(12) United States Patent
Bar-Even et al.

(10) Patent No.: US 10,781,456 B2
(45) Date of Patent: Sep. 22, 2020

(54) CARBON-NEUTRAL AND CARBON-POSITIVE PHOTORESPIRATION BYPASS ROUTES SUPPORTING HIGHER PHOTOSYNTHETIC RATE AND YIELD

(71) Applicants: Max-Planck-Gesellschaft zur Förderung der Wissenschaften e.V., Munich (DE); Yeda Research and Development Co. Ltd., at the Weizmann Institute of Science, Rehovot (IL)

(72) Inventors: Arren Bar-Even, Berlin (DE); Tobias Erb, Marburg (DE); Steffen Lindner, Berlin (DE); Philippe Marliere, Tournai (BE); Dan S. Tawfik, Jerusalem (IL)

(*) Notice: Subject to any disclaimer, the term of this patent is extended or adjusted under 35 U.S.C. 154(b) by 19 days.

(21) Appl. No.: 15/737,558

(22) PCT Filed: Jun. 22, 2016

(86) PCT No.: PCT/EP2016/064420
§ 371 (c)(1),
(2) Date: Dec. 18, 2017

(87) PCT Pub. No.: WO2016/207219
PCT Pub. Date: Dec. 29, 2016

(65) Prior Publication Data
US 2018/0223302 A1 Aug. 9, 2018

(30) Foreign Application Priority Data
Jun. 23, 2015 (EP) .................................. 15173354
Feb. 17, 2016 (EP) .................................. 16156189

(51) Int. Cl.
*C12N 15/82* (2006.01)

(52) U.S. Cl.
CPC ..... *C12N 15/8269* (2013.01); *C12N 15/8261* (2013.01); *Y02A 40/146* (2018.01)

(58) Field of Classification Search
CPC ............ C12N 15/8269; C12N 15/8261; Y02A 40/146
USPC .......................................................... 435/92
See application file for complete search history.

(56) References Cited

FOREIGN PATENT DOCUMENTS

WO WO2013130394 A1 9/2013
WO WO2015120343 A2 8/2015

OTHER PUBLICATIONS

Shih et al., Introduction of a Synthetic CO2-fixing Photorespiratory Bypass into a Cyanobacterium, The Journal of Biological Chemistry, vol. 289, No. 14, pp. 9493-9500.*
MicrobeWiki, Ralstonia eutropha, Accessed Sep. 27, 2019, Online at: microbewiki.kenyon.edu/index.php/Ralstonia_eutropha.*
International Preliminary Report on Patentability for International Application No. PCT/EP2016/064420.
Trudeau Devin L et al: "Design and in vitro realization of carbon-conserving photorespiration", Proceedings of the National Academy of Sciences of the United States of America, vol. 115, No. 49, Dec. 4, 2018 (Dec. 4, 2018), pp. E11455-E11464, ISSN: 0027-8424.
Bar-Even Arren Ed—Tiburcio Antonio Fernandez et al:"Daring metabolic designs for enhanced plant carbon fixation", Plant Science, vol. 273 , pp. 71-83, ISSN: 0168-9452, DOI: 10.1016/J.PLANTSCI.2017.12.00.
Peterhansel Christoph et al., "Photorespiration Redesigned", Plant Physiology, vol. 155, No. 1, Jan. 2011, pp. 49-55.
Chang-Peng Xin et al., "The Benefits of Photorespiratory Bypasses: How Can They Work?", Plant Physiology, vol. 167, No. 2, Feb. 2015, pp. 574 - 585.

* cited by examiner

*Primary Examiner* — Jennifer M.H. Tichy
(74) *Attorney, Agent, or Firm* — Perdue IP Law, APC

(57) ABSTRACT

The present invention relates to an organism, a tissue, a cell or an organelle expressing enzymes which allow the conversion of 2-phosphoglycolate (2-PG; also known as glycolate 2-phosphate,) into an intermediate compound of the Calvin-Benson-Bassham Cycle (CBBC) without releasing $CO_2$. The organism, tissue, cell or organelle of the invention may be genetically engineered, transgenic and/or transplastomic so as to express at least one enzyme which is involved in this conversion. The present invention further relates to an organism, tissue, cell or organelle which comprises/expresses at least one enzyme which is involved in this conversion. The present invention further relates to a method for producing an organism, tissue, cell or organelle of the invention. The present invention further relates to a method of enzymatically converting 2-PG into an intermediate compound of the CBBC without releasing $CO_2$. The present invention further relates to the use of an organism, tissue, cell or organelle of the invention for enzymatically converting 2-PG into an intermediate compound of the CBBC without releasing $CO_2$.

28 Claims, 34 Drawing Sheets

Figure 1:
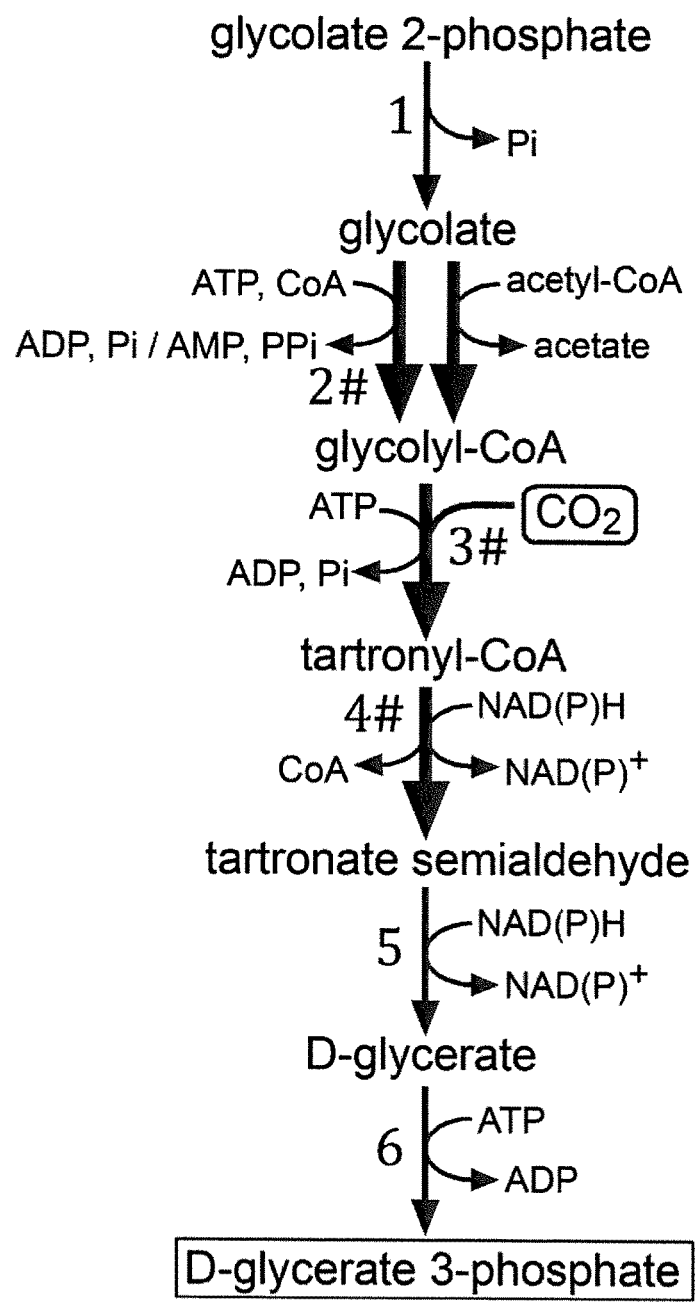
Figure 1:
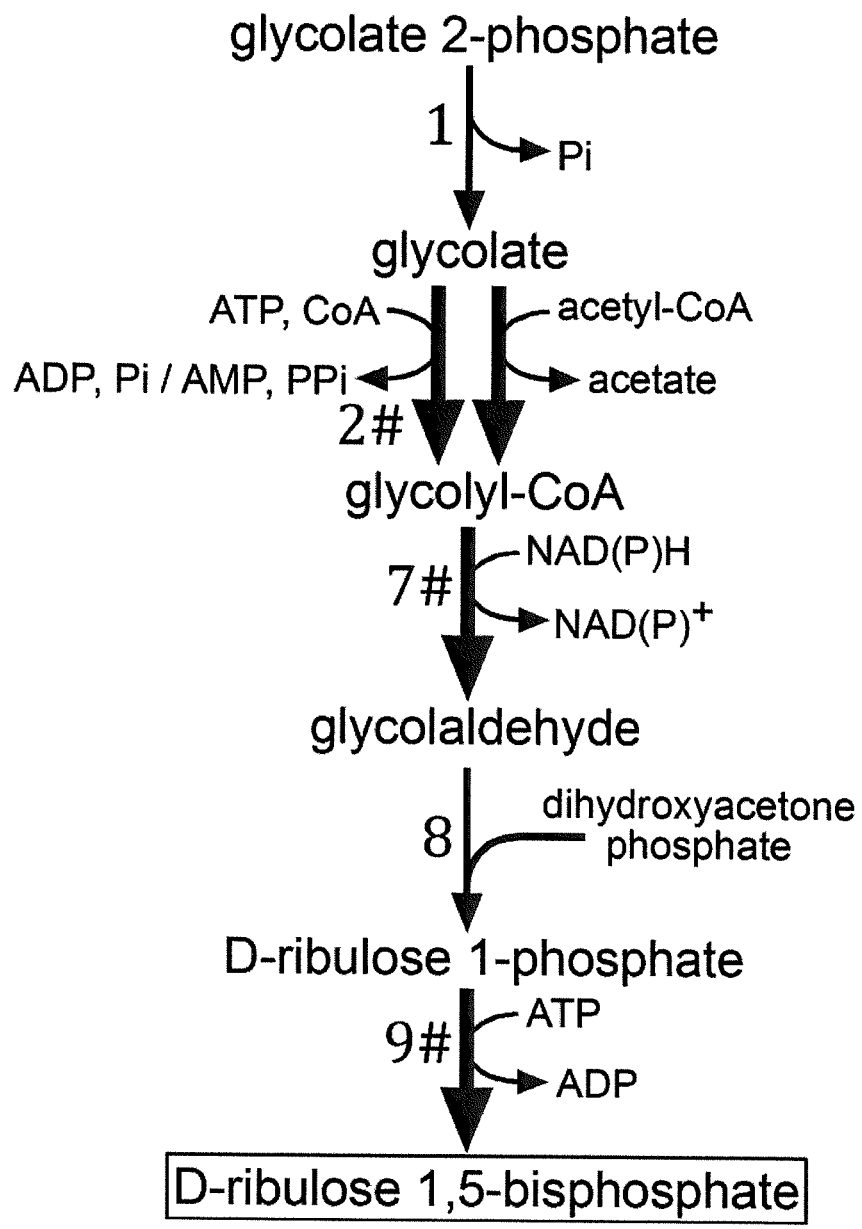
Figure 1:
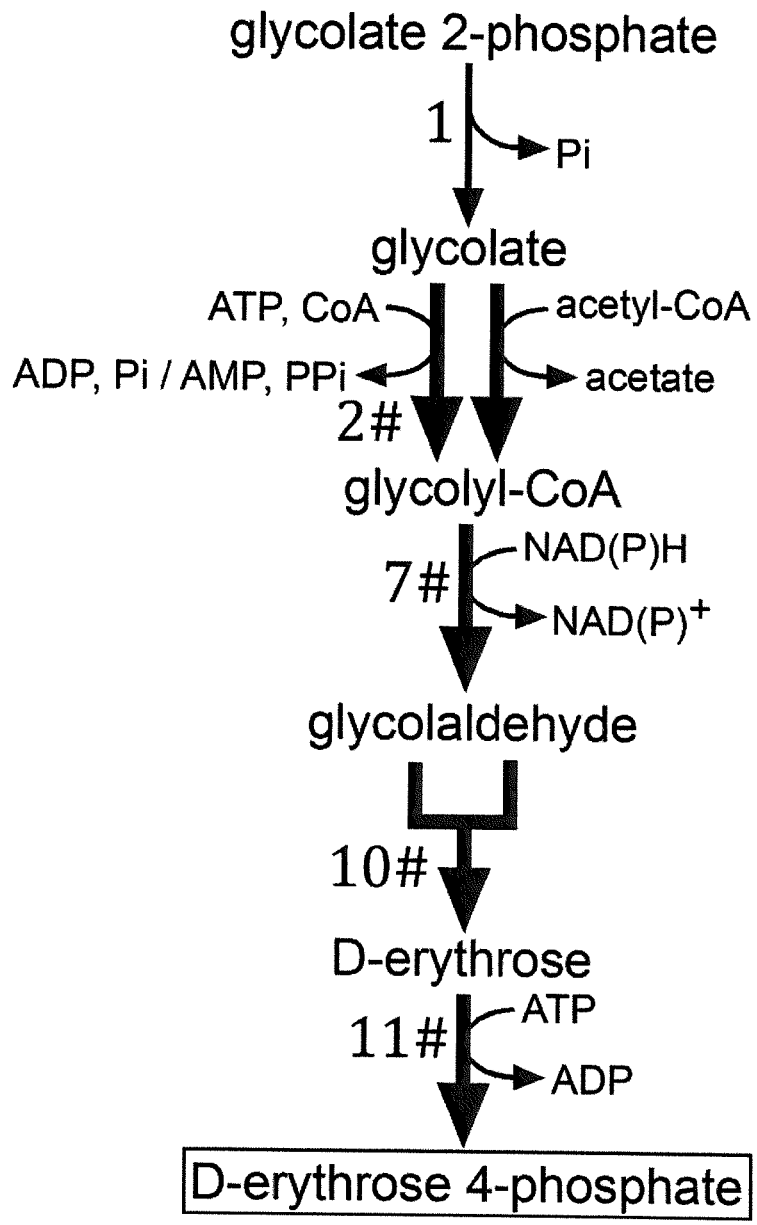
Figure 1:
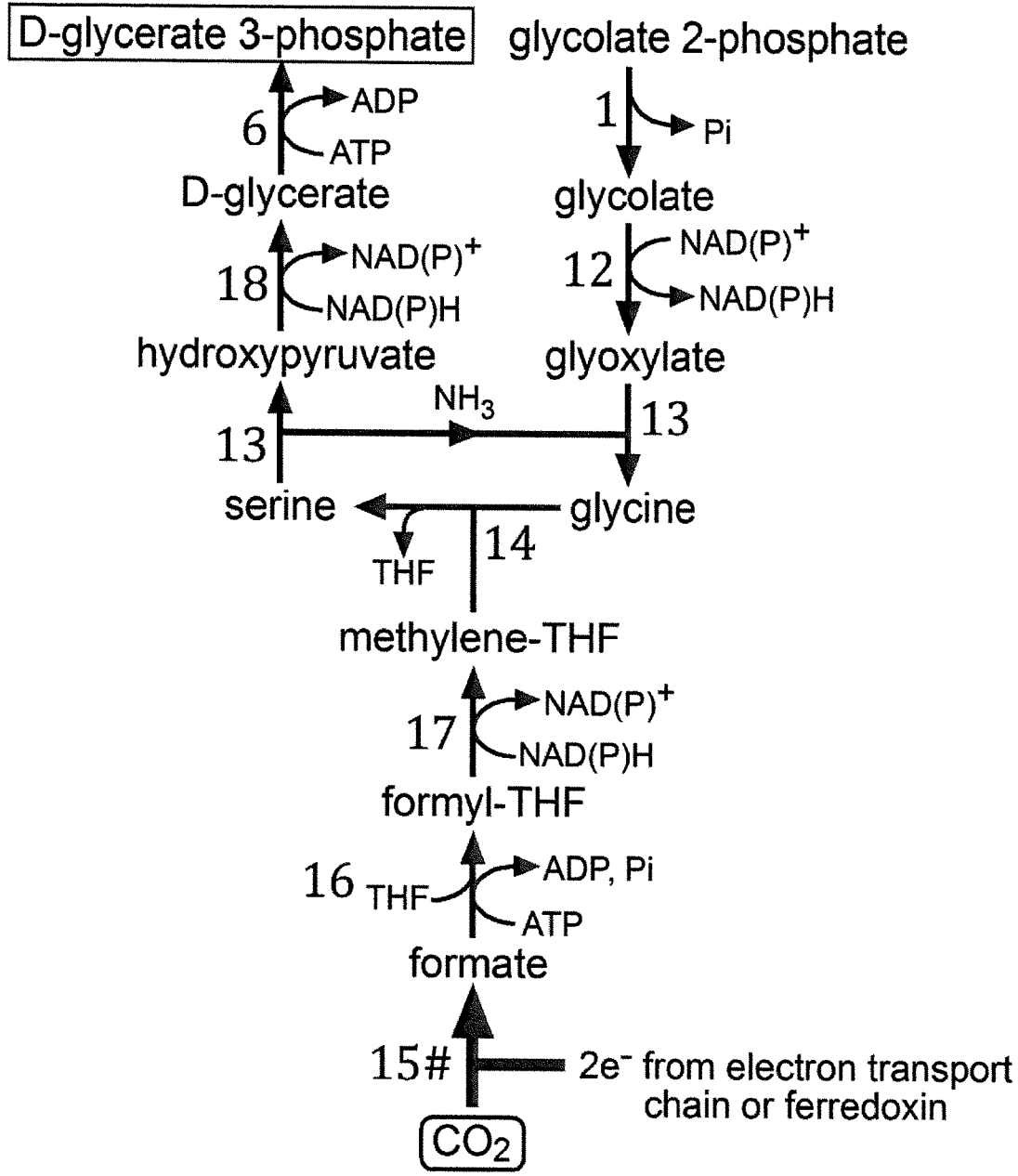
Figure 1:
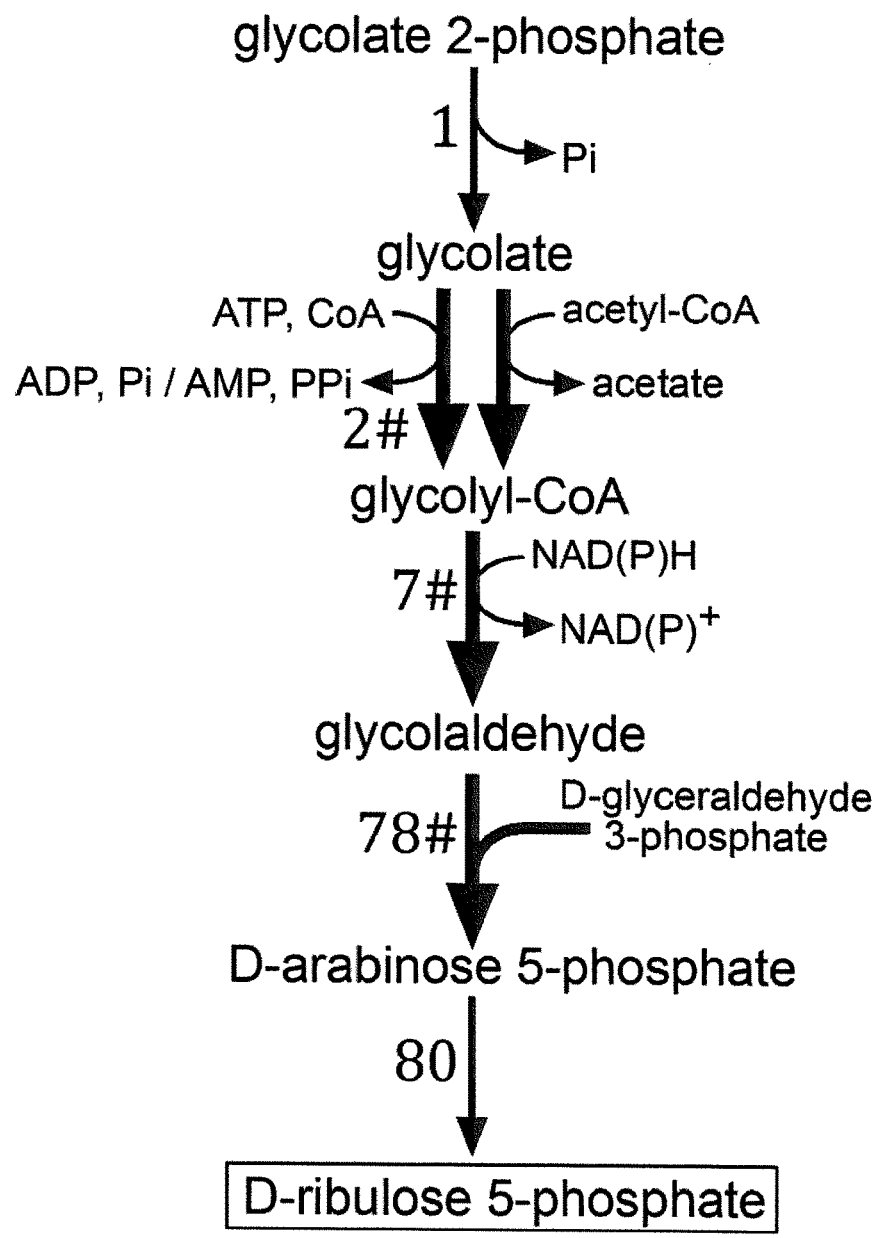
Figure 1:
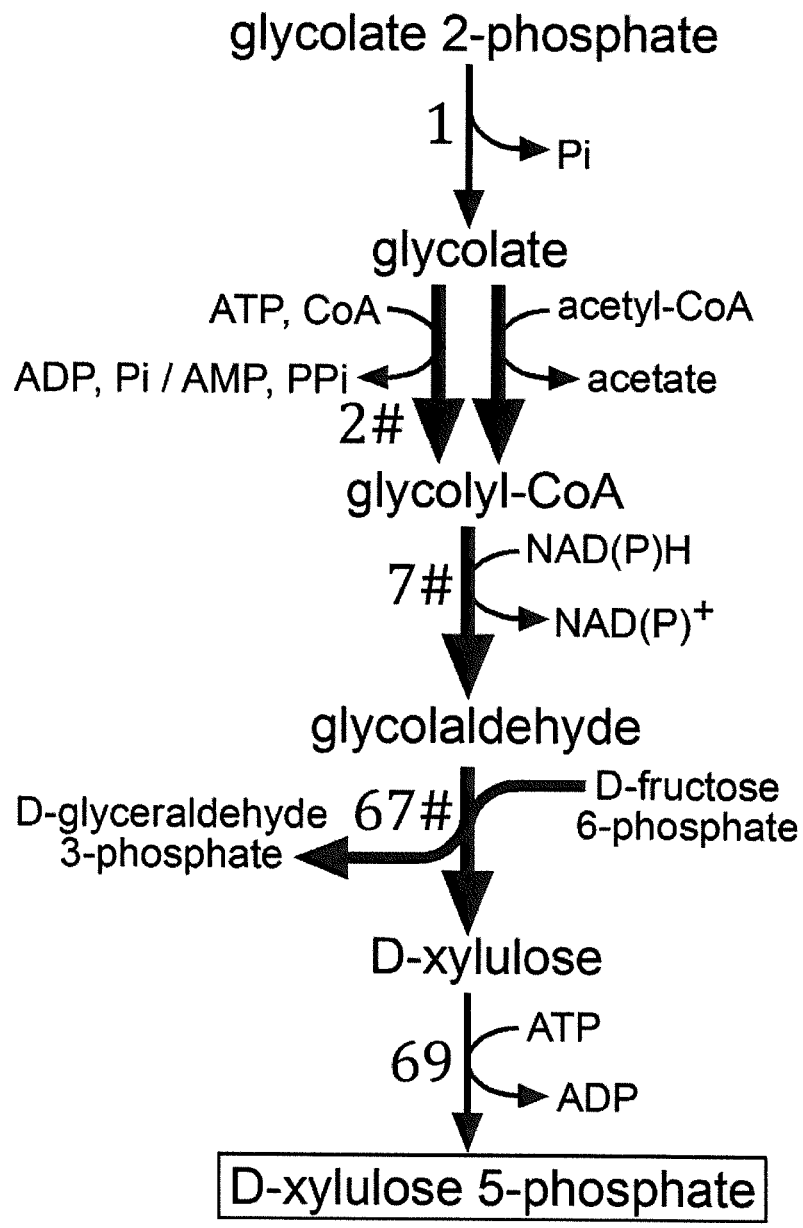
Figure 1:
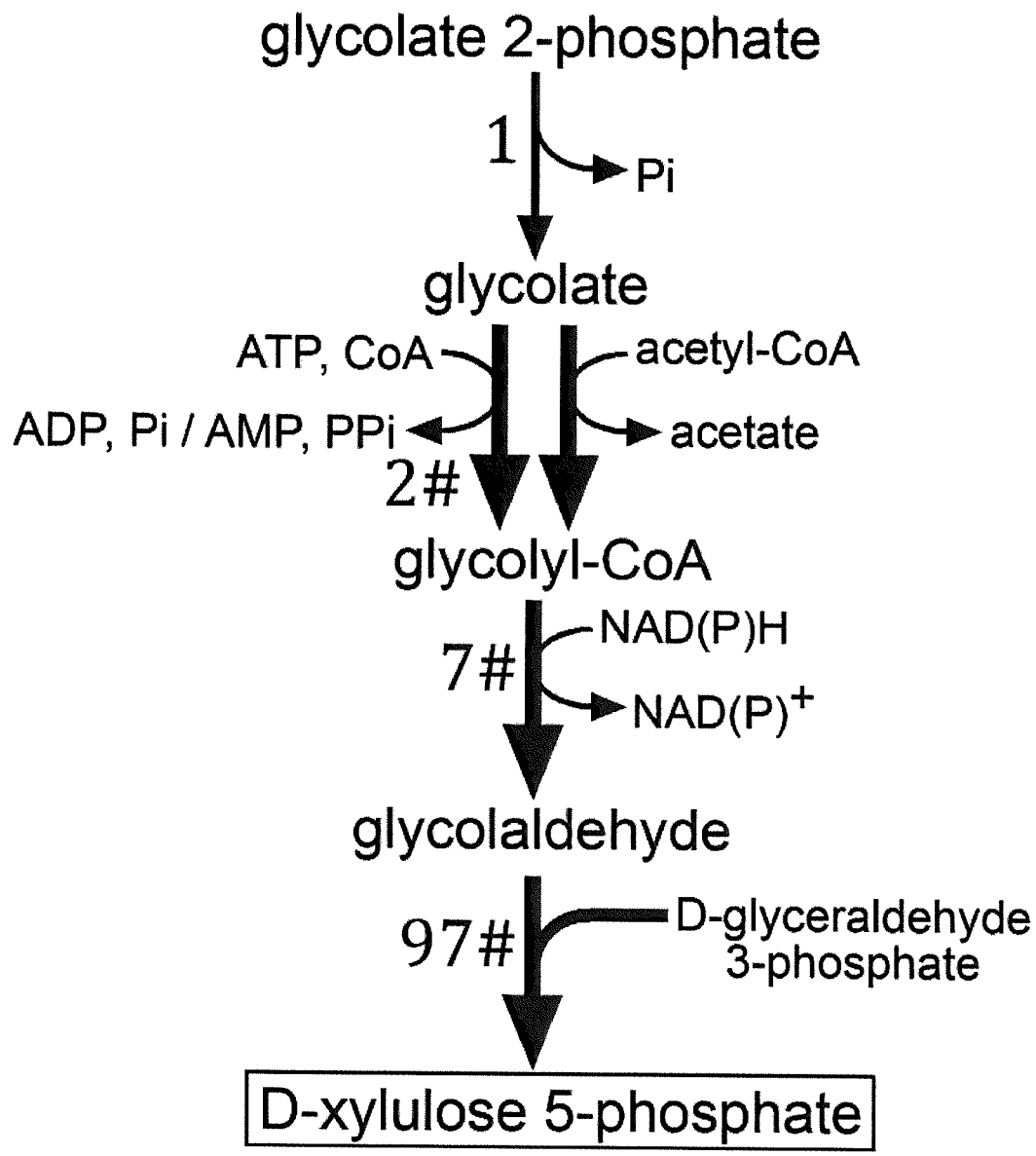

Specification includes a Sequence Listing.

(E), second page

(F), second page

(G)
Aldolase with glycolaldehyde (phosphate) as an acceptor (J), second page

(L)

Dihydroxyacetone/glyceraldehyde/erythrose production & tetrose rearrangement

(L), second page

Calvin-Benson-Bassham Cycle

CARBON-NEUTRAL AND CARBON-POSITIVE PHOTORESPIRATION BYPASS ROUTES SUPPORTING HIGHER PHOTOSYNTHETIC RATE AND YIELD

SUBMISSION OF SEQUENCE LISTING

The sequence listing associated with this application is filed in electronic format via EFS-Web and is hereby incorporated by reference into the specification in its entirety. The text file containing the sequence listing, created on Dec. 14, 2017, is named "1111_106_seq_list.TXT" and is 143 kB in size.

The present invention relates to an organism, a tissue, a cell or an organelle expressing enzymes which allow the conversion of 2-phosphoglycolate (2-PG; also known as glycolate 2-phosphate) into an intermediate compound of the Calvin-Benson-Bassham Cycle (CBBC) without releasing $CO_2$. The organism, tissue, cell or organelle of the invention may be genetically engineered, transgenic and/or transplastomic so as to express at least one enzyme which is involved in this conversion. The present invention further relates to an organism, tissue, cell or organelle which comprises/expresses at least one enzyme which is involved in this conversion. The present invention further relates to a method for producing an organism, tissue, cell or organelle of the invention. The present invention further relates to a method of enzymatically converting 2-PG into an intermediate compound of the CBBC without releasing $CO_2$. The present invention further relates to the use of an organism, tissue, cell or organelle of the invention for enzymatically converting 2-PG into an intermediate compound of the CBBC without releasing $CO_2$.

In the today's world, one in seven people is malnourished (Foley, 2011, *Nature* 478, 337-342). This situation is expected to worsen as human population keeps increasing at a staggering rate (Lee R., 2011, *Science* 333, 569-573). Feeding 10-15 billion people at the year 2100 is a tremendously challenging task that will only be met by the implementation of drastic measures to increase agricultural productivity (Godfray, H. C. et al., 2010, *Science* 327, 812-818; Tester M. and Langridge P., 2010, *Science* 327, 818-822). Hence, the seed industry seeks sustainable and economically viable solutions to increase crop yield despite numerous challenges, such as finite arable land and water resources, deleterious environmental conditions (e.g., drought, salinity), reduced availability of fertilizers, climate volatility and depletion of soil nutrients. A fundamental way to improve plant productivity and performance is through the use of plant genomics.

The reductive pentose phosphate cycle (rPP), also known as the Calvin-Benson-Bassham Cycle (CBBC), is responsible for the vast majority of the carbon fixed in the biosphere (Hugler M. and Sievert S. M., 2011, *Ann Rev Mar Sci* 3, 261-289). This cycle operates in higher plants, algae and many bacteria. Although under an immensely strong selective pressure for eons, this process, however, still displays major inefficiencies (Zhu X. G. et al., 2010, *Rev Plant Biol* 61, 235-261). A major constraint limiting the carbon fixation efficiency of the CBBC relates to its $CO_2$-fixing enzyme: ribulose-1,5-bisphosphate carboxylase/oxygenase (Rubisco). Rubisco exhibits low catalytic rate and hence is required at high cellular concentrations. Moreover, Rubisco's partial selectivity towards $CO_2$ results in $O_2$ being also accepted. This further reduces the CBBC's effective rate and leads to the formation of 2-PG, a compound which is toxic to plants (Spreitzer R. J. and Salvucci M. E., 2002, *Annu Rev Plant Biol* 53, 449-475). Due to an inherent mechanistic trade-off, any decrease in the cross-reactivity towards $O_2$ leads to a decrease in catalytic rate and vice versa. This makes improvements in photosynthetic yield by engineering Rubisco a daunting challenge (Savir Y. et al., 2010, *Proc Natl Acad Sci USA* 107, 3475-3480; Raines C. A., 2006, *Plant Cell Environ* 29, 331-339).

In a process termed photorespiration, 2-PG is detoxified and reassimilated into the CBBC at the expense of cellular energy, i.e., ATP and NADPH equivalents (Maurino V. G. et al., 2010, *Current Opinion in Plant Biology* 13, 249-256). However, the plant photorespiration pathway is inefficient for several reasons (Maurino V. G. et al., 2010, *Current Opinion in Plant Biology* 13, 249-256): (i) it dissipates reducing equivalents via the oxidation of glycolate with $O_2$; (ii) it releases $NH_3$ that needs to be reassimilated at an energetic cost; (iii) it releases $CO_2$, thereby counteracting the function of Rubisco and reducing the effective rate of the CBBC.

Previous studies indicated that photosynthetic rate and yield can be increased by implementing alternative photorespiration routes in plants (Kebeish R. et al., 2007, *Nat Biotechnol* 25, 593-599; Carvalho Jde F. et al., 2011, *BMC Biotechnol* 11, 111; Maier A. et al., 2012, *Frontiers in plant science* 3, 38). However, these routes focused only on (i) decreasing the ATP cost of photorespiration; (ii) bypassing the release of $NH_3$; (iii) avoiding dissipation of reducing power; and (iv) releasing $CO_2$ in the chloroplast, instead of the mitochondria, to increase the local $CO_2$ concentration in the vicinity of Rubisco and reduce the effect of $O_2$. In spite of their partial benefits (Peterhansel C. et al., 2013, *Plant Biol (Stuttg)* 15, 754-758; Peterhansel C. et al., 2013, *J Exp Bot* 64, 709-715), all these bypass routes have, just as natural photorespiration, the major drawback of resulting in the release of $CO_2$, thereby counteracting the function of Rubisco and reducing the effective rate of the CBBC.

WO2003/100066A1 discloses the re-use of 2-PG produced in photorespiration in a pathway that converts 2-PG into P-glycerate. Further, WO2009/103782A1 describes the conversion of glycolate into malate. However, similar to other alternative photorespiration routes, also the pathways disclosed in WO2003/100066A1 and WO2009/103782A1 result in the release of $CO_2$ and therefore do not remedy the major deficit of natural photorespiration.

Another suggested photorespiration bypass, which was, however, never fully implemented, tried to address this problem by introducing a carboxylation step (Shih P. M., 2014, *J Biol Chem* 289, 9493-9500). In this bypass route, glyoxylate, a photorespiration intermediate, is supposedly assimilated via reactions of the carbon fixing 3-hydroxypropionate bicycle (Herter S. et al., 2002, *J Biol Chem* 277, 20277-20283). This bypass, however, converts 2-PG into pyruvate, which is not an intermediate of the CBBC. Moreover, it considerably overlaps with the central metabolism, thereby demanding complex regulation.

Accordingly, there is a very high unmet need for engineering improved photorespiratory bypass routes, which reduce the deficits and inefficiencies of natural photorespiration and, therefore, a need for providing improved means and methods for reducing the deficits, inefficiencies and resulting negative impacts of photorespiration. It is thereby particularly envisaged that the photosynthetic rate and yield is increased.

This need is addressed by providing the embodiments characterized in the claims.

Accordingly, in a first aspect, the present invention relates to an organism, a tissue, a cell or an organelle expressing enzymes which allow the conversion of 2-PG into an intermediate compound of the CBBC without releasing $CO_2$.

In particular, the present invention provides enzymatic pathways that allow for the conversion of 2-PG into an intermediate compound of the CBBC with less deficits, inefficiencies and resulting negative impacts than natural photorespiration or previously suggested photorespiration bypass pathways. The assembled enzymatic pathways are therefore improved photorespiration bypass pathways, which can support a significantly higher photosynthetic rate and yield. It is the major advantage of these pathways that no $CO_2$ is released. Consequently, these pathways can support a significantly higher photosynthetic rate and yield.

In the context of the present invention, "without releasing $CO_2$" means that no net $CO_2$ is released/produced (as compared to the normal/natural, i.e. the non-alternative, photorespiration). Consequently, the conversion of 2-PG into an intermediate compound of the CBBC without releasing $CO_2$ may be carbon-neutral, i.e. no net $CO_2$ is fixed or released, or may even be carbon-positive, i.e. net $CO_2$ is fixed (both as compared to the normal/natural, i.e. the non-alternative, photorespiration). In the context of a carbon-positive conversion, at least 1 net $CO_2$ molecule(s) may be fixed per converted 2-PG molecule.

Thus, in one embodiment an enzymatic pathway for converting 2-PG into an intermediate compound of the CBBC, as described herein, is carbon-neutral. In another embodiment such a pathway is carbon-positive.

The conversion of 2-PG into an intermediate compound of the CBBC without releasing $CO_2$ in accordance with the invention may further enable/allow for a reduced ATP and/or NAD(P)H consumption (as compared to (an organism/tissue/cell/organelle with) normal/natural, i.e. non-alternative pathway of photorespiration). "Reduced . . . consumption" in this context means, for example, that at least 1, at least 2, at least 3, at least 4 or at least 5 less ATP molecule(s) and/or at least 1 molecule(s), at least 2, at least 3, at least 4, at least 5 less NAD(P)H molecule(s) is/are required/consumed per production of 1 triose phosphate via the CBBC. In principle, a lower ATP/NAD(P)H consumption are/is preferred. In this context, it is particularly envisaged that the pathway remains thermodynamically feasible and operates under strong thermodynamic motive force.

One particular advantage provided by the means and method of the present invention is that the alternative photorespiration pathway is short, i.e. comprises only a few enzymes (or enzymatic activities) and enzymatic conversions/reactions, respectively. In particular, 10 or less enzymatic conversions or reactions, respectively, are envisaged, wherein lower numbers are preferred. Particular, but non-limiting, examples of numbers of enzymes (or enzymatic activities) and enzymatic conversions or reactions, respectively, in accordance with the invention are 3, 4, 5, 6, 7, 8, 9 or 10. In principle, lower numbers are preferred. The different enzymatic routes provided by the present invention are described in more detail further below.

As a general feature, all pathways according to the present invention convert 2-PG into an intermediate compound of the CBBC. In principle any intermediate compound of the CBBC may be the resulting product/end-product of the conversion of 2-PG in accordance with the invention. The intermediate compounds of the CBBC are known in the art and are, for example, described in the FIGS. 2.1.33 and 2.1.35 of Strasburger, Lehrbuch der Botanik (33. Ed. 1991). Likewise, the intermediate compounds of the CBBC are described herein in FIG. 5. In particular, an intermediate compound of the CBBC resulting from the conversion of 2-PG to be employed in accordance with the invention is selected from the group consisting of: D-glycerate 3-phosphate, D-glycerate 1,3-bisphosphate, D-glyceraldehyde 3-phosphate, dihydroxyacetone phosphate (aka glycerone phosphate), D-fructose 1,6-bisphosphate, D-fructose 6-phosphate, D-sedoheptulose 7-phosphate, D-sedoheptulose 1,7-bisphosphate, D-erythrose 4-phosphate, D-xylulose 5-phosphate, D-ribose 5-phosphate, D-ribulose 5-phosphate, and D-ribulose 1,5-bisphosphate. Preferred intermediates are selected from the group consisting of: D-glycerate 3-phosphate; D-ribulose 5-phosphate; D-ribulose 1,5-bisphosphate; D-erythrose 4-phosphate; D-ribose 5-phosphate; D-xylulose 5-phosphate; D-fructose 6-phosphate; D-fructose 1,6-bisphosphate, D-sedoheptulose 1,7-bisphosphate and dihydroxyacetone phosphate. More preferred intermediate compounds are selected from the group consisting of: D-glycerate 3-phosphate, D-ribose 5-phosphate, D-ribulose 1,5-bisphosphate, D-ribulose 5-phosphate, D-xylulose 5-phosphate and D-erythrose 4-phosphate.

Examples of compounds which are not to be seen as intermediate compounds of the CBBC in accordance with the invention are, for example, intermediate compounds of the 3-hydroxypropionate cycle and intermediate compounds of the central metabolism. Examples of such non-envisaged compounds are 3-hydroxypropionate, malate, succinate, pyruvate, glycerate 2-phosphate and glucose 6-phosphate. Hence, in one aspect, it is envisaged that the conversion of 2-PG into an intermediate compound of the CBBC in accordance with the invention does not involve (parts of) and/or does not (considerably) overlap with the 3-hydroxypropionate bicycle. This means that (the) respective enzymes are not used in accordance with the invention (i.e. are not encompassed by the (cascade/series of) enzymes to be employed in accordance with the invention) and/or that no respective intermediate compounds occur. For example, it is envisaged that only 3 or less, preferably only 2 or less, more preferably only 1 and most preferably 0 enzyme(s) and/or intermediate compound(s) overlap with the 3-hydroxypropionate cycle.

It is in particular also envisaged that an organism, a tissue, a cell or an organelle may employ a pathway of the present invention, wherein said pathway does not involve any of the enzymes and/or metabolites of lower glycolysis (i.e. the pathways of the present invention do not overlap with the lower glycolysis). The term "lower glycolysis" refers to any conversions in glycolysis downstream of 2-phosphoglycerate. Possible end points of glycolysis are known in the art. Non-limiting examples for endpoints are lactate, ethanol or acetate. Enzymes that are involved in lower glycolysis but are not-envisaged in the pathways of the present invention are preferably selected from the group consisting of enolase; pyruvate kinase; pyruvate phosphate dikinase; and pyruvate water dikinase. Metabolites of lower glycolysis are known in the art. Preferably, metabolites that are involved in lower glycolysis but are not-envisaged in the pathways of the present invention are selected from phosphoenolpyruvate (PEP) and pyruvate. In other words, the enzymes expressed by an organism, a tissue, a cell or an organelle of the present invention that allow for conversion of 2-PG into an intermediate of the CBBC do not comprise any enzymes and/or metabolites of lower glycolysis. The enzyme(s) of the lower glycolysis are preferably selected from the group consisting of enolase; pyruvate kinase; pyruvate phosphate dikinase; and pyruvate water dikinase. The metabolites of the lower glycolysis are preferably selected from the group consisting of phosphoenolpyruvate (PEP) and pyruvate.

Similarly, it is in particular also envisaged that an organism, a tissue, a cell or an organelle may employ a pathway of the present invention, wherein said pathway does not involve any of the enzymes and/or metabolites of the citric acid/TCA cycle (i.e. the pathways of the present invention do not overlap with the citric acid/TCA cycle). Enzymes and metabolites of the citric acid/TCA cycle are known in the art. Preferably, metabolites that are involved in the citric acid/TCA cycle but are not-envisaged in the pathways of the present invention are selected from the group consisting of citrate, isocitrate, 2-keto-glutarate, succinyl-CoA, succinate, fimarate, malate and oxaloacetate. In other words the enzymes expressed by an organism, a tissue, a cell or an organelle of the present invention that allow for conversion of 2-PG into an intermediate of the CBBC do not comprise any enzymes and/or metabolites of the citric acid/TCA cycle. The metabolites of the citric assay/TCA cycle are preferably selected from the group consisting of citrate, isocitrate, 2-keto-glutarate, succinyl-CoA, succinate, fimarate, malate and oxaloacetate.

Furthermore, it is also envisaged that an organism, a tissue, a cell or an organelle may employ a pathway of the present invention, wherein said pathway does not involve any anaplerotic/cataplerotic enzymes and/or reaction. An anaplerotic enzyme is an enzyme that catalyzes an anaplerotic reaction. An anaplerotic reaction is a reaction in which a metabolite from lower glycolysis (preferably PEP or pyruvate) is converted into a metabolite of the citric acid/TCA cycle. A cataplerotic enzyme is an enzyme that catalyzes a cataplerotic reaction. A cataplerotic reaction is a reaction in which a metabolite from the TCA cycle is converted into a metabolite of lower glycolysis (preferably PEP or pyruvate). Anaplerotic/cataplerotic enzymes that are not-envisaged in the pathways of the present invention are preferably selected from the group consisting of PEP carboxylase, PEP carboxykinase, pyruvate carboxylase and malic enzyme. In other words the enzymes expressed by an organism, a tissue, a cell or an organelle of the present invention that allow for conversion of 2-PG into an intermediate of the CBBC do not comprise any anaplerotic/cataplerotic enzymes and/or reactions. Anaplerotic/cataplerotic enzymes may comprise or consist of PEP carboxylase, PEP carboxykinase, pyruvate carboxylase and malic enzyme.

The pathways according to the present invention as described in the following comprise enzymatic conversions which as such occur in nature and are part of the normal metabolism of certain organisms and for which corresponding enzymes have been described as being able to catalyze the reactions. Other enzymatic conversions which form part of the described pathways have as such not yet been described to occur in nature and, in particular, not in the context of a pathway as described herein. Such enzymatic reactions are sometimes referred herein as "non-native" (enzymatic) conversions or "non-native" reactions. In the appended Figures and elsewhere herein, these enzymatic conversions are indicated by hash keys or bold arrows. The present invention describes options for achieving these enzymatic conversions by using certain enzymes described in the prior art. Thus, in the context of the present invention, the term "non-native conversion" or "non-native reaction" means a chemical transformation for which no specific enzyme has been described so far, but which are expected to be promiscuously catalyzed, to some extent, by an existing enzyme or a variant thereof. Such existing enzyme is originally known to catalyze a different but chemically related reaction and is known or expected to also promiscuously accept the substrate of the non-native reaction. In particular, also mutant variants of one or more of the promiscuous existing enzymes for catalyzing one or more of the non-native reactions may be employed. Such mutant variants may, for example, be derived by the introduction of mutations or other alterations which, for example, alter or improve the enzymatic activity, so as to catalyze the non-native enzymatic conversion more efficiently. In particular, the person skilled in the art may thereby readily achieve higher rates of one or more non-native reaction(s) out of the promiscuous activity(ies). Methods for modifying and/or improving the enzymes or in other words enzyme evolution/engineering techniques are known by the person skilled in the art and are, for example, described herein elsewhere. By combining the different enzymatic conversions described herein, the present invention provides efficient photorespiration bypass pathways.

A pathway according to the present invention as described in the following is preferably characterized by the features that 2-PG is converted into an intermediate compound of the CBBC without releasing $CO_2$ and that this conversion involves as an intermediate
glycolyl-CoA and/or glycolaldehyde; or
glycolaldehyde 2-phosphate;
or that this conversion consumes methylene-THF that results from enzymatic conversion of $CO_2/HCO_3^-$.

As mentioned above, one of the preferred intermediates of the CBBC into which 2-PG is converted according to the present invention is D-glycerate 3-phosphate. In the following, the possible pathways will be described which allow the conversion of 2-PG into D-glycerate 3-phosphate according to preferred embodiments of the present invention. The pathway which allows converting 2-PG into D-glycerate 3-phosphate will be referred to as option "A)" in the following. According to option A) the intermediate compound of the CBBC is D-glycerate 3-phosphate, and the conversion of 2-PG is preferably achieved by:
a) enzymatic conversion of 2-PG into glycolyl-CoA, further enzymatic conversion of glycolyl-CoA into tartronyl-CoA, further enzymatic conversion of tartronyl-CoA into tartronate semialdehyde, further enzymatic conversion of tartronate semialdehyde into D-glycerate, and further enzymatic conversion of D-glycerate into D-glycerate 3-phosphate (a respective illustrative example is provided by FIG. 1A); or
enzymatic conversion of 2-PG into glycolyl-CoA, further enzymatic conversion of glycolyl-CoA into tartronyl-CoA, further enzymatic conversion of tartronyl-CoA into tartronate semialdehyde, further enzymatic conversion of tartronate semialdehyde into hydroxypyruvate, further enzymatic conversion of hydroxypyruvate into D-glycerate, and further enzymatic conversion of D-glycerate into D-glycerate 3-phosphate (a respective illustrative example is provided by FIG. 3A; pathway: 2-PG conversion into glycolyl CoA as shown in FIG. 2+enzymes 3#, 4#, 25, 18, 6); or by
b) enzymatic conversion of 2-PG into glycolate, further enzymatic conversion of glycolate into glyoxylate, further enzymatic conversion of glyoxylate into glycine, further enzymatic conversion of glycine into serine, further enzymatic conversion of serine into hydroxypyruvate, further enzymatic conversion of hydroxypyruvate into D-glycerate, and further enzymatic conversion of D-glycerate into D-glycerate 3-phosphate,
wherein said enzymatic conversion of glycine into serine consumes methylene-THF resulting from enzymatic conversion of $CO_2$ into formate, further enzymatic conversion of formate into formyl-THF, and further enzymatic conversion of formyl-THF into said methylene-THF (a respective illustrative example is provided by FIG. 1D); or by c) enzymatic conversion of 2-PG into glycolyl-CoA, further enzymatic conversion of glycolyl-CoA into hydroxypyruvate, further enzymatic conversion of hydroxypyruvate into D-glycerate, and further enzymatic conversion of D-glycerate into D-glycerate 3-phosphate (respective illustrative examples are provided by FIG. 4; pathways: 2-PG conversion into glycolyl CoA as shown in FIG. 2+enzymes 55#, 18, 6; 2-PG conversion into glycolyl CoA as shown in FIG. 2+enzymes 55#, 25, 5, 6; 2-PG conversion into glycolyl CoA as shown in FIG. 2+enzymes 15, 54#, 18, 6; 2-PG conversion into glycolyl CoA as shown in FIG. 2+enzymes 15, 54#, 25, 5, 6).

The enzymatic conversions as described in A)a), above, can be achieved as described in the following:

The enzymatic conversion of 2-PG into glycolyl-CoA as described in A)a), above, can be achieved by different pathways as will be described further below.

The further enzymatic conversion of glycolyl-CoA into tartronyl-CoA (reaction 3#) as described above in A)a), can, for example, be achieved by a biotin-dependent acyl-CoA carboxylase (EC 6.4.1.X) (this enzyme is an example of enzyme 3#, mentioned herein). In principle, any acyl-CoA carboxylase (EC 6.4.1.X) can be employed for such a conversion. In a preferred embodiment, a promiscuous biotin-dependent acyl-CoA carboxylase (e.g. see Tran T. H. et al., 2015, *Nature* 518, 120-124) is used. In a particularly preferred embodiment, the acyl-CoA carboxylase (EC 6.4.1.X) is a propionyl-CoA carboxylase (EC 6.4.1.3) (Hügler M. et al., 2003, *Eur. J. Biochem.* 270, 736-744). In one embodiment a propionyl-CoA carboxylase of *Methylobacterium extorquens* (the enzyme is herein also referred to as $PCC_{Me}$) may be employed. This enzyme comprises two subunits, generally referred to as propionyl-CoA carboxylase alpha and propionyl-CoA carboxylase beta, respectively, which are encoded by two separate genes. The amino acid sequence of propionyl-CoA carboxylase alpha (pccA) is known and available, e.g., under NCBI accession no.: WP_003599287.1 (nucleic acid sequence encoding the enzyme shown in SEQ ID NO: 1; amino acid sequence shown in SEQ ID NO: 2) The amino acid sequence of propionyl-CoA carboxylase beta (pccB) is known and available, e.g., under NCBI accession no.: WP_003597263.1 (nucleic acid sequence encoding the enzyme shown in SEQ ID NO: 3; amino acid sequence shown in SEQ ID NO: 4). It is of course not only possible to employ in the enzymatic conversion of glycolyl-CoA into tartronyl-CoA an enzyme having the subunits showing the amino acid sequences of SEQ ID NO: 2 and 4, respectively, but it is also possible to employ an enzyme, which has subunits showing related sequences, provided that the enzyme still shows the activity of converting glycolyl-CoA into tartronyl-CoA.

The term "related sequences" preferably means sequences showing at least 60%, preferably at least 65%, more preferably at least 70%, more preferably at least 75%, more preferably at least 80%, more preferably at least 85%, more preferably at least 90%, more preferably at least 95%, more preferably at least 99% and most preferably at least 99.5% sequence identity to the amino acid sequences shown in SEQ ID NO: 2 or 4, respectively.

Those having skill in the art will know how to determine percent identity between/among sequences using, for example, algorithms such as those based on CLUSTALW computer program (Thompson (1994) Nucl. Acids Res. 2:4673-4680), CLUSTAL Omega (Sievers (2014) Curr. Protoc. Bioinformatics 48:3.13.1-3.13.16) or FASTDB (Brutlag (1990) Comp App Biosci 6: 237-245). Also available to those having skill in this art are the BLAST, which stands for Basic Local Alignment Search Tool, and BLAST 2.0 algorithms (Altschul, (1997) Nucl. Acids Res. 25:3389-3402; Altschul (1990) J. Mol. Biol. 215:403-410). The BLASTN program for nucleic acid sequences uses as defaults a word length (W) of 11, an expectation (E) of 10, M=5, N=4, and a comparison of both strands. The BLOSUM62 scoring matrix (Henikoff (1992) Proc. Natl. Acad. Sci. U.S.A. 89:10915-10919) uses alignments (B) of 50, expectation (E) of 10, M=5, N=4, and a comparison of both strands.

How to design assays for determining the enzymatic activity of converting glycolyl-CoA into tartronyl-CoA is known to the skilled person. It is for instance possible to use an in vitro assay as described in the appended examples for determining whether an enzyme has the activity of converting glycolyl-CoA into tartronyl-CoA. In one embodiment the assay as described in the example may also be modified with respect to concentration of any components used and/or modification of buffer compositions based on the common general knowledge of skilled person.

Such above-mentioned related sequences may, for example also comprise mutated variants showing improved properties. In a preferred embodiment a mutated version of a propionyl-CoA carboxylase of *Methylobacterium extorquens* is employed, which shows an improved activity catalyzing the conversion of glycolyl-CoA into tartronyl-CoA in comparison to the wild-type enzyme. The present invention provides for a non-limiting example of such mutant variant, which has surprisingly been found to have improved activity for catalyzing the conversion of glycolyl-CoA into tartronyl-CoA in comparison to the wild-type enzyme. This non-limiting example is a mutant variant of $PCC_{Me}$ comprising a pccB mutant variant subunit that comprises the amino acid substitution from aspartate (D) to isoleucine (I) at a position corresponding to position 407 of the pccB amino acid sequence (see SEQ ID NO: 4) and/or the amino acid substitution from tyrosine (Y) to histidine (H) at a position corresponding to position 143 of the pccB amino acid sequence (see SEQ ID NO: 4). For example, a mutant variant of $PCC_{Me}$ that comprises the two above-mentioned amino acid substitutions but otherwise corresponds to the wild-type sequences may be employed (also referred to herein as $PCC_{Me}$_D407I_Y143H or pccB_D407I_Y143H_pccA, coding nucleic acid sequence is shown in SEQ ID NO: 5; amino acid sequence is shown in SEQ ID NO: 6) for converting glycolyl-CoA into tartronyl-CoA. The nucleic acid sequence encoding the pccB_D407I_Y143H subunit and the corresponding amino acid sequence are depicted in SEQ ID NO: 5 and 6, respectively. The improved activity of this mutant variant of $PCC_{Me}$ provided herein to catalyze the enzymatic conversion of glycolyl-CoA into tartronyl-CoA (reaction 3#) is also illustrated in the appended examples.

In another embodiment also any other propionyl-CoA carboxylase (EC 6.4.1.3) may be employed which comprises an amino acid substitution at a position corresponding to position 143 of SEQ ID NO: 4 and/or a amino acid substitution at a position corresponding to position 407 of SEQ ID NO: 4. Preferably, the substitution results in an amino acid which is similar to the amino acid substitutions described above for positions 143 and 407 of SEQ ID NO: 4. "Similar" in this context means that the amino acid introduced has a related chemical structure and/or chemical properties. Amino acids with related chemical structures and/or chemical properties are well known in the art. The corresponding positions in the amino acid sequence can, for example be identified by alignments of the amino acid sequences and/or corresponding nucleic acid sequences with the amino acid sequence of pccB (SEQ ID NO: 4) or the nucleic acid sequence (SEQ ID NO: 3) encoding the pccB protein.

In order to determine whether a nucleotide residue/position or a amino acid residue/position in a given nucleotide sequence or amino acid sequence, respectively, corresponds to a certain position compared to another nucleotide sequence or amino acid sequence, respectively, the skilled person can use means and methods well known in the art, e.g., alignments, either manually or by using computer programs such as those mentioned herein. For example, BLAST 2.0 can be used to search for local sequence alignments. BLAST or BLAST 2.0, as discussed above, produces alignments of nucleotide sequences to determine sequence similarity. Because of the local nature of the alignments, BLAST or BLAST 2.0 is especially useful in determining exact matches or in identifying similar or identical sequences. Similarly, alignments may also be based on the CLUSTALW computer program (Thompson (1994) Nucl. Acids Res. 2:4673-4680) or CLUSTAL Omega (Sievers (2014) Curr. Protoc. Bioinformatics 48:3.13.1-3.13.16).

The further enzymatic conversion of tartronyl-CoA into tartronate semialdehyde (reaction 4#) as described above in A)a) can, for example, be achieved by an acylating aldehyde dehydrogenase (EC 1.2.1.X) (this enzyme is an example of enzyme 4#, mentioned herein). In principle, any acylating aldehyde dehydrogenase (EC 1.2.1.X) can be employed for such a conversion, preferably a nonspecific acylating aldehyde dehydrogenase enzyme (e.g. see Baker P. et al., 2012, Biochemistry 51, 4558-4567). In a preferred embodiment, the acylating aldehyde dehydrogenase is a malonyl-CoA reductase (EC 1.2.1.75) (Hügler M et al., 2002, Journal of Bacteriology May 2002, p. 2404-2410). In particular, the malonyl-CoA reductase may be a malonyl-CoA reductase of Chloroflexus aurantiacus or a malonyl-CoA reductase Erythrobacter sp. NAP1. The amino acid sequence of malonyl CoA reductase of Chloroflexus aurantiacus ($MCR_{Ca}$) is known and is available, e.g., under NCBI accession no. AAS20429.1 (nucleic acid sequence is shown in SEQ ID NO: 7; amino acid sequence is shown in SEQ ID NO: 8). The amino acid sequence of malonyl CoA reductase of Erythrobacter sp. NAP1 ($MCR_E$) is known and is available, e.g., under NCBI accession no. WP_007163680.1 (nucleic acid sequence is shown in SEQ ID NO: 9; amino acid sequence is shown in SEQ ID NO: 10). The capability of a $MCR_E$ and $MCR_{Ca}$ to catalyze the enzymatic conversion of tartronyl-CoA into tartronate semialdehyde (reaction 4#) is also illustrated in the appended examples. It is of course not only possible to employ in the enzymatic conversion of tartronyl-CoA into tartronate semialdehyde an enzyme having the amino acid sequences of SEQ ID NO: 8 or 10, respectively, but it is also possible to employ an enzyme showing a related sequence, provided that the enzyme still shows the activity of converting tartronyl-CoA into tartronate semialdehyde.

The term "related sequences" preferably means sequences showing at least 60%, preferably at least 65%, more preferably at least 70%, more preferably at least 75%, more preferably at least 80%, more preferably at least 85%, more preferably at least 90%, more preferably at least 95%, more preferably at least 99% and most preferably at least 99.5% sequence identity to the amino acid sequences shown in SEQ ID NO: 8 or 10, respectively.

As regards the determination of percent identity the same applies as has been described herein above.

Such above-mentioned related sequences may, for example also comprise mutated variants showing improved properties. In particular, also any mutant variants created by the evolution and optimization strategies described herein elsewhere are included in the related sequences. In a preferred embodiment a mutated version of a malonyl-CoA reductase of Chloroflexus aurantiacus or a malonyl-CoA reductase Erythrobacter sp. NAP1 is employed, which shows an improved activity catalyzing the conversion of tartronyl-CoA into tartronate semialdehyde (reaction 4#) in comparison to the respective wild-type enzyme.

How to design assays for determining the enzymatic activity of converting tartronyl-CoA into tartronate semialdehyde is known to the skilled person. It is, for instance, possible to use an in vitro assay as described in the appended examples for determining whether an enzyme has the activity of converting tartronyl-CoA into glycerate with the exception that instead of detecting the formation of glycerate the formation of the product tartronate semialdehyde is detected. The formation of tatronate semialdehyde can, for example, be detected by an HPLC-MS based assay that uses phenylhydrazine. In such assays the tartronate semialdehyde can be covalently derivatized with phenylhydrazine to a phenylhydrazone, which can be detected by its absorbance at 324 nm and confirmed by its corresponding mass spectrum. Concentrations of any components used and/or buffer compositions can be selected analogous to the assay for detecting the activity to convert tartronyl-CoA into glycerate as described in the appended Examples or can also be based on the common general knowledge of a skilled person. Alternatively, the enzymatic activity of converting tartronyl-CoA into tartronate semialdehyde can, for example, also be detected by another assay. In the first step of such an assay the substrate tatronyl CoA is contacted with the respective enzyme (e.g. as described in the appended examples for the assay to measure the conversion from tartronyl-CoA into glycerate) and incubated for a defined time (e.g. as described in the appended examples for the assay to measure the conversion from tartronyl-CoA into glycerate). After the incubation the reaction is stopped, e.g. by heat inactivation, removal of the enzyme or any other means that do not interfere with the downstream analysis and are known to a skilled person. Subsequently, the formation of tatronate semialdehyde is detected by adding the enzyme tartronate semialdehyde reductase from E. coli (GarR) and NADH to the inactivated reaction mixture. After further incubation at 30° C. or 37° C. (e.g. for 1 min, 2 min, 3 min, 4 min, 5 min, 6 min, 7 min, 8 min, 9 min, 10 min, 15 min, 20 min, 30 min, 40 min) the decrease in absorbance at 340 nM is spectrophotometrically analyzed to indicate how much NADH was consumed. The measured NADH consumption is directly proportional to the level of tatronate semialdehyde in the initial solution (the reaction is basically irreversible). Further information can be found in THE JOURNAL OF BIOLOGICAL CHEMISTRY Vol. 275, No. 49, Issue of December 8, pp. 38780-38786, 2000 (Reuben K. Njau, Carter A. Herndon, and John W. Hawes, Novel b-Hydroxyacid Dehydrogenases in Escherichia coli and Haemophilus influenzae). In this article an assay, which detects the reverse, unfavorable direction, namely tatronate semialdehyde oxidation is described.

The further enzymatic conversion of tartronate semialdehyde into D-glycerate as described in A)a), above, is a conversion which does naturally occur and for which enzymes which catalyze this conversion are known.

Examples for corresponding enzymes which are known to catalyze this conversion are mentioned in Table 2 and corresponding enzymes can be employed in the context of the present invention. According to one embodiment the conversion can be achieved by directly converting tartronate semialdehyde into D-glycerate (reaction 5). In addition to the enzymes listed in Table 2 also any acylating aldehyde dehydrogenase (EC 1.2.1.X) may be employed for such a conversion. In a preferred embodiment an acylating aldehyde dehydrogenase having alcohol dehydrogenase activity is used. Preferably a nonspecific acylating aldehyde dehydrogenase enzyme (e.g. see Baker P. et al., 2012, *Biochemistry* 51, 4558-4567) is employed. In one embodiment, the acylating aldehyde dehydrogenase may be a malonyl-CoA reductase (EC 1.2.1.75 and/or 1.1.1.298) (Hügler M et al., 2002, Journal of Bacteriology May 2002, p. 2404-2410). In a preferred embodiment, the malonyl-CoA reductase may be a malonyl-CoA reductase of *Chloroflexus aurantiacus* or a malonyl-CoA reductase of *Erythrobacter* sp. NAP1. The amino acid sequence of malonyl-CoA reductase of *Chloroflexus aurantiacus* ($MCR_{Ca}$) is known and is available, e.g., under NCBI accession no. AAS20429.1 (nucleic acid sequence is shown in SEQ ID NO: 7; amino acid sequence is shown in SEQ ID NO: 8). The amino acid sequence of malonyl CoA reductase of *Erythrobacter* sp. NAP1 ($MCR_E$) is known and is available, e.g., under NCBI accession no. WP_007163680.1 (nucleic acid sequence is shown in SEQ ID NO: 9; amino acid sequence is shown in SEQ ID NO: 10). The general capability of both $MCR_E$ and $MCR_{Ca}$ to catalyze the enzymatic conversion of tartronate semialdehyde into glycerate (reaction 5) is also illustrated in the appended examples. It is of course not only possible to employ in the enzymatic conversion of tartronate semialdehyde into D-glycerate (reaction 5) an enzyme having the amino acid sequences of SEQ ID NO: 8 or 10, respectively, but it is also possible to employ an enzyme showing a related sequence, provided that the enzyme still shows the activity of converting tartronate semialdehyde into D-glycerate (reaction 5).

The term "related sequences" preferably means sequences showing at least 60%, preferably at least 65%, more preferably at least 70%, more preferably at least 75%, more preferably at least 80%, more preferably at least 85%, more preferably at least 90%, more preferably at least 95%, more preferably at least 99% and most preferably at least 99.5% sequence identity to the amino acid sequences shown in SEQ ID NO: 8 or 10, respectively.

As regards the determination of percent identity the same applies as has been described herein above.

Such above-mentioned related sequences may, for example also comprise mutated variants showing improved properties. In particular, also any mutant variants created by the evolution and optimization strategies described herein elsewhere are included in the related sequences. In a preferred embodiment a mutated version of a malonyl-CoA reductase of *Chloroflexus aurantiacus* or a malonyl-CoA reductase *Erythrobacter* sp. NAP1 is employed, which shows an improved activity catalyzing the conversion of tartronate semialdehyde into D-glycerate in comparison to the respective wild-type enzyme.

How to design assays for determining the enzymatic activity of converting tartronate semialdehyde into D-glycerate is known to the skilled person. It is, for instance, possible to use an in vitro assay as described in the appended examples for determining whether an enzyme has the activity of converting tatronyl-CoA into D-glycerate (reaction 5) with the only exception that tartronate semialdehyde is employed as substrate instead of tatronyl-CoA. In one embodiment the assay as described in the example may also be modified with respect to concentration of any components used and/or modification of buffer compositions based on the common general knowledge of skilled person. In one embodiment the substrate tatronate semialdehyde may not be provided directly but rather be formed as the product of a second enzymatic reaction (e.g. coupled to the above assay). For instance, an assay in which tatronyl-CoA is provided as substrate and the reaction mixture further comprises a respective enzyme for converting tatronyl-CoA to tatronate semialdehyde (as described herein or known in the art) may be employed (see appended Examples). In principle also any other reaction known in the art resulting in tatronate semialdehyde could also be coupled in order to provide the tatronate semialdehyde substrate In another embodiment, the enzymatic conversion can be achieved by first converting tartronate semialdehyde into hydroxypyruvate (reaction 25) and then further enzymatically converting hydroxypyruvate into D-glycerate (reaction 18). Also these conversions occur naturally (in particular enzymes for converting hydroxypyruvate into D-glycerate occur also in plants) and examples for the corresponding enzymes which can be employed are listed in Table 2. Preferably enzymes for converting hydroxypyruvate into D-glycerate derived from plants are employed.

In a preferred embodiment the enzymatic conversion of tartronyl-CoA into tartronate semialdehyde (reaction 4#) and tartronate semialdehyde into D-glycerate (reaction 5) may also be achieved by a single enzyme or enzyme complex that is capable of accepting both tartronyl-CoA and tatronate semialdehyde as substrate for reduction. In principle, any acylating aldehyde dehydrogenase (EC 1.2.1.X) can be employed for such a conversion. Preferably, a nonspecific acylating aldehyde dehydrogenase enzyme (e.g. see Baker P. et al., 2012, *Biochemistry* 51, 4558-4567) is employed. In particular, an acylating aldehyde dehydrogenase enzyme with alcohol dehydrogenase activity is used. In a preferred embodiment, the acylating aldehyde dehydrogenase is a malonyl-CoA reductase (EC 1.2.1.75 and/or EC 1.1.1.298) (Hügler M et al., 2002, Journal of Bacteriology May 2002, p. 2404-2410). In a preferred embodiment, the malonyl-CoA reductase may be a malonyl-CoA reductase of *Chloroflexus aurantiacus* or a malonyl-CoA reductase of *Erythrobacter* sp. NAP1. The amino acid sequence of malonyl CoA reductase of *Chloroflexus aurantiacus* ($MCR_{Ca}$) is known and is available, e.g., under NCBI accession no. AAS20429.1 (nucleic acid sequence is shown in SEQ ID NO: 7; amino acid sequence is shown in SEQ ID NO: 8). The amino acid sequence of malonyl CoA reductase of *Erythrobacter* sp. NAP1 ($MCR_E$) is known and is available, e.g., under NCBI accession no. WP_007163680.1 (nucleic acid sequence is shown in SEQ ID NO: 9; amino acid sequence is shown in SEQ ID NO: 10). The capability of both $MCR_E$ and $MCR_{Ca}$ to catalyze an enzymatic conversion of tartronyl-CoA into tartronate semialdehyde (reaction 4#) and tartronate semialdehyde into glycerate (reaction 5) is also illustrated in the appended examples.

It is of course not only possible to employ in the enzymatic conversion of tartronyl-CoA into tartronate semialdehyde (reaction 4#) and tartronate semialdehyde into D-glycerate (reaction 5) an enzyme having the amino acid sequences of SEQ ID NO: 8 or 10, respectively, but it is also possible to employ an enzyme showing a related sequence, provided that the enzyme still shows the activity of converting tartronyl-CoA into tartronate semialdehyde (reaction 4#) and tartronate semialdehyde into D-glycerate (reaction 5).

The term "related sequences" preferably means sequences showing at least 60%, preferably at least 65%, more preferably at least 70%, more preferably at least 75%, more preferably at least 80%, more preferably at least 85%, more preferably at least 90%, more preferably at least 95%, more preferably at least 99% and most preferably at least 99.5% sequence identity to the amino acid sequences shown in SEQ ID NO: 8 or 10, respectively.

As regards the determination of percent identity the same applies as has been described herein above.

Such above-mentioned related sequences may, for example also comprise mutated variants showing improved properties. In particular, also any mutant variants created by the evolution and optimization strategies described herein elsewhere are included in the related sequences. In a preferred embodiment a mutated version of a malonyl-CoA reductase of *Chloroflexus aurantiacus* or a malonyl-CoA reductase *Erythrobacter* sp. NAP1 is employed, which shows an improved activity catalyzing the conversion of tartronyl-CoA into tartronate semialdehyde (reaction 4#) and/or tatronate semialdehyde into D-glycerate (reaction 5) in comparison to the respective wild-type enzyme.

How to design assays for determining the enzymatic activity of converting tartronyl-CoA into tartronate semialdehyde (reaction 4#) and tatronate semialdehyde into D-glycerate (reaction 5) is known to the skilled person. In principle the enzymatic activity of the enzyme can be tested by testing for the conversions of tartronyl-CoA into tartronate semialdehyde (reaction 4#) and tatronate semialdehyde into D-glycerate (reaction 5) separately (as described above) or by testing for the capability of an enzyme to convert tartronyl-CoA into D-glycerate (reaction 4# and 5 combined). To test the enzymatic activity of converting tartronyl-CoA into tartronate semialdehyde (reaction 4#) and tatronate semialdehyde into D-glycerate (reaction 5) it is, for instance, possible to use any of the in vitro assays as described in the appended examples for determining whether an enzyme has the activity of converting tartronyl-CoA into tartronate semialdehyde (reaction 4#) and tatronate semialdehyde into D-glycerate (reaction 5). In one embodiment the assay as described in the example may also be modified with respect to concentration of any components used and/or modification of buffer compositions based on the common general knowledge of skilled person.

Similarly, the enzymatic conversion of D-glycerate into D-glycerate 3-phosphate (reaction 6) as described in A)a), above, is a conversion which does naturally occur and for which enzymes which catalyze this conversion are known, in particular also in plants. Examples for corresponding enzymes which are known to catalyze this conversion are mentioned in Table 2 and corresponding enzymes, preferably enzymes derived from plants, can be employed in the context of the present invention.

The enzymatic conversions as described in A)b), above, can be achieved as described in the following:

The enzymatic conversion of 2-PG into glycolate (reaction 1) as described in A)b), above, is a conversion which does naturally occur and for which enzymes which catalyze this conversion are known, in particular also in plants. Examples for corresponding enzymes which are known to catalyze this conversion are mentioned in Table 2 and corresponding enzymes, preferably enzymes derived from plants, can be employed in the context of the present invention.

The further enzymatic conversion of glycolate into glyoxylate (reaction 12) as described in A)b), above, is a conversion which does naturally occur and for which enzymes which catalyze this conversion are known. Examples for corresponding enzymes which are known to catalyze this conversion are mentioned in Table 2 and corresponding enzymes can be employed in the context of the present invention.

Similarly, the enzymatic conversion of glyoxylate into glycine (reaction 13) as described in A)b), above, is a conversion which does naturally occur and for which enzymes which catalyze this conversion are known. Examples for corresponding enzymes which are known to catalyze this conversion are mentioned in Table 2 and corresponding enzymes can be employed in the context of the present invention.

The further enzymatic conversion of glycine into serine (reaction 14) as described in A)b), above, is a conversion which does naturally occur and for which enzymes which catalyze this conversion are known, in particular also in plants. Examples for corresponding enzymes which are known to catalyze this conversion are mentioned in Table 2 and corresponding enzymes, preferably enzymes derived from plants, can be employed in the context of the present invention. The enzymatic conversion of glycine into serine (reaction 14) as described in A)b), above, is preferably a conversion which consumes methylene-THF resulting from the enzymatic conversion of $CO_2$ into formate (reaction 15#), further enzymatic conversion of formate into formyl-THF (reaction 16), and further enzymatic conversion of formyl-THF into said methylene-THF (reaction 17).

The enzymatic conversion of $CO_2$ into formate can, for example, be achieved by any type of formate dehydrogenase, preferably ferredoxin-dependent formate dehydrogenase (EC 1.1.99.X) (these enzymes are examples of enzyme 15# mentioned herein) (Hyunjun Choe et al., 2015, *Acta Cryst. D*71, 313-323; Schuchmann K. et al., 2014, *Nat. Rev. Microbiol.* 12 (12), 809-21). In principle, any ferredoxin-dependent formate dehydrogenase (EC 1.1.99.X) can be employed for such a conversion. When a ferredoxin-dependent formate dehydrogenase is used, ferredoxin can be reduced by electrons donated directly from components of the electron transport chain, including one of the photosystems. The enzymatic conversions of formate into formyl-THF (reaction 16), of formyl-THF into said methylene-THF (reaction 17) occur naturally (in particular enzymes occur also in plants) and examples for the corresponding enzymes which can be employed are listed in Table 2. Preferably enzymes derived from plants are employed.

The further enzymatic conversion of serine into hydroxypyruvate (reaction 13) as described in A)b), above, is a conversion which does naturally occur and for which enzymes which catalyze this conversion are known. Examples for corresponding enzymes which are known to catalyze this conversion are mentioned in Table 2 and corresponding enzymes can be employed in the context of the present invention.

The further enzymatic conversion of hydroxypyruvate into D-glycerate (reaction 18) as described in A)b), above, is a conversion which does naturally occur and for which enzymes which catalyze this conversion are known, in particular also in plants. Examples for corresponding enzymes which are known to catalyze this conversion are mentioned in Table 2 and corresponding enzymes, preferably enzymes derived from plants, can be employed in the context of the present invention.

The further enzymatic conversion of D-glycerate into D-glycerate 3-phosphate (reaction 6) as described in A)b) above, can be achieved as described in connection with A)a) above.

The enzymatic conversions as described in A)c), above, can be achieved as described in the following:

The enzymatic conversion of 2-PG into glycolyl-CoA as described in A)c), above, can be achieved by different pathways as will be described further below.

The further enzymatic conversion of glycolyl-CoA into hydroxypyruvate as described in A)c) above can be achieved in different ways. Preferably, this enzymatic conversion is designed in a manner that it consumes directly or indirectly $CO_2$. A direct consumption of $CO_2$ means that the enzymatic conversion of glycolyl-CoA into hydroxypyruvate involves the direct incorporation of (the carbon atom of) $CO_2$. An indirect consumption of $CO_2$ means that (the carbon atom of) $CO_2$ is first converted (e.g. preferably reduced to formic acid) and/or incorporated into another compound and then incorporated into glycolyl-CoA. Examples for a direct or indirect consumption of $CO_2$ by the conversion of glycolyl-CoA into hydroxypyruvate will be described in the following and are represented by reactions 54# and 55#. For example, the conversion of glycolyl-CoA into hydroxypyruvate can be achieved by a (reversible) pyruvate:ferredoxin oxidoreductase enzyme (EC 1.2.7.1) (this enzyme is an example of enzyme 55#) resulting in a consumption of $CO_2$ due to a direct incorporation. Alternatively, the conversion of glycolyl-CoA into hydroxypyruvate can be achieved by a (fully reversible) pyruvate formate lyase enzyme (EC 2.3.1.54) (this enzyme is an example of enzyme 54#, mentioned herein).

Thus, in one embodiment the enzymatic conversion of glycolyl-CoA into hydroxypyruvate as described in A)c), above, can, for example, be achieved by a (reversible) pyruvate:ferredoxin oxidoreductase enzyme (EC 1.2.7.1) (this enzyme is an example of enzyme 55#, mentioned herein), also referred to as pyruvate synthase (EC 1.2.7.1) (Furdui C. et al., 2000, *J Biol Chem* 275: 28494-28499). Some pyruvate:ferredoxin oxidoreductase (EC 1.2.7.1) variants are known to be promiscuous in the substrates that they can accept (e.g. Fukuda E. et al., 2002, *Biochim Biophys Acta* 1597: 74-80). Accordingly, it is expected that glycolyl-CoA can also serve as a substrate for pyruvate:ferredoxin oxidoreductase (EC 1.2.7.1) or at least for some pyruvate:ferredoxin oxidoreductase variants. In principle, any pyruvate:ferredoxin oxidoreductase enzyme (EC 1.2.7.1) can be employed for such a conversion. In the context of the present invention, preferably pyruvate:ferredoxin oxidoreductase (EC 1.2.7.1) variants that accept glycolyl-CoA (at a high frequency) are employed. The enzymatic conversion of glycolyl-CoA into hydroxypyruvate achieved by a (reversible) pyruvate:ferredoxin oxidoreductase enzyme (EC 1.2.7.1) preferably (directly) consumes $CO_2$.

While pyruvate:ferredoxin oxidoreductase enzymes (EC 1.2.7.1) are typically oxygen sensitive, several bacteria and archea exist that operate this enzyme under full microaerobic or aerobic conditions. For the enzymatic conversion of glycolyl-CoA into hydroxypyruvate in the context of the present invention, in particular, a pyruvate:ferredoxin oxidoreductase enzyme (EC 1.2.7.1) which is not or minimally oxygen sensitive and/or exhibits enzymatic activity under aerobic conditions (e.g. a pyruvate:ferredoxin oxidoreductase enzyme (EC 1.2.7.1) originating from *Hydrogenobacter thermophilus* TK-6, *Sulfolobus* sp. strain 7 or *Halobacterium halobium*) is employed. Several bacteria and archea, including but not limited to *Hydrogenobacter thermophilus* TK-6 (Yoon K. S. et al., 1997, *Arch Microbiol* 167: 275-279), *Sulfolobus* sp. strain 7 (Fukuda E. et al., 2002, *Biochim Biophys Acta* 1597: 74-80) and *Halobacterium halobium* (Plaga W. et al., 1992, *Eur J Biochem* 205: 391-397), express pyruvate:ferredoxin oxidoreductase enzymes (EC 1.2.7.1) that operate under full microaerobic or aerobic conditions and are not or minimally oxygen sensitive. In another embodiment, a pyruvate:ferredoxin oxidoreductase enzyme (EC 1.2.7.1) originating from a host different from the organism, tissue thereof, cell thereof or organelle thereof of the current invention is employed for the enzymatic conversion of glycolyl-CoA into hydroxypyruvate. Multiple studies indicate that the maturation of a pyruvate:ferredoxin oxidoreductase enzyme can occur correctly under aerobic conditions when expressed in a foreign host (Fukuda E. et al., 2002, loc. cit.; Yamamoto M., 2003, *Biochem Biophys Res Commun* 312: 1297-1302).

The enzymatic conversion of glycolyl-CoA into hydroxypyruvate achieved, for example, by a pyruvate:ferredoxin oxidoreductase enzyme (EC 1.2.7.1), can involve the oxidation of ferredoxin. In the context of this embodiment, preferably a pyruvate:ferredoxin oxidoreductase enzyme (EC 1.2.7.1), capable of accepting the ferredoxin of the organism/tissue/cell/organelle used in the context of the present invention, is employed. For example, several studies indicate that plant-like ferredoxin can replace the native ferredoxin used by pyruvate:ferredoxin oxidoreductase enzymes (EC 1.2.7.1) with only a little effect on activity (Pieulle L. et al., 2004, *Biochemistry* 43: 15480-15493).

In the context of a plant/plant tissue/plant cell/plant organelle according to the current invention, preferably a pyruvate:ferredoxin oxidoreductase (EC 1.2.7.1) accepting plant ferredoxin is employed. The pyruvate:ferredoxin oxidoreductase (EC 1.2.7.1) from *Desulfovibrio africanus* is for example known to accept e.g. algal ferredoxin, resulting in 60% of the original rate (Pieulle L. et al., 2004, *Biochemistry* 43: 15480-15493). Alternatively, pyruvate:ferredoxin oxidoreductase enzyme (EC 1.2.7.1) variants that use NADPH as electron donor, instead of ferredoxin, are employed for the enzymatic conversion of glycolyl-CoA into hydroxypyruvate. An example for an NADPH-dependent pyruvate:ferredoxin oxidoreductase enzyme which is, however, non-limiting, is the pyruvate:ferredoxin oxidoreductase enzyme (EC 1.2.7.1) from *Euglena gracilis* (Inui H., 1987, *J Biol Chem* 262: 9130-9135). Preferably, an NADPH-dependent pyruvate: ferredoxin oxidoreductase enzyme (EC 1.2.7.1) employed in the current invention is also capable of operating under (micro)aerobic conditions.

In another embodiment, the further enzymatic conversion of glycolyl-CoA into hydroxypyruvate as described in A)c), above, may, for example, be achieved by a (fully reversible) pyruvate formate lyase enzyme (EC 2.3.1.54) (this enzyme is an example of enzyme 54#, mentioned herein) (Buis J. M. et al., 2005, *Arch Biochem Biophys* 433: 288-296). Some variants of pyruvate formate lyase (EC 2.3.1.54) are known to have broad substrate specificity (Hesslinger C. et al., 1998, *Mol Microbiol* 27: 477-492; Sawers G. et al., 1998, *J Bacteriol* 180: 3509-3516) and hence pyruvate formate lyase enzymes (EC 2.3.1.54) or at least some variants thereof are expected to accept glycolyl-CoA. In principle, any pyruvate formate lyase enzyme (EC 2.3.1.54) may be employed for the enzymatic conversion of glycolyl-CoA into hydroxypyruvate. Preferably, in the context of the current invention a pyruvate formate lyase enzyme variant (EC 2.3.1.54) that accepts glycolyl-CoA (at a high frequency) is employed.

The reaction catalyzed by pyruvate formate lyase (EC 2.3.1.54) takes place via a radical mechanism, which involves a glycyl radical (Becker A. et al., 1999, *Nat Struct Biol* 6: 969-975; Plaga W. et al., 2000, *FEBS Lett* 466: 45-48; Becker A. et al., 2002, *J Biol Chem* 277: 40036-40042). In a preferred embodiment, a pyruvate formate lyase activating enzyme (PFL-AE) is employed to generate the stable and catalytically essential glycyl radical for the reaction catalyzed by pyruvate formate lyase (EC 2.3.1.54) (Buis J. M. et al., 2005, loc. cit.; Vey J. L. et al., 2008, *Proc Natl Acad Sci USA* 105: 16137-16141). The glycyl radical is in principle susceptible to destruction by oxygen, which results in irreversible cleavage of the polypeptide and inactivation of pyruvate formate lyase (EC 2.3.1.54) (Sawers G. et al., 1998, *Mol Microbiol* 29: 945-954; Zhang W. et al., 2001, *Biochemistry* 40: 4123-4130). However, previous studies have shown that, for example, *E. coli* cells grown under microaerobic conditions produce a significant amount of formate, indicating that pyruvate formate lyase (EC 2.3.1.54) retains its activity in the presence of oxygen (Alexeeva S. et al., 2000, *J Bacteriol* 182: 4934-4940; Levanon S. S. et al., 2005, *Biotechnol Bioeng* 89: 556-564; Zhu J. et al., 2007, *Biotechnol Bioeng* 97: 138-143). In the context of the current invention, preferably pyruvate formate lyase (EC 2.3.1.54) variants that have increased oxygen tolerance/enzymatic activity under aerobic conditions (e.g. evolved by methods as described elsewhere) are employed. In particular, for example, the product of the yfiD gene in *E. coli* may also be employed to increase the oxygen tolerance/enzymatic activity under aerobic conditions of pyruvate formate lyase (EC 2.3.1.54). The product of the yfiD gene in *E. coli* was shown to reactivate pyruvate formate lyase (EC 2.3.1.54) in the presence of oxygen by replacing its fragmented part (Zhu J. et al., 2007, loc. cit.; Wagner A F, 2001, *Biochem Biophys Res Commun* 285: 456-462).

The enzymatic conversion of glycolyl-CoA into hydroxypyruvate achieved by a (fully reversible) pyruvate formate lyase enzyme (EC 2.3.1.54) is preferably a conversion which consumes formic acid resulting from the enzymatic conversion of $CO_2$ into formate (reaction 15#). The enzymatic conversion of $CO_2$ into formate (reaction 15#) in this context, may be achieved by a ferredoxin-dependent formate dehydrogenase (EC 1.1.99.X) or another type of formate dehydrogenase as described in A)b) above.

The further enzymatic conversion of hydroxypyruvate into D-glycerate as described in A)c), above, is a conversion which does naturally occur and for which enzymes catalyzing this conversion are known. Examples for corresponding enzymes which are known to catalyze this conversion are mentioned in Table 2 and corresponding enzymes may be employed in the context of the present invention.

According to one embodiment the conversion of hydroxypyruvate into D-glycerate as described above in A)c) can be achieved by directly converting hydroxypyruvate into D-glycerate (reaction 18). Examples for corresponding enzymes which are known to catalyze this conversion occur naturally, in particular also in plants. Preferably enzymes for converting hydroxypyruvate into D-glycerate derived from plants are employed in the context of the current invention.

In another embodiment, the enzymatic conversion of hydroxypyruvate into D-glycerate as described in A)c), above, can be achieved by first enzymatically converting hydroxypyruvate into tartronate semialdehyde (reaction 25) and further enzymatically converting tartronate semialdehyde into D-glycerate (reaction 5). Both conversions occur naturally and enzymes which catalyze this conversion are known. Examples for corresponding enzymes which are known to catalyze this conversion are mentioned in Table 2 and corresponding enzymes may be employed in the context of the present invention.

The further enzymatic conversion of D-glycerate into D-glycerate 3-phosphate (reaction 6) as described in A)c) above, can be achieved as described in connection with A)a) above.

As mentioned above, in another embodiment one of the preferred intermediates of the CBBC into which 2-PG is converted according to the present invention is D-ribulose 1,5-bisphosphate. In the following, the possible pathways will be described which allow the conversion of 2-PG into D-ribulose 1,5-bisphosphate according to preferred embodiments of the present invention. The pathway which allows converting 2-PG into D-ribulose 1,5-bisphosphate will be referred to as option "B)" in the following. According to option B) the intermediate compound of the CBBC is D-ribulose 1,5-bisphosphate, and the conversion of 2-PG is preferably achieved by:

a) enzymatic conversion of 2-PG into glycolaldehyde, further enzymatic conversion of glycolaldehyde into D-ribulose 1-phosphate, and further enzymatic conversion of D-ribulose 1-phosphate into D-ribulose 1,5-bisphosphate (a respective illustrative example is provided by FIG. 1B); or b) enzymatic conversion of 2-PG into glycolaldehyde, further enzymatic conversion of glycolaldehyde into D-ribulose 1-phosphate, further enzymatic conversion of D-ribulose 1-phosphate into D-ribose 1-phosphate, further enzymatic conversion of D-ribose 1-phosphate into D-ribose 1,5-bisphosphate, and further enzymatic conversion of D-ribose 1,5-bisphosphate into D-ribulose 1,5-bisphosphate (a respective illustrative example is provided by FIG. 3B; pathway: 2-PG conversion into glycolaldehyde as shown in FIG. 2+enzymes 8, 29#, 31, 32); or c) enzymatic conversion of 2-PG into 2-phosphoglycolyl phosphate, further enzymatic conversion of 2-phosphoglycolyl phosphate into glycolaldehyde 2-phosphate, and further enzymatic conversion of glycolaldehyde 2-phosphate into D-ribulose 1,5-bisphosphate (a respective illustrative example is provided by FIG. 3B; pathway: 2-PG conversion into glycolaldehyde 2-phosphate as shown in FIG. 2 (enzymes 23# and 24#)+enzyme 28#).

The enzymatic conversions as described in B)a), above, can be achieved as described in the following:

The enzymatic conversion of 2-PG into glycolaldehyde as described in B)a), above, can be achieved by different pathways as will be described further below.

The enzymatic conversion of glycolaldehyde into D-ribulose 1-phosphate (reaction 8), which can be achieved, for example, by condensation of glycolaldehyde with dihydroxyacetone phosphate, as described in B)a), above, is a conversion which does naturally occur and for which enzymes catalyzing this conversion are known. Examples for corresponding enzymes which are known to catalyze this conversion are mentioned in Table 2 and corresponding enzymes can be employed in the context of the present invention.

The enzymatic conversion of D-ribulose 1-phosphate into D-ribulose 1,5-bisphosphate (reaction 9#) as described in B)a), above, can for example be achieved by a 1-phosphofructokinase (EC 2.7.1.56) or a ribulokinase (EC 2.7.1.16) (these enzymes are examples for enzyme 9# mentioned herein). In principle any 1-phosphofructokinase (EC 2.7.1.56) or a ribulokinase (EC 2.7.1.16) can be employed for this purpose.

As regards 1-phosphofructokinase, it is known that several of these enzymes confuse D-ribulose and D-fructose—e.g., fructose 1,6-bisphosphatase can dephosphorylate ribulose 1,5-bisphosphate (Mizunuma H. et al., 1980, *Arch*

*Biochem Biophys* 201, 296-303; Donahue J. L. et al., 2000, *J Bacteriol* 182, 5624-5627) and phosphoribulokinase can phosphorylate fructose 6-phosphate (Siebert K. et al., 1981, *Biochim Biophys Acta* 658, 35-44). Thus, these enzymes are suitable for the described conversion of D-ribulose 1-phosphate into D-ribulose 1,5-bisphosphate.

As regards ribulokinase, it is preferred to employ in the present invention a promiscuous variant of D-ribulose 5-kinase (e.g. see Lee L. V. et al., 2001, *Arch Biochem Biophys* 396, 219-224) which can accept D-ribulose 1-phosphate as an alternative substrate.

The enzymatic conversions as described in B)b), above, can be achieved as described in the following:

The enzymatic conversion of 2-PG into glycolaldehyde as described in B)b), above, can be achieved by different pathways as will be described further below.

The enzymatic conversion of glycolaldehyde into D-ribulose 1-phosphate (reaction 8), for example by condensation of glycolaldehyde with dihydroxyacetone phosphate, as described in B)b) above, can be achieved as described in connection with B)a) above.

The enzymatic conversion of D-ribulose 1-phosphate into D-ribose 1-phosphate (reaction 29#) as described in B)b), above, can for example be achieved by a 5-methylthio-D-ribulose 1-phosphate 1,2-isomerase (this enzyme is an example for enzyme 29# mentioned herein). In principle any 5-methylthio-D-ribulose 1-phosphate 1,2-isomerase can be employed for this purpose, preferably a promiscuous 5-methylthio-D-ribulose 1-phosphate 1,2-isomerase. An example is the enzyme referred to as Rru_A0360 (Saito Y. et al., 2007, *Biochem* 71, 2021-2028; Erb T. J. et al., 2012, *Nat Chem Biol* 8, 926-932).

Figure 3:
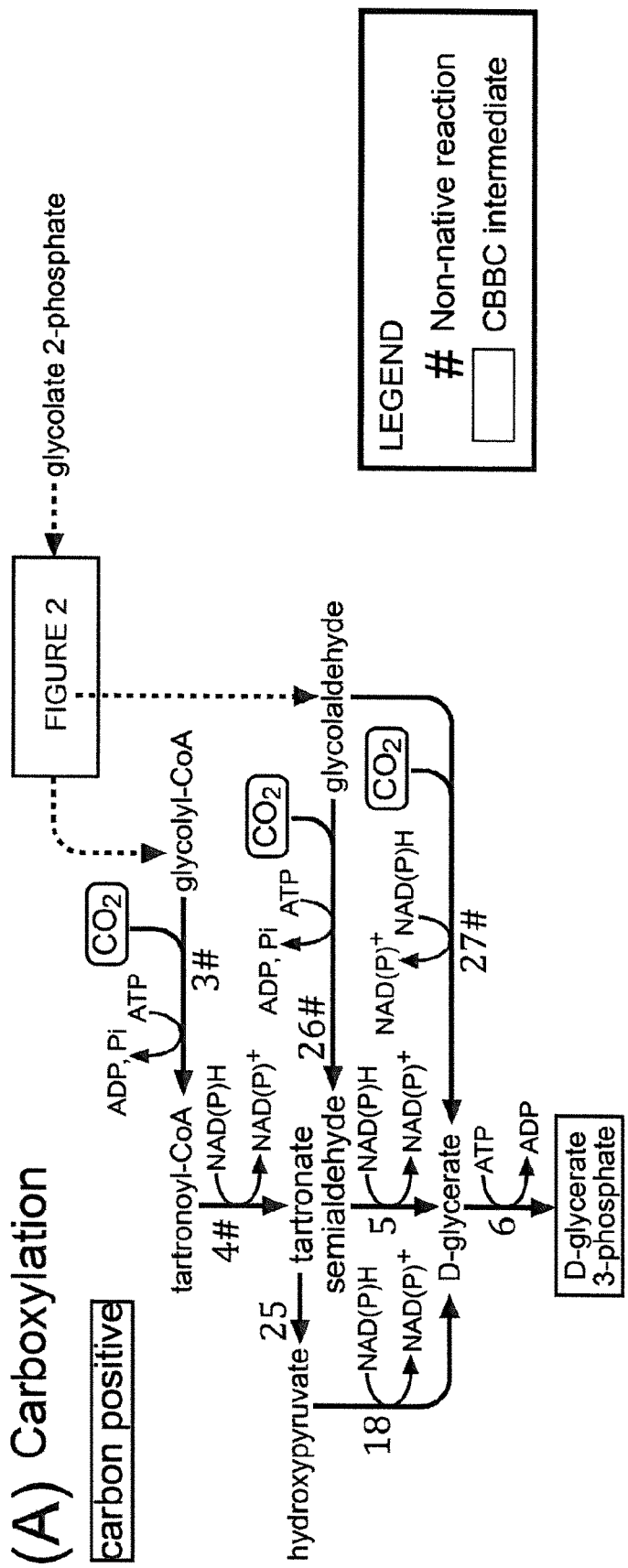
Figure 3:
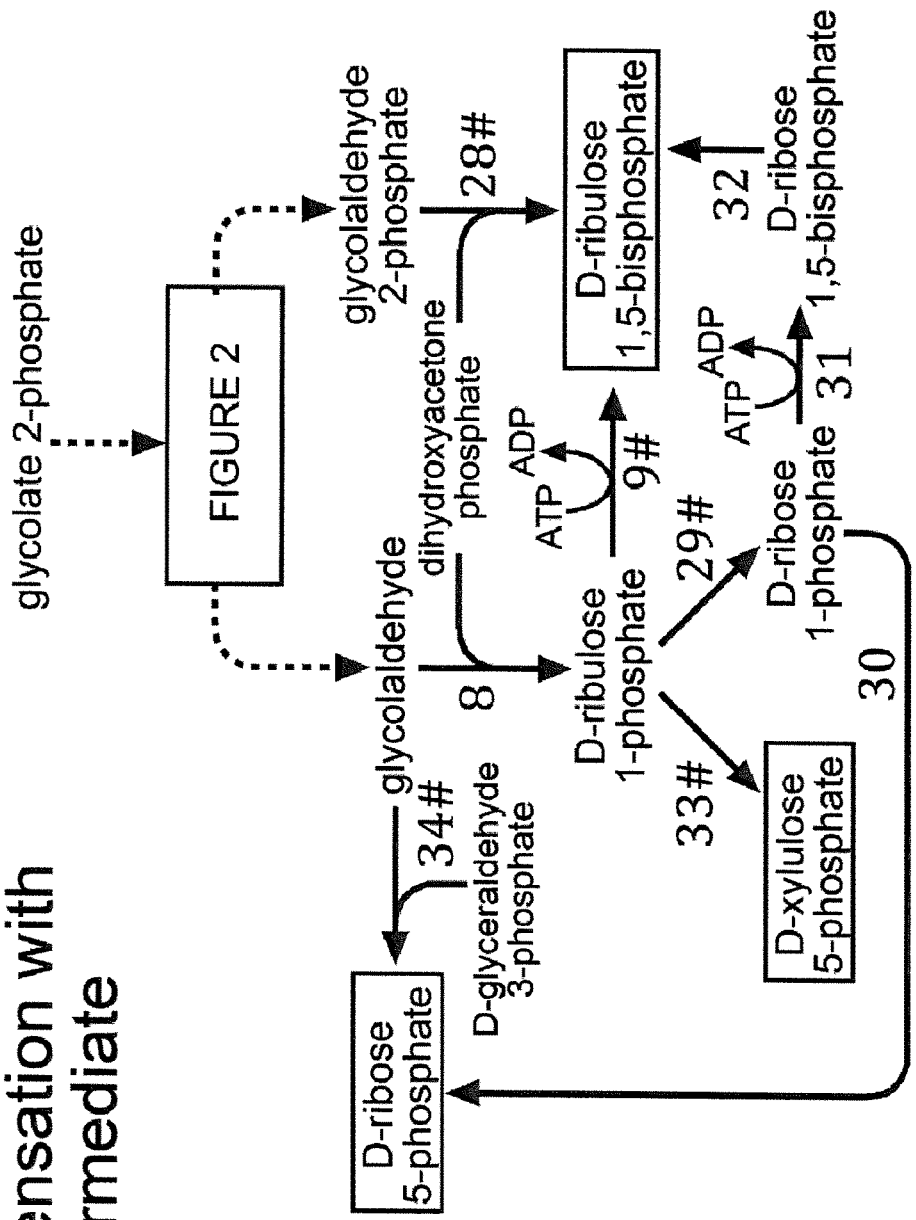
Figure 3:
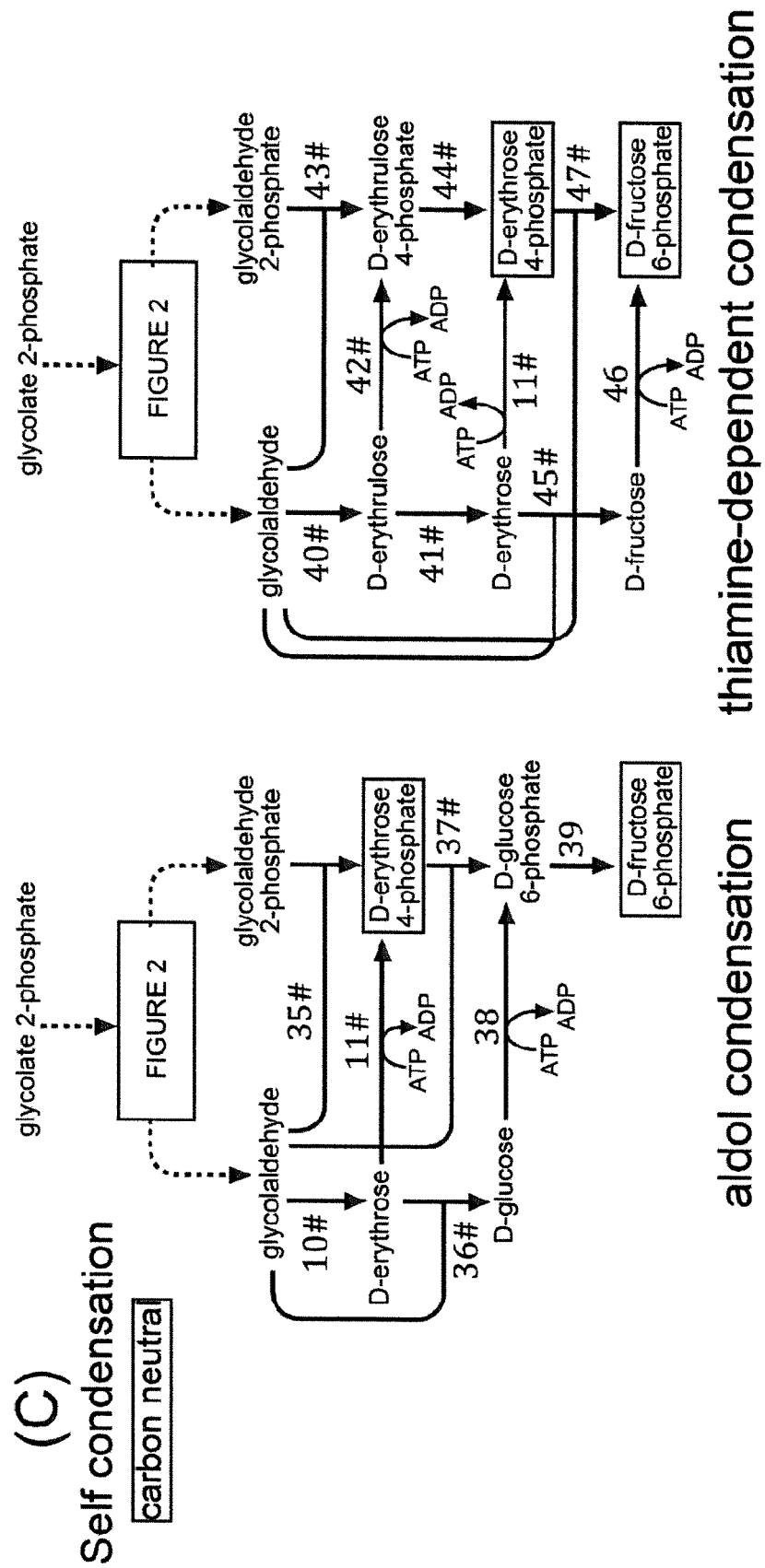
Figure 3:
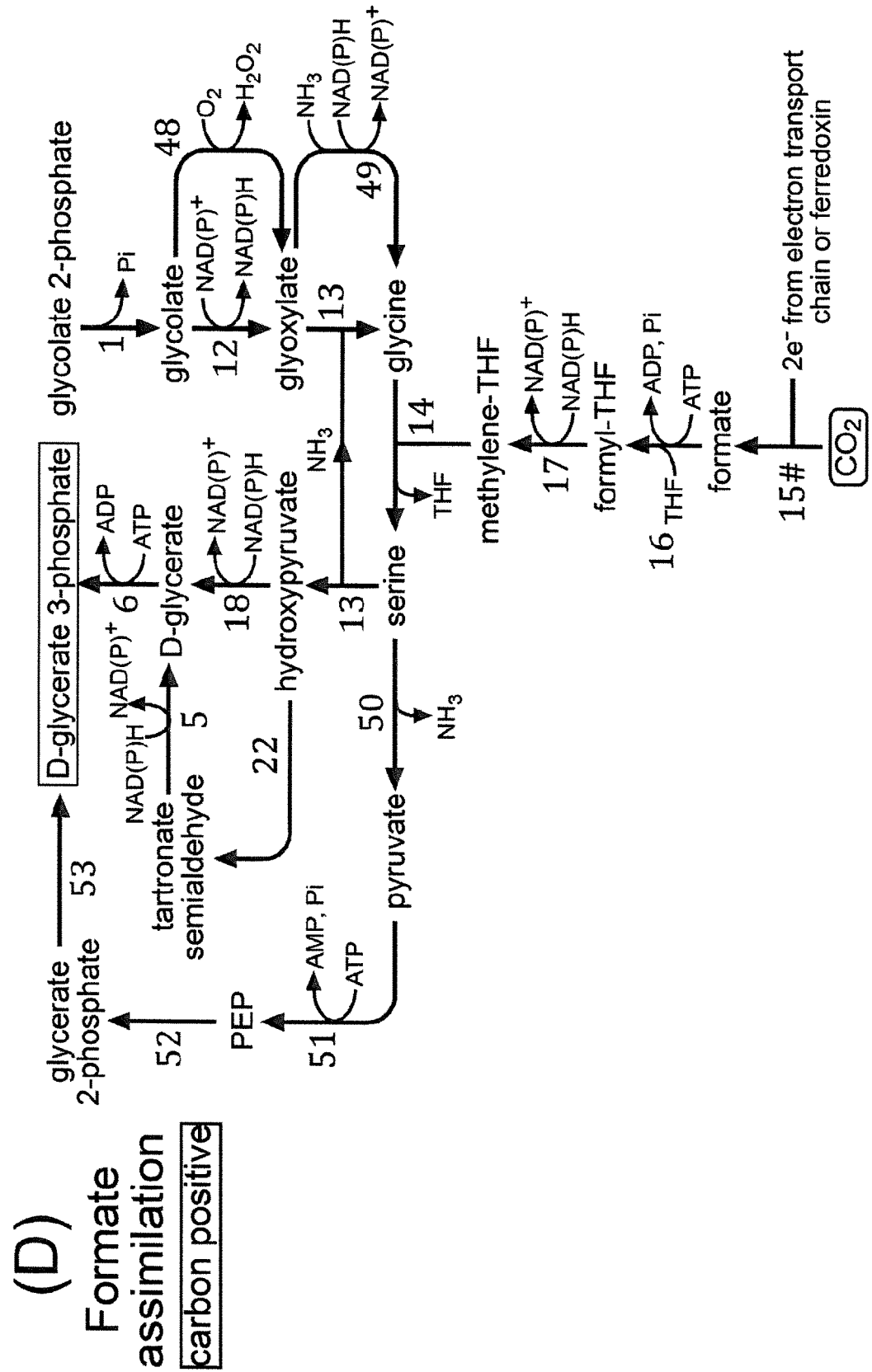
Figure 3:
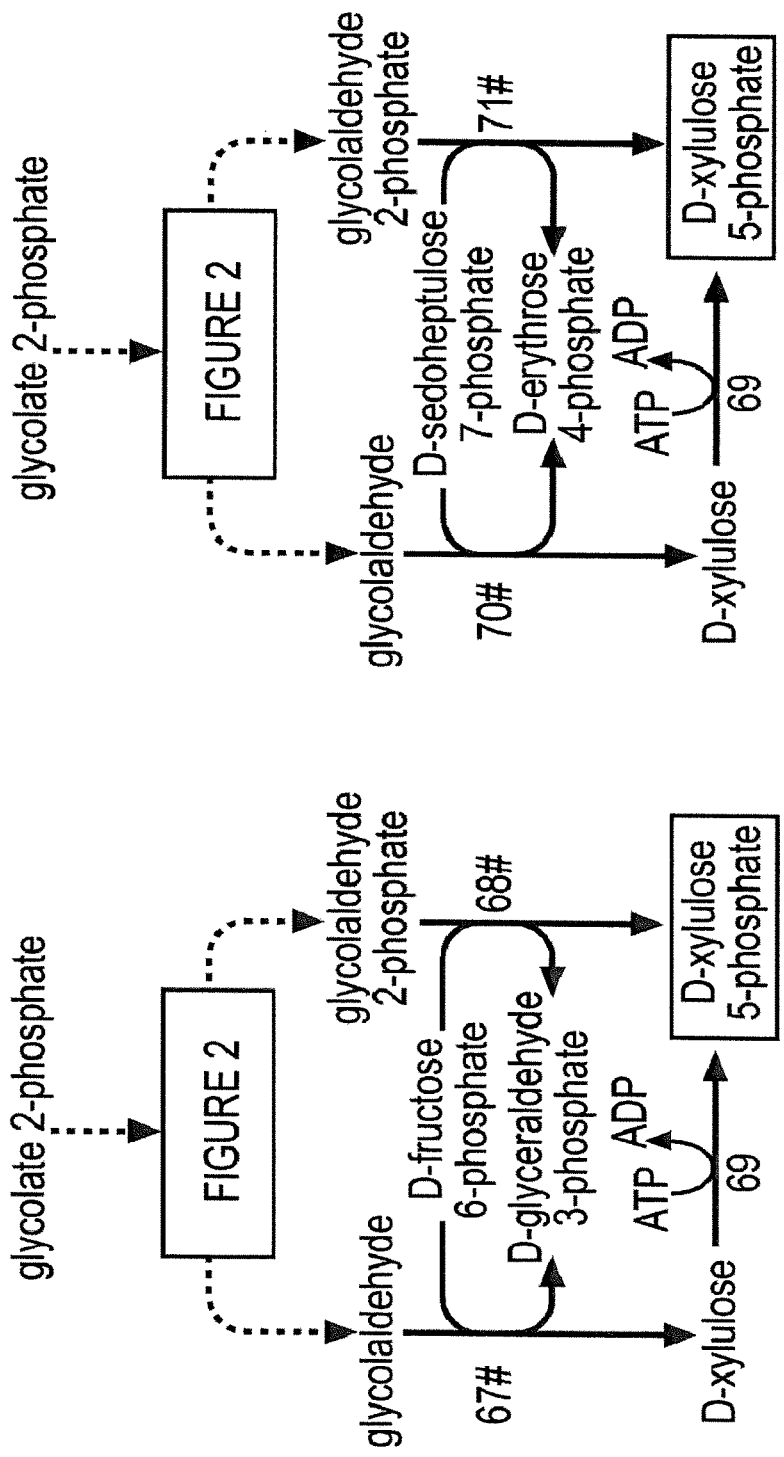
Figure 3:
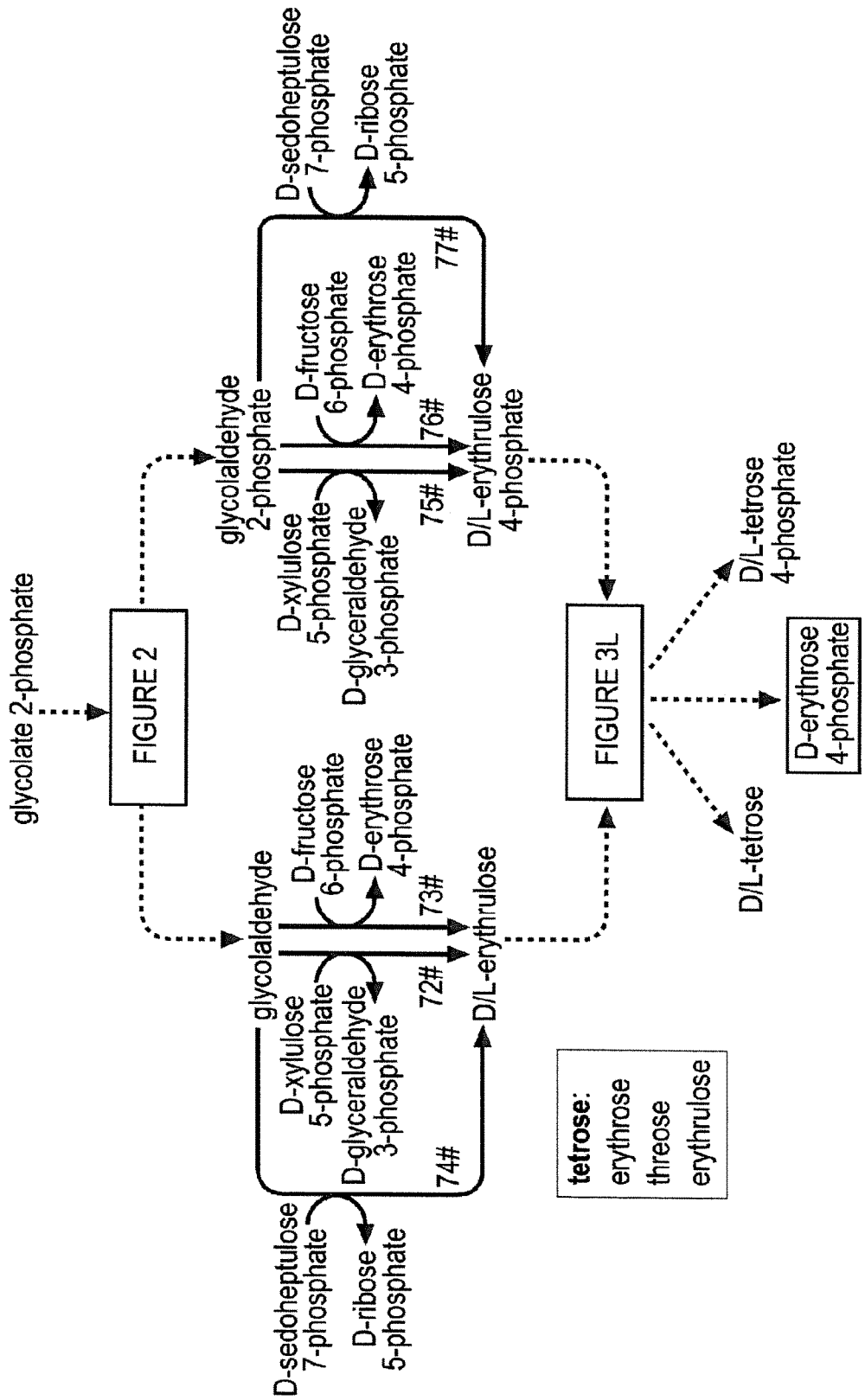
Figure 3:
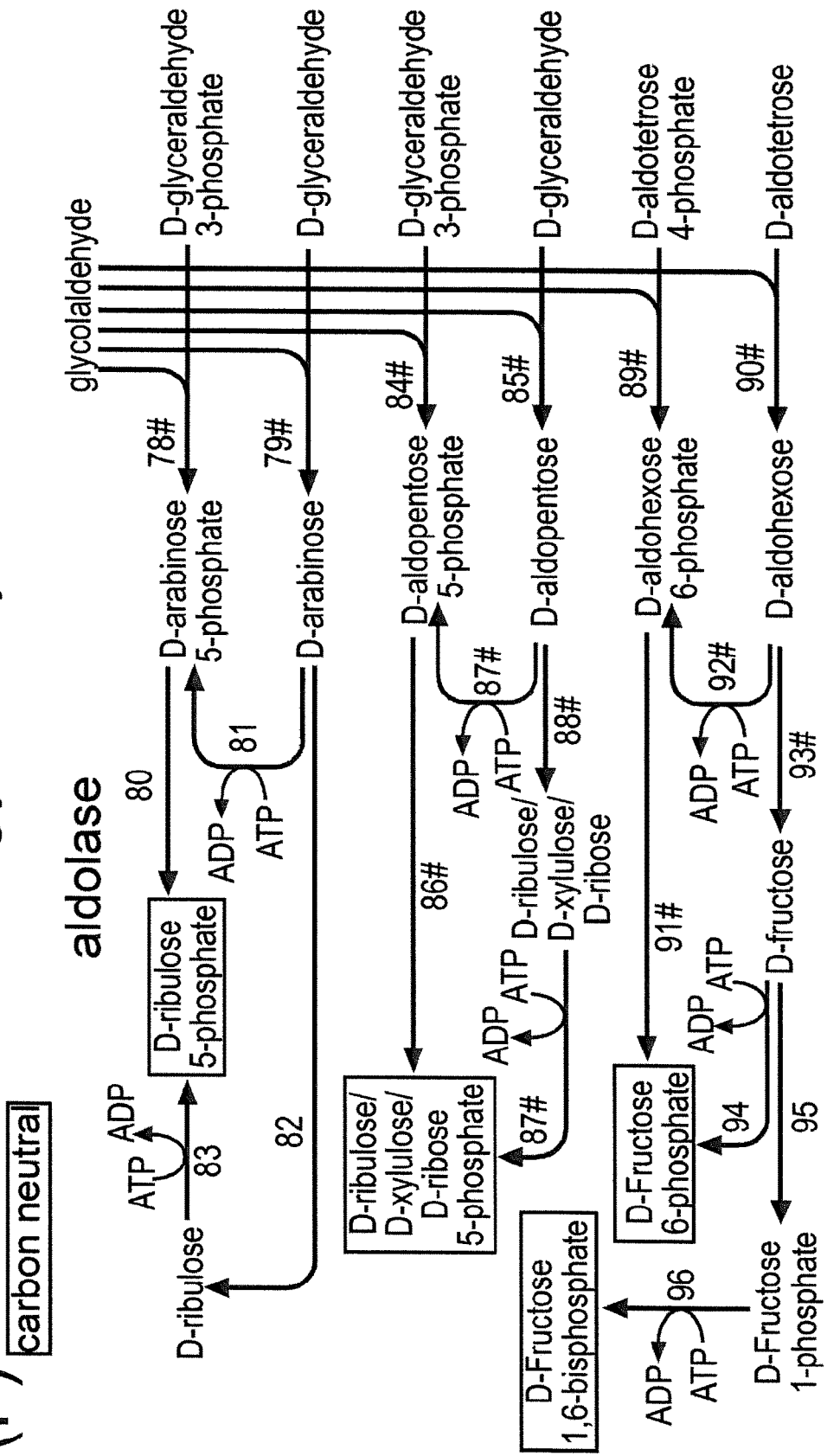
Figure 3:
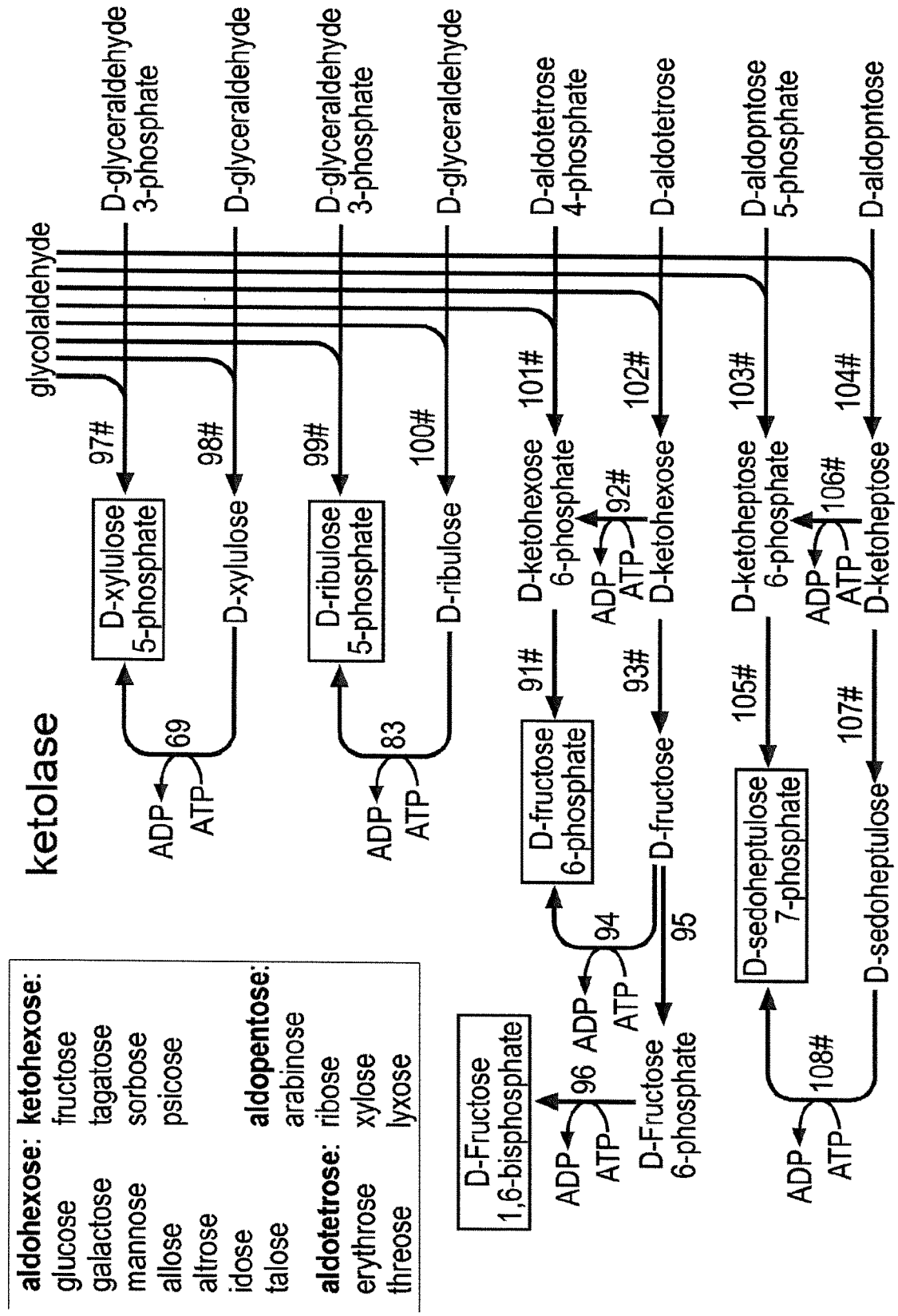
Figure 3:
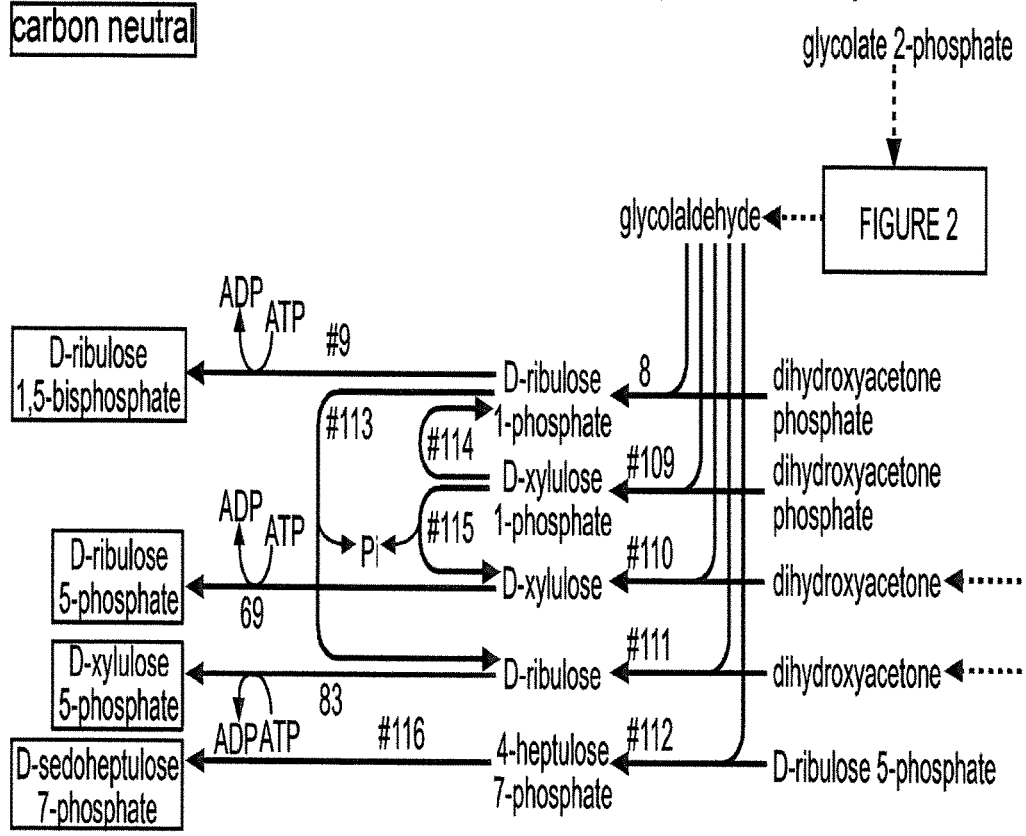
Figure 3:
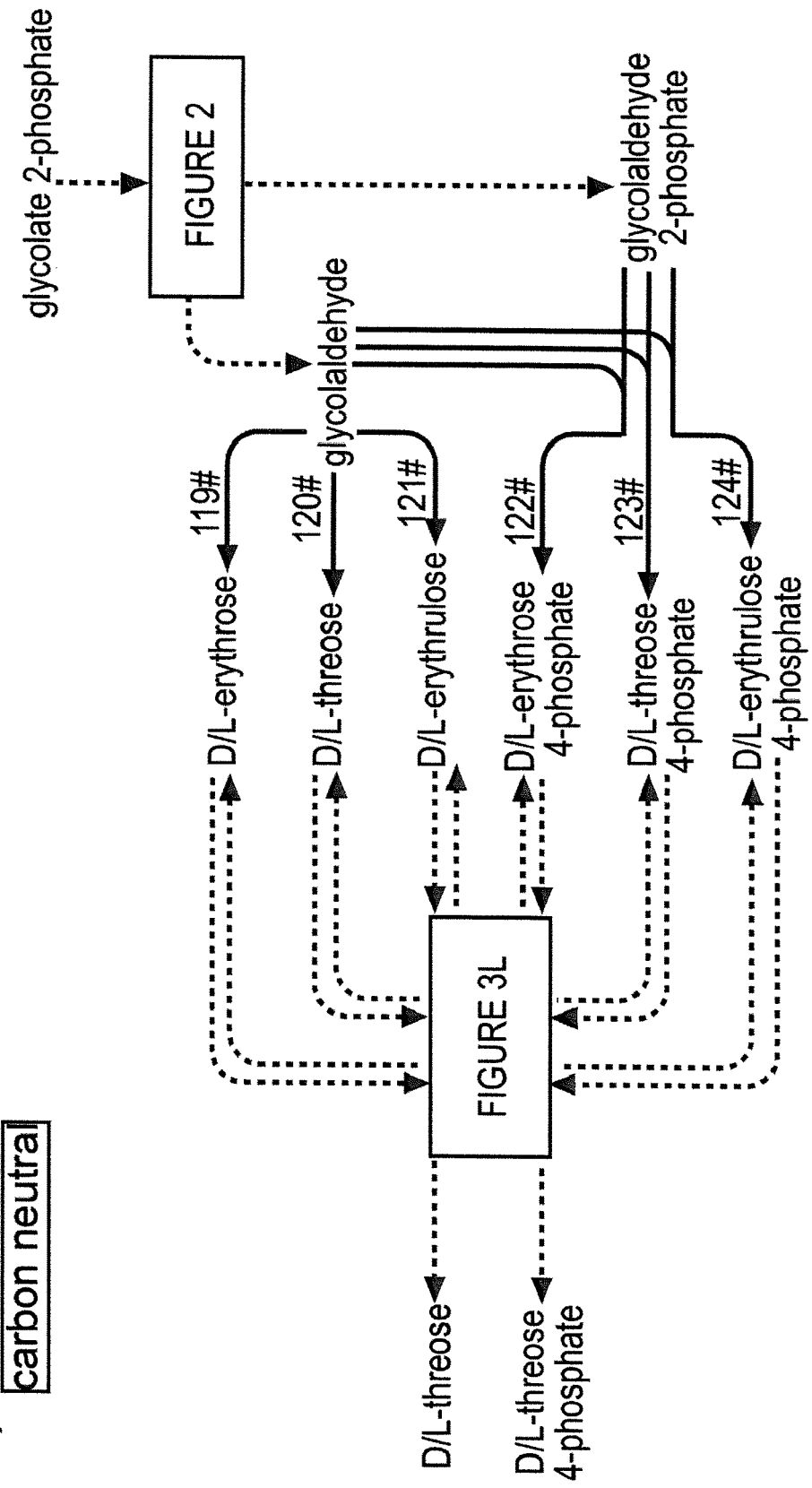
Figure 3:
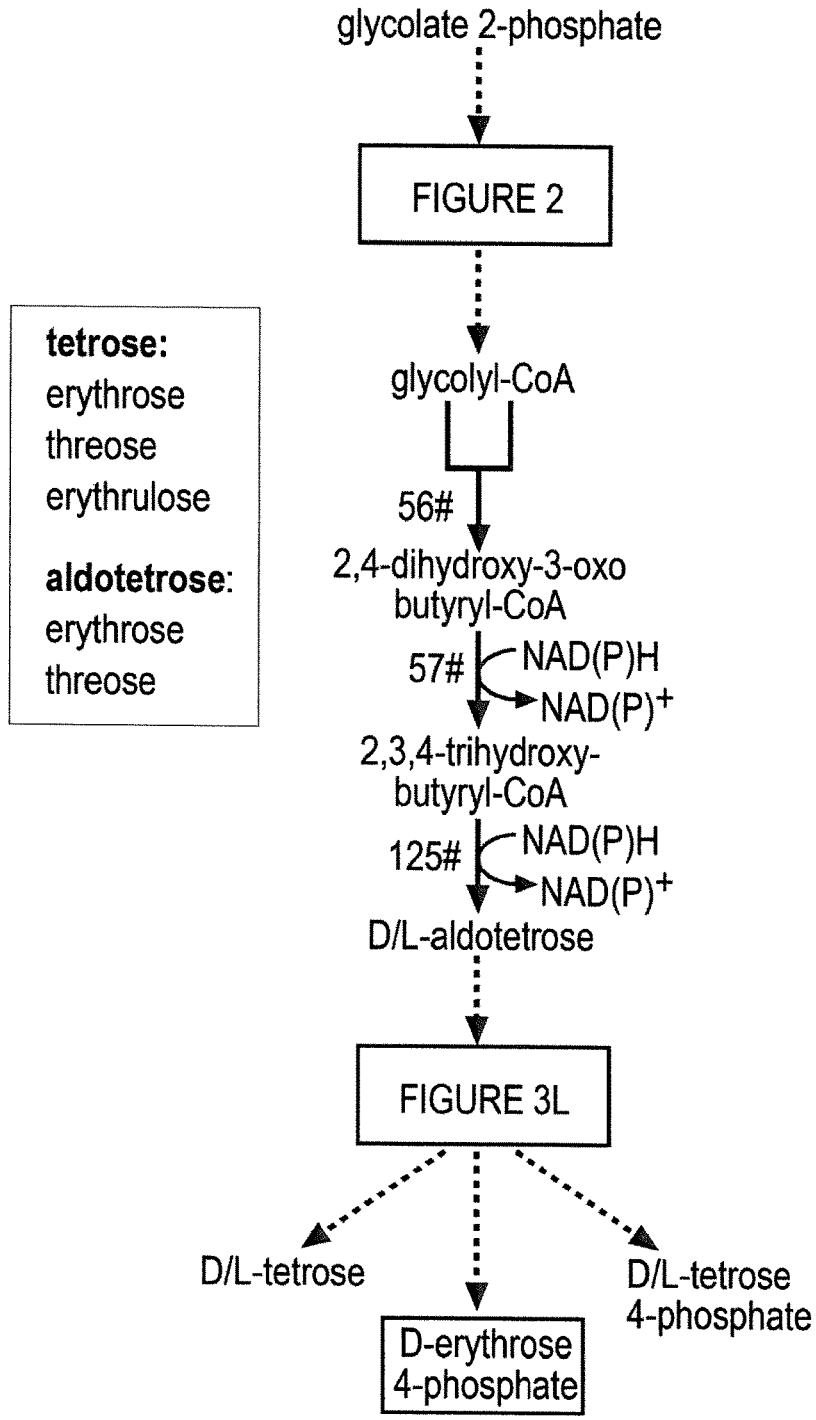
Figure 3:
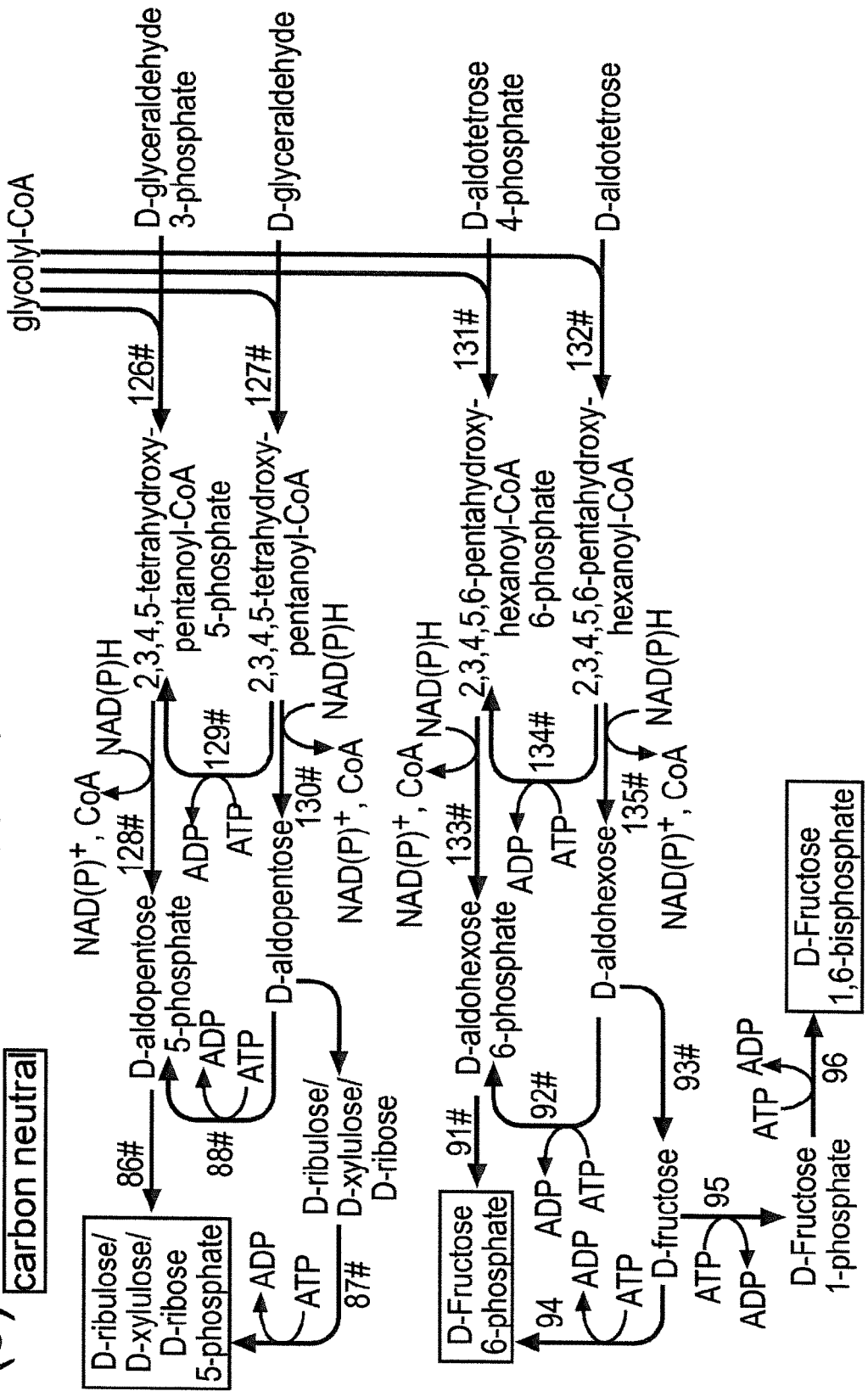
Figure 3:
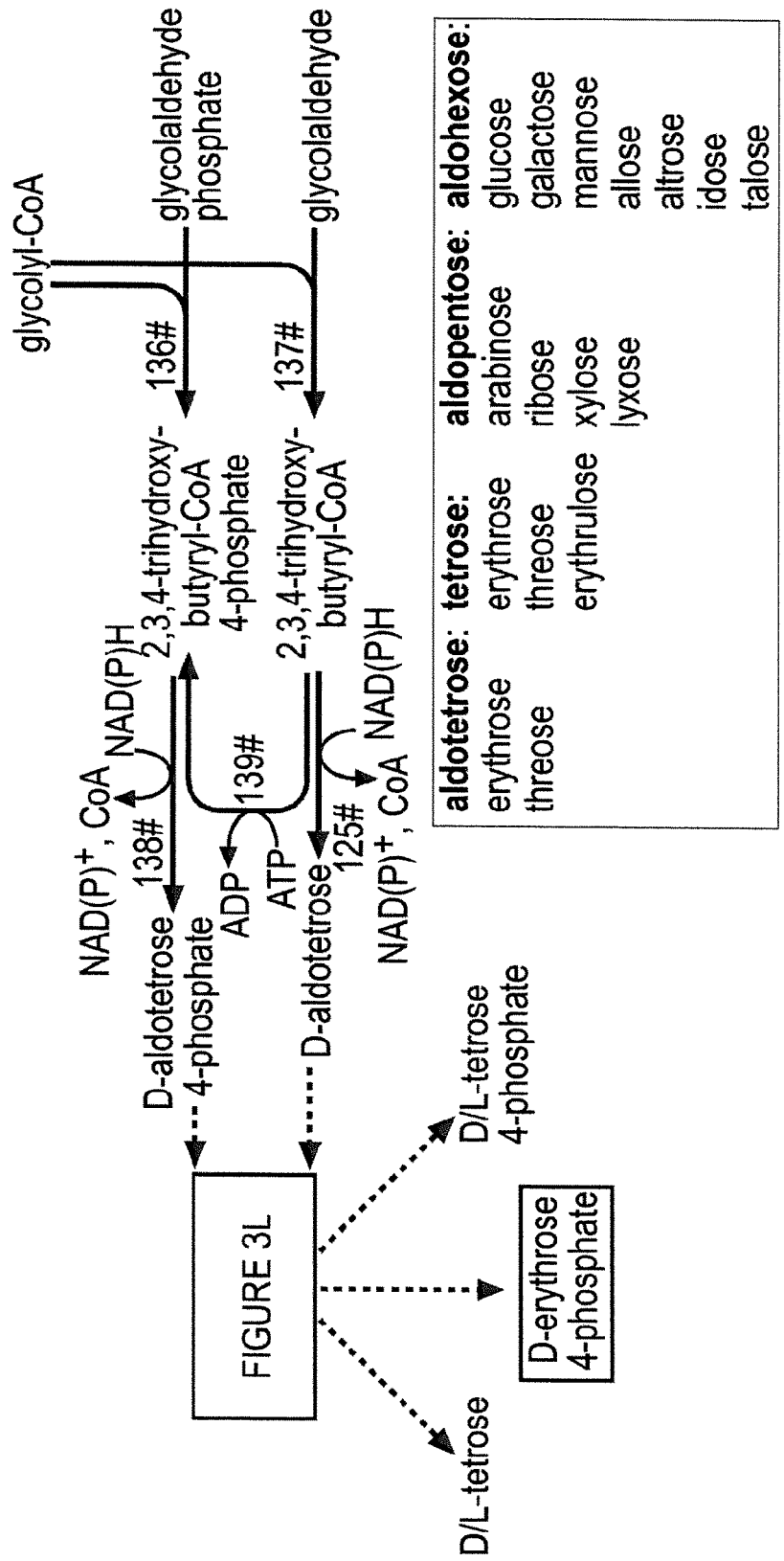
Figure 3:
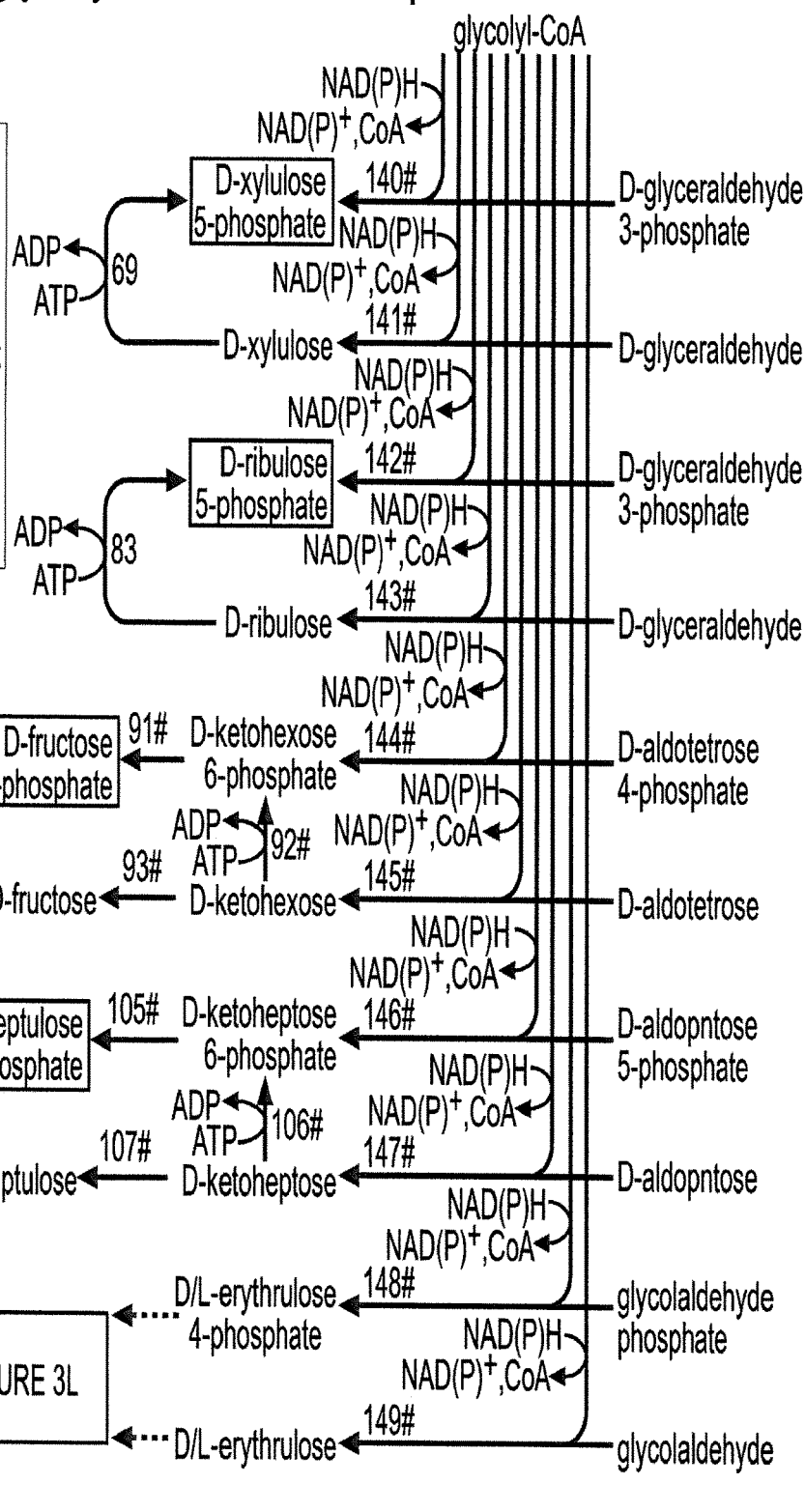
Figure 3:
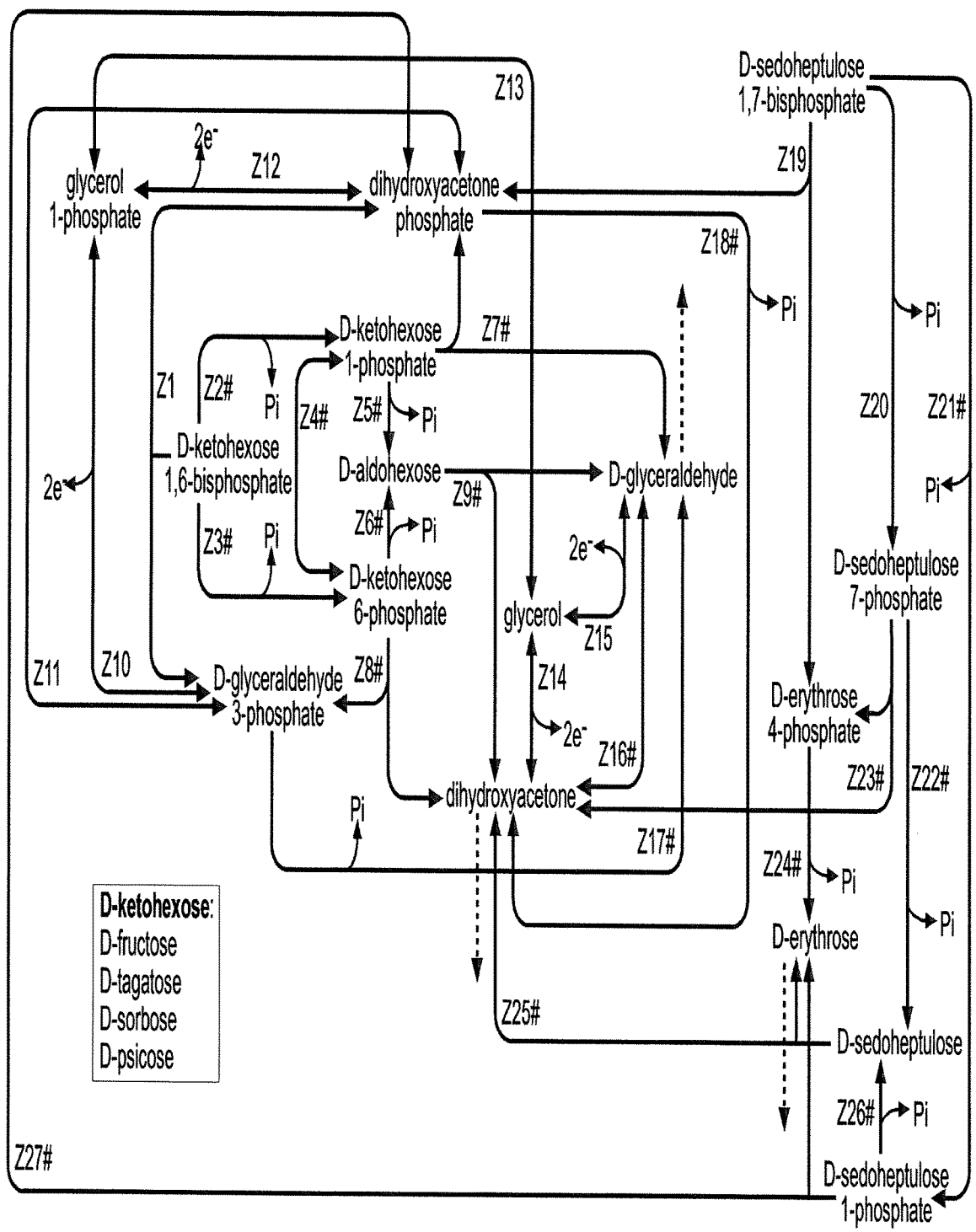
Figure 3:
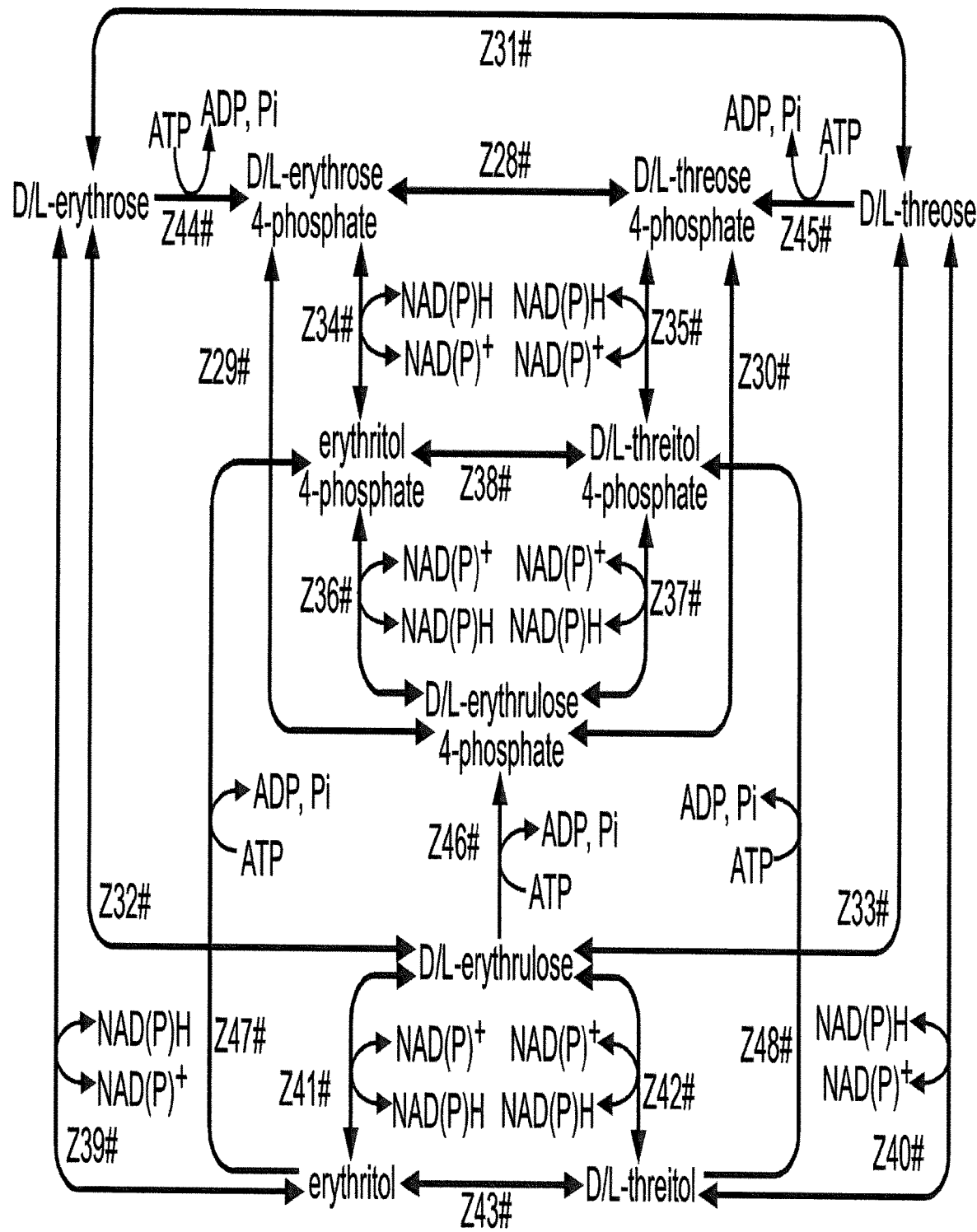

According to this embodiment, D-ribulose 1-phosphate can also be assimilated to the CBBC via its isomerisation to D-ribose 1-phosphate (reaction 29# in FIG. 3). In a preliminary study it was found that this reaction can be catalyzed by the enzyme Rru_A0360 with measurable rate ($k_{cat}$=0.03 s$^{-1}$, $k_{cat}/K_M$<20 M$^{-1}$s$^{-1}$). Preferably, such rate can even be evolutionary further optimized as described herein elsewhere.

The enzymatic conversion of D-ribose 1-phosphate into D-ribose 1,5-bisphosphate (reaction 31) as described in B)b), above, is a conversion which does naturally occur and for which enzymes which catalyze this conversion are known. Examples for corresponding enzymes which are known to catalyze this conversion are mentioned in Table 2 and corresponding enzymes can be employed in the context of the present invention. In particular, D-ribose 1-phosphate can be phosphorylated to D-ribose 1,5-bisphosphate (reaction 31) by an ADP-dependent ribose-1-phosphate kinase.

The enzymatic conversion of D-ribose 1,5-bisphosphate into D-ribulose 1,5-bisphosphate (reaction 32) as described in B)b), above, is a conversion which does naturally occur and for which enzymes which catalyze this conversion are known.

Examples for corresponding enzymes which are known to catalyze this conversion are mentioned in Table 2 and corresponding enzymes can be employed in the context of the present invention. In particular, D-ribose 1,5-bisphosphate can be isomerised to D-ribulose 1,5-bisphosphate (reaction 32) by ribose-1,5-bisphosphate isomerase (Aono R. et al., 2015, *Nat Chem Biol* 11, 355-360).

The enzymatic conversions as described in B)c), above, can be achieved as described in the following:

The enzymatic conversion of 2-PG into 2-phosphoglycolyl phosphate (reaction 23#) as described in B)c), above, can for example be achieved by transferring a phosphate group from another carboxylic acid or by utilizing a kinase enzyme such as 3-phosphoglycerate kinase: 2-PG was found to be a competitive inhibitor of this enzyme (Tompa P. et al., 1986, *Eur J Biochem* 154, 643-649; Vas M., 1990, *Eur J Biochem* 194, 639-645; Szilagyi A. N. et al., 1998, *Biochemistry* 37, 8551-8563), indicating that it can also serve as a substrate for at least some enzyme variants. Accordingly, in a preferred embodiment the enzymatic conversion of 2-PG into 2-phosphoglycolyl phosphate as described in B)c), above, can for example be achieved by a 3-phosphoglycerate kinase (EC 2.7.2.3) (this enzyme is an example for enzyme 23# mentioned herein). In principle any 3-phosphoglycerate kinase (EC 2.7.2.3) can be employed for this conversion.

The enzymatic conversion of 2-phosphoglycolyl phosphate into glycolaldehyde 2-phosphate (reaction 24#) as described in B)c), above, can for example be achieved by a phosphorylating glyceraldehyde 3-phosphate dehydrogenase (EC 1.2.1.12) (this enzyme is an example for enzyme 24# mentioned herein). A phosphorylating glyceraldehyde 3-phosphate dehydrogenase (EC 1.2.1.12) is known to catalyze the reduction of glycolyl phosphate (Fife T. H. et al., 1970, *Biochemistry* 9, 4064-4067; Armstrong J. M. et al., 1976, *Biochem J* 159, 513-527; Byers L. D., 1978, *Arch Biochem Biophys* 186, 335-342) and the presence of a terminal phosphate moiety is known to enhance the reactivity (Byers L. D., 1978 loc. cit.). In principle, any phosphorylating glyceraldehyde 3-phosphate dehydrogenase (EC 1.2.1.12) can be employed for this conversion.

The enzymatic conversion of glycolaldehyde 2-phosphate into D-ribulose 1,5-bisphosphate (reaction 28#) as described in B)c), above, can be achieved by a L-fuculose-phosphate aldolase (EC 4.1.2.17) (this enzyme is an example for enzyme 28# mentioned herein), an enzyme that can also condense glycolaldehyde and dihydroxyacetone phosphate (Ghalambor M. A. et al., 1962, *J Biol Chem* 237, 2427-2433; Ghalambor, M. A. et al., 1966, *Methods Enzymol* 9, 538-542). In principle, any L-fuculose-phosphate aldolase (EC 4.1.2.17) can be employed for this conversion. Preferably, an L-fuculose-phosphate aldolase (EC 4.1.2.17) derived from *E. coli* can be employed for this conversion.

As mentioned above, in another embodiment one of the preferred intermediates of the CBBC into which 2-PG is converted according to the present invention is D-erythrose 4-phosphate. In the following, the possible pathways will be described which allow the conversion of 2-PG into D-erythrose 4-phosphate according to preferred embodiments of the present invention. The pathway which allows converting 2-PG into D-erythrose 4-phosphate will be referred to as option "C)" in the following. According to option C) the intermediate compound of the CBBC is D-erythrose 4-phosphate, and the conversion of 2-PG is preferably achieved by:

a) enzymatic conversion of 2-PG into glycolaldehyde, further enzymatic conversion of glycolaldehyde into D-erythrose, and further enzymatic conversion of D-erythrose into D-erythrose 4-phosphate (a respective illustrative example is provided by FIG. 1C);

b) enzymatic conversion of 2-PG into glycolyl-CoA, further enzymatic conversion of glycolyl-CoA into 2,4-dihydroxy-3-oxo-butyryl-CoA, further enzymatic conversion of 2,4-dihydroxy-3-oxo-butyryl-CoA into 2,3,4-trihydroxy-3-oxo-butyryl-CoA, further enzymatic conversion of 2,3,4-trihydroxy-3-oxo-butyryl-CoA into a D-aldotetrose or a L-aldotetrose, and further enzymatic conversion of said D-aldotetrose or said L-aldotetrose into D-erythrose 4-phosphate, wherein said D-aldotetrose is D-erythrose or D-threose, and wherein said L-aldotetrose is L-erythrose or L-threose.

The enzymatic conversions as described in C)a), above, can, for example, be achieved as described in the following:

The enzymatic conversion of 2-PG into glycolaldehyde as described in C)a), can be achieved by different pathways as will be described further below.

The further enzymatic conversion of glycolaldehyde into D-erythrose (reaction 10#) as described in C)a) can, for example, be achieved by an aldolase (EC 4.1.2.X) (this enzyme is an example for enzyme 10# mentioned herein). In principle, any aldolase (EC 4.1.2.X) can be employed for this conversion. Preferably, a nonspecific aldolase, which can accept unphosphorylated donor and acceptor, and catalyze a reaction with glycolaldehyde as an acceptor (e.g. see Schürmann M. et al., 2001, *J. Mol. Catal. B: Enzym.* 19-20, 247-252; Chiu T. H. et al., 1969, *Biochemistry* 8, 98-108) is employed in the context of the present invention. In a preferred embodiment the aldolase employed is a fructose 6-phosphate aldolase or a xylulose 1-phosphate aldolase (Schirmann M., 2002, *Journal of Molecular Catalysis B: Enzymatic* 19-20, 247-252).

The further enzymatic conversion of D-erythrose into D-erythrose 4-phosphate (reaction 11#) as described in C)a) can, for example, be achieved by a dihydroxyacetone kinase (EC 2.7.1.29; Herz S. et al., 2002, *Phytochemistry* 60, 3-11) (this enzyme is an example for enzyme 11# mentioned herein). In principle, any dihydroxyacetone kinase (EC 2.7.1.29) can be employed for this conversion.

The enzymatic conversions as described in C)b), above, can, for example, be achieved as described in the following:

The enzymatic conversion of 2-PG into glycolyl-CoA as described in C)b), can be achieved by different pathways as will be described further below.

The further enzymatic conversion of glycolyl-CoA into 2,4-dihydroxy-3-oxo-butyryl-CoA (reaction 56#) as described in C)b) can, for example, be achieved by an acetyl-CoA C-acetyltransferase (EC 2.3.1.9) (this enzyme is an example for enzyme 56# mentioned herein). In principle, any acetyl-CoA C-acetyltransferase (EC 2.3.1.9) can be employed for this conversion. Preferably, two molecules of glycolyl-CoA are enzymatically converted by an acetyl-CoA C-acetyltransferase (EC 2.3.1.9) into 2,4-dihydroxy-3-oxo-butyryl-CoA. Preferably, an acetyl-CoA C-acetyltransferase (EC 2.3.1.9), which can accept glycolyl-CoA as donor and/or can accept glycolyl-CoA as an acceptor is employed in the context of the present invention. In a preferred embodiment the acetyl-CoA C-acetyltransferase (EC 2.3.1.9) bktB (UniProt accession code Q0KBP1; entry version 66 (9 Dec. 2015)) from *Cupriavidus necator* H16 (formerly known as *Ralstonia eutropha* H16) is employed. This acetyl-CoA C-acetyltransferase can substitute the donor acetyl-CoA with glycolyl-CoA and can further substitute the acceptor acetyl-CoA with glycolyl-CoA (Martin C H et al., 2013, *Nat Commun* 4, 1414). Hence, this enzyme can catalyze the condensation of two glycolyl-CoA molecules to generate 2,4-dihydroxy-3-oxobutyryl-CoA.

The further enzymatic conversion of 2,4-dihydroxy-3-oxo-butyryl-CoA into 2,3,4-trihydroxy-3-oxo-butyryl-CoA (reaction 57#) as described in C)b) can, for example, be achieved by a 3-hydroxybutyryl-CoA dehydrogenase (EC 1.1.1.157) (this enzyme is an example for enzyme 57# mentioned herein). In principle, any 3-hydroxybutyryl-CoA dehydrogenase (EC 1.1.1.157) can be employed for this conversion. Preferably, a 3-hydroxybutyryl-CoA dehydrogenase, which has a high specificity for 2,4-dihydroxy-3-oxo-butyryl-CoA as a substrate is employed.

Moreover, the further enzymatic conversion of 2,3,4-trihydroxy-3-oxo-butyryl-CoA into a D-aldotetrose or a L-aldotetrose (reaction 125#) as described in C)b) can, for example, be achieved by an aldehyde dehydrogenase (acetylating, EC. 1.2.1.X). This enzyme is an example for enzyme 125# mentioned herein). A preferred D-aldotetrose is D-erythrose or D-threose. In principle, any aldehyde dehydrogenase (acetylating, EC. 1.2.1.X) can be employed for the enzymatic conversion of 2,3,4-trihydroxy-3-oxo-butyryl-CoA into a D-aldotetrose or a L-aldotetrose. Preferably, an aldehyde dehydrogenase (acetylating, EC. 1.2.1.X), which has a high specificity for 2,3,4-trihydroxy-3-oxo-butyryl-CoA as a substrate is employed.

The further enzymatic conversion of a D-aldotetrose or a L-aldotetrose into D-erythrose 4-phosphate as described in C)b) can, for example, be achieved by any of the interconversion pathways shown in FIG. 3L (lower panel; respective enzymes and further information as regards the reactions of these pathways are provided in Table 3). As mentioned above, a preferred D-aldotetrose is D-erythrose or D-threose.

In particular, the enzymatic conversion of D-erythrose (a preferred D-aldotetrose) into D-erythrose 4-phosphate (reaction Z44#; also referred to as 11# herein) can, for example, be achieved by a sugar kinase (EC 2.7.1.X) (this enzyme is an example for enzyme Z44# and enzyme 11# mentioned herein). In principle, any sugar kinase (EC 2.7.1.X) can be employed for this conversion. Preferably, a dihydroxyacetone kinase (EC 2.7.1.29; Herz S. et al., 2002, *Phytochemistry* 60, 3-11) (this enzyme is an example for enzyme Z44# and enzyme 11# mentioned herein) is employed. In principle, any dihydroxyacetone kinase (EC 2.7.1.29) can be employed for this conversion. A respective example is described in Herz et al.

Furthermore, the enzymatic conversion of D-threose (a preferred D-aldotetrose) into D-erythrose 4-phosphate can, for example, be achieved by the enzymatic conversion of D-threose into D-erythrose (reaction Z31#), and the further enzymatic conversion of D-erythrose into D-erythrose 4-phosphate (reaction Z44#; also referred to as 11# herein). The enzymatic conversion of D-threose into D-erythrose (reaction Z31#) can, for example, be achieved by a sugar epimerase (EC 5.1.3.X) (this enzyme is an example for enzyme Z31# mentioned herein). In principle, any sugar epimerase (EC 5.1.3.X) can be employed for this conversion. Similarly, in principle also any sugar isomerase (EC 5.3.1.X) having sugar epimerase activity can be can be employed. Preferably, a xylose isomerase (EC 5.3.1.5; see, e.g., Vuolanto A et al., 2002, *Biocatalysis and Biotransformation* 20, 235-240) and/or a L-rhamnose isomerase (5.3.1.14; see, e.g., Leang K et al., 2004, *Biochim Biophys Acta* 1674, 68-77) is/are employed for this conversion. In principle any xylose isomerase and/or any L-rhamnose isomerase can be employed for this conversion. Preferably, an enzyme referred to in Vuolanto A et al. or Leang K et al. such as the xylose isomerase from *Streptomyces rubiginosus* (UniProt: P24300; entry version 119 (20 Jan. 2016)) is employed. The enzymatic conversion of D-erythrose into D-erythrose 4-phosphate (reaction Z44#; also referred to as 11# herein) can, for example, be achieved as described further above.

Alternatively, the enzymatic conversion of D-threose (a preferred D-aldotetrose) into D-erythrose 4-phosphate can, for example, be achieved by the enzymatic conversion of D-threose into D-threose 4-phosphate (reaction Z45#), and further enzymatic conversion of D-threose 4-phosphate into D-erythrose 4-phosphate (reaction Z28#).

The enzymatic conversion of D-threose into D-threose 4-phosphate (reaction Z45#) can, for example, be achieved by a sugar kinase (EC 2.7.1.X) (this enzyme is an example for enzyme Z45# mentioned herein). In principle any sugar kinase (EC 2.7.1.X) can be employed for this conversion. Preferably, a sugar kinase (EC 2.7.1.X), which has a high specificity for D-threose as a substrate is employed.

The further enzymatic conversion of D-threose 4-phosphate into D-erythrose 4-phosphate (reaction Z28#) can, for example, be achieved by a sugar epimerase (EC 5.1.3.X) (this enzyme is an example for enzyme Z28# mentioned herein). In principle any sugar epimerase (EC 5.1.3.X) can be employed for this conversion. Preferably, a sugar epimerase (EC 5.1.3.X), which has a high specificity for D-threose 4-phosphate as a substrate is employed.

In an embodiment, in which an L-aldotetrose (L-threose or L-erythrose) is enzymatically converted to D-erythrose 4-phosphate, for example one of the enzymatic pathways shown in FIG. 3L (lower panel; respective enzymes and further information as regards the reactions of these pathways are provided in Table 3), which comprises the conversion of erythritol 4-phosphate to D-erythrose 4-phosphate (reaction Z34#) can be employed. This reaction can, for example, be achieved by an alcohol-sugar dehydrogenase (EC 1.1.1.X).

As mentioned above, in another embodiment one of the preferred intermediates of the CBBC into which 2-PG is converted according to the present invention is D-ribose 5-phosphate. In the following, the possible pathways will be described which allow the conversion of 2-PG into D-ribose 5-phosphate according to preferred embodiments of the present invention. The pathway which allows converting 2-PG into D-ribose 5-phosphate will be referred to as option "D)" in the following. According to option D) the intermediate compound of the CBBC is D-ribose 5-phosphate, and the conversion of 2-PG is preferably achieved by:

enzymatic conversion of 2-PG into glycolaldehyde, further enzymatic conversion of glycolaldehyde into D-ribulose 1-phosphate, further enzymatic conversion of D-ribulose 1-phosphate into D-ribose 1-phosphate, and further conversion of D-ribose 1-phosphate into D-ribose 5-phosphate (a respective illustrative example is provided by FIG. 3B; pathway: 2-PG conversion into glycolaldehyde as shown in FIG. 2+enzymes 8, 29#, 30).

The enzymatic conversion of 2-PG into glycolaldehyde as described in D) can, for example, be achieved by different pathways as will be described further below.

The enzymatic conversion of glycolaldehyde into D-ribulose 1-phosphate (reaction 8) as described in D), is a conversion which does naturally occur and can, for example, be achieved as described above for B)a) or B)b).

The further enzymatic conversion of D-ribulose 1-phosphate into D-ribose 1-phosphate (reaction 29#) as described in D) can, for example, be achieved by a 5-methylthio-D-ribulose 1-phosphate 1,2-isomerase as described in connection with B), above.

The further enzymatic conversion of D-ribose 1-phosphate into D-ribose 5-phosphate (reaction 30) as described in D) is a conversion which does naturally occur and for which enzymes which catalyze this conversion are known (Hammer-Jespersen K. et al., 1970, *Eur J Biochem* 17, 397-407). Examples for corresponding enzymes which are known to catalyze this conversion are mentioned in Table 2 and corresponding enzymes can be employed in the context of the present invention.

As mentioned above, in another embodiment one of the preferred intermediates of the CBBC into which 2-PG is converted according to the present invention is D-ribulose 5-phosphate. In the following, the possible pathways will be described which allow the conversion of 2-PG into D-ribulose 5-phosphate according to preferred embodiments of the present invention. The pathway which allows converting 2-PG into D-ribose 5-phosphate will be referred to as option "E)" in the following. According to option E) the intermediate compound of the CBBC is D-ribulose 5-phosphate, and the conversion of 2-PG is preferably achieved by:

enzymatic conversion of 2-PG into glycolaldehyde, further enzymatic conversion of glycolaldehyde into D-arabinose 5-phosphate, and further enzymatic conversion of D-arabinose 5-phosphate into D-ribulose 5-phosphate (a respective illustrative example is provided by FIG. 1E).

The enzymatic conversion of 2-PG into glycolaldehyde as described in E) can, for example, be achieved by different pathways as will be described further below.

The further enzymatic conversion of glycolaldehyde into D-arabinose 5-phosphate (reaction 78#) as described in E) can, for example, be achieved by an aldolase (EC 4.1.2.X). Preferably, the enzymatic conversion of glycolaldehyde into D-arabinose 5-phosphate is achieved by the aldol condensation of glycolaldehyde (as a donor) with D-glyceraldehyde 3-phosphate (as an acceptor). In principle, any aldolase (EC 4.1.2.X) can be employed for the conversion of glycolaldehyde into D-arabinose 5-phosphate. Preferably, an aldolase, which is able to catalyze the aldol condensation of glycolaldehyde (as a donor) with D-glyceraldehyde 3-phosphate (as an acceptor), thus yielding D-arabinose 5-phosphate, is employed. An example for such an enzyme is a D-fructose 6-phosphate aldolase (an enzyme belonging to EC 4.1.2.X, which has not yet been assigned to a own EC number within this class of enzymes) (this enzyme is in particular a representative example for enzyme 78# mentioned herein). Even more preferably, an aldolase that has a substrate affinity that is characterized by a $K_M$ below 1 mM towards glycolaldehyde (as a donor) and D-glyceraldehyde 3-phosphate (as an acceptor) and/or that achieves the condensation with $16.5<k_{cat}<173$ sec$^{-1}$ is employed. Particularly preferred is an aldolase that is further characterized in that the affinity of the enzyme towards dihydroxyacetone (as a donor) is considerably worse/lower than for glycolaldehyde (as a donor). Preferred is a ratio of at least 5 times, preferably at least 10 times, even more preferably at least 15 times and most preferably at least 20 times between the respective affinities (defined by $K_M$, wherein a higher $K_M$ indicates a lower affinity). Similarly, a particularly preferred aldolase is characterized and/or further characterized in that the affinity of the enzyme towards D-fructose 6-phosphate as a substrate is considerably worse/lower than those for D-arabinose 5-phosphate as substrate. Preferred is a ratio of at least 5 times, preferably at least 10 times, even more preferably at least 15 times and most preferably at least 20 times between the respective affinities (as indicated by $K_M$). In other words, it is particularly preferred to employ an aldolase that catalyzes the conversion of glycolaldehyde and D-glyceraldehyde 3-phosphate into D-arabinose 5-phosphate (and/or the reverse reaction) more efficiently (as, e.g. characterized by a ratio of at least 5 times, preferably at least 10 times, even more preferably at least 15 times and most preferably at least 20 times between the $k_{cat}/K_M$ values of the respective reaction(s) than the conversion of dihydroxyaceton and D-glyceraldehyde 3-phosphate into D-fructose 6-phosphate (and/or the reverse reaction).

Most preferably, an enzyme that is encoded by the *E. coli* gene fsaA (UniProt accession code: P78055; entry version 138 (20 Jan. 2016)) or by the *E. coli* gene fsaB (UniProt accession code: P32669; Entry version 125 (20 Jan. 2016)) is employed. As previously shown, these enzymes are able to catalyze the aldol condensation of glycolaldehyde (as a donor) with D-glyceraldehyde 3-phosphate (as an acceptor) to yield D-arabinose 5-phosphate (Garrabou X et al., 2009, *Angew Chem Int Ed Engl* 48(30), 5521-5525; Samland A K et al., 2011, *Chembiochem* 12(10), 1454-1474; Sánchez-Moreno I et al., 2012, *J Mol Catal B: Enzym* 2012 84; 9-14; Guérard-Hélaine C et al., 2015, *ChemCatChem* 7(12), 1871-1879). The affinities of the enzymes encoded by fsaA and fsaB genes towards the substrates glycolaldehyde (as a donor) with D-glyceraldehyde 3-phosphate (as an acceptor) are characterized by a $K_M$ below 1 mM and the condensation is expected to have $16.5 < k_{cat} < 173$ $sec^{-1}$ (Garrabou X et al., 2009, loc. cit.; Sánchez-Moreno I et al., 2012, loc. cit.). It has further been reported that the affinities of these enzymes towards D-fructose 6-phosphate ($K_M > 6$ mM (Garrabou X et al., 2009, loc. cit.; Sánchez-Moreno I et al., 2012, loc. cit.)) as a substrate and dihydroxyacetone phosphate ($K_M > 25$ mM (Garrabou X et al., 2009, loc. cit.; Sánchez-Moreno I et al., 2012, loc. cit.)) as a substrate are considerably lower (as indicated by an increased $K_M$) than those for D-arabinose 5-phosphate ($K_M \approx 0.5$ mM (Garrabou X et al., 2009, loc. cit.)) and glycolaldehyde ($K_M \approx 0.2$ mM (Garrabou X et al., 2009, loc. cit.; Sánchez-Moreno I et al., 2012, loc. cit.)). Accordingly, an overexpressed enzyme encoded by the fsaA or fsaB gene will predominantly catalyze the reversible glycolaldehyde assimilation rather than the reversible D-fructose 6-phosphate cleavage. While the enzyme encoded by the fsaA or fsaB gene may in principle catalyzes the condensation of two glycolaldehyde molecules, the affinity towards glycolaldehyde as an acceptor is too low ($K_M > 60$ mM (Garrabou X et al., 2009, loc. cit.; Sánchez-Moreno I et al., 2012, loc. cit.)) to compete with D-arabinose 5-phosphate synthesis in vivo. Thus, also this alternative reaction does not significantly compete with the conversion of glycolaldehyde into D-arabinose 5-phosphate.

The further enzymatic conversion of D-arabinose 5-phosphate into D-ribulose 5-phosphate (reaction 80) as described in E) is a conversion which does naturally occur and for which enzymes that catalyze this conversion are known (Meredith T C et al., 2005, *Journal of Bacteriology* 187(20), 6936-6942; Smyth K M et al., 2013 *Carbohyd Res* 380, 70-75). In particular, such enzymes are known from *E. coli* and have also been suggested in planta. Examples for corresponding enzymes which are known to catalyze this conversion are mentioned in Table 2 and corresponding enzymes can be employed in the context of the present invention. The enzymatic conversion of D-arabinose 5-phosphate into D-ribulose 5-phosphate (reaction 80) can for example be achieved by a D-arabinose 5-phosphate isomerase (EC 5.3.1.13). Variants of this isomerase are, for example, known from *E. coli* (Meredith T C et al., 2005, loc. cit.) and a corresponding candidate enzyme was also suggested in planta (Smyth K M et al., 2013, loc. cit.).

As mentioned above, in another embodiment one of the preferred intermediates of the CBBC into which 2-PG is converted according to the present invention is D-xylulose 5-phosphate. In the following, possible pathways will be described which allow the conversion of 2-PG into D-xylulose 5-phosphate according to preferred embodiments of the present invention. The pathways which allow converting 2-PG into D-xylulose 5-phosphate will be referred to as option "F" in the following. According to option F) the intermediate compound of the CBBC is D-xylulose 5-phosphate, and the conversion of 2-PG is preferably achieved by:
a) enzymatic conversion of 2-PG into glycolaldehyde, further enzymatic conversion of glycolaldehyde into D-xylulose, and further enzymatic conversion of D-xylulose into D-xylulose 5-phosphate (a respective illustrative example is provided by FIG. 1F); or
b) enzymatic conversion of 2-PG into glycolaldehyde, further enzymatic conversion of glycolaldehyde into D-xylulose 5-phosphate (a respective illustrative example is provided by FIG. 1G); or
c) enzymatic conversion of 2-PG into 2-phosphoglycolyl phosphate, further enzymatic conversion of 2-phosphoglycolyl phosphate into glycolaldehyde 2-phosphate, and further enzymatic conversion of glycolaldehyde 2-phosphate into D-xylulose 5-phosphate (respective illustrative examples are provided by FIG. 3E: pathway 1: 2-PG conversion into glycolaldehyde 2-phosphate as shown in FIG. 2+enzyme/reaction 68#; pathway 2: 2-PG conversion into glycolaldehyde 2-phosphate as shown in FIG. 2+enzyme/reaction 71#).

The enzymatic conversions as described in F)a), above, can, for example, be achieved as described in the following:

The enzymatic conversion of 2-PG into glycolaldehyde as described in F)a), above, can, for example, be achieved by different pathways as will be described, below.

The further enzymatic conversion of glycolaldehyde into D-xylulose as described in F)a) can, for example, be achieved by a transaldolase (EC 2.2.1.2). In principle, any transaldolase can be employed. Preferably, one or more of the transaldolases mentioned in the context of the two alternative reactions (reactions 67# and 70#), further below, is/are employed.

The enzymatic conversion of glycolaldehyde into D-xylulose can, for example be achieved by the transaldolase reaction between D-fructose 6-phosphate and glycolaldehyde (reaction 67#). For this conversion, preferably a transaldolase which accepts D-fructose 6-phosphate and glycolaldehyde as substrates is employed. Preferably, a transaldolase enzyme (EC 2.2.1.2) from *E. coli*, *B. subtilis* or *C. glutamicum* is employed. In particular, a transaldolase (EC 2.2.1.2) selected from the group consisting of the following enzymes can be employed: TalB from *E. coli* (UniProt accession code: P0A870; entry version 109 (20 Jan. 2016)); Tal from *B. subtilis* (UniProt accession code: P19669) and Tal from *C. glutamicum* (UniProt accession code: Q8NQ64; entry version 109 (9 Dec. 2015)) (Samland A K et al., 2012, *FEBS J* 279(5), 766-778). These enzymes are known to catalyze the transaldolase reaction between D-fructose 6-phosphate and glycolaldehyde, in which the former transfers a dihydroxyacetone moiety to the latter, resulting in the formation of D-glyceraldehyde 3-phosphate and D-xylulose (reaction 67#) (Samland A K et al., 2012, loc. cit.). The $V_{max}$ of this reaction is in reasonable scale (1.6-8.8 μmol/min/mg) if catalyzed by these enzyme(s). The affinity of the enzyme(s) towards glycolaldehyde has been reported to be characterized in a $K_M > 60$ mM. Preferably, an enzyme, which is based on said enzymes but has been engineered and/or evolved to an even higher activity and/or affinity towards glycolaldehyde (characterized in a lower $K_M$) is employed. Methods for modifying and/or improving the desired enzymes are well-known to the person skilled in the art and are described elsewhere herein. Most preferably, a respective improved enzyme, which has a high affinity to glycolaldehyde, wherein the high affinity is reflected by a low $K_M$ value ($K_M < 1$ mM), is employed. Such enzyme allows for particularly efficient glycolaldehyde assimilation.

Alternatively, the enzymatic conversion of glycolaldehyde into D-xylulose as described in F)a) can also be achieved by the transaldolase reaction between D-sedoheptulose 7-phosphate and glycolaldehyde (reaction 70#). In such a case, preferably a transaldolase which accepts D-sedoheptulose 7-phosphate and glycolaldehyde as substrates is employed.

Finally, the further enzymatic conversion of D-xylulose into D-xylulose 5-phosphate (reaction 69) as described in F)a), above, is a conversion which does naturally occur and for which enzymes which catalyze this conversion are known. Examples for corresponding enzymes which are known to catalyze this conversion are mentioned in Table 2 and corresponding enzymes can be employed in the context of the present invention. In particular, the enzymatic conversion of D-xylulose into D-xylulose 5-phosphate (reaction 69) can, for example, be achieved by a D-xylulokinase enzyme (EC 2.7.1.17) (Di Luccio E et al., 2007, *J Mol Biol* 365(3), 783-798; Hemmerlin A et al., 2006, *Plant Physiol* 142(2), 441-457).

The enzymatic conversions as described in F)b), above, can, for example, be achieved as described in the following: The enzymatic conversion of 2-PG into glycolaldehyde as described in F)b), above, can, for example, be achieved by different pathways as will be described further below.

The enzymatic conversion of 2-PG into glycolaldehyde as described in F)b), above, can, for example, be achieved by different pathways as will be described further below.

The further enzymatic conversion of glycolaldehyde into D-xylulose 5-phosphate as described in F)b) can, for example, be achieved by a transketolase enzyme (EC 2.2.1.1). In principle, any transketolase can be employed. Preferably, one or more of the transketolases mentioned in the context of the two alternative reactions (reactions 97# and 98#), further below, is/are employed.

The enzymatic conversion of glycolaldehyde into D-xylulose 5-phosphate can, for example, be achieved by the (reversible) condensation of glycolaldehyde (as a donor) and D-glyceraldehyde 3-phosphate (as an acceptor) (reaction 97#). This conversion can, for example, be achieved with the transketolase (EC 2.2.1.1) TKL1 from *S. cerevisiae* (UniProt accession code: P23254; entry version 168 (20 Jan. 2016)), which was found to catalyze the reversible condensation of glycolaldehyde (as a donor) and D-glyceraldehyde 3-phosphate (as an acceptor), yielding the CBBC's intermediate D-xylulose 5-phosphate (Fiedler E et al., 2001, *J Biol Chem* 276(19), 16051-16058). Preferably, a transketolase, which is, for example, based on the above mentioned enzyme, and which has been engineered and/or evolved to an even higher affinity towards its substrates, in particular glycolaldehyde as a donor (characterized in a lower $K_M$), is employed. Methods for modifying and/or improving the desired enzyme are well-known to the person skilled in the art and are described elsewhere herein. Most preferably, a respective improved enzyme, which has a high affinity of glycolaldehyde as a donor ($K_M$<1 mM), is employed. Even more preferably, since glycolaldehyde can also serve as an acceptor, which results in the formation of erythrulose (Fiedler E et al., 2001, loc. cit.; Sprenger G A et al., 1995, *Eur J Biochem* 230(2), 525-532; Sevostyanova I A et al., 2004, *Biochem Biophys Res Commun* 313(3), 771-774), a transketolase employed for the above mentioned conversion is preferably engineered and/or evolved to a high affinity of glycolaldehyde as a donor ($K_M$<1 mM) but low affinity for glycolaldehyde as an acceptor ($K_M$>10 mM).

Alternatively, the enzymatic conversion of glycolaldehyde into D-xylulose 5-phosphate can also be achieved by the enzymatic conversion of glycolaldehyde into D-xylulose and the subsequent enzymatic conversion of D-xylulose into D-xylulose 5-phosphate. The enzymatic conversion of glycolaldehyde into D-xylulose can, for example, be achieved by the condensation of glycolaldehyde (as a donor) and D-glyceraldehyde (as an acceptor) (reaction 98#). For such conversion, preferably a transketolase which accepts glycolaldehyde (as a donor) and D-glyceraldehyde (as an acceptor) is employed. The subsequent enzymatic conversion of D-xylulose into D-xylulose 5-phosphate (reaction 69) can, for example, be achieved as described in F)a), above.

The enzymatic conversions as described in F)c), above, can, for example, be achieved as described in the following:

The enzymatic conversion of 2-PG into 2-phosphoglycolyl phosphate (reaction 23#) as described in F)c) can, for example, be achieved as described in connection with B)c), above.

The further enzymatic conversion of 2-phosphoglycolyl phosphate into glycolaldehyde 2-phosphate (reaction 24#) as described in F)c) can, for example, be achieved as described in connection with B)c), above.

The enzymatic conversion of glycolaldehyde 2-phosphate into D-xylulose 5-phosphate as described in F)c) can, for example, be achieved by a transaldolase (EC 2.2.1.2). In principle, any transaldolase can be employed. Preferably, one of the transaldolase mentioned in the context of the two alternative reactions (reactions 68# and 71#), below, is/are employed.

The enzymatic conversion of glycolaldehyde 2-phosphate into D-xylulose 5-phosphate can, for example, be achieved by the condensation of D-fructose 6-phosphate (as a donor) and glycolaldehyde 2-phosphate (as an acceptor) (reaction 68#). In such a case, preferably a transaldolase which accepts D-fructose 6-phosphate (as a donor) and glycolaldehyde 2-phosphate (as an acceptor), is employed.

Alternatively, the enzymatic conversion of glycolaldehyde 2-phosphate into D-xylulose 5-phosphate can, for example, be achieved by the condensation of D-sedoheptulose 7-phosphate (as a donor) and glycolaldehyde 2-phosphate (as an acceptor) (reaction 71#). In such a case, preferably a transaldolase which accepts D-sedoheptulose 7-phosphate (as a donor) and glycolaldehyde 2-phosphate (as an acceptor) is employed.

Some of the pathways for the conversion of 2-PG into an intermediate compound of the CBBC of the present invention as described above comprise the enzymatic conversion of 2-PG into glycolyl-CoA. In the following, the possible pathways will be described which allow the conversion of 2-PG into glycolyl-CoA according to preferred embodiments of the present invention. The enzymatic conversion of 2-PG into glycolyl-CoA can, for example, be achieved by:
a) enzymatic conversion of 2-PG into glycolate and further enzymatic conversion of glycolate into glycolyl-CoA (a respective illustrative example is provided by FIG. 2; enzyme 1 and 2#); or
b) enzymatic conversion of 2-PG into glycolate, further enzymatic conversion of glycolate into glycolyl phosphate, and further enzymatic conversion of glycolyl phosphate into glycolyl-CoA (a respective illustrative example is provided by FIG. 2; enzymes 1, 19# and 21#); or
c) enzymatic conversion of 2-PG into glycolate, further enzymatic conversion of glycolate into glycolyl phosphate, further enzymatic conversion of glycolyl phosphate into glycolaldehyde, and further enzymatic conversion of glycolaldehyde into glycolyl-CoA (a respective illustrative example is provided by FIG. 2; enzymes 1, 19#, 20# and 7#); or
d) enzymatic conversion of 2-PG into glycolate, further enzymatic conversion of glycolate into glycolaldehyde, and further enzymatic conversion of glycolaldehyde into glycolyl-CoA (a respective illustrative example is provided by FIG. 2; enzymes 1, 22# and 7#).

The enzymatic conversion of 2-PG into glycolyl-CoA as described in a), above, can be achieved as described in the following:

The enzymatic conversion of 2-PG into glycolate (reaction 1) as described in a), above, is a conversion which does naturally occur and for which enzymes catalyzing this conversion are known, in particular also in plants. Examples for corresponding enzymes which are known to catalyze this conversion are mentioned in Table 2 and corresponding enzymes, preferably enzymes derived from plants, can be employed in the context of the present invention.

The further enzymatic conversion of glycolate into glycolyl-CoA (reaction 2#) as described above in a) can, for example, be achieved by a CoA-transferase (EC 2.8.3.X) (Volodina E. et al., 2014, Appl Microbiol Biotechnol 98, 3579-3589; Dhamankar H. et al., 2014, Metab Eng 25C, 72-81) or an ADP-forming or AMP-forming CoA ligase (EC 6.2.1.X) (Awano T. et al., 2014, J Bacteriol 196, 140-147; US 2011/0118434 A1) (these enzymes are an example for enzyme 2# mentioned herein). In principle, any ADP-forming or AMP-forming CoA ligase (EC 6.2.1.X) or CoA-transferase (EC 2.8.3.X) can be employed for such a conversion. In a preferred embodiment, the ADP-forming or AMP-forming CoA ligase (EC 6.2.1.X) is a propionate-CoA ligase (EC 6.2.1.17) (Awano T. et al., 2014, J Bacteriol 196, 140-147; US 2011/0118434 A1). In another preferred embodiment the CoA-transferase (EC 2.8.3.X) is a propionyl-CoA transferase (EC 2.8.3.1). In one embodiment a propionyl-CoA tranferase of Ralstonia eutropha or a propionyl-CoA tranferase of Clostridium propionicum is employed. The amino acid sequence of (the wild-type) propionyl-CoA tranferase of Ralstonia eutropha ($PCT_{Re}$) is known and is available, e.g., under NCBI accession no. CAJ93797.1 (encoding nucleic acid sequence is shown in SEQ ID NO: 11; amino acid sequence is shown in SEQ ID NO: 12). The amino acid sequence of (the wild-type) propionyl-CoA tranferase of Clostridium propionicum ($PCT_{Cp}$) is known and is available, e.g., under NCBI accession no. CAB77207.1 (encoding nucleic acid sequence is shown in SEQ ID NO: 13; amino acid sequence is shown in SEQ ID NO: 14). Notably, the capability of both enzymes to catalyze the conversion of glycolate into glycolyl-CoA (reaction 2#) is also shown in the appended examples.

It is of course not only possible to employ in the enzymatic conversion of glycolate into glycolyl-CoA (reaction 2#) an enzyme having the amino acid sequences of SEQ ID NOs: 12 or 14, respectively, but it is also possible to employ an enzyme showing a related sequence, provided that the enzyme still shows the activity of converting glycolate into glycolyl-CoA (reaction 2#).

The term "related sequences" preferably means sequences showing at least 60%, preferably at least 65%, more preferably at least 70%, more preferably at least 75%, more preferably at least 80%, more preferably at least 85%, more preferably at least 90%, more preferably at least 95%, more preferably at least 99% and most preferably at least 99.5% sequence identity to the amino acid sequences shown in SEQ ID NO: 12 or 14, respectively.

As regards the determination of percent identity the same applies as has been described herein above.

Such above-mentioned related sequences may, for example also comprise mutated variants showing improved properties. In particular, also any mutant variants created by the evolution and optimization strategies described herein elsewhere and showing improved properties are included in the related sequences. In a preferred embodiment a mutated version of a propionyl-CoA tranferase of Ralstonia eutropha or a propionyl-CoA tranferase of Clostridium propionicum is employed, which shows an improved activity catalyzing the conversion of glycolate into glycolyl-CoA (reaction 2#) in comparison to the respective wild-type enzyme.

How to design assays for determining the enzymatic activity of converting glycolate into glycolyl-CoA (reaction 2#) is well known in the art. It is, for instance, possible to use an in vitro assay as described in the appended examples for determining whether an enzyme has the activity of converting glycolate into glycolyl-CoA (reaction 2#). In one embodiment the assay as described in the example may also be modified with respect to concentration of any components used and/or modification of buffer compositions based on the common general knowledge of skilled person.

The enzymatic conversion of 2-PG into glycolyl-CoA as described in b), above, can be achieved as described in the following:

The enzymatic conversion of 2-PG into glycolate (reaction 1) as described above in b) can, for example, be achieved as described in connection with a) above.

The further enzymatic conversion of glycolate into glycolyl phosphate (reaction 19#) as described above in b) can, for example, be achieved by a carboxyl kinase (EC 2.7.2.X) (this enzyme is an example for enzyme 19# mentioned herein). In principle, any carboxyl kinase (EC 2.7.2.X) can be employed for such a conversion. In a preferred embodiment, the carboxyl kinase (EC 2.7.2.X) is an acetate kinase (EC 2.7.2.1) (Lyer, P. et al., 2005, Microbial Enzymes and Biotransformations (Barredo, J. L., Ed.), pp 239-246, ISBN: 9781588292537) or, in another embodiment, a butyrate kinase (Hartmanis M. G., 1987, J Biol Chem 262, 617-621) (EC 2.7.2.7). Even more preferably the carboxyl kinase (EC 2.7.2.X) is an acetate kinase (EC 2.7.2.1).

The further enzymatic conversion of glycolyl phosphate into glycolyl-CoA (reaction 21#) as described above in b) can, for example, be achieved by a phosphate acyltransferase (EC 2.3.1.X) (this enzyme is an example for enzyme 21# mentioned herein), as some glucosamine 6-phosphate acetyltransferase variants can accept glycolyl-CoA instead of acetyl-CoA (Macauley M. S., 2012, J Biol Chem 287, 28882-28897). In principle, any phosphate acyltransferase (EC 2.3.1.X) can be employed for such a conversion. In a preferred embodiment, the phosphate acyltransferase (EC 2.3.1.X) is a phosphate acetyltransferase (EC 2.3.1.8).

The enzymatic conversion of 2-PG into glycolyl-CoA as described in c), above, can be achieved as described in the following:

The enzymatic conversion of 2-PG into glycolate (reaction 1) as described above in c) can, for example, be achieved as described in connection with a) above.

The further enzymatic conversion of glycolate into glycolyl phosphate (reaction 19#) as described above in c) can, for example, be achieved as described in connection with b) above.

The further enzymatic conversion of glycolyl phosphate into glycolaldehyde (reaction 20#) as described above in c) can, for example, be achieved by a phosphorylating glyceraldehyde 3-phosphate dehydrogenase (EC 1.2.1.12) (this enzyme is an example for enzyme 20# mentioned herein) (Fife T. H. et al., 1970, Biochemistry 9, 4064-4067; Armstrong J. M. et al., 1976, Biochem J 159, 513-527; Byers L. D., 1978, Arch Biochem Biophys 186, 335-342). In principle, any phosphorylating glyceraldehyde 3-phosphate dehydrogenase (EC 1.2.1.12) can be employed for such a conversion.

The further enzymatic conversion of glycolaldehyde into glycolyl-CoA (reaction 7#) as described above in c) can, for example, be achieved by an acylating aldehyde dehydrogenase (EC 1.2.1.X) (this enzyme is an example for enzyme 7# mentioned herein) (Burton R. M. et al., 1953, *J Biol Chem* 202, 873-890; Sohling B. et al., 1993, *Eur J Biochem* 212, 121-127). In principle, any acylating aldehyde dehydrogenase (EC 1.2.1.X) can be employed for such a conversion. In a preferred embodiment, the acylating aldehyde dehydrogenase (EC 1.2.1.X) is an acetaldehyde dehydrogenase (acylating) (EC 1.2.1.10).

The enzymatic conversions for the enzymatic conversion of 2-PG into glycolyl-CoA as described in d), above, can be achieved as described in the following:

The enzymatic conversion of 2-PG into glycolate (reaction 1) as described above in d) can, for example, be achieved as described in connection with a) above.

The further enzymatic conversion of glycolate into glycolaldehyde (reaction 22#) as described above in d) can, for example, be achieved by an ATP- and NAD(P)H-dependent carboxylic acid reductase (EC 1.2.1.X) (this enzyme is an example for enzyme 22# mentioned herein). Several ATP- and NAD(P)H-dependent carboxylic acid reductase (EC 1.2.1.X) variants were shown to catalyze the reduction of acetate and lactate at high rate (Venkitasubramanian P., 2006, *Biocatalysis in the Pharmaceutical and Biotechnology Industries* (Patel, R. N., Ed.), ISBN: 9781588292537; Napora-Wijata K., 2014, *Biotechnol J* 9, 822-843) strongly indicating that glycolate can also be accepted as substrate. In principle, any ATP- and NAD(P)H-dependent carboxylic acid reductase (EC 1.2.1.X) can be employed for such a conversion.

The further enzymatic conversion of glycolaldehyde into glycolyl-CoA (reaction 7#) as described above in d) can, for example, be achieved as described in connection with c) above.

Some of the pathways for the conversion of 2-PG into an intermediate compound of the CBBC of the present invention as described above comprise the enzymatic conversion of 2-PG into glycolaldehyde. In the following, the possible pathways will be described which allow the conversion of 2-PG into glycolaldehyde according to preferred embodiments of the present invention. The enzymatic conversion of 2-PG into glycolaldehyde can, for example, be achieved by:
i) enzymatic conversion of 2-PG into glycolyl-CoA (by any of the pathways for enzymatic conversion of 2-PG into glycolyl-CoA as described above) and further enzymatic conversion of glycolyl-CoA into glycolaldehyde (respective illustrative examples are provided by FIG. 2; enzymes 1, 2# and 7#; or FIG. 2; enzymes 1, 19#, 21# and 7#, respectively); or
ii) enzymatic conversion of 2-PG into glycolate, further enzymatic conversion of glycolate into glycolyl phosphate and further enzymatic conversion of glycolyl phosphate into glycolaldehyde (a respective illustrative example is provided by FIG. 2; enzymes 1, 19# and 20#, respectively); or
iii) enzymatic conversion of 2-PG into glycolate, further enzymatic conversion of glycolate into glycolaldehyde (a respective illustrative example is provided by FIG. 2; enzymes 1 and 22#, respectively); or
iv) enzymatic conversion of 2-PG into glycolyl-CoA (by any of the pathways for enzymatic conversion of 2-PG into glycolyl-CoA as described above), further enzymatic conversion of glycolyl-CoA into glycolyl phosphate and further enzymatic conversion of glycolyl phosphate into glycolaldehyde (a respective illustrative example is provided by FIG. 2; enzymes 1, 2#, 21# and 20#, respectively); or The enzymatic conversions for the enzymatic conversion of 2-PG into glycolaldehyde as described in i), above, can be achieved as described in the following:

The enzymatic conversion of 2-PG into glycolyl-CoA as described above in i) can, for example, be achieved as described above. In the context of i) the enzymatic conversion of 2-PG into glycolyl-CoA is preferably achieved by the pathways a) and b) as described above.

The further enzymatic conversion of glycolyl-CoA into glycolaldehyde (reaction 7#) as described above in i) can, for example, be achieved by an acylating aldehyde dehydrogenase (EC 1.2.1.X) (this enzyme is an example for enzyme 7# mentioned herein) (Burton R. M. et al., 1953, *J Biol Chem* 202, 873-890; Sohling B. et al., 1993, *Eur J Biochem* 212, 121-127). In principle, any acylating aldehyde dehydrogenase (EC 1.2.1.X) can be employed for such a conversion. In a preferred embodiment, the acylating aldehyde dehydrogenase (EC 1.2.1.X) is an acetaldehyde dehydrogenase (acylating) (EC 1.2.1.10).

The enzymatic conversions for the enzymatic conversion of 2-PG into glycolaldehyde as described in ii), above, can be achieved as described in the following:

The enzymatic conversion of 2-PG into glycolate as described above in ii) can, for example, be achieved as described above.

The further enzymatic conversion of glycolate into glycolyl phosphate (reaction 19#) as described above in ii) can, for example, be achieved by a carboxyl kinase (EC 2.7.2.X) (this enzyme is an example for enzyme 19# mentioned herein) as described above. In principle, any carboxyl kinase (EC 2.7.2.X) can be employed for such a conversion. In a preferred embodiment, the carboxyl kinase (EC 2.7.2.X) is an acetate kinase (EC 2.7.2.1.) (Lyer P. et al., 2005, loc. cit.) or, in another embodiment, a butyrate kinase (Hartmanis M. G., 1987, loc. cit.) (EC 2.7.2.7). Even more preferably the carboxyl kinase (EC 2.7.2.X) is an acetate kinase (EC 2.7.2.1.).

The further enzymatic conversion of glycolyl phosphate into glycolaldehyde (reaction 20#) as described above in ii) can, for example, be achieved by a phosphorylating glyceraldehyde 3-phosphate dehydrogenase (EC 1.2.1.12) (this enzyme is an example for enzyme 20# mentioned herein) (Fife T. H. et al., 1970, loc. cit.; Armstrong J. M. et al., 1976, loc. cit.; Byers L. D., 1978, loc. cit.). In principle, any phosphorylating glyceraldehyde 3-phosphate dehydrogenase (EC 1.2.1.12) can be employed for such a conversion.

The enzymatic conversions for the enzymatic conversion of 2-PG into glycolaldehyde as described in iii), above, can be achieved as described in the following:

The enzymatic conversion of 2-PG into glycolate as described above in iii) can, for example, be achieved as described above.

The further enzymatic conversion of glycolate into glycolaldehyde (reaction 22#) as described above in iii) can, for example, be achieved by an ATP- and NAD(P)H-dependent carboxylic acid reductase (EC 1.2.1.X) (this enzyme is an example for enzyme 22# mentioned herein). Several ATP- and NAD(P)H-dependent carboxylic acid reductase (EC 1.2.1.X) variants were shown to catalyze the reduction of acetate and lactate at high rate (Venkitasubramanian P., 2006, *Biocatalysis in the Pharmaceutical and Biotechnology Industries* (Patel, R. N., Ed.), ISBN: 9781588292537; Napora-Wijata K., 2014, *Biotechnol J* 9, 822-843) strongly indicating that glycolate can also be accepted as substrate. In principle, any ATP- and NAD(P)H-dependent carboxylic acid reductase (EC 1.2.1.X) can be employed for such a conversion.

The enzymatic conversions for the enzymatic conversion of 2-PG into glycolaldehyde as described in iii), above, can be achieved as described in the following:

The enzymatic conversion of 2-PG into glycolyl-CoA as described above in iv) can, for example, be achieved as described above. In the context of iv) the enzymatic conversion of 2-PG into glycolyl-CoA is preferably achieved by enzymatic conversion of 2-PG into glycolate, further enzymatic conversion of glycolate into glycolyl-CoA. These enzymatic conversions are achieved as described above.

The enzymatic conversion of glycolyl-CoA into glycolyl phosphate (reaction 21#) as described above in iv) can, for example, be achieved by a phosphate acyltransferase (EC 2.3.1.X) (this enzyme is an example for enzyme 21# mentioned herein). It has, for example, been shown that some glucosamine 6-phosphate acetyltransferase variants can accept glycolyl-CoA instead of acetyl-CoA (Macauley M. S., 2012, loc. cit.). In principle, any phosphate acyltransferase (EC 2.3.1.X) can be employed for such a conversion. In a preferred embodiment, the phosphate acyltransferase (EC 2.3.1.X) is a phosphate acetyltransferase (EC 2.3.1.8).

The further enzymatic conversion of glycolyl phosphate into glycolaldehyde as described above in iv) can, for example, be achieved as described above in b).

Preferred, but non-limiting examples of photorespiration bypass routes in accordance with the invention are those depicted in the appended FIGS. 1 to 4. The bypass routes shown in FIG. 1 and mentioned above are particularly preferred.

Figure 2:
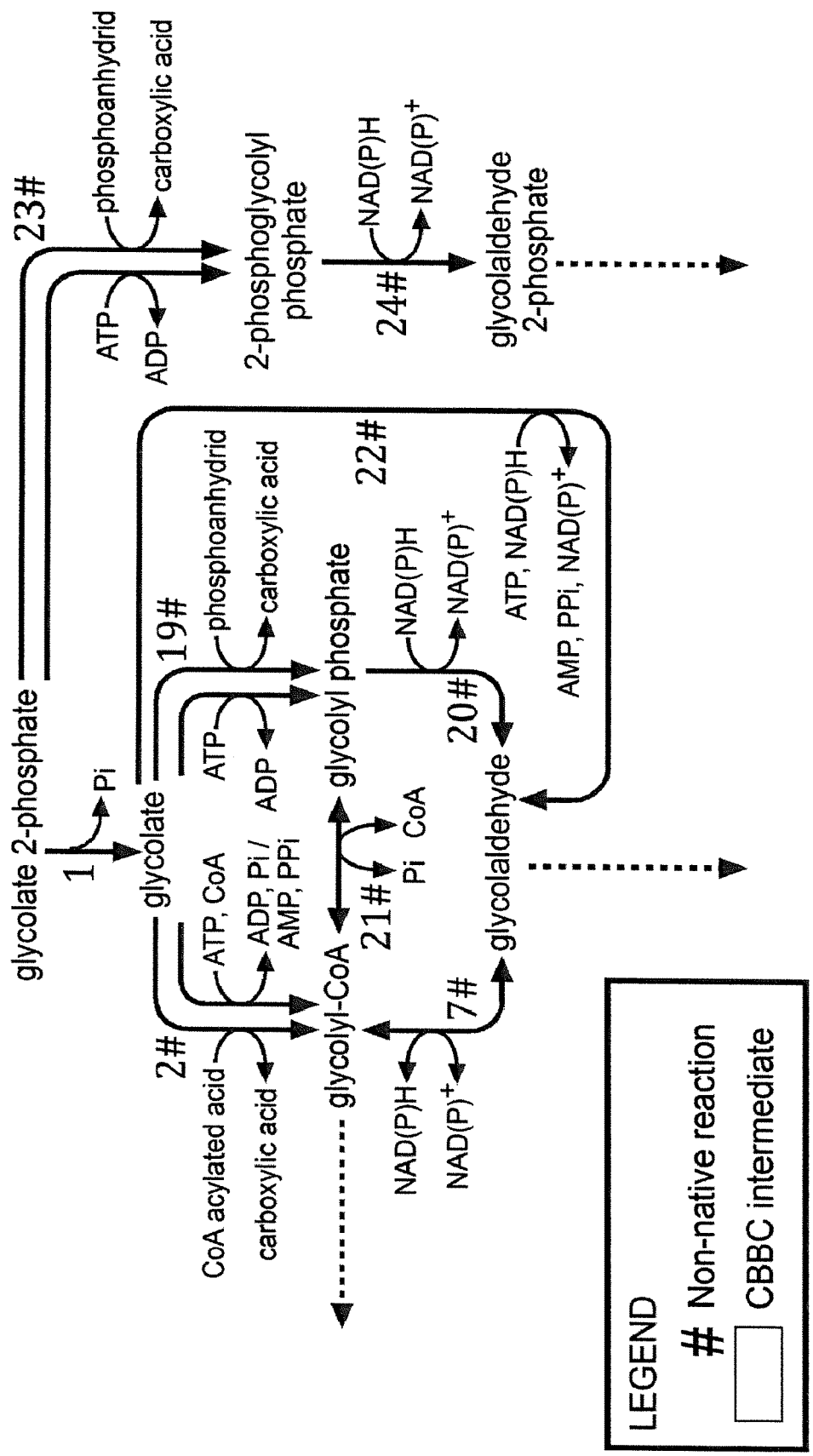
Figure 4:
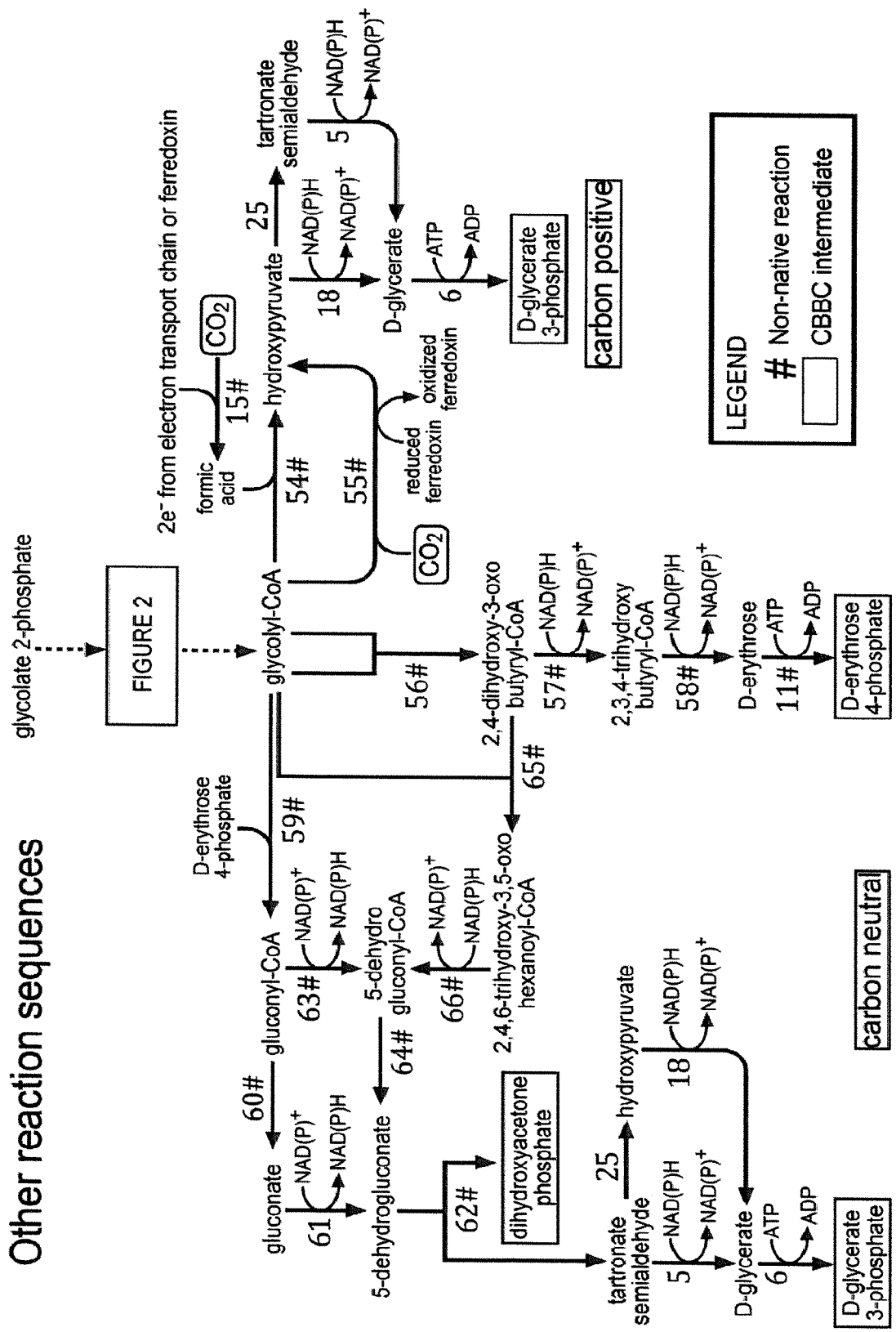

Notably, there are multiple alternative implementation schemes of the pathways shown in FIGS. 1A, B, C, and D as discussed above and/or further presented in, for example FIG. 2 and FIG. 3. Furthermore, other types of bypass routes are shown in FIG. 4; all these routes provide alternative approaches to support increased yield of photorespiration. All these pathways, and their possible combinations, are included in the current invention, but are non-limiting. Examples for enzymes that can, for example, achieve the enzymatic conversions of these pathways are given for each enzymatic conversion in Tables 2 and 3. The respective reactions/enzymes/enzymatic conversions are identified with the same Arabic numbers in the FIGS. 1 to 4 and in the Tables 2 and 3. Of course, also respective organisms, tissues, cells, or organelles, in which one or more of said pathways for the conversion of 2-PG into an intermediate compound of the Calvin-Benson-Bassham Cycle (CBBC) are included in the present invention.

As indicated in the FIGS. 1 to 4 and/or as described, above, some of the photorespiration bypass are listed in Tables 2 and 3). The invention, of course, also relates to corresponding organisms, tissues, cells, or organelles which express the corresponding enzyme(s).

Furthermore, some of the photorespiration bypass pathways (as shown in FIGS. 1 to 4 and/or described above) of the present invention require tetrose rearrangement. Tetrose rearrangement can, for example, be achieved by one of the pathways and/or enzymes/enzymatic conversions/reactions shown in FIG. 3L. Thus, the current invention also relates to one or more of the pathways and/or enzymes/enzymatic conversions/reactions for tetrose rearrangement, as shown in FIG. 3L (respective enzymes/enzymatic conversions/reactions are listed in Tables 2 and 3). The invention, of course, also relates to corresponding organisms, tissues, cells, or organelles which express the corresponding enzyme(s).

As it is evident from FIGS. 1 to 4 and the description herein, the present invention provides pathways that achieve the conversion of 2-PG into an intermediate of the CBBC without releasing $CO_2$ by:

a) the enzymatic conversion of 2-PG into glycolyl-CoA (e.g. by one of the pathways shown in FIG. 2 and/or described above) and the further enzymatic conversion of glycolyl-CoA into an intermediate of the CBBC (e.g. by one or more of the pathways shown in FIG. 1A, 3A; 31, 3J, 3K or 4); or b) the enzymatic conversion of 2-PG into glycolaldehyde (preferably by one of the pathways shown in FIG. 2 and/or described above) and the further enzymatic conversion of glycolaldehyde into an intermediate of the CBBC (e.g. by one or more of the pathways shown in FIG. 1B, 1C, 1E, 1F, 1G, 3A, 3B, 3C, 3E, 3F, 3G, 3H, 3J or 3K); or c) the enzymatic conversion of 2-PG into glycolaldehyde 2-phosphate (preferably by one of the pathways shown in FIG. 2 and/or described above) and the further enzymatic conversion of glycolaldehyde 2-phosphate into an intermediate of the CBBC (e.g. by one or more of the pathways shown in FIG. 3B, 3C, 3E, 3G, 3H, 3J or 3K); or d) the enzymatic conversion of 2-PG into an intermediate of the CBBC, wherein said conversion involves methylene-THF that results from enzymatic conversion of $CO_2$/$HCO_3^-$ (e.g. by one or more of the pathways shown in FIGS. 1D, 3D).

The enzymes/reactions/enzymatic conversions are listed in Tables 2 and 3. Similarly, the present invention also provides respective organisms, tissues, cells, or organelles expressing enzymes which allow for the conversion of 2-PG into an intermediate compound of the CBBC by one or more of the pathways as listed, above, in a) to d). In particular said organisms, tissues, cells, or organelles can be genetically engineered so as to express the respective enzymes (as long as they are not already naturally expressed and/or expressed in a sufficient amount).

The present invention further provides pathways that allow for enzymatic conversion of 2-PG into glycolyl-CoA, 2-PG into glycolaldehyde and/or 2-PG into glycolaldehyde 2-phosphate (e.g. as shown in FIG. 2 and/or described above). Similarly, the present invention also relates to a respective organisms, tissues, cells, or organelles expressing enzymes which allow for the conversion of 2-PG into glycolyl-CoA, 2-PG into glycolaldehyde and/or 2-PG into glycolaldehyde 2-phosphate. The respective pathways offer the possibility of converting 2-PG into glycolyl-CoA, 2-PG into glycolaldehyde and/or 2-PG into glycolaldehyde 2-phosphate. In particular, by the pathways of the present invention, the respective conversion can be achieved in a highly efficient manner (i.e. with low NAD(P)H consumption (less than 4 molecules, less than 3 molecules, preferably less than 2 molecules, most preferably less than 1 molecule) and/or ATP consumption (less than 4 molecules, less than 3 molecules, preferably less than 2 molecules, most preferably less than 1 molecule) and/or without releasing $CO_2$). In addition, the pathways allow for establishing photorespiration bypass pathways according to the current invention.

Furthermore the present invention also provides pathways that allow for enzymatic conversion of glycolyl-CoA into an intermediate of the CBBC, glycolaldehyde into an intermediate of the CBBC and/or glycolaldehyde 2-phosphate into an intermediate of the CBBC. Similarly, the present invention also relates to a respective organisms, tissues, cells, or organelles expressing enzymes which allow for the conversion of 2 glycolyl-CoA into an intermediate of the CBBC, glycolaldehyde into an intermediate of the CBBC and/or glycolaldehyde 2-phosphate into an intermediate of the CBBC. The respective pathways offer the possibility of converting glycolyl-CoA into an intermediate of the CBBC, glycolaldehyde into an intermediate of the CBBC and/or glycolaldehyde 2-phosphate into an intermediate of the CBBC. In particular, by the pathways of the current invention conversion can be achieved in a highly efficient manner (i.e. with low NAD(P)H consumption (less than 4 molecules, less than 3 molecules, preferably less than 2 molecules, most preferably less than 1 molecule) and/or ATP consumption (less than 4 molecules, less than 3 molecules, preferably less than 2 molecules, most preferably less than 1 molecule) and/or without releasing $CO_2$). In addition, the pathways allow for establishing photorespiration bypass pathways according to the current invention.

Similarly, as shown in FIG. 1D, the present invention also relates to a pathway for enzymatically converting $CO_2$ (thereby fixing the same) to methylene-THF. The present invention further provides respective organisms, tissues, cells, or organelles expressing enzymes which allow for the conversion of $CO_2$ to methylene-THF The respective enzymatic conversions and enzymes are explained in the context of option A)b). This pathway has the advantage of fixing $CO_2$.

In any of the above mentioned embodiments which employ one or more concrete enzymes for which the corresponding amino acid sequence(s) is/are identified herein or incorporated by reference to a prior art document or a database entry, it is also envisaged that any enzyme variant (s) (having the same activity as the concrete enzyme(s); as determined e.g. by in vitro conversion assays such as the assays as depicted in Example 6 (or analogous thereto)) having at least 60%, preferably at least 65%, preferably at least 70%, preferably at least 75%, preferably at least 80%, preferably at least 85%, preferably at least 90%, preferably at least 95% and most preferably 99% identity in the amino acid sequence (compared to the respective wilde-type enzyme(s)) are employed.

Those having skill in the art will know how to determine percent identity between/among sequences using, for example, algorithms such as those based on CLUSTALW computer program (Thompson (1994) Nucl. Acids Res. 2:4673-4680), CLUSTAL Omega (Sievers (2014) Curr. Protoc. Bioinformatics 48:3.13.1-3.13.16) or FASTDB (Brutlag (1990) Comp App Biosci 6: 237-245). Also available to those having skill in this art are the BLAST, which stands for Basic Local Alignment Search Tool, and BLAST 2.0 algorithms (Altschul, (1997) Nucl. Acids Res. 25:3389-3402; Altschul (1990) J. Mol. Biol. 215:403-410). The BLASTN program for nucleic acid sequences uses as defaults a word length (W) of 11, an expectation (E) of 10, M=5, N=4, and a comparison of both strands. The BLOSUM62 scoring matrix (Henikoff (1992) Proc. Natl. Acad. Sci. U.S.A. 89:10915-10919) uses alignments (B) of 50, expectation (E) of 10, M=5, N=4, and a comparison of both strands.

The photorespiration bypasses of the current invention have the particular advantageous property of recycling 2-PG to an intermediate compound of the CBBC in a $CO_2$-neutral (without releasing $CO_2$) or even a $CO_2$-positive (supporting net carbon fixation) manner. This is achieved by avoiding a decarboxylation reaction and/or including a (at least one) carboxylation reaction. In particular, inorganic carbon ($CO_2$) will not be lost as described for natural or other synthetic photorespiration reactions. In particular, inorganic carbon ($CO_2$) will not be lost in the mitochondria as described for natural photorespiration. Accordingly, such pathways can increase the carbon fixation rate of the CBBC and thereby the photosynthetic rate and yield. In particular, this applies to organisms, which naturally exhibit the CBBC such as plants, algae, cyanobacteria or other bacteria (e.g. *Pseudomonas oxalaticus, Paracoccus denitrificans, Ralstonia eutropha, Rhizobium japonicum, Thiobacillus ferrooxidans*). By contrast, natural photorespiration, as well as photorespiration bypass routes known in the art have the major disadvantage of releasing $CO_2$ during enzymatic recycling of 2-PG, which decreases the effective carbon fixation rate of the CBBC and thereby limits photosynthetic rate and yield.

Another particular advantage of the 2-PG converting pathways of this invention is to combine the advantageous feature of avoiding $CO_2$ release with direct recycling of 2-PG in a CBBC intermediate. Moreover, the bypass routes of the current invention further combine the advantageous feature of avoiding $CO_2$ release with any other of the further advantageous features listed herein.

A further advantage of the photorespiration bypass routes of the current invention is that they are short, i.e. require only ten or less enzymatic conversions. Notably, high numbers of enzymes would increase the risk of interfering with the non-photorespiratory metabolism. Furthermore, implementing such longer pathways in organisms that do not naturally express the corresponding enzymes requires more steps of genetic engineering.

Notably, the photorespiration bypass pathways of the current invention have the advantage of minimally overlapping and interfering with non-photorespiratory central metabolism or the 3-hydroxypropionate bicycle.

As a further advantageous property, the photorespiration bypass pathways of the current invention allow recycling of 2-PG into an intermediate compound of the CBBC without releasing $NH_3$. In contrast, natural photorespiration leads to the loss of $NH_3$, which needs to be reassimilated at an energetic cost.

The current invention further reduces the energetic costs for recycling 2-PG into the CBBC compared to natural photorespiration and alternative photorespiration bypass pathways by decreasing the consumption of ATP and/or the consumption of reduction equivalents for recycling 2-PG into a CBBP intermediate. Thereby the current invention allows increasing not only the carbon fixation efficiency but also the energetic efficiency of the CBBC.

The exact fraction of Rubisco's oxygenation reaction is debated, however, multiple studies determined independently that, for C3 plants, this fraction is in the range of 20% to 30% (Zhu X. G., et al. (2010) Annu Rev Plant Biol 61, 235-261; Peterhansel C., et al. (2013) Plant Biol (Stuttg) 15, 754-758; Ogren W. L. (1984) Annu Rev Plant Physiol 35, 415-442; Sharkey T. D. (1988) Physiol. Plant. 73, 147-152; Cegelski L., et al. (2006) J Magn Reson 178, 1-10; Zhu X. G., et al. (2007) Plant Physiol 145, 513-526; Andersson I. (2008) J Exp Bot 59, 1555-1568; Sage R. F., et al. (2012) Annu Rev Plant Biol 63, 19-47; Busch F. A. (2013) Plant Biol (Stuttg) 15, 648-655; Szecowka M., et al. (2013) Plant Cell 25, 694-714; Ma F., et al. (2014) Proc Natl Acad Sci USA 111, 16967-16972; Misra J. B. (2014) J Plant Physiol 171, 319-328). For example, in C3 plants, assuming an average fraction of Rubisco's oxygenation reaction of 25%, the photorespiration bypass routes of this invention can support up to 10%, 15%, 20%, 25%, 30%, 40%, 50% or 60% increased CBBP efficiency, as regarding, in this context particularly, the iterations/cycles of the CBBC that are required to produce 1 triose phosphate via the CBBC.

Moreover, they can increase the efficiency of ATP and consumption up to 10%, 15%, 20%, 25%, 30%, 35%, 39%, 45% or 49% and/or the efficiency of NAD(P)H consumption up to 5%, 10%, 15%, 20%, 25% or 28%. In other words, to produce one triose phosphate via the CBBC, the photorespiration bypass routes of this invention reduce the required iterations/cycles of the CBBC (e.g. to 3 or less or 4 or less, as compared to 4.8 for natural photorespiration), the ATP consumption (e.g. to 10.5 or less, 11 or less or 12 or less molecules as compared to 15.6 molecules for natural photorespiration) and/or the NAD(P)H consumption (e.g. to 7.5 or less or 8 or less molecules as compared to 9.6 molecules for natural photorespiration) as compared to C3 plants exhibiting natural photorespiration. Calculated per iteration/cycle of the CBBC, the bypass routes of the present invention support an up to 40%, 45%, 50%, 55% or 60% higher biomass yield and/or an up to 16%, 20%, 25%, 30%, 38%, or 49% higher yield per ATP. For comparison, the photorespiration bypass routes presented in the prior art support much lower decreases in ATP and/or NADPH consumption (≤8% and ≤14%, respectively) with no improvement in the productivity of the CBBC.

These calculations show that the $CO_2$-neutral and $CO_2$-positive photorespiration pathways of this invention have a significant advantage over their natural counterparts and previously suggested bypass routes. This applies to strong illumination, where growth is mainly limited by the activity of the CBBC, as well as to low light conditions, where growth is limited by the supply of ATP and NADPH (Xin C. et al., 2014, *Plant Physiol* dx.doi.org/10.1104/pp.114.248013). The implementation of this bypass routes in CBBC-exhibiting/Rubico-using organisms/tissues/cells/organelles (e.g. C3 plants/tissues/cells/organelles) is thus expected to significantly increase photosynthetic efficiency, growth rate and/or biomass yield under various environmental conditions. This provides for example the basis for increasing photosynthetic efficiency and agricultural productivity of many cultivated crops such as rice, wheat, barley, oat, soybean, cotton and potato. Consequently, significantly higher agricultural yields are supported. Furthermore, the current invention can for example also establish increased growth rates of other organisms exhibiting the CBBC (e.g. algae, cyanobacteria and other bacteria).

In particular, because of the enhanced photosynthetic potential, an organism/tissue/cell/organelle having the photorespiration bypass pathways of the present invention achieves one or more of the following properties: elevated yield of harvestable parts (e.g. fruits, seeds, shoots, leaves, roots, etc. per dry weight of the whole organism, improved drought and heat resistance, enhanced nitrogen-use efficiency, and reduced requirements for fertilization.

The present invention further relates to an organism, tissue, cell or organelle expressing an improved photorespiration bypass route in accordance with the invention, for example an improved photorespiration bypass route as depicted in the enclosed Figures, preferably an improved photorespiration bypass route as depicted in FIG. 1A, B, C or D. As mentioned, it is particularly envisaged that the bypass route according to the invention converts 2-PG into an intermediate compound of the CBBC without releasing $CO_2$. The term "expressing an improved photorespiration bypass route in accordance with the invention" means that the organism, tissue, cell or organelle contains the respective enzymes which form part of such a pathway.

Thus, the present invention further relates to an organism, tissue, cell or organelle expressing (a cascade of/series of) enzymes which allow/which are required for an improved photorespiration bypass route in accordance with the invention.

In a specific aspect, in the organism/tissue/cell/organelle of the invention, the normal/natural photorespiration is inactivated, for example by inactivating/knock out/suppressing one or more of the respective enzymes like, for example, glycolate oxidase and/or enzymes of the glycine cleavage system. Respective means and methods for inactivating/knock out/suppressing certain enzymes in plants are known in the art.

However, the improved photorespiration bypass routes of the invention also operate alongside the natural one and still have a positive effect—without even interfering with the natural pathway. Respective embodiments are also covered by the invention.

In particular, the (cascade of/series of) enzymes to be employed in accordance with the invention (is) are meant to be (a cascade of/series of) enzymes which catalyze(s) the steps and conversions, respectively, which are required to convert 2-PG into an intermediate compound of the CBBC without releasing $CO_2$ as described herein. Respective enzymes are, for example, those enzymes which are marked by Arabic numerals in the appended Figures like, for example, in FIG. 1A, B, C or D or in Tables 2 and 3.

In principle, the organism, tissue, cell or organelle of the present invention may be any organism, tissue, cell or organelle which exhibits and/or is capable of exhibiting an alternative photorespiration pathway as disclosed herein, i.e. which expresses the respective enzymes (the enzymes which allow/are required for the conversion 2-PG into an intermediate compound of the CBBC without releasing $CO_2$).

In particular, the organism, tissue, cell or organelle of the present invention is an organism, tissue, cell or organelle which exhibits the CBBC, in particular under aerobic conditions, i.e which comprises Rubisco that is active in the presence of $O_2$, i.e. which, at least to some extent, also accept $O_2$ instead of $CO_2$. The organism, tissue, cell or organelle of the present invention is also an organism, tissue, cell or organelle (the wild-type of) which exhibits (suffers from) photorespiration and, in particular, (the wild-type of) which suffers from (a) product(s)/intermediate(s) of photorespiration like, for example, 2-PG, and/or (the wild-type of) which requires to convert from (a) product(s)/intermediate(s) of photorespiration like, for example, 2-PG into an intermediate, like an intermediate of the CBBC. In a preferred embodiment, the organism/tissue/cell/organelle according to the present invention is a photosynthetically active organism/tissue/cell/organelle, i.e. an organism/tissue/cell/organelle which is capable of photosynthesis.

As mentioned above, the (wild-type) organism/tissue/cell/organelle in accordance with the invention may have an inactivated normal/natural photorespiration.

In another aspect, the invention relates to a cell of an organism comprising the organelle (e.g. the plastid) of the invention.

It is especially envisaged that the organism, tissue or cell of the present invention comprises (an) organelle(s) (e.g. (a) plastid such as (a) chloroplast(s)) of the invention or are itself of a organelle-like, plastid-like or chloroplast-like nature (like, for example, a cyanobacterium).

In principle, any step (sub-conversion) of, any subset of steps of, or all steps of the (entire) conversion of 2-PG into an intermediate of the CBBC, i.e. of the alternative photorespiratory pathways in accordance with the invention, may take place in any compartment of a cell/cell organelle. However, a particular compartmentation of one or more single step, one or more subset of steps, or all steps may be advantageous as can readily be comprehended by the skilled person. It is, for example, preferred that one or more single step, one or more subsets of steps, or all steps take place in the plastids (e.g. chloroplasts), in particular in the stroma (matrix) thereof. It is particularly preferred that all steps take place in the plastids (e.g. chloroplasts), in particular in the stroma (matrix) thereof. The person skilled in the art is readily able to choose for any step, any subset of steps, or all steps the respective most advantageous compartmentation. For example, the compartmentation may be chosen in a photorespiration-like a manner, i.e. the different steps and/or sub sets of steps may be split into the chloroplast, the peroxisome and the mitochondrion, as the case may be. The compartmentation may also be chosen according to the column "Natural plant localization" as referred to in Table 2. In particular, the compartmentation may be chosen so that the respective intermediates can easily be transported from and/or to (an)other relevant compartment(s).

For example, at least a first step, for example of converting 2-PG into glycolate, and a last step which eventually results in the intermediate compound of the CBBC (for example the step of converting D-gycerate into D-glycerate 3-phosphate or D-erythrose into D-erythrose 4-phosphate) may take place in the plastid (e.g. chloroplast). It is, however, preferred that all steps of the conversion, i.e. the entire conversion, of 2-PG, i.e. of the alternative photorespiratory pathway, in accordance with the invention take(s) place in the plastid (e.g. chloroplast), in particular in the plastid's stroma (matrix). Consequently, it is preferred that the plastid (e.g. chloroplast), in particular in its stroma (matrix), comprises (by way of expression or targeting) the enzymes which are required for the entire conversion of 2-PG, i.e. of the alternative photorespiratory pathway, in accordance with the invention.

The invention also relates to such (a) plastid(s). In addition, the invention relates to (a) plastid(s) comprising, in particular in the stroma (matrix), (by way of expression or targeting) a subset of, but at least one of, the enzymes which are required for the entire conversion of 2-PG, i.e. of the alternative photorespiratory pathway, in accordance with the invention.

In principle, any plastid is envisaged in the context of the invention i.e, any plastid may comprise (express) (an) enzyme(s) in accordance with the invention. However, a "green" plastid, i.e. a plastid which exhibits/is capable of exhibiting photosynthesis and, in particular, the CBBC and, more particular, the CBBC and photorespiration (the latter applies to the respective wild-type) is preferred. Hence, the most preferred plastid is a chloroplast. However, also other plastids are envisaged and may comprise (express) the enzyme(s) in accordance with the invention. Examples of such other plastids are plastids contained in the phloem (P-plastids), pro-plastids, chromoplasts, leucoplasts (e.g. amyloplasts, proteinoplasts, elaioplasts) and gerontoplasts.

The present invention also relates to a cell organelle comprising all, a subset of, but at least one of the enzymes which are required for the entire conversion of 2-PG, i.e. of the alternative photorespiration bypass pathway, in accordance with the present invention. In principle, any cell organelle is envisaged in this context (e.g. plastid, mitochondrium, peroxisome, ER, Golgi apparatus, nucleus, vacuole, cell wall, etc.). However, preferred organelles are those which are involved in natural photorespiration like, for example, chloroplasts, peroxisomes and mitochondria. As mentioned, plastids are the most preferred cell organelle.

The organism of the present invention may be a plant (including higher plants, ferns, mosses and algae), a cyanobacterium (e.g. *Synechocystis, Synechococcus*) or a bacterium of other bacterial lineages that utilizes the CBBC, such as *Pseudomonas oxalaticus, Paracoccus denitrificans, Ralstonia eutropha, Rhizobium japonicum, Thiobacillus ferrooxidans*. As mentioned above a cyanobacterium is particularly envisaged as a bacterium that utilizes the CBBC. The tissue or cell of the present invention may origin from these organisms. A "green" organism, i.e. an organism which exhibits/is capable of exhibiting photosynthesis and, in particular, the CBBC and, more particular, the CBBC and photorespiration (the latter applies at least to the respective wild-type), is preferred. Respective organisms are known in the art and are, for example, plants (including higher plants, ferns, mosses and algae) and cyanobacteria.

A preferred "green" organism in accordance with the invention is a plant (including higher plants, ferns, mosses and algae), in particular a higher plant or a vascular plant. A preferred plant in accordance with the invention is a C3 plant, i.e. a plant which fixes $CO_2$ (directly) via Rubisco and which does not exhibit another upstream $CO_2$ fixation and/or concentrating mechanism (like the C4 mechanism).

The plant of the invention (for example genetically engineered, transgenic and/or transplastomic) may, for example, be any monocot or dicot plant, such as, but not limited to, plants of commercial or agricultural interest, such as crop plants (especially crop plants used for human food or animal feed), wood- or pulp-producing trees, vegetable plants, fruit plants, and ornamental plants. Non-limiting examples of plants of interest include grain crop plants (such as wheat, oat, barley, maize, rye, triticale, rice, millet, sorghum, quinoa, amaranth, and buckwheat); forage crop plants (such as forage grasses and forage dicots including alfalfa, vetch, clover, and the like); oilseed crop plants (such as cotton, safflower, sunflower, soybean, canola, rapeseed, flax, peanuts, and oil palm); tree nuts (such as walnut, cashew, hazelnut, pecan, almond, and the like); sugarcane, coconut, date palm, olive, sugarbeet, tea, and coffee; wood- or pulp-producing trees; vegetable crop plants such as legumes (for example, beans, peas, lentils, alfalfa, peanut), lettuce, asparagus, artichoke, celery, carrot, radish, the brassicas (for example, cabbages, kales, mustards, and other leafy brassicas, broccoli, cauliflower, Brussels sprouts, turnip, kohlrabi), edible cucurbits (for example, cucumbers, melons, summer squashes, winter squashes), edible alliums (for example, onions, garlic, leeks, shallots, chives), edible members of the Solanaceae (for example, tomatoes, eggplants, potatoes, peppers, groundcherries), and edible members of the Chenopodiaceae (for example, beet, chard, spinach, quinoa, amaranth); fruit crop plants such as apple, pear, citrus fruits (for example, orange, lime, lemon, grapefruit, and others), stone fruits (for example, apricot, peach, plum, nectarine), banana, pineapple, grape, kiwifruit, papaya, avocado, and berries; and ornamental plants including ornamental flowering plants, ornamental trees and shrubs, ornamental groundcovers, and ornamental grasses. Preferred dicot plants include, but are not limited to, canola, cotton, potato, quinoa, amaranth, buckwheat, safflower, soybean, sugarbeet, and sunflower, more preferably soybean, canola, and cotton. Preferred monocots include, but are not limited to, wheat, oat, barley, maize, rye, triticale, rice, ornamental and forage grasses, sorghum, millet, and sugarcane. However, as mentioned, C4 plants are less preferred (but not excluded).

Preferred but non-limiting examples of a plant of the invention are the highly cultivated C3 plants like, for example, rice, wheat, barley, oat, soybean, cotton and potato.

In principle, it is envisaged that the tissue or cell of the present invention originate from the organism of the invention, i.e from the organisms described herein.

The (transgenic) cell of the invention may be an isolated cell (e. g., individual (plant) cell or cell grown in or on an artificial culture medium), or can be a (plant) cell in undifferentiated tissue (e. g., callus or any aggregation of (plant) cells). The transgenic (plant) cell can be a (plant) cell in at least one differentiated tissue, e.g. selected from the group consisting of leaf (e. g., petiole and blade), root, stem (e. g., tuber, rhizome, stolon, bulb, and corm) stalk (e. g., xylem, phloem), wood, seed, fruit (e. g., nut, grain, fleshy fruits), and flower (e. g., stamen, filament, anther, pollen, carpel, pistil, ovary, ovules). The (transgenic) organism (e.g. plant) of the invention includes organisms (e.g. plants) of any developmental stage, and includes a regenerated organism (e.g. plant) prepared from the (transgenic) cells claimed herein, or a progeny organism (which can be an inbred or hybrid progeny organism) of the regenerated organism, or progeny (e.g. seed) of such a transgenic organism (e.g. plant).

Also provided and claimed is a (genetically engineered, transgenic and/or transplastomic) progeny (e.g. seed) of the organism (e.g. plant) of the invention.

The present invention further relates to an organism, tissue, cell or organelle, in particular an organism, tissue, cell or organelle as described herein, which expresses, preferably in its organelle(s) (e.g. plastid(s)), at least one of the enzymes as defined herein, preferably the cascade of/series of enzymes as defined herein (the photorespiratory bypass route).

Means and methods to confirm that the alternative photorespiration pathway and the involved (cascade of/series of) enzymes, respectively, is/are functional inside the organism, tissue, cell or organelle (e.g. in the plant chloroplast) are known in the art and, for example, include:

- Studying whether respective encoding genes are expressed and the respectively encoded proteins/enzymes occur/accumulate inside the organism, tissue, cell or organelle (e.g. the chloroplast).
- Studying whether the respective metabolic intermediates of the pathway occur/accumulate in the organism, tissue, cell or organelle.
- Studying any changes in the photosynthetic properties of the organism, tissue, cell or organelle by measurement of a photosynthetic property. This may include the determination of the $CO_2$ compensation point by gas exchange measurements and/or the ATP and/or NAD(P)H consumption rates.
- Studying growth, biomass production and yield of the organism/tissue/cell/organelle under different growth conditions, such as under non-favourable conditions for C3-plants.

Examples of such methods are described herein elsewhere and in WO 2011/099006, WO 2003/100066, EP 2 093 283 and Shih (loc. cit.).

Subject-matter of the present invention also are organelles, cells, tissues or organisms (e.g. plant plastids, plant cells, plant tissues or plants) which comprise one or more nucleic acid(s) which encode (an) polypeptide(s) having the (cascade of/series of) enzymes/enzymatic activities in accordance with the invention, i.e. the enzymes/enzymatic activities as described herein.

The organism, tissue, cell or organelle of the invention may be a genetically engineered, transgenic, and/or transplastomic organism, tissue, cell or organelle (e.g. plastid), as the case may be.

In one aspect, the organism, tissue, cell or organelle may be genetically engineered transgenic and/or transplastomic so as to express an enzyme, or several or all of the (cascade of/series of) enzymes, by which an enzymatic conversion as defined herein is achieved, i.e. which allow for the photorespiration bypass route in accordance with the invention.

In a specific aspect, the organism, tissue, cell or organelle of the invention comprises, for example in its genome, one or more recombinant DNA constructs including DNA that can be transcribed into one or more mRNAs encoding the (cascade of/series of) enzyme(s) in accordance with the invention.

The present invention further relates to a method for producing an organism, a tissue, a cell or a organelle of the invention and as described herein. The method may comprise a step of genetically engineering an organism, a tissue, a cell or an organelle (e.g. a plant organelle (e.g. a plastid), plant cell, plant tissue or plant as defined herein).

The method of producing of the invention may, in particular, comprise the step of
(i) genetically engineering an organism, tissue, cell or organelle so as to comprise (express) (an) enzyme(s) as described and defined herein, preferably the entire cascade of/series of enzymes (the entire alternative photorespiratory bypass route).

The method of producing of the invention may further comprise the step of
(ii) (re)generating, for example, from said tissue, cell or organelle, the (transgenic and/or transplastomic) organism.

The invention further relates to the organism, tissue, cell or organelle as obtained or as obtainable by the method of producing of the invention. The invention further relates to the genetically engineered, transgenic and/or transplastomic organism, tissue, cell or organelle as obtained by or as obtainable by the method of producing of the invention.

In the context of the invention, genetically engineering an organism, tissue, cell and/or organelle so as to comprise/express (an) enzyme(s) as described and defined herein may be achieved by introducing into an organism, tissue, cell and/or organelle (for example as comprised or to be comprised in the organism, tissue, or cell) one or more nucleotide sequence(s) (e.g. (a) recombinant DNA construct(s)) encoding one or more of the enzymes to be employed in accordance with the invention. mRNA encoding the enzyme(s) may then be transcribed/expressed from said nucleotide sequence(s), preferably within said organelle, for example, where applicable, from the (organelle's) genome into which said nucleotide sequence(s) (e.g. (a) recombinant DNA construct(s)) has/have been integrated.

Further, the organism (e.g. plant) tissue or cell of the invention, and/or the organelle(s) (e.g. chloroplast(s)) comprised therein, may be genetically engineered so that (a) nucleotide sequence(s) (e.g. a recombinant DNA construct) encoding the enzyme(s) to be employed in accordance with the invention is comprised. mRNA encoding the enzyme(s) may then be transcribed/expressed from said nucleotide sequence.

When providing or producing the (genetically engineered, transgenic and/or transplastomic) organism, tissue, cell or organelle of the invention, the skilled person can readily rely on its common general knowledge and the teaching of the invention. In particular, respective means and methods for genetically engineering and transfecting/transforming, respectively are known in the art and are, for example, disclosed in WO 2011/099006, WO 03/100066, EP 2 093 283 and Shih et al., 2014 (loc. cit.).

Both, a transiently transformed/transfected and stably transformed/transfected organism, tissue, cell or organelle is encompassed by this invention. A stably transformed/transfected transgenic organism, tissue, cell or organelle is particularly preferred. In a preferred embodiment, the transgenic organism is a fertile transgenic plant from which seed can be harvested, and the invention further claims transgenic seeds of such a transgenic plant, wherein the seeds preferably also contain the enzymes and/or the respective recombinant construct(s) of this invention.

The transgenic tissue, cell or organelle or transgenic organism of the invention, e.g. comprising the (genetically engineered) organelle of the invention, can be obtained by use of any appropriate transient or stable, integrative or non-integrative transformation method known in the art or presently disclosed. The respective nucleotide sequences (e.g. recombinant DNA constructs) can in principle be transcribed in any cell, tissue or organelle or in a whole organism of any developmental stage. However, the herein elsewhere described compartmentation may be advantageous also in this context, The nucleotide sequence(s) encoding the enzyme(s) in accordance with the invention may be introduced into the organism's, tissue's, cell's or organelle's genome (where the organelle has a genome). The enzyme(s) may be expressed from this genome, for example from the mentioned introduced nucleotide sequence(s).

For example, the organelle may be genetically engineered so as to produce/express the enzyme(s) (see Bock R., 2014, Curr. Opin. Biotechnol. 26, 7-13 for genetical engineering of plastids). The enzyme(s) may be transcribed from the organelle's genome (where the organelle has a genome), for example from an encoding nucleotide sequence introduced therein (e.g. recombinant DNA construct). The organelle may comprise a nucleotide sequence which encodes and expresses the enzyme(s).

It is envisaged in the context of the invention that the enzymes may either be expressed directly in the organelle (e.g in the plastid and in particular in the plastid's stroma (matrix)) or may be targeted into the organelle (e.g in the plastid and in particular into the plastid's stroma (matrix)), e.g. after transcription/translation in the nucleus/cytosol.

As mentioned, in a preferred embodiment, the organelle to be comprised in the organism/tissue/cell of the invention, and the organelle of the invention, respectively, in particular the organelle which comprises (expresses) the enzyme(s) to be employed in accordance with the invention is a chloroplast. However, for example by choosing appropriate expression signals, it is also possible to express plastid transgenes encoding the enzyme(s) in non-green tissues, i.e. in other types of plastids (cf. Zhang, Plant J. 72 (2012) 115-128; Caroca, Plant J. 73 (2013) 368-379). Such other types of plastids are described herein elsewhere. For example, the enzyme(s) may be expressed from the mentioned nucleotide sequence(s) and/or from the plastids genome, respectively.

The skilled person is readily able to target (an) enzyme(s) in accordance with the invention into the relevant cell organelle/compartment. Thereby, the skilled person can, for example, rely on Emanuelsson (Nature Protocols 2, 953-971 2007), WO 2011/099006, WO 03/100066, EP 2 093 283 and Shih (loc. cit.). In particular, targeting domains for the desired cell organelles may be used and may, hence, be comprised in the nucleotide sequences/constructs described herein. The respective enzyme may then be translated as a respective precursor with an amino (N)-terminal extension (the targeting domain). Usually, in case the enzymes are to be targeted into the plastid, mitochondria or peroxisome, transit peptides (TP), pre-sequences or peroxisomal targeting signals (e.g. PTS1 and PTS2) are used as targeting domains, respectively.

In particular, if the enzymes are to be targeted into the plastid, N-terminal extensions acting as the "zip code" (also called "transit peptides") may be used. The targeting domains for plastids may be such which are recognized by Tocs (proteins of the outer membrane complex which shuttles the pre-protein through the outer membrane) and/or Tics (proteins of the inner membrane complex which shuttles the pre-protein through the inner membrane). The (pre-)proteins/enzymes may further be assembled with chaperons. In a preferred aspect the enzymes may be stroma (matrix)-targeted enzymes. Respective nucleic acid constructs may comprise stroma (matrix)-targeting domains.

The skilled person is further readily able to provide an organism (a plant) which comprises/expresses the enzyme(s) to be employed in accordance with the invention in certain plastids (e.g. in chloroplasts), and, optionally, not to comprise/express the enzyme(s) in other plastids (e.g. amyloplasts), as the case may be. For example, such a selective expression/production of the enzyme(s) in the respective plastids can readily be achieved by the choice of, for example, (a) respective suitable element(s) like (a) promoter(s) and/or (a) signaling sequence(s) (targeting domain(s)), and the like.

Means and methods to genetically engineer an organism, tissue, cell (e.g. a plant) and/or a plastid are well known in the art and are, for example, described in Valkov, Transgenic Res. 20, 137 (2011) and Svab, Proc. Natl. Acad. Sci. USA 90, 913 (1993), WO 2011/099006, WO 2003/100066, EP 2 093 283, Shih et al. 2014 (loc. cit.) and Bock R., Curr. Opin. Biotechnol. 26, 7-13 (2014). An example of such a method is biolistic transformation (particle bombardment), for example with gold particles coated with the nucleotide sequence (s) (e.g. recombinant DNA construct) encoding the enzyme(s) in accordance with the invention. The respective means may, for example be a PDS1000/He particle delivery system, for example equipped with a Hepta adaptor (Bio-Rad, Hercules, Calif., USA).

Where a nucleotide sequence (e.g. recombinant DNA construct) is used to produce a (genetically engineered transgenic, e.g. transplastomic, organism (e.g. plant, or transgenic, e.g. transplastomic, tissue, cell or plastid thereof, of this invention), genetic engineering, transfection and transformation, respectively, can include any of the well-known and demonstrated methods and compositions. Suitable methods for, for example, plant transformation include virtually any method by which DNA can be introduced into a (plant) cell, in particular into a plastid, such as by direct delivery of DNA (e. g., by PEG-mediated transformation of protoplasts, by electroporation, by agitation with silicon carbide fibers, and by acceleration of DNA coated particles), by Agrobacterium-mediated transformation, by viral or other vectors, etc. One preferred method of plant transformation is microprojectile bombardment, for example, as illustrated in U.S. Pat. No. 5,015,580 (soy), U.S. Pat. No. 5,550,318 (maize), U.S. Pat. No. 5,538,880 (maize), U.S. Pat. No. 6,153,812 (wheat), U.S. Pat. No. 6,160,208 (maize), U.S. Pat. No. 6,288,312 (rice) and U.S. Pat. No. 6,399,861 (maize), and U.S. Pat. No. 6,403,865 (maize).

In particular, the mRNA encoding the enzyme(s) may be expressed by transcription from a nucleotide sequence (for example DNA) following a promoter.

In various embodiments, the nucleotide sequence encoding the enzyme(s) (e.g. the recombinant DNA construct) as employed in the context of the invention include, in addition to the transcribable nucleotide sequence (coding for the enzyme(s)), one or more of the following elements:

(a) a(n) (organelle (e.g. plastid)) promoter or a promoter from a heterologous source organism that is active (e.g. in organelles (e.g. plastids), cells, organisms, tissues of the invention) (e.g. from a bacterium or phage);
(b) a signal/targeting sequence capable of targeting (expression of) the enzyme(s) into the relevant compartment/organelle (e.g. plastid); and
(c) at least one gene expression element.

These elements are, for example, described in more detail herein elsewhere and in WO 2007/011479, WO 2011/099006, WO 03/100066, EP 2 093 283 and Shih (loc. cit.).

For the purpose of expressing the nucleic acids which encode the polypeptides having the enzymatic activities as required for the present invention in, for example, (plant) cells or organelles (e.g. plastids) any convenient regulatory sequences can be used. The regulatory sequences will provide transcriptional and translational initiation as well as termination regions, where the transcriptional initiation may be constitutive or inducible. The coding region is operably linked to such regulatory sequences. Suitable regulatory sequences, in particular for plants, are represented by the constitutive 35S promoter. This may, in particular, be used for dicotyledonous plants. For monocotyledonous plants the constitutive ubiquitin promoter may be used, in particular the maize ubiquitin promoter (GenBank: gil9700915). Examples for inducible promoters represent the light inducible promoters of the small subunit of Rubisco, in particular the tomato rbcS promoter (GenBank: gi22624), and the promoters of the "light harvesting complex binding protein (Ihcb)", in particular the tobacco Ihcb promoter (GenBank: gil 890636).

Generally, a nucleotide sequence (e.g. a recombinant DNA construct) which encodes (an) enzyme(s) to be expressed in accordance with the invention may include a promoter operably linked to the transcribable nucleotide sequence. In various embodiments, the promoter may be selected from the group consisting of a constitutive promoter, a spatially specific promoter, a temporally specific promoter, a developmentally specific promoter, and an inducible promoter. Non-constitutive promoters suitable for use with the nucleotide sequence to be employed (e.g. recombinant DNA construct) of the invention include spatially specific promoters, temporally specific promoters, and inducible promoters. Spatially specific promoters can include cell-, tissue-, or organ-specific promoters. Temporally specific promoters can include promoters that tend to promote expression during certain developmental stages in an organism's (e.g. plant's) growth cycle, or during different times of day or night, or at different seasons in a year. Inducible promoters include promoters induced by chemicals or by environmental conditions such as, but not limited to, biotic or abiotic stress (e. g., water deficit or drought, heat, cold, high or low nutrient or salt levels, high or low light levels, or pest or pathogen infection). An expression-specific promoter can also include promoters that are generally constitutively expressed but at differing degrees or "strengths" of expression, including promoters commonly regarded as "strong promoters" or as "weak promoters".

A particular but non-limiting example of a promoter which may be used to express (an) enzyme(s) to be expressed in accordance with the invention in the plastid (e.g. in the chloroplast) is the Prrn promoter. Other suitable promoters are, for example, the plastid psbA, psbD, rbcL and rp132 promoters (see, for example, Staub (1993) EMBO J. 12, 601-606; Allison (1995) EMBO J. 14, 3721-3730; Eibl (1999) Plant J. 19, 333-345). In principle, heterologous promoters from other organisms (e.g. bacteria and phages) may also be used (see, for example, Newell (2003) Transgenic Res. 12, 631-634).

This invention also provides a transgenic organism, tissue or cell thereof, having in its genome, in particular in the genome of its organelles (e.g. plastid(s)), a recombinant DNA construct (e.g. for (plant) cell transformation), including DNA that can be transcribed into an RNA encoding the enzyme(s) to be employed. In a preferred embodiment at least one of the enzymes of a pathway according to the present invention expressed in such a transgenic organism is heterologous with respect to the organism, i.e. it is not naturally expressed in said organism but is naturally expressed in a different organism. More preferably, at least 2, at least 3 or at least 5 of the enzymes of a pathway of the present invention present in such a transgenic plant are heterologous to the transgenic organism and are expressed from nucleic acid sequences which have been introduced into said organism by way of genetic engineering.

The polypeptides having the enzymatic activities as required for the present invention may comprise an amino acid sequence targeting them into organelles (e.g. a plastid (e.g. a chloroplast), preferably to the stroma (matrix) of the plastid (e.g. chloroplast)), but also to the organelle (e.g. plastid) membrane and/or the cytoplasm. Suitable targeting sequences are known in the art. Preferably, the chloroplast transit peptide derived from the ribulose-I,5-bisphosphate carboxylase gene (e.g. from *Solanum tuberosum* (GenBank: G68077, amino acids 1-58)) is used for targeting the polypeptides according to the present invention to the plastids.

Alternatively, the polypeptides are directly targeted to the plastid using transformation of the plastid genome by particle bombardment (for example of leaf sections) and integration by homologous recombination. Suitable vectors and selection systems are known in the art. The coding sequences for the polypeptides may either be transferred in individual vectors or in one construct, where the individual open reading frames may be fused to one or several polycistronic RNAs with ribosome binding sites added in front of each individual open reading frame in order to allow independent translation.

Some enzymes, for example enzymes of the CBBC and/or photorespiration, e.g., Rubisco, glyceraldehyde 3-phosphate dehydrogenase, glycolate 2-phosphatase, are abundant enzymes inside plant plastids/chloroplasts and thus do not have to be transferred to the organism, cell, tissue or plastids to enable function of the biochemical pathway of the invention.

The present invention further relates to an organism, tissue, cell or organelle expressing at least one of the enzymes as defined herein. The expression is particularly meant to be a heterologous expression.

The present invention further relates to a method of enzymatically converting 2-PG into an intermediate compound of the CBBC without releasing $CO_2$ comprising the step of providing an organism, a tissue, a cell or a organelle of the invention. What has been said with respect to the features of this method herein elsewhere also applies here, *mutatis mutandis*.

The present invention further relates to a use of an organism, a tissue, a cell or a organelle of the invention for enzymatically converting 2-PG into an intermediate compound of the CBBC without releasing $CO_2$. What has been said with respect to the features of this use herein elsewhere also applies here, mutatis mutandis.

As described herein above, the pathways of the present invention may comprise so called "non-native conversion" or "non-native reactions" which can be catalyzed by enzymes as described above. Preferably, the non-native reactions of the photorespiration bypass pathways of the current invention (cf., for example, the bold arrows in the appended Figures) are catalyzed by the respective enzymes depicted in Table 3. It is of course also possible to employ enzymes, which are derived from any of the listed existing enzymes, e.g. by the introduction of mutations or other alterations which, for example, alter or improve the enzymatic activity so as to be more efficient in the desired enzymatic conversion.

Methods for modifying and/or improving the desired enzymes are well-known to the person skilled in the art and include, e.g., random mutagenesis or site-directed mutagenesis and subsequent selection of enzymes having the desired properties or approaches of the so-called "directed evolution", DNA shuffling or in vivo evolution.

For example, for genetic engineering in prokaryotic cells, a nucleic acid molecule encoding a enzyme can be introduced into plasmids which permit mutagenesis or sequence modification by recombination of DNA sequences. Standard methods (see Sambrook and Russell (2001), Molecular Cloning: A Laboratory Manual, CSH Press, Cold Spring Harbor, N.Y., USA) allow base exchanges to be performed or natural or synthetic sequences to be added. DNA fragments can be connected to each other by applying adapters and linkers to the fragments. Moreover, engineering measures which provide suitable restriction sites or remove surplus DNA or restriction sites can be used. In those cases, in which insertions, deletions or substitutions are possible, in vitro mutagenesis, "primer repair", restriction or ligation can be used. In general, a sequence analysis, restriction analysis and other methods of biochemistry and molecular biology are carried out as analysis methods. The resulting enzyme variants are then tested for their enzymatic activity.

In particular, in the current invention, modifying and/or improving the desired enzymes can be achieved by systematically screening orthologs and close paralogs of the respective enzymes for the highest activity in catalyzing the respective non-native reactions. To this end enzyme variants are recombinantly overexpressed in an expression host, preferably E. coli and are subsequently assessed for their promiscuous enzyme activity. For this purpose, the respective enzyme can be expressed in E. coli according to methods well-known in the art and the cells, cell extracts or purified protein can be assessed in corresponding enzymatic assays which are also well-known to the person skilled in the art for the desired enzymatic activity.

If the activity of an enzyme for a particular reaction is below the detection limit of the activity assay, directed evolution towards similar substrates that do show some promiscuity can be applied, thus obtaining 'generalists' that often show non-native activities (Rockah-Shmuel L. et al. (2012) Nucleic Acids Res 40, 11627-11637; Tokuriki N. et al. (2012) Nature communications 3, 1257). A similar strategy can also be applied if the substrate for a reaction can neither be purchased nor chemically synthesized.

Further, the activity of a promiscuous enzyme can be optimized towards catalyzing a desired non-native reaction by directed evolution the respective enzyme. To this end, recently developed strategies for the design and construction of enzyme libraries including phylogenetic (Goldsmith M. et al. (2013) Methods Enzymol 523, 257-283) and computational methods (Khersonsky O. et al. (2012) Proc Natl Acad Sci USA 109, 10358-10363) are used; such libraries deliver improved enzyme variants upon screening of $\leq 10^3$ variants (Goldsmith M. et al. (2013), loc. cit.; Rockah-Shmuel L. et al. (2014) Methods Mol Biol 1179, 129-137). It has been previously demonstrated for a range of enzymes that are not related to this invention that $k_{cat}/K_M$ improvements in the order of $10^2$-$10^5$ could be achieved (Tokuriki N. et al. (2012), loc. cit.; Khersonsky O. et al. (2012), loc. cit.; Cherny I. et al. (2013) ACS Chem Biol 8, 2394-2403) using these methods, even in cases in which the activity was below the detection limit in the starting enzyme (Rockah-Shmuel L. et al. (2012), loc. cit.). By applying libraries designed by using a consensus, phylogenetic approach (Goldsmith M. et al. (2013), loc. cit.; Khersonsky O. et al. (2009) Biochemistry 48, 6644-6654) the enzyme structure can be further optimized for improved folding and stability (Khersonsky O. et al. (2012), loc. cit.; Aharoni A. et al. (2004) Proc Natl Acad Sci USA 101, 482-487).

To drive the use of NADP(H) as the sole electron donor/acceptor, either enzymes that natively use NADPH are selected, or the cofactor specificity of NADH-dependent paralog enzymes are switched, as previously described for many oxidoreductases (e.g. see Watanabe S. et al. (2005) J Biol Chem 280, 10340-10349; Ehsani M. et al. (2009) Biotechnol Bioeng 104, 381-389).

To additionally improve pathway flux, co-localization of different enzymes can be enforced by fusion of two or more enzymes, into complexes that funnel intermediates between the different components. The folding of such constructs can be optimized by directed evolution as described above. Alternatively, scaffolding using engineered protein-protein interactions is implemented (Dueber J. E. et al. (2009) Nat Biotechnol 27, 753-759; Moon T. S. et al. (2010) Metab Eng 12, 298-305). The cellulosome provides a potential source of scaffolding proteins that can be grafted onto our metabolic systems (Smith S. P. et al. (2013) Curr Opin Struct Biol 23, 686-694).

Thus, in one embodiment, the organism, tissue, cell or organelle of the present invention expresses at least one fusion protein comprising at least two of the enzymes of a pathway according to the present invention.

The enzymes capable of catalyzing the non-native reactions listed in the Table 3, highlighted in the Figures and/or mentioned herein elsewhere comprise existing enzymes having the promiscuous activity of catalyzing the respective non-native conversions. In addition, the enzymes if unmodified have affinity to their natural substrates. The enzymes capable of catalyzing the non-native reactions listed in the Table 3, highlighted in the Figures or mentioned elsewhere further comprise improved variants of these existing enzymes that have improved enzymatic activity for the non-native reactions and lowered affinity for their native substrates. Furthermore also enzyme variants that are only capable of catalyzing the non-native reactions, but no longer have affinity for their natural substrates are included.

The present invention is further described by reference to the following non-limiting figures and examples.

The Figures show:

FIG. 1 (A) shows a carbon-positive photorespiration bypass pathway in which 2-PG (2-phosphoglycolate, here referred to as glycolate 2-phosphate) is enzymatically converted into the CBBC intermediate compound D-glycerate 3-phosphate. The enzymatic conversion of 2-PG into D-glycerate 3-phosphate involves the enzymatic conversion of 2-PG into glycolate (reaction 1, as indicated in the Figure), further enzymatic conversion of glycolate into glycolyl-CoA (reaction 2#, as indicated in the Figure), further enzymatic conversion of glycolyl-CoA into tartronytl-CoA (reaction 3#, as indicated in the Figure), further enzymatic conversion of tartronytl-CoA into tartronate semialdehyde (reaction 4#, as indicated in the Figure), further enzymatic conversion of tartronate semialdehyde into D-glycerate (reaction 5, as indicated in the Figure), and further enzymatic conversion of D-glycerate into D-glycerate 3-phosphate (reaction 6, as indicated in the Figure). The reactions as indicated above and in the Figure can, for example, be catalyzed by the enzymes as listed in Tables 2 and 3 under the respective reaction number.

FIG. 1 (B) shows a carbon-neutral photorespiration bypass pathway in which 2-PG (2-phosphoglycolate, here referred to as glycolate 2-phosphate) is enzymatically converted into the CBBC intermediate compound D-ribulose 1,5-bisphosphate. The enzymatic conversion of 2-PG into D-ribulose 1,5-bisphosphate involves the enzymatic conversion of 2-PG into glycolate (reaction 1, as indicated in the Figure), further enzymatic conversion of glycolate into glycolyl-CoA (reaction 2#, as indicated in the Figure), further enzymatic conversion of glycolyl-CoA into glycolaldehyde (reaction 7#, as indicated in the Figure), further enzymatic conversion of glycolaldehyde into D-ribulose 1-phosphate (reaction 8, as indicated in the Figure), and further enzymatic conversion of D-ribulose 1-phosphate into D-ribulose 1,5-bisphosphate (reaction 9#, as indicated in the Figure). The reactions as indicated above and in the Figure can, for example, be catalyzed by the enzymes as listed in Tables 2 and 3 under the respective reaction number.

FIG. 1 (C) shows a carbon-neutral photorespiration bypass pathway in which 2-PG (2-phosphoglycolate, here referred to as glycolate 2-phosphate) is enzymatically converted into the CBBC intermediate compound D-erythrose 4-phosphate. The enzymatic conversion of 2-PG into D-ribulose 1,5-bisphosphate involves the enzymatic conversion of 2-PG into glycolate (reaction 1, as indicated in the Figure), further enzymatic conversion of glycolate into glycolyl-CoA (reaction 2#, as indicated in the Figure), further enzymatic conversion of glycolyl-CoA into glycolaldehyde (reaction 7#, as indicated in the Figure), further enzymatic conversion of glycolaldehyde into D-erythrose (reaction 10#, as indicated in the Figure), and further enzymatic conversion of D-erythrose into D-erythrose 4-phosphate (reaction 11#, as indicated in the Figure). The reactions as indicated above and in the Figure can, for example, be catalyzed by the enzymes as listed in Tables 2 and 3 under the respective reaction number.

FIG. 1 (D) shows a carbon-positive photorespiration bypass pathway in which 2-PG (2-phosphoglycolate, here referred to as glycolate 2-phosphate) is enzymatically converted into the CBBC intermediate compound D-glycerate 3-phosphate. The enzymatic conversion of 2-PG into D-glycerate 3-phosphate involves the enzymatic conversion of 2-PG into glycolate (reaction 1, as indicated in the Figure), further enzymatic conversion of glycolate into glyoxylate (reaction 12, as indicated in the Figure), further enzymatic conversion glyoxylate into glycine (reaction 13, as indicated in the Figure), further enzymatic conversion of glycine into serine (reaction 14, as indicated in the Figure), further enzymatic conversion of serine into hydroxypyruvate (reaction 13, as indicated in the Figure), further enzymatic conversion of hydroxypyruvate to glycerate (reaction 18, as indicated in the Figure), and further enzymatic conversion of D-glycerate into D-glycerate 3-phosphate (reaction 6, as indicated in the Figure). The enzymatic conversion of glycine into serine is dependent on the enzymatic conversion of $CO_2$ into formate (reaction 15#, as indicated in the Figure), further enzymatic conversion of formate into formyl-tetrahydrofolate (reaction 16, as indicated in the Figure), and further enzymatic conversion of formyl-tetrahydrofolate into methylene-tetrahydrofolate (reaction 17, as indicated in the Figure). The reactions as indicated above and in the Figure can, for example, be catalyzed by the enzymes as listed in Tables 2 and 3 under the respective reaction number.

FIG. 1 (E) shows a carbon-neutral photorespiration bypass pathway in which 2-PG (2-phosphoglycolate, here referred to as glycolate 2-phosphate) is enzymatically converted into the CBBC intermediate compound D-ribulose 5-phosphate. The enzymatic conversion of 2-PG into D-ribulose 5-phosphate involves the enzymatic conversion of 2-PG into glycolate (reaction 1, as indicated in the Figure), further enzymatic conversion of glycolate into glycolyl-CoA (reaction 2#, as indicated in the Figure), further enzymatic conversion of glycolyl-CoA into glycolaldehyde (reaction 7#, as indicated in the Figure), further enzymatic conversion of glycolaldehyde into D-arabinose 5-phosphate (reaction 78# as indicated in the Figure), and further enzymatic conversion of D-arabinose 5-phosphate into D-ribulose 5-phosphate (reaction 80, as indicated in the Figure). The reactions as indicated above and in the Figure can, for example, be catalyzed by the enzymes as listed in Tables 2 and 3 under the respective reaction number.

FIG. 1 (F) shows a carbon-neutral photorespiration bypass pathway in which 2-PG (2-phosphoglycolate, here referred to as glycolate 2-phosphate) is enzymatically converted into the CBBC intermediate compound D-xylulose 5-phosphate. The enzymatic conversion of 2-PG into D-xylulose 5-phosphate involves the enzymatic conversion of 2-PG into glycolate (reaction 1, as indicated in the Figure), further enzymatic conversion of glycolate into glycolyl-CoA (reaction 2#, as indicated in the Figure), further enzymatic conversion of glycolyl-CoA into glycolaldehyde (reaction 7#, as indicated in the Figure), further enzymatic conversion of glycolaldehyde into D-xylulose (reaction 67#, as indicated in the Figure), and further enzymatic conversion of D-xylulose into D-xylulose 5-phosphate (reaction 69, as indicated in the Figure). The reactions as indicated above and in the Figure can, for example, be catalyzed by the enzymes as listed in Tables 2 and 3 under the respective reaction number.

FIG. 1 (G) shows a carbon-neutral photorespiration bypass pathway in which 2-PG (2-phosphoglycolate, here referred to as glycolate 2-phosphate) is enzymatically converted into the CBBC intermediate compound D-xylulose 5-phosphate. The enzymatic conversion of 2-PG into D-xylulose 5-phosphate involves the enzymatic conversion of 2-PG into glycolate (reaction 1, as indicated in the Figure), further enzymatic conversion of glycolate into glycolyl-CoA (reaction 2#, as indicated in the Figure), further enzymatic conversion of glycolyl-CoA into glycolaldehyde (reaction 7#, as indicated in the Figure), and further enzymatic conversion of glycolaldehyde into D-xylulose 5-phosphate (reaction 97#, as indicated in the Figure). The reactions as indicated above and in the Figure can, for example, be catalyzed by the enzymes as listed in Tables 2 and 3 under the respective reaction number.

FIG. 2 shows multiple metabolic transformation that convert 2-PG (2-phosphoglycolate, here referred to as glycolate 2-phosphate) to glycolyl-CoA, glycolaldehyde and glycolaldehyde 2-phosphate (see Tables 2 and 3 for the identity of the reactions and for enzymes that can, for example catalyze these reactions).

FIG. 3 shows variants of the photorespiration bypass pathways shown in FIG. 1. (see Tables 2 and 3 for the identity of the reactions and for enzymes that can, for example catalyze these reactions) and additional photorespiration bypass pathways provided by the present application.

Specifically, FIG. 3H presents multiple ways to self-condense glycolaldehyde or to condense glycolaldehyde with glycolaldehyde phosphate to generate tetrose or tetrose phosphate, respectively, where tetrose can either be erythrose, erythrulose or threose. These tetroses can be interconverted one to another as shown in FIG. 3L.

Specifically, FIG. 3L presents metabolic conversions that can lead to the conversion of an intermediate of the CBBC to dihydroxyacetone, glyceraldehyde and/or erythrose, which can further be used by some of the pathways shown in FIG. 3A-K to assimilate 2-PG to the CBBC. FIG. 3L (second page) further present interconversions of tetroses and tetroses phosphate, where tetrose can either be erythrose, erythrulose or threose.

FIG. 4 shows further alternative photorespiration bypass pathways that do not release $CO_2$. (see Tables 2 and 3 for the identity of the reactions and for enzymes that can, for example, catalyze these reactions)

Figure 5:
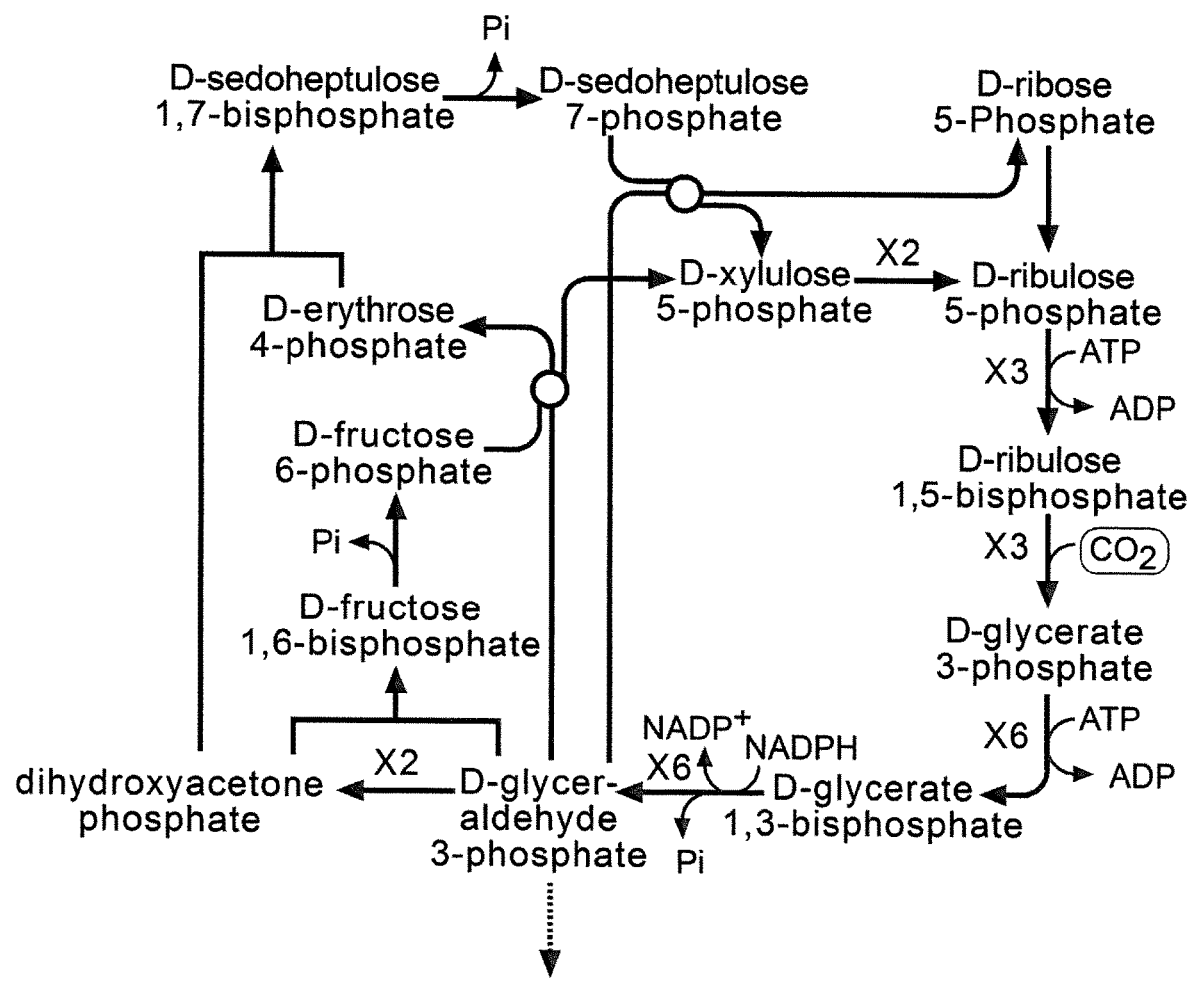

FIG. 5 shows the CBBC and all of its metabolic intermediates: D-glycerate 3-phosphate, D-glycerate 1,3-bisphosphate, D-glyceraldehyde 3-phosphate, dihydroxyacetone phosphate (also referred to as glycerone phosphate), D-fructose 1,6-bisphosphate, D-fructose 6-phosphate, D-sedoheptulose 7-phosphate, D-sedoheptulose 1,7-bisphosphate, D-erythrose 4-phosphate, D-xylulose 5-phosphate, D-ribose 5-phosphate, D-ribulose 5-phosphate, and D-ribulose 1,5-bisphosphate.

Figure 6:
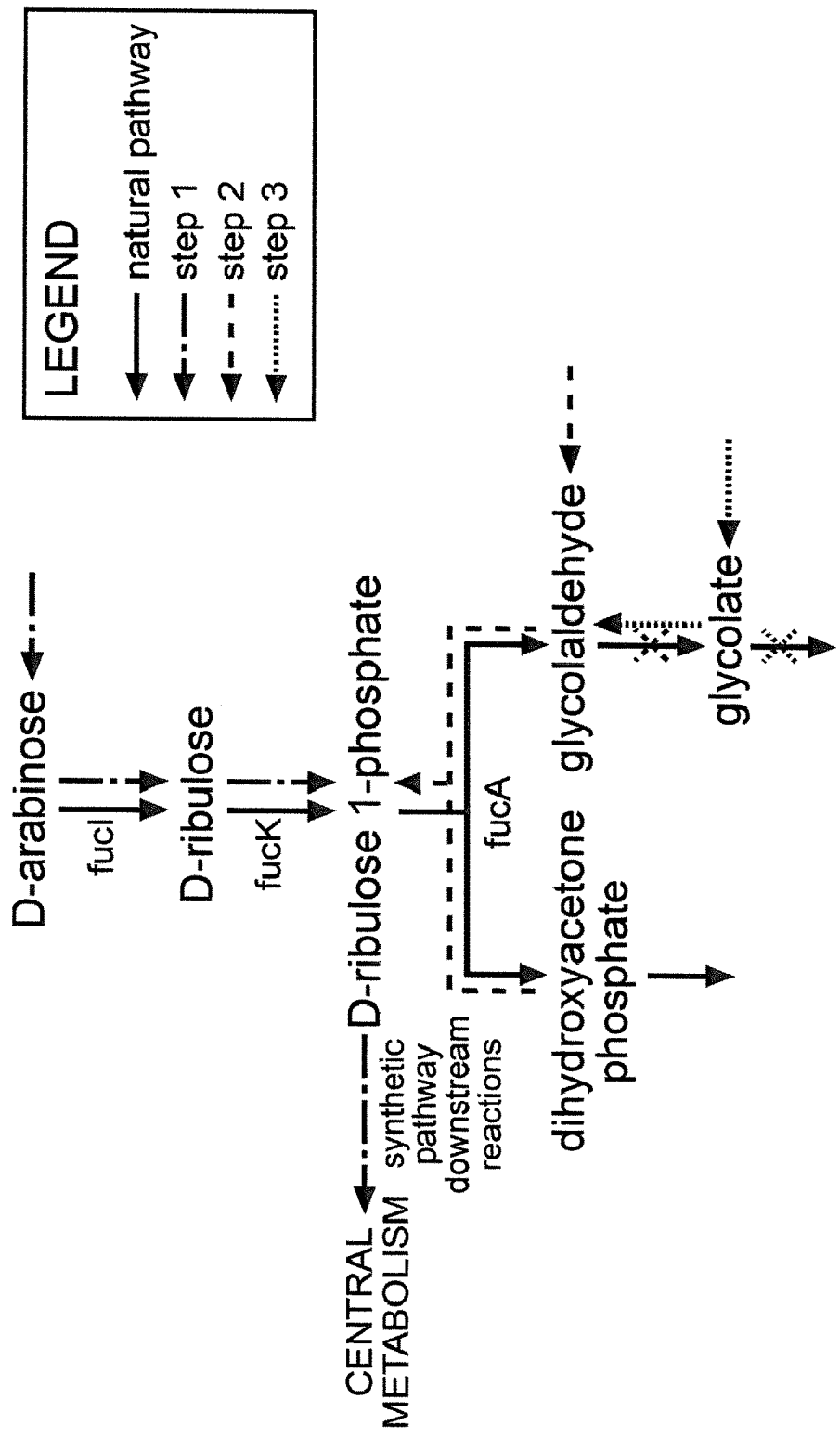

FIG. 6 shows a metabolic strategy to select for the activities of segments of the pathway shown in FIG. 1B in a heterotrophic host. Full line arrows show the natural D-arabionase degradation pathway. First selection step (semi-dashed arrows) involves deleting fucA, overexpressing the enzyme catalyzing reaction 9 (see Table 3) together with Rubisco, and feeding the cells with D-arabinose. In the second selection step (dashed arrows) the expression of fucA is reestablished, and the enzymes supporting glycoladehyde oxidation and growth on glycolate are deleted. This strain is fed with glycolaldehyde as sole carbon source. In the third and final selection step (dotted arrows), the enzymes catalyzing reactions 2 and 7 (see Table 3) are expressed in the above strain and glycolate is added as sole carbon source.

Figure 7:
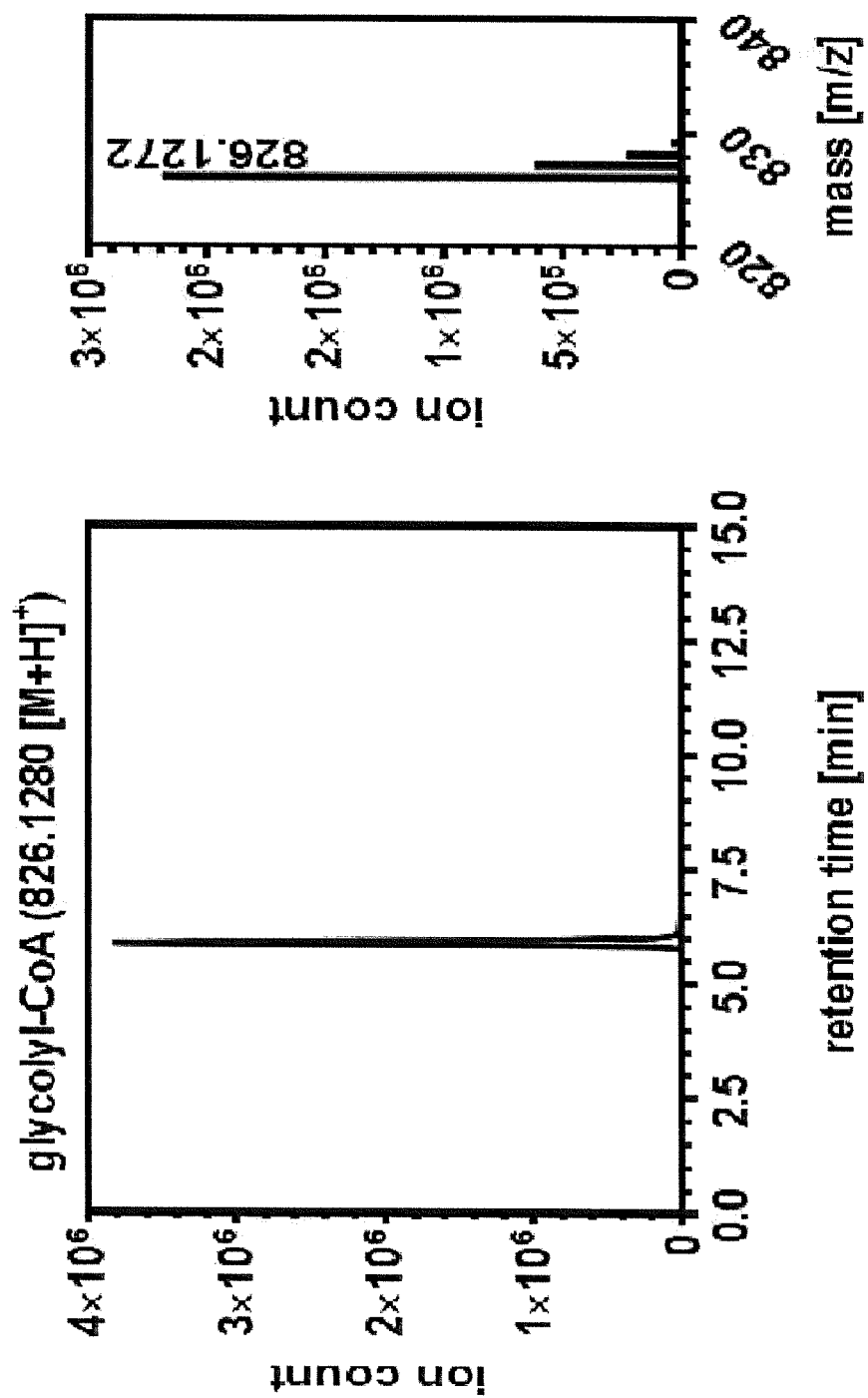

FIG. 7: UPLC-hrMS analysis of glycolyl-CoA formed within reaction of PCT. A: Extracted ion chromatogram of glycolyl-CoA. B: Mass spectrum of glycolyl-CoA.

Figure 8:
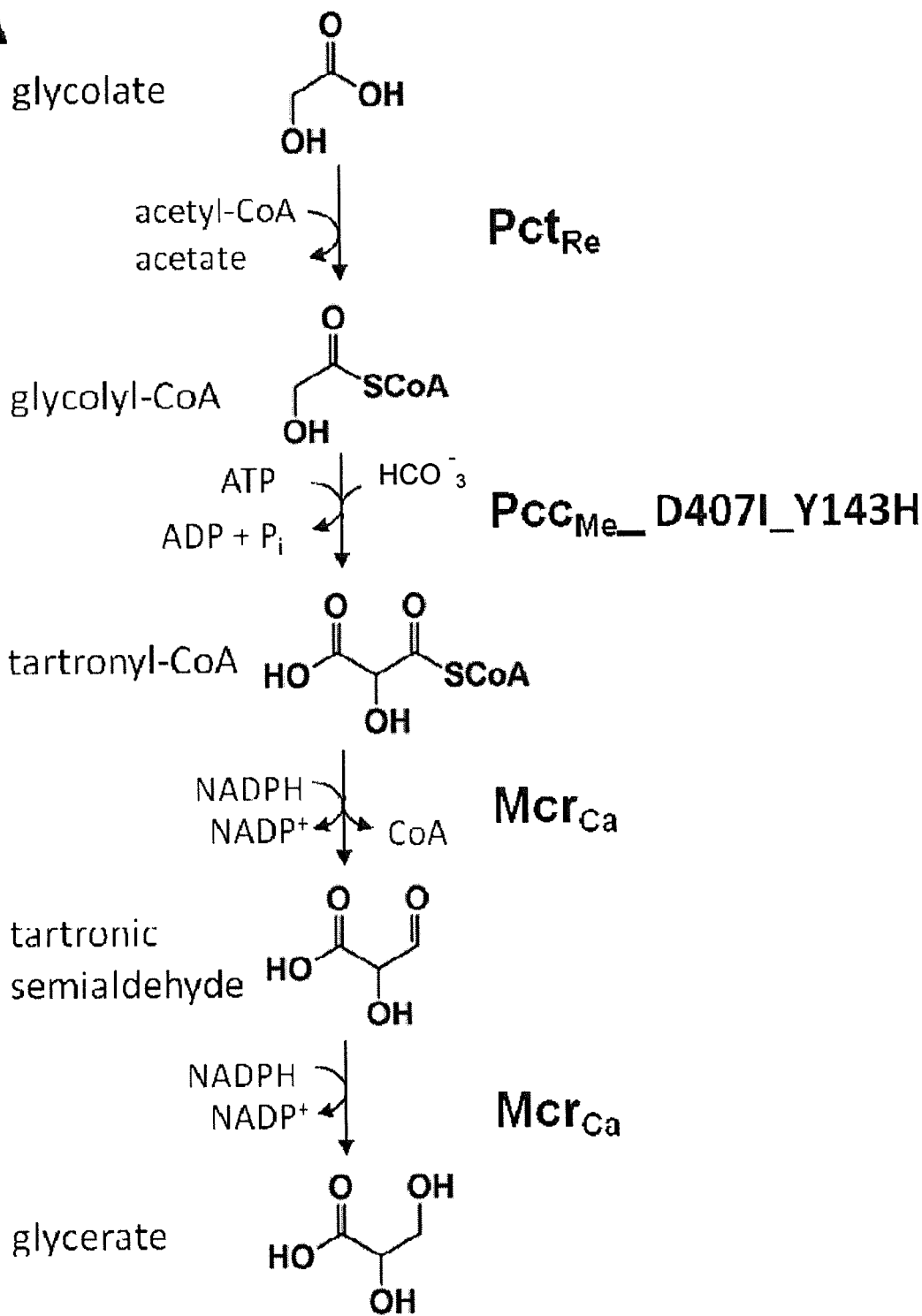
Figure 8:
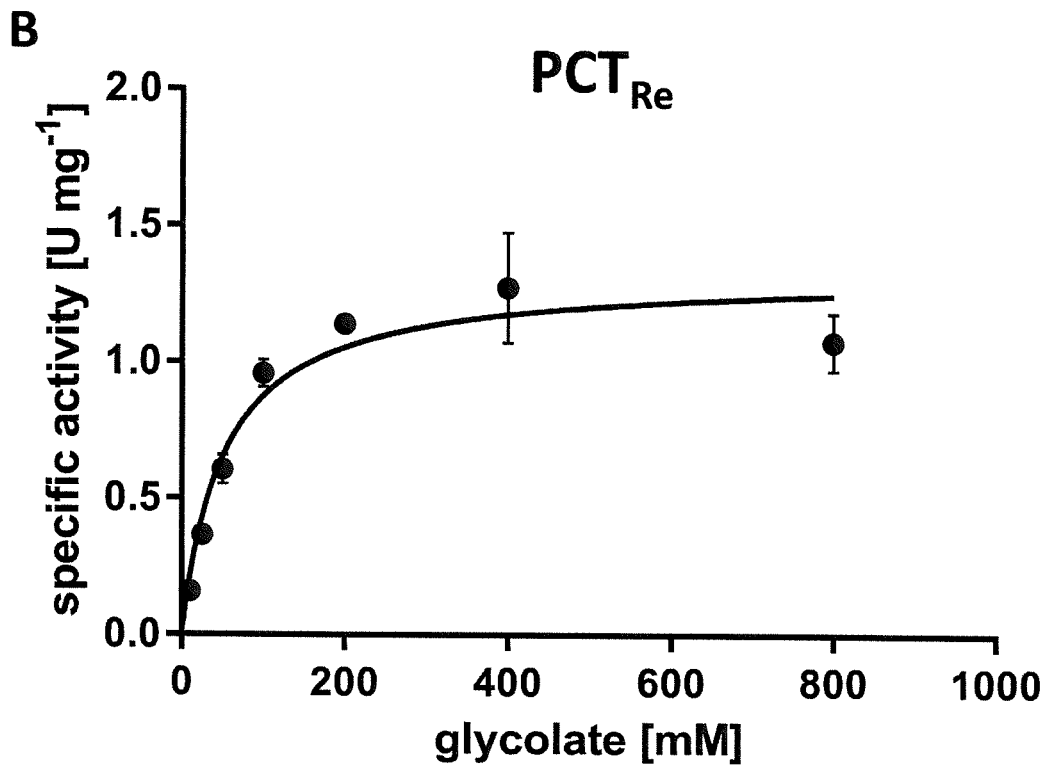
Figure 8:
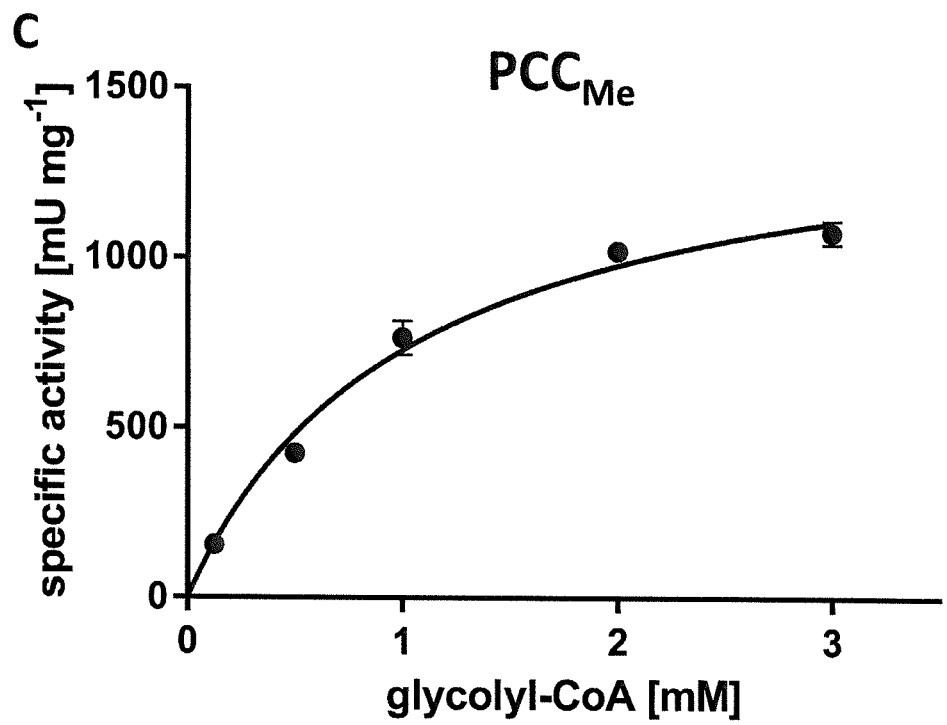
Figure 8:
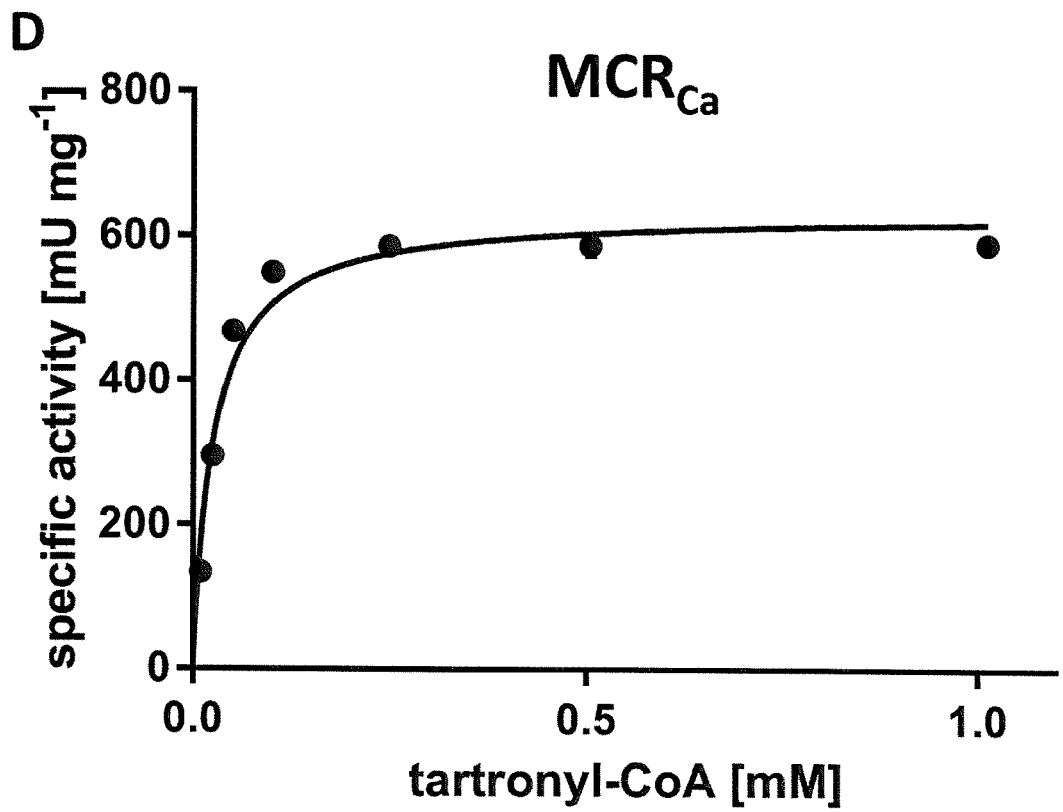

FIG. 8: A: Reactions of the synthetic photorespiratory bypass with the corresponding enzymes. B: Michaelis-Menten kinetics for $PCT_{Re}$. The corresponding $K_m$ for glycolate is 51.7±9.6 mM, $v_{max}$ is 1.3±0.07 U mg$^{-1}$. n=3. C: Michaelis-Menten kinetics for PCC double mutant ($PCC_{Me}\_D407I\_Y143H$). The corresponding $K_m$ is 1.0±0.15 mM, $v_{max}$ is 1.5±0.09 U mg$^{-1}$. n=2. D: Michaelis-Menten kinetics for $MCR_{Ca}$. The corresponding $K_m$ for tartronyl-CoA is 0.03±0.003 mM, $v_{max}$ is 0.6±0.01 U mg$^{-1}$. n=3.

The curves were fitted in Graph Pad Prism 6.

Figure 9:
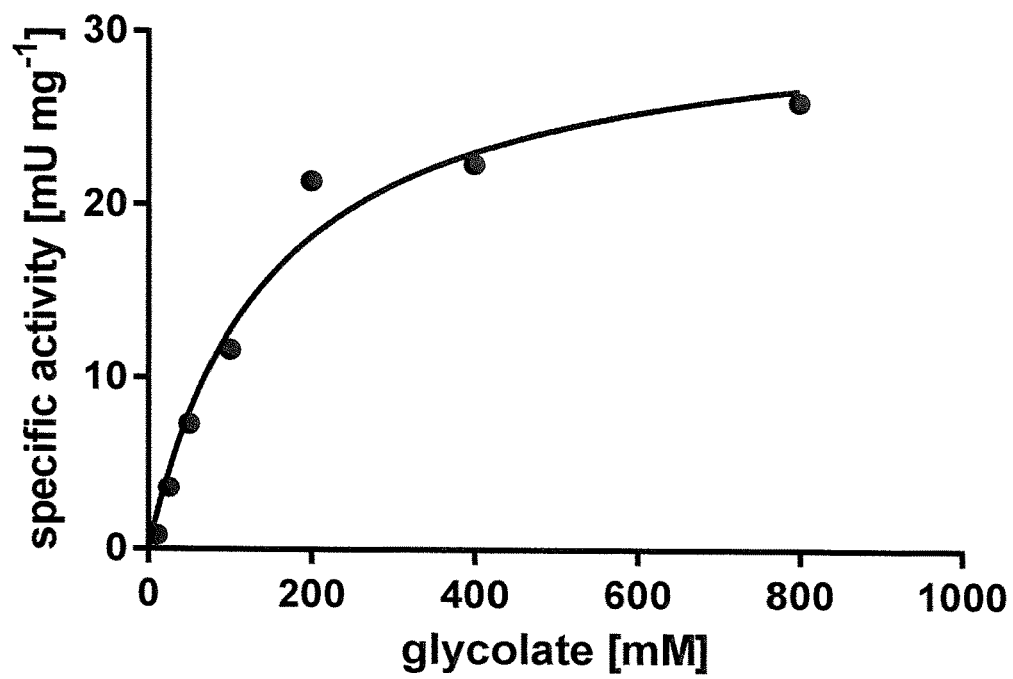

FIG. 9: Michaelis-Menten kinetics for $PCT_{Cp}$. The curve was fitted in Graph Pad Prism 6. The corresponding $K_m$ for glycolate is 149±35 mM, $v_{max}$ is 31.6±2.7 mU mg$^{-1}$. n=1 (preliminary result).

Figure 10:
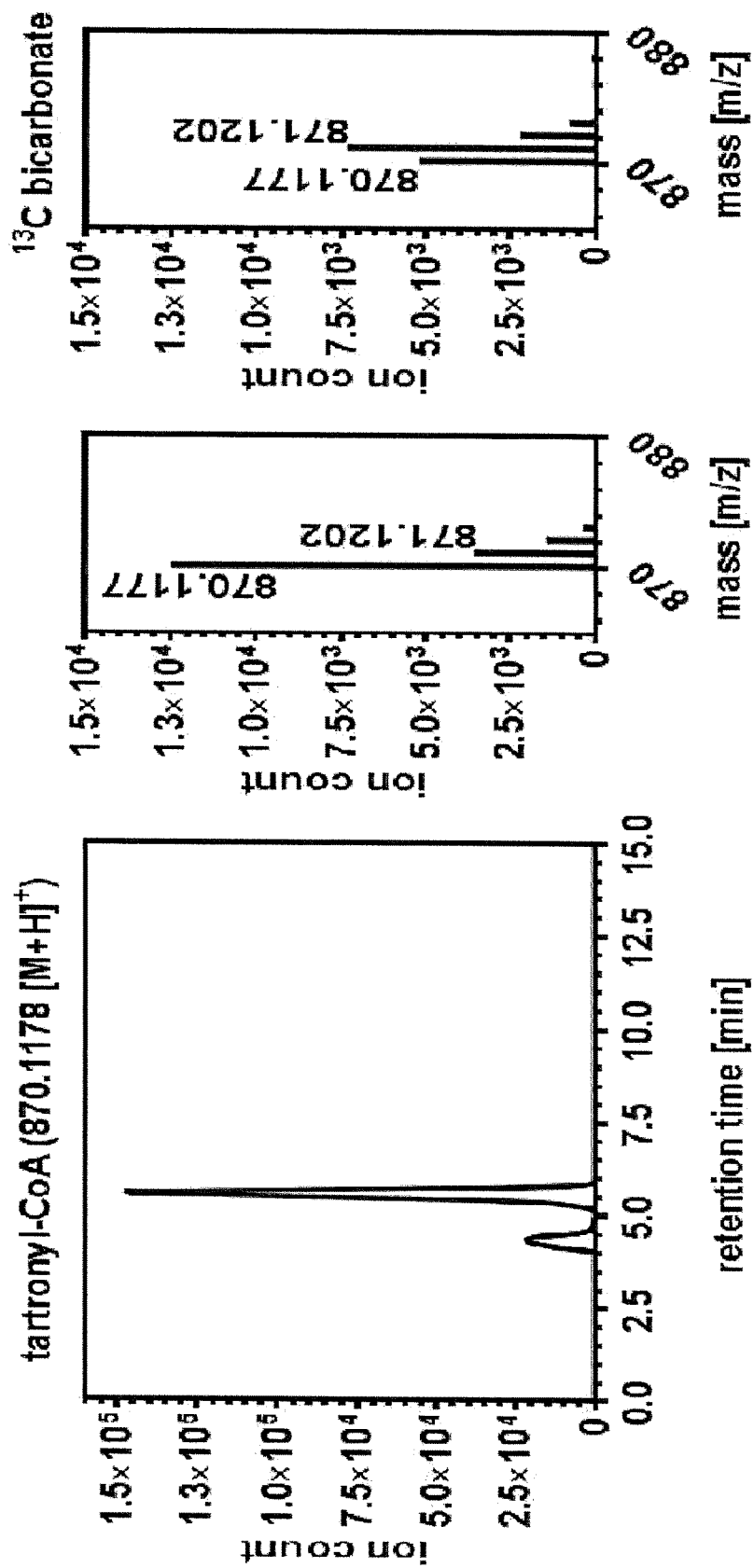

FIG. 10: UPLC-hrMS analysis of tartronyl-CoA formed by $PCC_{Me}\_D407I\_Y143H$. A: Extracted ion chromatogram of tartronyl-CoA. B: Mass spectrum of tartronyl-CoA. C: Mass spectrum of tartronyl-CoA. The reaction was performed with $^{13}C$ labeled bicarbonate.

Figure 11:
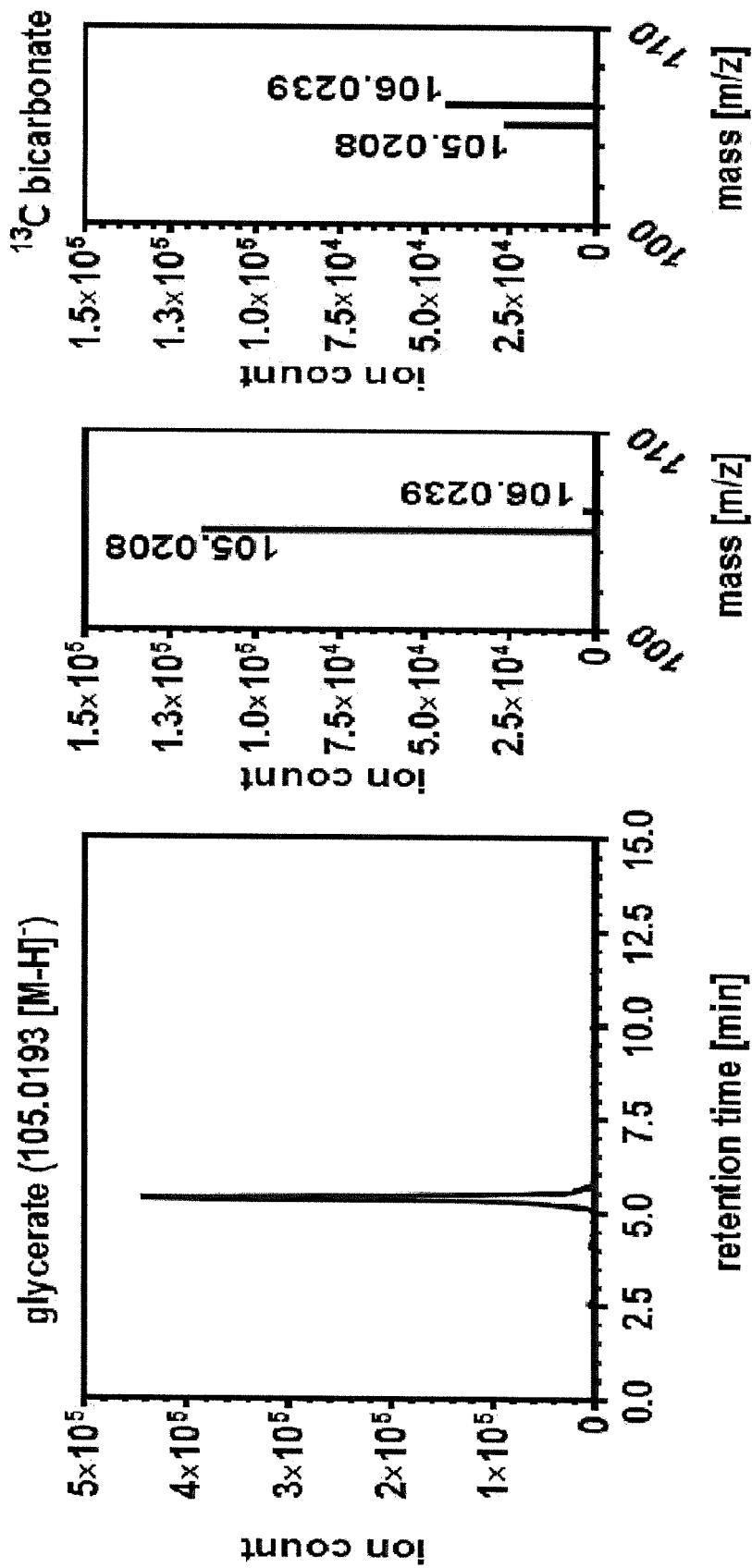

FIG. 11: UPLC-hrMS analysis of glycerate formed of glycolyl-CoA by $PCC_{Me}$ and $MCR_{Ca}$. A: Extracted ion chromatogram of glycerate. B: Mass spectrum of glycerate. C: Mass spectrum of glycerate. The reaction was performed with $^{13}C$ labeled bicarbonate.

Figure 12:
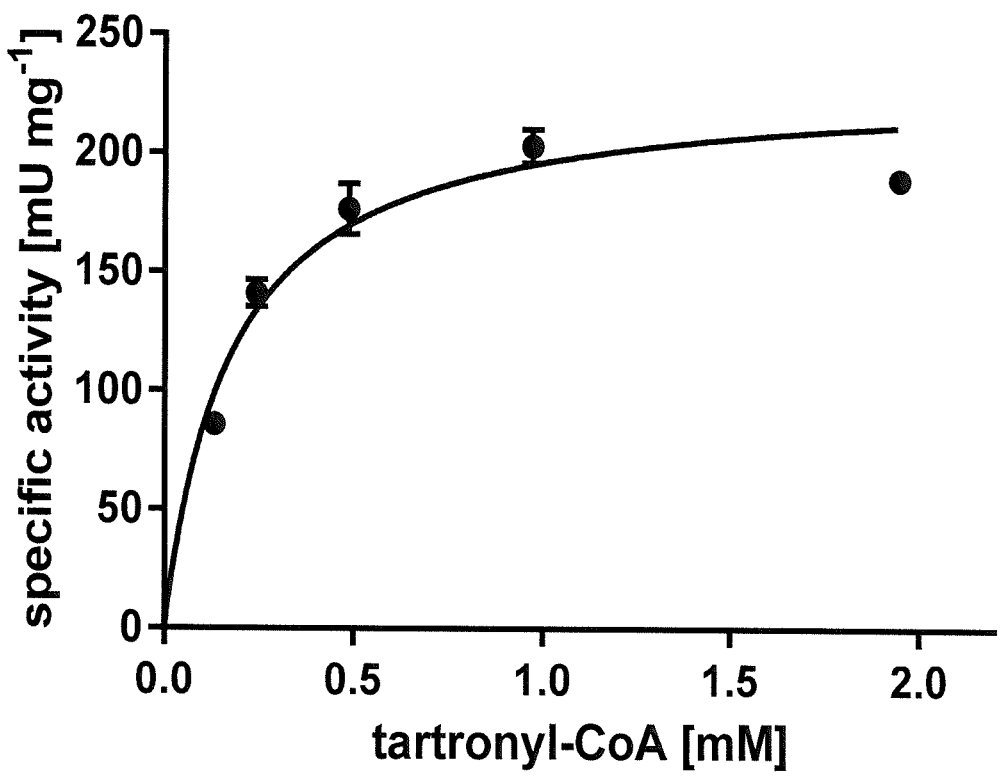

FIG. 12: Michaelis-Menten kinetics for $MCR_E$. The curve was fitted in Graph Pad Prism 6. The corresponding $K_m$ for tartronyl-CoA is 0.18±0.04 mM, $v_{max}$ is 0.23±0.01 U mg$^{-1}$ (n=2).

In this specification, a number of documents including patent applications are cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

The invention will now be described by reference to the following examples which are merely illustrative and are not to be construed as a limitation of the scope of the present invention.

EXAMPLE 1: EXPLORATION OF SYNTHETIC PHOTORESPIRATION BYBASS ROUTES

Four highly advantageous photorespiration bypass pathways according to the present invention are shown in FIG. 1. They contain between one to four non-native reactions (as defined above) and are either $CO_2$-neutral (FIG. 1B, C) or $CO_2$-positive (supporting net carbon fixation, FIG. 1A, D). These pathways are all short, thermodynamically favourable, energetically efficient, and overlap only minimally with non-photorespiratory central metabolism. The enzymatic conversions employed in the pathways described herein are characterized in that they are thermodynamically feasible, i.e. they are thermodynamically feasible conversions, which can in principle be catalyzed by enzymes. Moreover, the enzymatic conversions, as described herein, shall have a high driving force and will therefore generally not limit the pathway flux, thereby leading to high pathway efficiency.

Notably, there are multiple alternative implementation schemes of the pathways shown in FIGS. 1A, B, C, and D as discussed above and further presented in, for example FIG. 2 and FIG. 3. Furthermore, other types of photorespiration bypass routes are shown in FIG. 4; these all provide alternative approaches to support increased yield of photorespiration.

The non-native reactions of the pathways shown in FIG. 1 and some alternatives thereof shown in the other Figures as well as exemplifying promiscuous enzymes capable of catalyzing these non-native reactions are described in more detail in the following:

Glycolate can be converted into Glycolyl-CoA (reaction 2#) by a range of enzymes, including a CoA-transferase (Volodina E. et al., 2014, Appl Microbiol Biotechnol 98, 3579-3589; Dhamankar H. et al., 2014, Metab Eng 25C, 72-81), an ADP-forming CoA ligase (Awano T. et. al., 2014, loc. cit.), or an AMP-forming CoA ligase (Soucaille P. et al., 2012, loc. cit.). Glycolyl-CoA can be further reduced to glycolaldehyde (reaction 7#) by several acylating aldehyde dehydrogenases (Burton R. M. et al., 1953, loc. cit.; Sohling, B. et. al., 1993, loc. cit.). FIG. 2 presents multiple alternative reaction sequences that can generate glycolyl-CoA and glycolaldehyde from glycolate. For example, glycolate can be converted to glycolyl phosphate (reaction 19#) by a promiscuous carboxyl kinase enzyme, such as acetate kinase (Lyer P. et al., 2005, loc. cit.) or butyrate kinase (Hartmanis M. G., 1987, loc. cit.), or by the transfer of a phosphate group from another carboxylic acid. Glycolyl phosphate can then be reduced to glycolaldehyde (reaction 20#) by a phosphorylating glyceraldehyde 3-phosphate dehydrogenase (Fife T. H. et al., 1970, *Biochemistry* 9, 4064-4067; Armstrong J. M. et al., 1976, *Biochem J* 159, 513-527; Byers L. D., 1978, *Arch Biochem Biophys* 186, 335-342), or converted to glycolyl-CoA (reaction 21#) via a non-specific phosphate acetyltransferase enzyme (as some glucosamine 6-phosphate acetyltransferase variants can accept glycolyl-CoA instead of acetyl-CoA (Macauley M. S., 2012, loc. cit.). Another possibility is the direct reduction of glycolate to glycolaldehyde by an ATP- and NAD(P)H-dependent carboxylic acid reductase (CAR; reaction 22#). Several variants of this enzyme were shown to catalyze the reduction of acetate and lactate at high rate (Venkitasubramanian P., 2006, loc. cit.; Napora-Wijata K., 2014, loc. cit.), strongly indicating that glycolate can also be accepted as substrate.

Carboxylation of glycoyl-CoA to tartronyl-CoA (reaction 3#) can be catalyzed by a promiscuous biotin-dependent acyl-CoA carboxylase (e.g. see Tran T. H. et al., 2015, loc. cit.). Tartronyl-CoA can be reduced to tartronate semialdehyde (reaction 4#) by a nonspecific acylating aldehyde dehydrogenase enzyme (e.g. see Baker P. et al., 2012, loc. cit.).

The phosphorylation of D-ribulose 1-phosphate to D-ribulose 1,5-bisphosphate (reaction 9#) is expected to be catalyzed by two enzyme families: (i) Variants of 1-phosphofructokinase given that several enzymes confuse D-ribulose and D-fructose—e.g., fructose 1,6-bisphosphatase can dephosphorylate ribulose 1,5-bisphosphate (Mizunuma H. et al., 1980, *Arch Biochem Biophys* 201, 296-303; Donahue J. L. et al., 2000, *J Bacteriol* 182, 5624-5627) and phosphoribulokinase can phosphorylate fructose 6-phosphate (Siebert, K., 1981, loc cit.); (ii) Nonspecific variants of D-ribulose 5-kinase (e.g. see Lee L. V. et al., 2001, loc. cit.) which can accept D-ribulose 1-phosphate as an alternative substrate.

D-ribulose 1-phosphate can also be assimilated to the CBBC via its isomerisation to D-ribose 1-phosphate (reaction 29# in FIG. 3), catalyzed promiscuously by a 5-methylthio-D-ribulose 1-phosphate 1,2-isomerase, such as Rru_A0360 (Saito Y. et al., 2007, loc. cit.; Erb T. J. et al., 2012, loc. cit.): in a preliminary study we found that this reaction occurs with measurable rate ($k_{cat}$=0.03 s$^{-1}$, $k_{cat}/K_M$<20 M$^{-1}$s$^{-1}$). Preferably, such rate can even be evolutionary further optimized. D-ribose 1-phosphate can then be converted to the CBBC's intermediate D-ribose 5-phosphate (reaction 30) by D-ribose 1,5-phosphomutase (Hammer-Jespersen K. et al., 1970, loc. cit.). Alternatively, D-ribose 1-phosphate can be phosphorylated to D-ribose 1,5-bisphosphate (reaction 31) by ADP-dependent ribose-1-phosphate kinase and then isomerised to D-ribulose 1,5-bisphosphate (reaction 32) by ribose-1,5-bisphosphate isomerise (Aono R. et al., 2015, loc. cit.).

A notable variant of the pathway shown in FIG. 1B bypasses the initial dephosphorylation of 2-PG and instead reduce it to glycolaldehyde phosphate via 2-phospohglycolyl phosphate intermediate (reactions 23# and 24# in FIG. 2). 2-PG conversion into 2-phospohglycolyl phosphate can proceed by transferring a phosphate group from another carboxylic acid or by utilizing a kinase enzyme such as 3-phosphoglycerate kinase: 2-PG was found to be a competitive inhibitor of this enzyme (Tompa P. et al., 1986, loc. cit.; Vas M., 1990, loc. cit.; Szilagyi A. N. et al., 1998, loc. cit.), indicating that it can also serve as a substrate for at least some enzyme variants. The reduction of 2-phosphoglycolyl phosphate can be catalyzed by a phosphorylating glyceraldehyde 3-phosphate dehydrogenase: this enzyme catalyzes the reduction of glycolyl phosphate (Fife T. H. et al., 1970, loc. cit.; Armstrong J. M. et al., 1976, loc. cit.; Byers L. D., 1978, loc. cit.) and the presence of a terminal phosphate moiety enhances the reactivity (Byers L. D., 1978, loc. cit.). Glycolaldehyde 2-phosphate can be then condensed with dihydroxyacetone phosphate to give the CBBC intermediate D-ribulose 1,5-bisphosphate (reaction 28#). This reaction is known to be catalyzed L-fuculose 1-phosphate aldolase, the same enzyme that can also condense glycolaldehyde and dihydroxyacetone phosphate (Ghalambor M. A. et al., 1962, loc. cit.; Ghalambor, M. A. et al., 1966, loc. cit.).

The condensation of glycolaldehyde molecules to form D-erythrose (reaction 10#) can be catalyzed by an aldolase enzyme. Nonspecific aldolases, which can accept unphosphorylated donor and acceptor, and catalyze a reaction with glycolaldehyde as an acceptor (e.g. see Schirmann M. et al., 2001, loc. cit.; Chiu T. H. et al., 1969, loc. cit.), are expected to catalyze this reaction.

The phosphorylation of D-erythrose to D-erythrose 4-phosphate (reaction 11#) can be catalyzed by dihydroxyacetone kinase (Herz S. et al., 2002, loc. cit.).

The reduction of $CO_2$ to formate (reaction 15#) can be supported by a ferredoxin-dependent formate dehydrogenase, where the ferredoxin is reduced by photosystem 1, or by electrons donated directly from components of the electron transport chain, including one of the photosystems.

Two other $CO_2$-positive photorespiration bypass pathways can be established by the direct conversation of glycolyl-CoA to hydroxypyruvate (which is then reduced to D-glycerate, either directly or via initial isomerization to tartronate semialdehyde, and further phosphorylated to D-glycerate 3-phosphate).

In the first approach, glycolyl-CoA is converted to hydroxypyruvate via a (reversible) pyruvate:ferredoxin oxidoreductase enzyme (also referred to as pyruvate synthase, reaction 55#) (Furdui C. et al., 2000, loc. cit.). While this enzyme is generally oxygen sensitive, there exist several bacteria and archea that operate this enzyme under full microaerobic or aerobic conditions. These include *Hydrogenobacter thermophilus* TK-6 (Yoon K. S. et al., 1997, loc. cit.), *Sulfolobus* sp. strain 7 (Fukuda E. et al., 2002, loc. cit.), and *Halobacterium halobium* (Plaga W. et al., 1992, loc. cit.). Moreover, multiple studies indicate that enzyme maturation can occur correctly under aerobic condition when expressed in a foreign host (Fukuda E. et al., 2002, loc. cit.; Yamamoto M. et al., 2003, loc. cit.). Further, several studies indicates that plant-like ferredoxin can replace the native ferredoxin with only a little effect on activity. For example, pyruvate:ferredoxin oxidoreductase from *Desulfovibrio africanus* can accept algal ferredoxin, resulting in 60% of the original rate (Pieulle L. et al., 2004, *Biochemistry* 43: 15480-15493). As some variants of pyruvate:ferredoxin oxidoreductase are known to by promiscuous in the substrates they can accept (e.g. Fukuda E. et al., 2002, loc. cit.), glycolyl-CoA is expected to serve as a substrate for at least some of the enzymes. Finally, some enzyme variants use NADPH as the electron acceptor, instead of ferredoxin, and can operate under (micro)aerobic conditions (e.g., the enzyme from *Euglena gracilis* (Inui H., 1987, loc. cit.)); these enzymes are also likely to support the conversion of glycolyl-CoA to hydroxypyruvate.

In the second approach, $CO_2$ is first reduced to formate (reaction 15#) by a ferredoxin-dependent formate dehydrogenase or by electrons donated directly from components of the electron transport chain, including one of the photosystems. Glycolyl-CoA is then converted to hydroxypyruvate via a (fully reversible) pyruvate formate lyase enzyme (reaction 54#) (Buis J. M. et al., 2005, loc. cit.). The reaction of pyruvate formate lyase (PFL) takes place via a radical mechanism, which involves a glycyl radical (Becker A. et al., 1999, loc. cit.; Plaga W. et al., 2000, loc. cit.; Becker A. et al., 2002, loc. cit.). Pyruvate formate lyase activating enzyme (PFL-AE) generates the stable and catalytically essential glycyl radical (Buis J. M. et al., 2005, loc. cit.; Vey J. L. et al., 2008, loc. cit.). The glycyl radical is susceptible to destruction by oxygen, which results in irreversible cleavage of the polypeptide and inactivation of PFL (Sawers G. et al., 1998, loc. cit.; Zhang W. et al., 2001, loc. cit.). However, previous studies have shown that E. coli cells grown under microaerobic conditions produce a significant amount of formate, indicating that PFL retains its activity in the presence of oxygen (Alexeeva S. et al., 2000, *J Bacteriol* 182: 4934-4940; Levanon S. S. et al., 2005, *Biotechnol Bioeng* 89: 556-564; Zhu J. et al., 2007, *Biotechnol Bioeng* 97: 138-143) and could be further evolved to become more oxygen tolerant. The product of the yfiD gene in E. coli was shown to reactivate PFL in the presence of oxygen by replacing its fragmented part (Zhu J. et al., 2007, loc. cit.; Wagner A F, 2001, loc. cit.). Some variants of pyruvate formate lyase have broad substrate specificity (Hesslinger C. et al., 1998, loc. cit.; Sawers G. et al., 1998, loc. cit.) and hence are expected to accept glycolyl-CoA.

EXAMPLE 2: CALCULATED IMPROVEMENTS OF CBBC ACHIEVED BY THE PHOTORESPIRATION BYPASS PATHWAYS OF FIG. 1

The exact fraction of Rubisco's oxygenation reaction is debated; however, multiple studies determined independently that, for, for example, C3 plants, this fraction is in the range of 20% to 30% (Zhu X. G., et al. (2010) loc. cit.; Peterhansel C., et al. (2013) loc. cit.; Ogren W. L. (1984) loc. cit.; Sharkey T. D. (1988) loc. cit.; Cegelski L., et al. (2006) loc. cit.; Zhu X. G., et al. (2007) loc. cit.; Andersson I. (2008) loc. cit.; Sage R. F., et al. (2012) loc. cit.; Busch F. A. (2013) loc. cit.; Szecowka M., et al. (2013) loc. cit.; Ma F., et al. (2014) loc. cit.; Misra J. B. (2014) loc. cit.). Assuming an average oxygenation fraction of 25%, the photorespiration bypass routes shown in FIG. 1 can support substantially higher carbon fixation and photosynthetic efficiency (Table 1). For comparison, the previously suggested photorespiration bypass routes support, at best, minimal decreases in ATP and NADPH consumption ($\leq 8\%$ and $\leq 14\%$, respectively) with no improvement in the productivity of the CBBC.

These calculations show that the $CO_2$-neutral and $CO_2$-positive photorespiration pathways of this invention (as, for example, in FIG. 1) have a significant advantage over their natural counterparts, both under strong illumination, where growth is mainly limited by the activity of the CBBC, and under low light, where growth is limited by the supply of ATP and NADPH (Xin C. et al., 2014, *Plant Physiol* dx.doi.org/10.1104/pp. 114.248013). Accordingly, the calculations indicate that implementation of these novel bypass routes in e.g. C3 plants would significantly increase plant growth rate and biomass yield under various environmental conditions.

EXAMPLE 3: ENGINEERING OF INDIVIDUAL ENZYME COMPONENTS

Enzymes that promiscuously catalyze non-native reactions as described herein can be evolved so as to catalyzing the respective non-native reactions with higher efficiency in order to further increase the efficiency of the photorespiration bypass pathways of this invention.

Given that the level of promiscuity typically varies dramatically between homologues (Khersonsky O. et al. (2010) *Annu Rev Biochem* 79, 471-505; Afriat L. et al. (2006) *Biochemistry* 45, 13677-13686; Bar-Rogovsky H. et al. (2013) *J Biol Chem* 288, 23914-23927), this is for example achieved by systematically screening orthologs and close paralogs of the respective enzymes for the highest activity in catalyzing the respective non-native reactions. To this end enzyme variants are recombinantly overexpressed in an expression host, preferably E. coli and are subsequently assessed for their promiscuous enzyme activity. If the activity of an enzyme for a particular reaction is below the detection limit of the activity assay, directed evolution towards similar substrates that do show some promiscuity can be applied, thus obtaining 'generalists' that show desired non-native activities (Rockah-Shmuel L. et al. (2012) loc. cit.; Tokuriki N. et al. (2012), loc. cit.). A similar strategy can also be applied if the substrate for a reaction can neither be purchased nor chemically synthesized.

Further, the activity of a promiscuous enzyme can be optimized towards catalyzing a desired non-native reaction by directed evolution of the respective enzyme. To this end, recently developed strategies for the design and construction of enzyme libraries including phylogenetic (Goldsmith, M., et al. (2013), loc. cit.) and computational methods (Khersonsky O. et al. (2012), loc. cit.) are used; such libraries deliver improved enzyme variants upon screening of $\leq 10^3$ variants (Goldsmith, M., et al. (2013), loc. cit.; Rockah-Shmuel L. et al. (2014), loc. cit.). It has been previously demonstrated for a range of enzymes that are not related to this invention that $k_{cat}/K_M$ improvements in the order of $10^2$-$10^5$ could be achieved (Tokuriki N. et al. (2012), loc. cit.; Khersonsky O. et al. (2012), loc. cit.; Cherny I. et al. (2013), loc. cit.) using these methods, even in cases in which the activity was below the detection limit in the starting enzyme (Rockah-Shmuel L. et al. (2012) loc. cit.). By applying libraries designed by using a consensus, phylogenetic approach (Goldsmith, M., et al. (2013), loc. cit.; Khersonsky O. et al. (2009); loc. cit.) the enzyme structure can be further optimized for improved folding and stability (Khersonsky O. et al. (2012), loc. cit.; Aharoni, A., et al. (2004), loc. cit.).

The oxidoreductase enzymes employed in the context of the current invention are intended to preferably utilize NADP(H) and not other electron donor/acceptor. Unlike $NAD^+$, $NADP^+$ is directly reduced in photosynthesis, allowing photosynthetic electron flow to be directly coupled to an electron-consuming photorespiration bypass. Moreover, under illumination, the chloroplastic reduction potential of NADP(H) is considerably lower than that of NAD(H), which increases the driving force of electron-consuming reactions (Heineke D., et al., 1991, *Plant Physiol* 95, 1131-1137). To drive the use of NADP(H) as the sole electron donor/acceptor, either enzymes that natively use NADP(H) are selected, or the cofactor specificity of NAD(H)-dependent paralog enzymes are switched, as previously described for many oxidoreductases (e.g. see Watanabe S. et al. (2005) loc. cit.; Ehsani M. et al. (2009) loc. cit.).

To additionally improve pathway flux, co-localization of different enzymes can be enforced by fusion of two, or more enzymes, into complexes that funnel intermediates between the different components. The folding of such constructs can be optimized by directed evolution as described above. Alternatively, scaffolding using engineered protein-protein interactions is implemented (Dueber J. E. et al. (2009), loc. cit.; Moon T. S. et al. (2010), loc. cit.). The cellulosome provides a potential source of scaffolding proteins that can be grafted onto our metabolic systems (Smith S. P. et al. (2013), loc. cit.).

In the context of this invention, an enzyme activity test is performed by providing the respective substrate to living host cells expressing the respective enzyme, to a crude extract comprising the respective enzyme or to the respective purified enzyme, and the turnover of said substrate is measured by detecting directly or indirectly the appearance of the desired product and/or the turnover of the respective substrate. Suitable detection methods are LC-MS (Bennett B. D. et al., 2009, *Nat. Chem. Biol.* 5(8), 593-9) or spectrometric assays (e.g., formation of NAD(P)H results in increased fluorescence at a wavelength of 340 nm; Berrios-Rivera S J, 2002, *Metab Eng.* 4(3), 217-29). Respective substrates and products are either purchased or synthesized.

EXAMPLE 4: ESTABLISHING PATHWAY ACTIVITY IN VITRO AND IN VIVO

In Vitro Reconstitution and Optimization of the Pathways

A dedicated in vitro platform is used to systematically test and further optimize the synthetic photorespiration bypass pathways of this invention. The in vitro platform is similar in design to already described systems (Bujara M. et al. (2011) *Nat Chem Biol* 7, 271-277; Goh E. B. et al. (2014) *Metab Eng* 26C, 67-76). It consists of a small micro-reactor (1-20 ml in size), in which all purified enzymatic components, necessary cofactors (e.g., NAD(P)(H), ATP) and respective substrate(s) of the synthetic pathway are combined. The micro-reactor is directly coupled to a high resolution mass spectrometer (e.g., a QTOF-system) via an injection pump (operating at flow rates of 10-100 µl/min). The high resolution mass spectrometer allows identifying and quantifying the concentration of the metabolites of the synthetic pathway and their changes over time in the micro-reactor. With this setup, the rate(s) of product formation (i.e., pathway efficiency), as well as the pathway's boundary conditions can be tested systematically with changing parameters (different iso-enzymes, different enzyme concentrations, etc.) in a medium throughput approach. This allows to analyze enzymes and their optimal concentrations, thereby achieving highly efficient and robust operating pathways in vitro.

In Vivo Reconstitution and Optimization of the Pathways in *E. coli*

*E. coli* is easy to manipulate genetically and metabolically, and has a short doubling time, and can hence be used to evolutionary optimize the kinetics of the synthetic pathways. The pathways are incrementally established in *E. coli*, at each step selecting for enhanced activity of one pathway segment. For example, the realization of the bypass route in FIG. 1B is performed as follows (FIG. 6). Step 1: in a ΔglcDEF fuc+ *E. coli* strain that can metabolize D-arabinose but not glycolate (LeBlanc D. J. et al. (1971) *J Bacteriol* 106, 82-89; Zhu Y. et al. (1986) *J Mol Evol* 23, 259-266), fucA is deleted and the enzymes catalyzing the reactions downstream of D-ribulose 1-phosphate are introduced. These include the enzyme catalyzing reaction 9# (see Table 3) and Rubisco. Growth of this strain on D-arabinose is dependent on the activity of the introduced pathway segment. Step 2: fucA is reintroduced and the strain is cultivated with glycolaldehyde as a sole carbon source (glycerone phosphate is recycled). Step 3: the segment reducing glycolate to glycolaldehyde completes the synthetic pathway to support growth on glycolate as sole carbon source. At each step, evolution optimization towards high flux is performed.

Dedicated expression of all pathway enzymes may optimize the activity of the non-native pathways. To optimize the regulation of native genes, a rapid and modular methodology can be employed, in which genes of interest are combinatorially paired with a small set of ribosome binding sites along a synthetically assembled operon, modulating the expression levels of the genes by several orders of magnitude (Zelcbuch L. et al. (2013) *Nucleic Acids Res* 41, e98). Transformation methodologies as well as promoters, vectors and all other components required for a person skilled in the art to generate such bacteria are for example described in Zelcbuch L. et al. (2013) *Nucleic Acids Res* 41, e98.

The experimental methodology described here do not just confirm pathway activity in vivo, but further enable to directly evolve enhanced activity: continuous cultivation of glycolate-consuming *E. coli* within a turbidostat can support the evolution of the bacterium to higher growth rate and hence higher pathway activity (Flegr J., 1997, *Journal of Theoretical Biology* 188(1), 121-126).

In Vivo Reconstitution and Optimization of the Pathways in Cyanobacteria

The synthetic photorespiration bypass pathways in accordance with the invention are exemplary implemented in cyanobacteria, which are engineered to become highly dependent on photorespiration (e.g., DccmM *Synechocystis*, a carboxysome-less strain that is dependent on high $CO_2$ concentrations (for example 5% $CO_2$ atmosphere, which is >100 µM dissolved $CO_2$; Ogawa T. et al. (1994) *Photosynth Res* 39, 183-190) and/or that cannot operate one or more of the native photorespiration pathways (e.g., Dtsr that abolishes the glycerate pathway (Eisenhut M. et al. (2008) *Proc Natl Acad Sci USA* 105, 17199-17204)). This allows comparing the activity of the different synthetic pathways relative to natural photorespiration, and to directly selecting for high pathway activity in a photosynthetic organism that utilizes the CBBC. In particular. the growth rate, biomass yield, photosynthetic rate and flux via the CBBC in the cyanobacterial strains expressing the synthetic pathways are compared to those of wild-type strains.

EXAMPLE 5: ESTABLISHING PATHWAYS IN HIGHER PLANTS AND CHARACTERIZING THEIR PHENOTYPES

A high throughput in planta greenhouse screening platform is used to test different synthetic photorespiration pathways in parallel and in two different model species representing the two main classes of crop plants, monocots (*Brachypodium distachyon* (Brutnell T. P. et al. (2015) *Annu Rev Plant Biol.* 66, 465-485)) and dicots (*Arabidopsis thaliana*). To express several genes from a single construct, the repetitive nature of the construct is reduced, thus avoiding unwanted gene silencing and recombination. To this end, each gene is expressed in the construct using different regulatory elements (promoters, terminators). To identify promoters that are induced as early as the seedling stage and in all photosynthetic tissues the EVO's database and mining capabilities are utilized. These promoters are further validated in planta using promoter'::gus fusions (Blume B. et al. (1997) *Plant J* 12, 731-746).

Whole genome RNA sequencing is carried out to verify expression of the pathway genes in the plant. Where applicable, the chloroplast proteome is further analyzed to verify proper targeting of the expressed enzymes if desired. To comprehensively characterize the in planta responses to the synthetic pathways, changes in architecture, physiology and productivity of plants are measured. Furthermore, to demonstrate that the synthetic photorespiration bypass routes give rise to increased carbon fixation rates, growth rates or biomass yields, transgenic lines carrying the different synthetic pathways may be compared to plants carrying empty vectors.

EXAMPLE 6: IN VITRO ESTABLISHMENT OF THE SYNTHETIC PHOTORESPIRATORY BYPASS PATHWAY FROM GLYCOLATE TO GLYCERATE

The following example experimentally illustrates the implementation of the photorespiration pathways disclosed herein, in particular the photorespiration bypass pathway as shown in FIG. 1A. In particular, the example experimentally illustrates that the non-native enzymatic conversions 2#, 3# and 4# as well as the enzymatic conversion 5 can be achieved by using the enzymes described herein. These four enzymatic conversions form part of the photorespiration bypass pathway shown in FIG. 1A but also other photorespiration bypass pathways disclosed herein. In particular, the present example also illustrates that the non-native enzymatic conversion of glycolate into glycolyl-CoA (reaction 2#) can be achieved by the enzymes listed herein. Thereby the present example also demonstrates experimentally that 2-PG can be enzymatically converted to glycolyl-CoA (via glycolate) by the proposed enzymatic conversions, using in particular the enzymes provided herein, because reaction 1, which converts 2-PG into glycolate, is a reaction well known with the enzymes disclosed herein (in particular also in plants as part of the natural photorespiration). As mentioned elsewhere herein, the enzymatic conversion of 2-PG into glycolyl-CoA is the first step of a number of photorespiration bypass pathways disclosed herein, which are therefore also experimentally illustrated and supported by the present example.

Specifically, in the present example the enzymes listed in Table 4, which are enzymes disclosed in the context of the present invention, were recombinantly expressed and subjected to in vitro activity assays to illustrate their capability of catalyzing the respective enzymatic conversions. The capability of catalyzing the respective enzymatic conversions (see, e.g., FIG. 8A for which enzyme catalyzes which reaction) was assessed by different experimental means that are explained in more detail below. Furthermore, kinetic parameters for the respective reactions and enzymes were determined as described further below and are summarized in Table 5.

In the following the experimental analyses including the employed means and methods and results are explained in detail.

Construction of Expression Vectors for Heterologous Expression of the Enzymes $PCT_{Re}$, $PCT_{CP}$, $PCC_{Me}$, $PCC_{Me}$ D407I Y143H, $MCR_{Ca}$ and $MCR_E$ For the heterologous expression of the propionyl-CoA transferase from *Ralstonia eutropha* ($PCT_{Re}$; nucleic acid sequence shown in SEQ ID NO: 11; amino acid sequence shown in SEQ ID NO: 12), the previously described vector pET-19b::pct (Lindenkamp et al., 2013, *Applied Microbiology and Biotechnology*, 97(17), 7699-7709) was employed.

For the heterologous expression of the propionyl-CoA transferase from *Clostridium propionicum* ($PCT_{CP}$; nucleic acid sequence shown in SEQ ID NO: 13; amino acid sequence shown in SEQ ID NO: 14) a pET16b vector containing the gene encoding the $PCT_{CP}$ was employed (SEQ ID NO: 26).

The propionyl-CoA carboxylase enzyme from *Methylobacterium extorquens* ($PCC_{Me}$) comprises two independent protein subunits that are expressed by two different genes, namely pccA (nucleic acid sequence is shown in SEQ ID NO: 1; encoded amino acid sequence is shown in SEQ ID NO:2) and pccB (SEQ ID NO: 3; encoded amino acid sequence is shown in SEQ ID NO:4). Thus, to express $PCC_{Me}$ an expression vector for simultaneous heterologous expression of both the pccA gene and the pccB gene from the same vector with each gene under T7-lac promoter control, respectively was constructed. To this end, the pccA gene (SEQ ID NO: 1) was cloned from *Methylobacterium extorquens* genomic DNA into pTE100 (SEQ ID NO: 20) and the NcoI site within the pccA gene (SEQ ID NO: 1) at position 336 of SEQ ID NO: 1 was mutated by Quick Change PCR to remove a NcoI restriction site resulting in SEQ ID NO: 15.

For that, the following primers were used:

```
                              (SEQ ID NO: 16)
5'-GGTGCCATCGCCGCAATGGGCGACAAGATC-3';
and (SEQ ID NO: 17)
5'-GATCTTGTCGCCCATTGCGGCGATGGCACC-3'.
```

For amplification and introduction of NdeI and KpnI restriction sites of pccA with the modified NcoI site (SEQ ID NO:15) (for subsequent cloning into pCDFduet to construct the pCDFduet_pccB_pccA), the following primers were used:

```
                              (SEQ ID NO: 18)
5'-CGGCTGCCATATGTTCGATAAGATCCTGATTG-3';
and (SEQ ID NO: 19)
5'-CATGCGTGGTACCTCAGGCGAATTCCAGGATC-3'.
```

For amplification and introduction of NdeI and EcoR1 restriction sites of the pccB gene from *Methylobacterium extorquens* genomic DNA, the following primers were used:

```
                              (SEQ ID NO: 24)
5'-GACCGTGCATATGAAGGACATCCTCGAGAAGC-3';
and (SEQ ID NO: 25)
5'-GATACATGAATTCTCAGAGCGGGATGTTGTCGT-3'.
```

The pccA gene modified in the NcoI site (SEQ ID NO: 15) as well as the pccB gene (SEQ ID NO: 3) were cloned into the vector pCDFduet to yield the plasmid pCDFduet_pccB_pccA. This vector was employed for heterologous expression of the wilde-type $PCC_{Me}$.

To construct an expression vector for heterologous expression of the mutant variant $PCC_{Me}$_D407I_Y143H two point mutations (resulting in the amino acid exchanges D407I and Y143H) were introduced into the pccB gene of the above-mentioned pCDFduet_pccB_pccA vector. To this end single-oligo directed mutagenesis was performed (Shenoy and Visweswariah, 2003, *Analytical biochemistry*, 319 (2), 335-336). To introduce the nucleotide exchange resulting in the D407I amino acid exchange in the encoded pccB protein, the following primer was used:

(SEQ ID NO: 21)
5'-CAAGGCCTTCGGCGGCGCCTACATCGTCATGGCCTCCAAGCATG-3'.

After confirmation of the successful mutation via sequencing, another nucleic acid mutation was introduced in the mutated pccB gene resulting in the encoding of the second amino acid exchange, Y143H. For this second PCR the following primer was used:

(SEQ ID NO: 22)
5'-GCGCTCGGCGGCCACGGCGAGGTGTTCCGC-3'.

The final plasmid for the overexpression of the $PCC_{Me}$_D407I_Y143H doublemutant protein variant (consisting of pccA with the amino acid sequence shown in SEQ ID NO: 2; and pccB_D407I_Y143H with the amino acid sequence shown in SEQ ID NO: 6) was named pCDFduetpccB_D407I_Y143H_pccA and comprised the modified pccA gene with SEQ ID NO: 15 and the pccB gene encoding the pccB_D407I_Y143H mutant variant with the nucleic acid sequence shown in SEQ ID NO: 5.

For the heterologous expression of the $MCR_{Ca}$ protein (amino acid sequence is shown in SEQ ID NO: 8; corresponding nucleic acid sequence encoding the protein is depicted in SEQ ID NO: 7) the previously described pTRC-$MCR_{Ca}$ plasmid (Kröger et al., 2011, Analytical biochemistry, 411(1), 100-105) was employed.

For the heterologous expression of the $MCR_E$ protein (SEQ ID NO: 10; corresponding nucleic acid encoding the protein is depicted in SEQ ID NO: 9) an expression plasmid was cloned with the backbone pSEVA321 and an *E. coli* codon optimized insert that was provided by the Joint Genome Institute of the US Department of Energy (JGI-DOE), which synthesized the corresponding codon optimized insert comprising a codon optimized version of the gene encoding the $MCR_E$ protein. The complete sequence of the expression plasmid with the insert is depicted in SEQ ID NO: 23) and comprises the codon optimized nucleotide sequence of the gene the $MCR_E$ protein from nucleotide position 115 to 3827 of SEQ ID NO: 23.

Heterologous Expression and Purification of Recombinant Proteins

For the heterologous overexpression of the $PCT_{Re}$, the $PCT_{Cp}$, the $PCC_{Me}$, the $PCC_{Me}$_D407I_Y143H, the $MCR_{Ca}$ and the $MCR_E$ protein, respectively, the corresponding plasmid encoding the respective enzyme was first transformed into chemically competent *E. coli* BL21 (DE3) cells. The cells transformed with the respective plasmid encoding one of said enzymes were then grown on LB agar plates containing 100 µg mL$^{-1}$ ampicillin ($PCT_{Re}$, $PCT_{Cp}$ and $MCR_{Ca}$), 34 µg mL$^{-1}$ chloramphenicol ($MCR_E$) or 50 µg mL$^{-1}$ spectinomycin ($PCC_{Me}$, $PCC_{Me}$_D407I_Y143H) at 37° C. over night. Subsequently, for expression of the $PCC_{Me}$ and the $PCC_{Me}$_D407I_Y143H 1 L selective TB medium was inoculated with the colonies obtained from the overnight culture and grown at 25° C. for 24 h without addition of IPTG, as the T7-lac promoter showed already constitutive expression in the absence of the inducer. For the overexpression of $PCT_{Re}$, $PCT_{Cp}$, $MCR_E$ and $MCR_{Ca}$, cells were cultivated in 1 L selective LB medium at 37° C. to an $OD_{600}$ of 0.4 to 0.6, induced with 0.5 mM IPTG and grown over night at 18° C. to 25° C.

Cells were harvested at 10 000×g for 10 min and cell pellets were stored at −80° C. until purification of enzymes. Cell pellets of $MCR_{Ca}$ and $MCR_E$ overexpressing cells were resuspended in two-fold volume of buffer $A_{Strep}$ (50 mM Tris/HCl, 150 mM NaCl, pH 7.8) containing 0.1 mg mL$^{-1}$ DNAse I. The cell suspension was passed through a French pressure cell twice at a pressure of 137 MPa and centrifuged at 100 000×g and 4° C. for 1 h. The supernatant was filtered through a 0.45 µm syringe filter and loaded at a flow rate of 1 mL min$^{-1}$ onto a 1 mL StrepTrap™ HP column (GE healthcare) which had previously been equilibrated with 5 column volumes of buffer $A_{Strep}$. The column was washed with 20 column volumes of buffer $A_{Strep}$ and the protein was eluted with buffer $A_{Strep}$ containing 3 mM desthiobiotin. The enzyme was stored in buffer $A_{Strep}$ containing 20% glycerol.

$PCT_{Re}$, $PCT_{Cp}$, $PCC_{Me}$ and $PCC_{Me}$_D407I_Y143H overexpressing cells, respectively, were resuspended in two-fold volume of buffer $A_{His}$ (50 mM Tris/HCl, 500 mM NaCl, pH 7.8) containing 0.1 mg mL$^{-1}$ DNAse I. The cell suspension was passed through a French pressure cell twice at a pressure of 137 MPa and centrifuged at 100 000×g and 4° C. for 1 h. The supernatant was filtered through a 0.45 µm syringe filter and loaded at a flow rate of 1 mL min$^{-1}$ onto a 1 mL HisTrap™ FF column (GE healthcare) which had previously been equilibrated with 5 column volumes of buffer $A_{His}$. The column was washed with 20 column volumes of 90% buffer $A_{His}$ and 10% buffer $B_{His}$ (50 mM Tris/HCl, 500 mM NaCl, 500 mM imidazole, pH 7.8) and the respective protein was eluted with buffer $B_{His}$. The fraction containing the respective eluted enzyme was desalted using two 5 mL HiTrap™ Desalting columns (GE healthcare) and buffer $A_{Strep}$. The respective purified enzymes were stored at −20° C. in buffer $A_{Strep}$ containing 20% glycerol.

Activity Assays $PCT_{Re}$ Activity for Catalyzing the Conversion of Glycolate into Glycolyl-CoA (Reaction 2#)

The activity of the purified $PCT_{Re}$ protein to catalyze the conversion of glycolate into glycolyl-CoA (reaction 2#) was determined via analysis of the time dependent formation of glycolyl-CoA in an in vitro assay using ultra-high performance liquid chromatography coupled high resolution mass spectrometry (UPLC-hrMS, see FIG. 7).

Specifically, the enzyme assay was performed at 37° C. in a total volume of 60 µL. The reaction mixture contained 200 mM MOPS/KOH, 2 mM acetyl-CoA, 97 µg enzyme and 10 mM to 800 mM glycolate (pH 7.5). 10 µL aliquots were taken at time points 0.5, 1.0, 1.5 and 2.0 minutes and the reaction was immediately stopped by HCl (1% total concentration). The samples were centrifuged at 17 000×g and the supernatant diluted 1:20 for MS analysis. The measurements were done using an Agilent 6550 iFunnel Q-TOF LC-MS system equipped with an electrospray ionization source set to positive ionization mode.

Compounds were separated on a RP-18 column (50 mm×2.1 mm, particle size 1.7 µm, Kinetex XB-C18, Phenomenex) using a mobile phase system comprised of 50 mM ammonium formate pH 8.1 and methanol. Chromatographic separation was carried out using the following gradient condition at a flow rate of 250 µl/min: 0 min 0% methanol; 1 min 0% methanol, 3 min 2.5% methanol; 9 min 23% methanol; 14 min 80% methanol; 16 min 80% methanol. Capillary voltage was set at 3.5 kV and nitrogen gas was used for nebulizing (20 psig), drying (13 l/min, 225° C.) and sheath gas (12 l/min, 400° C.). The TOF was calibrated using an ESI-L Low Concentration Tuning Mix (Agilent) before measurement (residuals less than 2 ppm for five reference ions) and was recalibrated during a run using 922 m/z as reference mass. MS data were acquired with a scan range of 500-1200 m/z.

LC-MS data were analyzed using MassHunter Qualitative Analysis software (Agilent). The velocity of the particular reactions was calculated within the linear range of the reaction via the concentration of the formed glycolyl-CoA, that had been determined via LC-MS using a standard curve (25 µM to 100 µM glycolyl-CoA).

The $K_m$ for glycolate for the CoA transferase from *R. eutropha* ($PCT_{Re}$) was determined to 51.7±9.6 mM and the $v_{max}$ to 1.4±0.1 U mg$^{-1}$ using nonlinear regression (R$^2$: 0.91, GraphPad Prism 6, FIG. 8B).

$PCT_{Ca}$ Activity for Catalyzing the Conversion of Glycolate to Glycolyl-CoA (Reaction 2#)

As an alternative enzyme for catalyzing the conversion of glycolate to glycolyl-CoA (reaction 2#), the propionyl-CoA transferase of *Clostridium propionicum* ($PCT_{Cp}$) was tested. The activity assay using this enzyme was performed as described above for $PCT_{Re}$ with the only difference that instead of the $PCT_{Re}$ enzyme the $PCT_{Cp}$ enzyme was employed. The detected $K_m$ value of the $PCT_{Ca}$ enzyme for glycolate was 149±35 mM and the $v_{max}$ amounted to 31.6±2.7 mU mg$^{-1}$ (see FIG. 9).

$PCC_{Me}$ and $PCC_{Me}$ D407I Y143H Activity for Catalyzing the Conversion of Glycolyl-CoA into Tartonyl-CoA (Reaction 3#)

Next the activities of the purified $PCC_{Me}$ protein and the mutant variant $PCC_{Me\_}D407I\_Y143H$ for catalyzing the conversion of glycolyl-CoA into tartonyl-CoA (reaction 2#) was analyzed. The $PCC_{Me\_}D407I\_Y143H$ is a mutant variant of $PCC_{Me}$, which has been designed and tested for its activity to convert glycolyl-CoA into tartonyl-CoA for the first time in the context of the present invention. The amino acid substitutions D407I and Y143H were manually selected as potential target sited for mutagenesis in order to improve the catalytical activity for the conversion of glycolyl-CoA into tartonyl-CoA (reaction 2#). The selection of these amino acids was merely speculative and only supported by comparing existing structures of biotin-dependent propinyl-CoA-carboxylases and biotin-dependent methylmalonyl-CoA-decarboxylases. Specifically, these structures were evaluated in respect to residues potentially involved in binding propionyl-CoA.

As shown in the extracted ion chromatogram for tartronyl-CoA shown in FIG. 10, the purified $PCC_{Me\_}D407I\_Y143H$ protein indeed exhibited a glycolyl-CoA carboxylation activity. Similarly, as mentioned below, also the wilde-type $PCC_{Me}$ exhibited a glycolyl-CoA carboxylation activity, although the activity was lower as the activity of the $PCC_{Me\_}D407I\_Y143H$ protein. Thus, the introduced mutations surprisingly indeed improved the activity for converting glycolyl-CoA into tartonyl-CoA.

The activity of the $PCC_{Me\_}D407I\_Y143H$ protein as well as the $PCC_{Me}$ protein was determined spectrophotometrically at 37° C. The ATP hydrolysis reaction of the respective enzyme was coupled to ATP regeneration by pyruvate kinase (PK) with phosphoenolpyruvate (PEP) and subsequent reduction to lactate by lactate dehydrogenase (LDH). The oxidation of NADH by LDH was followed spectrophotometrically at 340 nm. The reaction mixture (300 µL) contained 200 mM NH$_4$HCO$_3$ buffer, pH 7.7, 5 mM MgCl$_2$, 1 mM ATP, 1 mM PEP, 4 U PK, 5.8 U LDH, 0.3 mM NADH and 48 µg of $PCC_{Me\_}D407I\_Y143H$ or $PCC_{Me}$. The reaction was initiated by addition of 1 mM glycolyl-CoA. Samples for UPLC-hrMS were withdrawn and stopped by acidification (5% formic acid) after most of the NADH was consumed. Precipitated protein was removed by centrifugation at 4° C. and 17 000×g. The supernatants were analyzed by UPLC-hrMS as described above. Glycolyl-CoA-dependent ATP-hydrolyis of the $PCC_{Me}$ wilde-type enzyme was detected at 0.4 U mg$^{-1}$ protein, whereas the $PCC_{Me\_}D407I\_Y143H$ enzyme showed a glycoyly-CoA-dependent ATP hydrolysis rate of 1.0 U mg$^{-1}$ protein. As mentioned above, and shown in FIG. 10, the glycolyl-CoA carboxylation activity of the $PCC_{Me\_}D407I\_Y143H$ enzyme was confirmed by direct detection of the product tartronyl-CoA by UPLC-hrMS.

In a second assay, the reaction mixture was slightly modified for a $^{13}$C labeling experiment. Here, the reaction mixture contained 50 mM NH$_4$HCO$_3$ buffer, pH 7.7 and 150 mM [$^{13}$C]NaHCO$_3$, pH 7.7 (otherwise as above-mentioned). The incorporation of the $^{13}$C label into the carboxylation product tartronyl-CoA is depicted by a shift in the mass spectrum (see FIG. 10C).

A similar assay was used to determine the $K_m$ value of the $PCC_{Me\_}D407I\_Y143H$ enzyme for the substrate glycolyl-CoA. The reaction mixture (300 µL) contained 200 mM NH$_4$HCO$_3$ buffer, pH 7.7, 8.3 mM MgCl$_2$, 1.7 mM ATP, 1.7 mM PEP, 4 U PK, 5.8 U LDH, 0.3 mM NADH and 24 µg of $PCC_{Me\_}D407I\_Y143H$. The reaction was started by addition of varying amounts of glycolyl-CoA (0.125-3 mM). For the $PCC_{Me\_}D407I\_Y143H$ double mutant, the $K_m$ for glycolyl-CoA was determined to be 1.0±0.15 mM with a $v_{max}$ 1.5±0.09 U mg$^{-1}$ (see FIG. 8C).

$MCR_{Ca}$ Activity for Catalyzing the Conversion of Tartonyl-CoA into Tartronate Semialdehyde (Reaction 4#) and the Subsequent Conversion of Tartronate Semialdehyde (Also Referred to as Tartronic Semialdehyde) into Glycerate (Reaction 5)

The kinetics of the $MCR_{Ca}$ enzyme for enzymatically converting the substrate tartonyl-CoA into glycerate (via reactions 4# and 5 both catalyzed by $MCR_{Ca}$) were determined spectrophotometrically at 365 nm following the oxidation of NADPH. Per molecule tartonyl-CoA, two molecules of NADPH are oxidized by $MCR_{Ca}$ (a first in reaction 4# and a second in reaction 5) The measurements were carried out at 37° C. in a total reaction volume of 200 µL containing 100 mM MOPS buffer (with 5 mM MgCl$_2$, pH 7.5) with an initial NADPH concentration of 0.4 mM NADPH and 23 µg $MCR_{Ca}$.

With its physiological substrate, malonyl-CoA, the enzyme exhibits a specific activity of approximately 7 U mg$^{-1}$ at 37° C. (0.3 mM substrate, Kröger et al. 2011, loc. cit.). With tartronyl-CoA (0.25 mM), the specific activity at 37° C. was 0.6 U mg$^{-1}$.

The determined kinetic values for tartronyl-CoA are (n=3, nonlinear regression with GraphPad Prism 6): $K_m$: 25.7±2.6 µM and $v_{max}$: 635±14 mU/mg (R$^2$: 0.96, FIG. 8D). The $K_m$ value for tartronyl-CoA is comparable to the apparent $K_m$ value for malonyl-CoA (30 µM, Hügler et al., 2002, Journal of Bacteriology, p. 2404-2410) and indicates in line with the usage of this enzyme in the present invention a high affinity for tartronyl-CoA. It is envisaged that the substrate specificity for tartronyl-CoA versus malonyl-CoA, can be further increased by enzyme engineering and evolution (as described elsewhere herein).

MCR$_E$ Activity for Catalyzing the Conversion of Tartonyl-CoA into Tartronate Semialdehyde (Reaction 4#) and the Subsequent Conversion of Tartronate Semialdehyde into Glycerate (Reaction 5)

An alternative enzyme for catalyzing the conversion of tartonyl-CoA into glycerate (via reactions 4# and 5) is the MCR from Erythrobacter sp. NAP1 (MCR$_E$). It was tested for its activity with malonyl-CoA and for tartronyl-CoA with the assay described above for MCR$_{Ca}$. The specific activity of MCR$_E$ for tartronyl-CoA is 6 times lower than that of MCR$_{Ca}$ (0.1 U mg$^{-1}$ with 0.25 mM tartronyl-CoA, see FIG. 12), but it also exhibits a 100 times lower specific activity for malonyl-CoA than MCR$_{Ca}$ (0.1 U mg$^{-1}$ with 0.25 mM malonyl-CoA). Thus, MCR$_E$ exhibits lower rates of catalysis than MCR$_{Ca}$, its substrate specificity is higher which could be advantageous for the in vivo application of the pathway. Coupling of the Conversion of Glycolyl-CoA into Tartronyl-CoA (Reaction 3#) by PCC$_{Me}$ D407I Y143H with the Conversions of Tartronyl-CoA into Tartronate Semialdehyde (Reaction 4#) and of Tartronate Semialdehyde into Glycerate (Reaction 5) by MCR$_{Ca}$ In addition to the above mentioned assays also another assay was performed in which the formation of tartronyl-CoA from glycolyl-CoA (reaction 3#) by the PCC$_{Me}$_D407I_Y143H enzyme was directly coupled to its subsequent two step reduction via tartronate-semialdehyde (reaction 4#) to glycerate (reaction 5) by use of the purified MCR$_{Ca}$ (Kröger et al., 2011, loc. cit.). The reaction mixture (300 µL) contained 200 mM NH$_4$HCO$_3$ buffer, pH 7.7, 5 mM MgCl$_2$, 1 mM ATP, 0.4 mM NADPH, 43 µg PCC$_{Me}$_D407I_Y143H, and 184 µg of MCR$_{Ca}$.

To determine whether MCR$_{Ca}$ was able to catalyze the two step reduction of tartonyl-CoA to glycerate (via tartronic semialdehyde), samples of the reaction mixture were withdrawn after all of the NADPH was consumed. The samples were stopped with formic acid (5% final concentration). The acidified samples were centrifuged at 4° C. and 17 000×g and the supernatants were analyzed by HPLC-hrMS.

The formation of glycerate was analyzed using an Agilent 6550 iFunnel Q-TOF LC-MS system equipped with an electrospray ionization source set to negative ionization mode. Compounds were separated on a Luna-NH2 column (100 mm×2.0 mm, particle size 3 µm, Phenomenex) using a mobile phase system comprised of 20 mM ammonium acetate, 20 mM NH$_4$OH, 95:5 H$_2$O/acetonitrile, pH 9.8 and acetonitrile. Chromatographic separation was carried out using the following gradient condition at a flow rate of 250 µl/min: 0 min 85% acetonitrile; 7 min 0% acetonitrile; 14 min 0% acetonitrile; 15 min 85% acetonitrile; 17.5 min 85% acetonitrile. Capillary voltage was set at 3.5 kV and nitrogen gas was used for nebulizing (20 psig), drying (13 l/min, 225° C.) and sheath gas (12 l/min, 400° C.). The TOF was calibrated using an ESI-L Low Concentration Tuning Mix (Agilent) before measurement (residuals less than 2 ppm for five reference ions) and was recalibrated during a run using 113 m/z as reference mass. MS data were acquired with a scan range of 50-200 m/z.

LC-MS data were analyzed using MassHunter Qualitative Analysis software (Agilent). MCR$_{Ca}$ was indeed able to reduce the tartronyl-CoA, produced by PCC$_{Me}$_D407I_Y143H, to glycerate (see FIG. 11). This indirectly also confirmed that MCR$_{Ca}$ reduced tartronyl-CoA to tatronate semialdehayde. To detect tatronate semialdehyde an HPLC-MS based assay can be employed that uses phenylhydrazine. In such assays the tartronate semialdehyde can be covalently derivatized with phenylhydrazine to a phenylhydrazone, which can be detected by its absorbance at 324 nm and confirmed by its corresponding mass spectrum.

The reaction mixture was slightly modified for an additional $^{13}$C labeling assay. For that the mixture contained 50 mM NH$_4$HCO$_3$ buffer, pH 7.7 and 150 mM [$^{13}$C]NaHCO$_3$, pH 7.7. A shift in the mass spectrum after incubation in the presence of $^{13}$C labeled bicarbonate (FIG. 11C) proves that the glycerate was formed from $^{13}$C labeled tartronyl-CoA, resulting from the carboxylation of glycolyl-CoA.

Notably, the results with respect to the enzyme kinetics of the PCC$_{Me}$_D407I_Y143H from the ATP hydrolysis assay for PCC$_{Me}$_D407I_Y143H and the MCR$_{Ca}$ coupled assay showed an ~10 fold discrepancy in the calculated specific activities of PCC$_{Me}$_D407I_Y143H, which was further investigated.

First, the option that this difference in the determined values resulted from an additional ATP hydrolysis during glycolyl-CoA carboxylation that is not directly related to the glycolyl-CoA carboxylation was assessed. The assay used for this analysis was performed in a reaction volume of 300 µL that contained 200 mM MOPS/KOH (pH 7.5), 1.6 mM MgCl$_2$, 50 mM KHCO$_3$, 0.33 mM ATP, 0.533 mM NADPH, 24 µg PCC$_{Me}$_D407I_Y143H, 138 µg MCR$_{Ca}$, 16 µg epimerase. The assay was started by the addition of 2 mM glycolyl-CoA. The amount of formed tartronyl-CoA was calculated based on the absorption difference of NADPH from start to end of the reaction. From 333 µM ATP applied to the reaction, 46 µM were used for actual carboxylation. This implies, that only 14% of the ATP hydrolysis lead to tartronyl-CoA formation, which would in turn explain the difference in the determined values. However, anyhow irrespective of the exact values of the enzyme kinetics it is clear from both experiments that PCC$_{Me}$_D407I_Y143H has glycolyl-CoA carboxylation activity and can convert glycolyl-CoA tartronyl-CoA.

The activity of the wildtype PCC$_{Me}$ with glycolyl-CoA, measured with ATP hydrolysis assay was 0.4 U mg$^{-1}$, whereas with the MCR$_{Ca}$ coupled assay, no activity could be measured. However, given the results of the PCC$_{Me}$_D407I_Y143H, the failure to detect activity of the wildtype PCC$_{Me}$ with glycolyl-CoA in the MCR$_{Ca}$ coupled assay probably results from the fact that the activity is below the detection limit of this assay. Thus, the PCC$_{Me}$_D407I_Y143H was indeed much more efficient in glycolyl-CoA carboxylation than the wild type enzyme. It may be advantageous to construct mutant variants of PCC$_{Me}$_D407I_Y143H (by enzyme evolution) which reduces the amount of hydrolyzed ATP independent of glycolyl-CoA conversion. Such efforts could focus on increasing interaction of the enzyme with the hydroxy group of glycolyl-CoA.

Summary of Activity Assays

In summary, the above mention activity assays illustrated that the respective reactions of the proposed pathway can be performed by the enzymes used and disclosed herein. In particular, FIG. 11 shows that the in vitro conversion of glycolyl-CoA to glycerate by the combined function of PCC$_{Me}$_D407I_Y143H and MCR$_{Ca}$ is possible and that the formed glycerate is $^{13}$C labeled if the reaction is performed in the presence of $^{13}$C labeled bicarbonate.

FIG. 8 gives an overview of the investigated enzymes and their Michaelis-Menten kinetics. The enzymes and their corresponding kinetic values are listed in Table 5.

The present invention refers to the following tables:

TABLE 1

Estimated efficiency advantages of the synthetic photorespiration bypass routes shown in FIG. 1 over the natural photorespiration pathway.

Requirements for the production of 1 triose phosphate via the CBBC

| Pathway | cycles/iterations of the CBBC # | relative efficiency | ATP molecules # | relative efficiency | NAD(P)H molecules # | relative efficiency |
|---|---|---|---|---|---|---|
| Native | 4.8 | 100% | 15.6 | 100% | 9.6 | 100% |
| FIG. 1A | 3 | 160% | 11.3-12† | 130-138% | 7.5 | 128% |
| FIG. 1B | 4 | 120% | 12-13† | 120-130% | 8 | 120% |
| FIG. 1C | 4 | 120% | 12.5-13.5† | 116-125% | 8 | 120% |
| FIG. 1D | 3 | 160% | 10.5 | 149% | 7.5†† | 128% |

†formation of glycolyl-CoA can consume either one or two ATP equivalents
††assuming that glycolate oxidation is NAD(P)-dependent
: signifies numbers of iterations/cycles of the CBBC or molecules consumed, respectively Table 2 and Table 3.

Table 2 and Table 3 summarize all reactions as shown in the FIGS. 1 to 4. In particular, Table 2 lists the non-native reactions/enzymes/enzymatic conversions and Table 3 lists all other reactions/enzymes/enzymatic conversions The first column of these Tables indicate the number of the reactions/enzymatic conversions/enzymes as shown in the Figures. In particular, the individual enzymatic reactions/enzymatic conversions are depicted with numbers in the Figures (e.g. the enzymatic conversion of 2-PG (2-phosphoglycolate, also known as glycolate 2-phosphate) into glycolate is depicted as "1"). In the context of this application, this number "X" is depicted as "reaction X" or "enzymatic conversion X", where it refers to the enzymatic conversion. Moreover, this number "X" is depicted as "enzyme X", where it refers to the respective enzyme catalysing the respective reaction.

In Tables 2 and 3, possible cofactors are indicated in brackets.

TABLE 2

| Reaction/Enzyme no. | EC no. of enzyme to be employed | Enzyme to be employed | Examples for organisms | Natural plant localization | Substrate(s) | Product(s) | Enzymatic activity within the photorespiration bypass pathways | Ref. |
|---|---|---|---|---|---|---|---|---|
| 1 | 3.1.3.18 | phosphoglycolate phosphatase | ubiquitous | chloroplast | 2-PG, H$_2$O | glycolate, phosphate | phosphoglycolate phosphatase | [1] |
| 5 | 1.1.1.60 | tartronate-semialdehyde reductase | Escherichia coli | | tartronate-semialdehyde (NAD(P)H) | glycerate (NAD(P)) | tartronate-semialdehyde reductase | [2] |
| 6 | 2.7.1.31 | glycerate kinase | ubiquitous | chloroplast | D-glycerate (ATP) | D-glycerate (ADP) | glycerate kinase | [3] |
| 8 | 4.1.2.17 | L-fuculose-phosphate aldolase | Escherichia coli | | dihydroxyacetone phosphate, glycolaldehyde | D-ribulose 1-phosphate | D-ribulose 1-phosphate aldolase | [4] |
| 12 | 1.1.1.26 | glyoxylate reductase | Arabidopsis thaliana | chloroplast | glycolate (NAD(P)) | glyoxylate (NAD(P)H) | glycolate dehydrogenase | [5] |
| 13 | 2.6.1.45 | serine-glyoxylate transaminase | Arabidopsis thaliana | peroxisome | L-serine, glyoxylate | Hydroxypyruvate, glycine | serine-glyoxylate transaminase | [6] |
| 14 | 2.1.2.1 | serine hydroxyl-methyltransferase | ubiquitous | mitochondria | methylene-THF, glycine | L-serine | serine hydroxymethyl-transferase | [7] |
| 16 | 6.3.4.3 | formate tetrahydrofolate ligase | ubiquitous | chloroplast | formate, THF (ATP) | formyl-THF (ADP, phosphate) | formate tetrahydrofolate ligase | [8] |
| 17 | 3.5.4.9 + 1.5.1.5 | methylene-tetrahydrofolate dehydrogenase & cyclohydrolase | ubiquitous | chloroplast | formyl-THF (NAD(P)H) | methylene-THF, H$_2$O (NAD(P)) | methylene-tetrahydrofolate dehydrogenase & cyclohydrolase | [8] |
| 18 | 1.1.1.81 | hydroxypyruvate reductase | ubiquitous | peroxisome | hydroxypyruvate (NAD(P)H) | glycerate (NAD(P)) | hydroxypyruvate reductase | [9] |
| 25 | 5.3.1.22 | hydroxypyruvate isomerase | Escherichia coli | | hydroxypyruvate | tartronate-semialdehyde | hydroxypyruvate isomerase | [10] |
| 30 | 5.4.2.7 | phosphopento-mutase | Escherichia coli | | D-ribose 1-phosphate | D-ribose 5-phosphate | D-ribose 1-phosphate mutase | [11] |
| 31 | 2.7.1.X | ADP-dependent #ribose-1-phosphate kinase | Thermococcus kodakarensis | | D-ribose 1-phosphate (ATP) | D-ribose 1,5-bisphosphate (ADP) | ADP-dependent ribose-1-phosphate kinase | [12] |
| 32 | 5.3.1.X | ribose-1,5-bisphosphate isomerase | Thermococcus kodakarensis | | D-ribose 1,5-bisphosphate | D-ribulose 1,5-bisphosphate | ribose-1,5-bisphosphate isomerase | [12] |
| 38 | 2.7.1.2 | glucokinase | ubiquitous | cytosol | D-glucose (ATP) | D-glucose 6-phosphate (ADP) | D-glucose 6-phosphate kinase | [13] |
| 39 | 5.3.1.9 | glucose-6-phosphate isomerase | ubiquitous | cytosol | D-glucose 6-phosphate | D-fructose 6-phosphate | glucose-6-phosphate isomerase | [14] |
| 46 | 2.7.1.4 | fructokinase | ubiquitous | cytosol | D-fructose (ATP) | D-fructose 6-phosphate (ADP) | D-fructose 6-phosphate kinase | [15] |

TABLE 2-continued

| Reaction/Enzyme no. | EC no. of enzyme to be employed | Enzyme to be employed | Examples for organisms | Natural plant localization | Substrate(s) | Product(s) | Enzymatic activity within the photorespiration bypass pathways | Ref. |
|---|---|---|---|---|---|---|---|---|
| 48 | 1.1.99.14 | glycolate oxidase | ubiquitous | peroxisome | glycolate, $O_2$ | glyoxylate, $H_2O_2$ | glycolate oxidase | [16] |
| 49 | 1.4.1.10 | glycine dehydrogenase | *Mycobacterium* sp. | | glyoxylate, $NH_3$, (NAD(P)H) | glycine, $H_2O$, (NAD(P)) | glycine dehydrogenase | [17] |
| 50 | 4.3.1.17 | L-serine ammonia-lyase | *Escherichia coli* | | L-serine | pyruvate, $NH_3$ | L-serine ammonia-lyase | [18] |
| 51 | 2.7.9.2 | pyruvate, water dikinase | *Escherichia coli* | | pyruvate, $H_2O$ (ATP) | PEP, phosphate, (AMP) | PEP synthetase | [19] |
| 52 | 4.2.1.11 | enolase | ubiquitous | plastid | PEP, $H_2O$ | D-glycerate 2-phosphate | PEP hydratase | [20] |
| 53 | 5.4.2.12 | phosphoglycerate mutase | ubiquitous | | D-glycerate 2-phosphate | D-glycerate 3-phosphate | phosphoglycerate mutase | [21] |
| 61 | 1.1.1.X | D-gluconate 5-dehydrogenase | *Gluconobacter oxydans* 621H | | D-gluconate | 5-keto D-gluconate | D-gluconate 5-dehydrogenase | [22] |
| 69 | 2.7.1.17 | D-xylulokinase | *Escherichia coli* | | D-xylulose (ATP) | D-xylulose 5-phosphate (ADP) | xylulokinase | [100] |
| 80 | 5.3.1.13 | D-arabinose 5-phosphate isomerase | ubiquitous | cytosol | D-arabinose 5-phosphate | D-ribulose 5-phosphate | Arabinose 5-phosphate isomerase | [23, 24] |
| 81 | 2.7.1.54 | D-arabinokinase | *Propionibacterium acidipropionici* | | D-arabinose | D-arabinose 5-phosphate | D-arabinokinase | [25] |
| 82 | 5.3.1.3 | D-arabinose isomerase | *Aeribacillus pallidus* | | D-arabinose | D-ribulose | arabinose isomerase | [26] |
| 83 | 2.7.1.47 | D-ribulokinase | *Escherichia coli* | | D-ribulose | D-ribulose 5-phosphate | D-ribulokinase | [27] |
| 94 | 2.7.1.4 | D-fructokinase | ubiquitous | chloroplast | D-fructose (ATP) | D-fructose 6-phosphate (ADP) | 6-fructokinase | [28] |
| 95 | 2.7.1.3 | ketohexokinase | *Homo sapiens* | | D-fructose (ATP) | D-fructose 1-phosphate (ADP) | 1-fructokinase | [29] |
| 96 | 2.7.1.56 | 1-phosphofructokinase | *Escherichia coli* | | D-fructose 1-phosphate (ATP) | D-fructose 1,6-bisphosphate (ADP) | 1-phosphofructokinase | [30] |
| 108 | 2.7.1.14 | D-sedoheptulokinase | *Mus musculus* | | D-sedoheptulose (ATP) | D-sedoheptulose 7-phosphate (ADP) | D-sedoheptulokinase | [31] |
| Z10 | 1.1.1.177 | glycerol-3-phosphate 1-dehydrogenase | *Archaeoglobus fulgidus* | | D-glyceraldehyde 3-phosphate | glycerol-1-phosphate | glycerol-3-phosphate 1-dehydrogenase | [32] |
| Z11 | 5.3.1.1 | triose-phosphate isomerase | ubiquitous | chloroplast | D-glyceraldehyde 3-phosphate | dihydroxyacetone phosphate | triose-phosphate isomerase | [33] |
| Z12 | 1.1.1.8/94 | glycerol-3-phosphate dehydrogenase | ubiquitous | cytosol | dihydroxyacetone phosphate | glycerol-1-phosphate | glycerol-3-phosphate 2-dehydrogenase | [34] |
| Z13 | 3.1.3.21 | glycerol-1-phosphatase | ubiquitous | cytosol | glycerol-1-phosphate | glycerol, phosphate | glycerol-1-phosphatase | [35] |
| Z14 | 1.1.1.6/156 | glycerol dehydrogenase | *Escherichia coli* | | glycerol | dihydroxyacetone | glycerol 2-dehydrogenase | [36] |
| Z15 | 1.1.1.21/72 | glycerol dehydrogenase | rabbit muscle | | glycerol | D-glyceraldehyde | glycerol 3-dehydrogenase | [36] |
| Z19 | 4.1.2.13 | fructose-bisphosphate aldolase | ubiquitous | chloroplast | D-sedoheptulose 1,7-bisphosphate | D-erythrose 4-phosphate, dihydroxyacetone phosphate | sedoheptulose-bisphosphate aldolase | [37] |
| Z20 | 3.1.3.37 | D-sedoheptulose 1,7-bisphosphatase | ubiquitous | chloroplast | D-sedoheptulose 1,7-bisphosphate | D-sedoheptulose 7-phosphate, phosphate | D-sedoheptulose 1,7-bisphosphate 1-phosphatase | [38] |

TABLE 3

| Reaction/Enzyme no. | EC no. of enzyme to be employed | Enzyme to be employed | Substrate(s) | Product(s) | Enzymatic activity within the photorespiration bypass pathways | Ref. |
|---|---|---|---|---|---|---|
| 2# | 6.2.1.17 | propionate-CoA ligase | glycolate, CoA (ATP)) | glycolyl-CoA (AMP, $PP_i$) | glycolate-CoA ligase | [39] |
| 3# | 6.4.1.3 | propionyl-CoA carboxylase or acyl-CoA carboxylase | glycolyl-CoA, $CO_2$ in form of bicarbonate (ATP) | tartronyl-CoA (ADP, phosphate) | glycolyl-CoA carboxylase | [40] |
| 4# | 1.2.1.75 | malonyl-CoA reductase | tartronyl-CoA (NAD(P)H) | tartronate semialdehyde (NAD(P)) | tartronyl-CoA reductase | [41] |

TABLE 3-continued

| Reaction/ Enzyme no. | EC no. of enzyme to be employed | Enzyme to be employed | Substrate(s) | Product(s) | Enzymatic activity within the photorespiration bypass pathways | Ref. |
|---|---|---|---|---|---|---|
| 7# | 1.2.1.10 | acetaldehyde dehydrogenase (acylating) | glycolyl-CoA (NAD(P)H) | glycolaldehyde, CoA (NAD(P)) | glycolaldehyde dehydrogenase (acylating) | [42, 43] |
| 9# | 2.7.1.56/ 2.7.1.16 | 1-phosphofructokinase or ribulokinase | D-ribulose 1-phosphate (ATP) | D-ribulose 1,5-bisphosphate (ADP) | 1-phosphoribulokinase | [30, 44] |
| 10# | 4.1.2.X | various aldolases (e.g., fructose 6-phosphate aldolase and/or xylulose 1-phosphate aldolase) | 2 glycolaldehyde | D-erythrose | D-erythrose aldolase | [45] |
| 11# | 2.7.1.29 | dihydroxyacetone kinase | D-erythrose (ATP) | D-erythrose 4-phosphate (ADP) | D-erythrose kinase | [46] |
| 15# | 1.1.99.33 | formate dehydrogenase | $CO_2$ (NAD(P)H) | formate (NAD(P)) | carbon dioxide reductase | [47] |
| 19# | 2.7.2.1 | acetate kinase | glycolate (ATP) | glycolyl-phosphate (ADP) | glycolate 1-kinase | [48] |
| 20# | 1.2.1.12 | phosphorylating glyceraldehyde 3-phosphate dehydrogenase | glycolyl-phosphate (NAD(P)H) | glycolaldehyde, phosphate (NAD(P)) | glycolaldehyde dehydrogenase (phosphorylating) | [49-51] |
| 21# | 2.3.1.8 | phosphate acetyltransferase | glycolyl-phosphate, CoA | glycolyl-CoA, phosphate | phosphate glycolyltransferase | [52] |
| 22# | 1.2.1.X | ATP- and NAD(P)H-dependent carboxylic acid reductase | glycolate (ATP, NAD(P)H) | glycolaldehyde (AMP, PPi, NAD(P)) | glycolate reductase | [53] |
| 23# | 2.7.2.3 | 3-phosphoglycerate kinase | 2-PG (ATP) | glycolate 1,2-bisphosphate (ADP) | phosphoglycolate kinase | [54-56] |
| 24# | 1.2.1.12 | phosphorylating glyceraldehyde 3-phosphate dehydrogenase | glycolate 1,2-bisphosphate (NAD(P)H) | glycolaldehyde 2-phosphate, phosphate (NAD(P)) | phosphoglycolaldehyde dehydrogenase (phosphorylating) | [49-51] |
| 26# | 6.4.1.1 | pyruvate carboxylase | glycolaldehyde, $CO_2$ in form of bicarbonate (ATP) | tartronate semialdehyde (ADP, phosphate) | glycolaldehyde carboxylase | [57] |
| 27# | 1.1.1.39 | malate dehydrogenase (decarboxylating) | glycolaldehyde, $CO_2$ (NAD(P)H) | glycerate (NADP) | glycerate dehydrogenase (decarboxylating) | [58] |
| 28# | 4.1.2.17 | L-fuculose-phosphate aldolase | glycolaldehyde 2-phosphate, dihydroxyacetone phosphate | D-ribulose 1,5-bisphosphate | D-ribuolse bisphosphate aldolase | [4, 59] |
| 29# | — | 5-methylthio-D-ribulose 1-phosphate 1,2-isomerase | D-ribulose 1-phosphate | D-ribose 1-phosphate | D-ribulose 1-phosphate 1,2-isomerase | [60] |
| 33# | — | 5-methylthio-D-ribulose 1-phosphate 1,3-isomerase | D-ribulose 1-phosphate | D-xylulose 5-phosphate | D-ribulose 1-phosphate 1,3-isomerase | [61, 62] |
| 34# | 4.1.2.X | various aldolases | glycolaldehyde, D-glyceraldehyde 3-phosphate | D-ribose 5-phosphate | D-ribose 5-phosphate aldolase | [63] |
| 35# | 4.1.2.X | various aldolases | glycolaldehyde, glycolaldehyde 2-phosphate | D-erythrose 4-phosphate | D-erythrose 4-phosphate aldolase | [45] |
| 36# | 4.1.2.X | various aldolases | D-erythrose, glycolaldehyde | D-glucose | D-glucose aldolase | [45] |
| 37# | 4.1.2.X | various aldolases | D-erythrose 4-phosphate, D-erythrose 4-phosphate | D-glucose 6-phosphate | D-glucose 6-phosphate aldolase | [45] |
| 40# | 4.1.1.X | transketolase, pyruvate decarboxylase or other thiamine dependent enzymes | 2 glycolaldehyde | D-erythrulose | D-erythrulose synthetase | [64-66] |
| 41# | 5.3.1.X | Various sugar isomerases; e.g. glucose isomerase | D-erythrulose | D-erythrose | D-erythrose isomerase | [67] |
| 42# | 2.7.1.X | Various sugar kinases | D-erythrulose | D-erythrulose 4-phosphate | D-erythrulose kinase | [68] |
| 43# | 4.1.1.X | pyruvate decartboxylase and other thiamine dependent enzymes | glycolaldehyde 2-phosphate, glycolaldehyde | D-erythrulose 4-phosphate | D-erythrulose 4-phosphate synthetase | [64-66] |
| 44# | 5.3.1.X | Various sugar isomerases | D-erythrulose 4-phosphate | D-erythrose 4-phosphate | D-erythrose 4-phosphate isomerase | [69] |
| 45# | 4.1.1.X | transketolase, pyruvate decarboxylase or other thiamine dependent enzymes | D-erythrose, glycolaldehyde | D-fructose | D-fructose synthetase | [64-66] |
| 47# | 4.1.1.X | transketolase, pyruvate decarboxylase or other thiamine dependent enzymes | D-erythrose 4-phosphate, glycolaldehyde | D-fructose 6-phosphate | D-fructose 6-phosphate synthetase | [64-66] |
| 54# | 2.3.1.54 | pyruvate formate lyase | glycolyl-CoA, formate | hydroxypyruvate | hydroxypyruvate formate lyase | [70, 71] |
| 55# | 1.2.7.1 | pyruvate synthase | glycolyl-CoA, $CO_2$ (2 reduced ferredoxin) | Hydroxypyruvate (2 oxidized ferredoxin) | hydroxypyruvate synthase | [72] |
| 56# | 2.3.1.9 | acetyl-CoA C-acetyltransferase | 2 glycolyl-CoA | 2,4-dihydroxy-3-oxo butyryl-CoA | glycolyl-CoA C-glycolyltransferase | [73] |

TABLE 3-continued

| Reaction/ Enzyme no. | EC no. of enzyme to be employed | Enzyme to be employed | Substrate(s) | Product(s) | Enzymatic activity within the photorespiration bypass pathways | Ref. |
|---|---|---|---|---|---|---|
| 57# | 1.1.1.X | various secondary-alcohol dehydrogenases | 2,4-dihydroxy-3-oxo butyryl-CoA | 2,3,4-trihydroxy butyryl-CoA | 2,3,4-trihydroxybutyryl-CoA dehydrogenase | [74] |
| 58# | 1.2.1.X | various aldehyde dehydrogenases (acylating) | 2,3,4-trihydroxy butyryl-CoA | D-erythrose | D-erythrose dehydrogenase | [42, 43] |
| 59# | 4.1.2.X | various aldolases | glycolyl-CoA, D-erythrose 4-phosphate | gluconyl-CoA | gluconyl-CoA aldolase | [45] |
| 60# | 3.1.2.X | various acyl-CoA hydrolases | gluconyl-CoA | Gluconate, CoA | gluconyl-CoA hydrolase | [75] |
| 62# | 4.1.2.X | various aldolases | Gluconate (NAD(P)) | 5-dehydrogluconate, (NAD(P)H) | 5-dehydro-gluconate aldolase | [45] |
| 63# | 1.1.1.X | various secondary-alcohol and sugar dehydrogenases | gluconyl-CoA (NAD(P)) | 5-dehydro gluconyl-CoA (NAD(P)H) | gluconyl-CoA 5-dehydrogenase | [74] |
| 64# | 3.1.2.X | various acyl-CoA hydrolases | 5-dehydro gluconyl-CoA | 5-dehydrogluconate, CoA | 5-dehydro-gluconyl-CoA hydrolase | [75] |
| 65# | 2.3.1.9 | acetyl-CoA C-acetyltransferase | 2,4-dihydroxy-3-oxo butyryl-CoA, glycolyl-CoA | 2,4,6-trihydroxy-3,5-oxo hexanoyl-CoA | 2,4-dihydroxy-3-oxo butyryl-CoA C-glycolyltransferase | [73] |
| 66# | 1.1.1.X | various secondary-alcohol and sugar dehydrogenases | 2,4,6-trihydroxy-3,5-oxo hexanoyl-CoA (NAD(P)H) | 5-dehydro gluconyl-CoA, (NADP) | 5-dehydro gluconyl-CoA dehydrogenase | [74] |
| 67# | 2.2.1.2 | transaldolase | glycolaldehyde, D-fructose 6-phosphate | D-xylulose, D-glyceraldehyde 3-phosphate | transaldolase with glycolaldehyde (acceptor) and D-fructose 6-phosphate (donor) | [76] |
| 68# | 2.2.1.2 | transaldolase | glycolaldehyde phosphate, D-fructose 6-phosphate | D-xylulose 5-phosphate, D-glyceraldehyde 3-phosphate | transaldolase with glycolaldehyde phosphate (acceptor) and D-fructose 6-phosphate (donor) | [76] |
| 70# | 2.2.1.2 | transaldolase | glycolaldehyde, D-sedoheptulose 7-phosphate | D-xylulose, D-erythrose 4-phosphate | transaldolase with glycolaldehyde (acceptor) and D-sedoheptulose 7-phosphate (donor) | [76] |
| 71# | 2.2.1.2 | transaldolase | glycolaldehyde phosphate, D-sedoheptulose 7-phosphate | D-xylulose 5-phosphate, D-erythrose 4-phosphate | transaldolase with glycolaldehyde phosphate (acceptor) and D-sedoheptulose 7-phosphate (donor) | [76] |
| 72# | 2.2.1.1 | transketolase | glycolaldehyde, D-xylulose 5-phosphate | D-erythrulose or L-erythrulose, D-glyceraldehyde 3-phosphate | transketolase with glycolaldehyde (acceptor) and D-xylulose 5-phosphate (donor) | [77] |
| 73# | 2.2.1.1 | transketolase | glycolaldehyde, D-fructose 6-phosphate | D-erythrulose or L-erythrulose, D-erythrose 4-phosphate | transketolase with glycolaldehyde (acceptor) and D-fructose 6-phosphate (donor) | [77] |
| 74# | 2.2.1.1 | transketolase | glycolaldehyde, D-sedoheptulose 7-phosphate | D-erythrulose or L-erythrulose, D-ribose 5-phosphate | transketolase with glycolaldehyde (acceptor) and D-fructose 6-phosphate (donor) | [77] |
| 75# | 2.2.1.1 | transketolase | glycolaldehyde, D-xylulose 5-phosphate | D-erythrulose 4-phosphate or L-erythrulose 4-phosphate, D-glyceraldehyde 3-phosphate | transketolase with glycolaldehyde phosphate (acceptor) and D-xylulose 5-phosphate (donor) | [77] |
| 76# | 2.2.1.1 | transketolase | glycolaldehyde phosphate, D-fructose 6-phosphate | D-erythrulose 4-phosphate or L-erythrulose 4-phosphate, D-erythrose 4-phosphate | transketolase with glycolaldehyde phosphate (acceptor) and D-fructose 6-phosphate (donor) | [77] |
| 77# | 2.2.1.1 | transketolase | glycolaldehyde phosphate, D-sedoheptulose 7-phosphate | D-erythrulose 4-phosphate or L-erythrulose 4-phosphate, D-ribose 5-phosphate | transketolase with glycolaldehyde phosphate (acceptor) and D-fructose 6-phosphate (donor) | [77] |
| 78# | 4.1.2.X | D-fructose 6-phosphate aldolase | glycolaldehyde, D-glyceraldehyde 3-phosphate | D-arabinose 5-phosphate | D-arabinose 5-phosphate aldolase | [78, 79] |
| 79# | 4.1.2.X | D-fructose 6-phosphate aldolase | glycolaldehyde, D-glyceraldehyde | D-arabinose | D-arabinose aldolase | [79, 80] |
| 84# | 4.1.2.X | Various aldolases (e.g., D-fructose 6-phosphate aldolase) | glycolaldehyde, D-glyceraldehyde 3-phosphate | D-aldopentose 5-phosphate | D-aldopentose 5-phosphate aldolase | [78, 79] |
| 85# | 4.1.2.X | Various aldolases (e.g., D-fructose 6-phosphate aldolase) | glycolaldehyde, D-glyceraldehyde | D-aldopentose | D-aldopentose aldolase | [79, 80] |

TABLE 3-continued

| Reaction/ Enzyme no. | EC no. of enzyme to be employed | Enzyme to be employed | Substrate(s) | Product(s) | Enzymatic activity within the photorespiration bypass pathways | Ref. |
|---|---|---|---|---|---|---|
| 86# | 5.3.1.X/ 5.1.3.X | Various phosphosugars isomerases and epimerases | D-aldopentose 5-phosphate | D-ribulose 5-phosphate/D-xylulose 5-phosphate/D-ribose 5-phosphate | D-aldopentose 5-phosphate isomerase/epimerase | [81, 82] |
| 87# | 2.7.1.X | Various sugar kinases | D-aldopentose (ATP) | D-aldopentose 5-phosphate (ADP) | D-aldopentose kinase | [68] |
| 88# | 5.3.1.X/ 5.1.3.X | Various sugars isomerases and epimerases | D-aldopentose | D-ribulose/D-xylulose/D-ribose | D-aldopentose isomerase/epimerase | [81, 82] |
| 89# | 4.1.2.X | Various aldolases (e.g., D-fructose 6-phosphate aldolase) | glycolaldehyde, D-aldotetrose 4-phosphate | D-aldohexose 6-phosphate | D-aldohexose 6-phosphate aldolase | [78, 79] |
| 90# | 4.1.2.X | Various aldolases (e.g., D-fructose 6-phosphate aldolase) | glycolaldehyde, D-aldotetrose | D-aldohexose | D-aldohexose aldolase | [79, 80] |
| 91# | 5.3.1.X | Various phosphosugars isomerases | D-aldohexose 6-phosphate | D-fructose 6-phosphate | D-aldohexose 6-phosphate isomerase | [81, 82] |
| 92# | 2.7.1.X | Various sugar kinases | D-aldohexose (ATP) | D-aldohexose 6-phosphate (ADP) | D-aldohexose kinase | [68] |
| 93# | 5.3.1.X | Various sugars isomerases | D-aldohexose | D-fructose | D-aldohexose isomerase | [81, 82] |
| 97# | 2.2.1.2 | transketolase | glycolaldehyde, D-glyceraldehyde 3-phosphate | D-xylulose 5-phosphate | transketolase with glycolaldehyde (donor) and D-glyceraldehyde 3-phosphate (acceptor) | [64] |
| 98# | 2.2.1.2 | transketolase | glycolaldehyde, D-glyceraldehyde | D-xylulose | transketolase with glycolaldehyde (donor) and D-glyceraldehyde (acceptor) | [64] |
| 99# | 2.2.1.2 | transketolase | glycolaldehyde, D-glyceraldehyde 3-phosphate | D-ribulose 5-phosphate | transketolase with glycolaldehyde (donor) and D-glyceraldehyde 3-phosphate (acceptor) | [64] |
| 100# | 2.2.1.2 | transketolase | glycolaldehyde, D-glyceraldehyde | D-ribulose | transketolase with glycolaldehyde (donor) and D-glyceraldehyde (acceptor) | [64] |
| 101# | 2.2.1.2 | transketolase | glycolaldehyde, D-aldotetrose 4-phosphate | D-ketohexose 6-phosphate | transketolase with glycolaldehyde (donor) and D-aldotetrose 4-phosphate (acceptor) | [64] |
| 102# | 2.2.1.2 | transketolase | glycolaldehyde, D-aldotetrose | D-ketohexose | transketolase with glycolaldehyde (donor) and D-aldotetrose (acceptor) | [64] |
| 103# | 4.1.2.X | Various aldolases (e.g., D-fructose 6-phosphate aldolase) | glycolaldehyde, D-aldopentose 4-phosphate | D-aldohexose 6-phosphate | D-aldoheptose 7-phosphate aldolase | [78, 79] |
| 104# | 4.1.2.X | Various aldolases (e.g., D-fructose 6-phosphate aldolase) | glycolaldehyde, D-tetrose | D-aldohexose | D-aldoheptose aldolase | [79, 80] |
| 105# | 5.3.1.X | Various phosphosugars isomerases and epimerases | D-aldoheptose 7-phosphate | D-sedoheptulose 7-phosphate | D-aldoheptose 7-phosphate isomerase | [81, 82] |
| 106# | 2.7.1.X | Various sugar kinases | D-aldoheptose (ATP) | D-aldoheptose 7-phosphate (ADP) | D-aldoheptose kinase | [68] |
| 107# | 5.3.1.X | Various sugars isomerases and epimerases | D-aldoheptose | D-sedoheptulose | D-aldoheptose isomerase | [81, 82] |
| 109# | 4.1.2.X | Various aldolases | dihydroxyacetone phosphate, glycolaldehyde | D-xylulose 1-phosphate | D-xylulose 1-phosphate aldolase | [45] |
| 110# | 4.1.2.X | Various aldolases | dihydroxyacetone, glycolaldehyde | D-xylulose | D-xylulose aldolase | [45] |
| 111# | 4.1.2.X | Various aldolases | dihydroxyacetone, | D-ribulose | D-ribulose aldolase | [4, 59] |
| 112# | 4.1.2.43 | 3-hexulose-6-phosphate synthase | glycolaldehyde, D-ribulose 5-phosphate | 4-heptulose 7-phosphate | 4-heptulose 7-phosphate synthase | [83] |
| 113# | 3.1.3.X | Various phosphatases | D-ribulose 1-phosphate | D-ribulose, phosphate | D-ribulose 1-phosphatase | [84] |
| 114# | 5.1.3.X | Various epimerases | D-xylulose-1-phosphate | D-ribulose-1-phosphate | D-ribulose-1-phosphate 3-epimerase | [85] |
| 115# | 3.1.3.X | Various phosphatases | D-xylulose 1-phosphate | D-xylulose (phosphate) | D-xylulose 1-phosphatase | [84] |
| 116# | 5.3.1.X | Various isomerases (e.g., 3-hexulose-6-phosphate isomerase) | 4-heptulose 7-phosphate | D-Sedoheptulose 7-phosphate | 4-heptulose 7-phosphate isomerases | [86] |
| 117# | 4.1.2.17 | L-fuculose-phosphate aldolase | glycolaldehyde 2-phosphate, dihydroxyacetone | D-ribulose 5-phosphate | D-ribuolse 5-phosphate aldolase | [4, 59] |

TABLE 3-continued

| Reaction/ Enzyme no. | EC no. of enzyme to be employed | Enzyme to be employed | Substrate(s) | Product(s) | Enzymatic activity within the photorespiration bypass pathways | Ref. |
|---|---|---|---|---|---|---|
| 118# | 4.1.2.X | Various aldolases | glycolaldehyde 2-phosphate, dihydroxyacetone | D-xylulose 5-phosphate | D-xylulose 5-phosphate aldolase | [45] |
| 119# | 4.1.2.X | various aldolases | 2 glycolaldehyde | D-erythrose or L-erythrose | (D-erythrose or L-erythrose) aldolase | [45] |
| 120# | 4.1.2.X | various aldolases (e.g., D-fructose 6-phosphate aldolase) | 2 glycolaldehyde | D-threose or L-threose | (D-threose or L-threose) aldolase | [45, 78] |
| 121# | 4.1.1.X | transketolase, pyruvate decarboxylase or other thiamine dependent enzymes | 2 glycolaldehyde | D-erythrulose or L-erythrulose | (D-erythrulose or L-erythrulose) synthetase | [64-66] |
| 122# | 4.1.2.X | various aldolases | 2 glycolaldehyde | D-erythrose 4-phosphate or L-erythrose 4-phosphate | (D-erythrose 4-phosphate or L-erythrose 4-phosphate) aldolase | [45] |
| 123# | 4.1.2.X | various aldolases (e.g., D-fructose 6-phosphate aldolase) | 2 glycolaldehyde | D-threose 4-phosphate or L-threose 4-phosphate | (D-threose 4-phosphate or L-threose 4-phosphate) aldolase | [45, 78] |
| 124# | 4.1.1.X | transketolase, pyruvate decarboxylase or other thiamine dependent enzymes | 2 molecules glycolaldehyde | D-erythrulose 4-phosphate or L-erythrulose 4-phosphate | (D-erythrulose 4-phosphate or L-erythrulose 4-phosphate) synthetase | [64-66] |
| 125# | 1.2.1.X | various aldehyde dehydrogenases (acylating) | 2,3,4-trihydroxy butyryl-CoA | D-erythrose or L-erythrose or D-threose or L-threose | (D-erythrose or L-erythrose or D-threose or L-threose) dehydrogenase | [42, 43] |
| 126# | 4.1.3.X | various lyases | glycolyl-CoA, D-glyceraldehyde 3-phosphate | 2,3,4,5-tetrahydroxy-pentanoyl-CoA 5-phosphate | 2,3,4,5-tetrahydroxy-pentanoyl-CoA 5-phosphate lyase | [87] |
| 127# | 4.1.3.X | various lyases | glycolyl-CoA, D-glyceraldehyde | 2,3,4,5-tetrahydroxy-pentanoyl-CoA | 2,3,4,5-tetrahydroxy-pentanoyl-CoA lyase | [87] |
| 128# | 1.2.1.X | various aldehyde dehydrogenases (acetylating) | 2,3,4,5-tetrahydroxy-pentanoyl-CoA 5-phosphate (NAD(P)H) | D-aldopentose 5-phosphate (NAD(P), CoA) | 2,3,4,5-tetrahydroxy-pentanoyl-CoA 5-phosphate reductase | [88] |
| 129# | 2.7.1.X | various kinases | 2,3,4,5-tetrahydroxy-pentanoyl-CoA (ADP) | 2,3,4,5-tetrahydroxy-pentanoyl-CoA 5-phosphate (ADP) | 2,3,4,5-tetrahydroxy-pentanoyl-CoA kinase | [68] |
| 130# | 1.2.1.X | various aldehyde dehydrogenases (acetylating) | 2,3,4,5-tetrahydroxy-pentanoyl-CoA (NAD(P)H) | D-aldopentose (NAD(P), CoA) | 2,3,4,5-tetrahydroxy-pentanoyl-CoA reductase | [88] |
| 131# | 4.1.3.X | various lyases | glycolyl-CoA, D-aldotetrose 4-phosphate | 2,3,4,5,6-pentahydroxy-hexanoyl-CoA 6-phosphate | 2,3,4,5,6-pentahydroxy-hexanoyl-CoA 6-phosphate lyase | [87] |
| 132# | 4.1.3.X | various lyases | glycolyl-CoA, D-aldotetrose | 2,3,4,5,6-pentahydroxy-hexanoyl-CoA | 2,3,4,5,6-pentahydroxy-hexanoyl-CoA lyase | [87] |
| 133# | 1.2.1.X | various aldehyde dehydrogenases (acetylating) | 2,3,4,5,6-pentahydroxy-hexanoyl-CoA (NAD(P)H) | D-aldohexose 6-phosphate (NAD(P), CoA) | 2,3,4,5,6-pentahydroxy-hexanoyl-CoA reductase | [88] |
| 134# | 2.7.1.X | various kinases | 2,3,4,5,6-pentahydroxy-hexanoyl-CoA (ATP) | 2,3,4,5,6-pentahydroxy-hexanoyl-CoA 6-phosphate (ADP) | 2,3,4,5,6-pentahydroxy-hexanoyl-CoA kinase | [68] |
| 135# | 1.2.1.X | various aldehyde dehydrogenases (acetylating) | 2,3,4,5,6-pentahydroxy-hexanoyl-CoA (NAD(P)H) | D-aldohexose (NAD(P), CoA) | 2,3,4,5,6-pentahydroxy-hexanoyl-CoA reductase | [88] |
| 136# | 4.1.3.X | various lyases | glycolyl-CoA, glycolaldehyde phosphate | 2,3,4-trihydroxy-butyryl-CoA 4-phosphate | 2,3,4-trihydroxy-butyryl-CoA 4-phosphate lyase | [87] |
| 137# | 4.1.3.X | various lyases | glycolyl-CoA, glycolaldehyde | 2,3,4-trihydroxy-butyryl-CoA | 2,3,4-trihydroxy-butyryl-CoA lyase | [87] |
| 138# | 1.2.1.X | various aldehyde dehydrogenases (acetylating) | 2,3,4-trihydroxy-butyryl-CoA (NAD(P)H) | D-aldotetrose 4-phosphate (NAD(P), CoA) | 2,3,4-trihydroxy-butyryl-CoA reductase | [88] |
| 139# | 2.7.1.X | various kinases | 2,3,4-trihydroxy-butyryl-CoA (ATP) | 2,3,4-trihydroxy-butyryl-CoA 4-phosphate (ADP) | 2,3,4-trihydroxy-butyryl-CoA kinase | [68] |
| 140# | 2.3.1.X | Thiamine-dependent dehydrogenase condensing glycolyl-CoA as an acceptor (e.g., evolved acetoin dehydrogenase complex) | glycolyl-CoA, D-glyceraldehyde 3-phosphate (NAD(P)H) | D-xylulose 5-phosphate (NAD(P), CoA) | D-xylulose 5-phosphate dehydrogenase complex | [89] |

TABLE 3-continued

| Reaction/ Enzyme no. | EC no. of enzyme to be employed | Enzyme to be employed | Substrate(s) | Product(s) | Enzymatic activity within the photorespiration bypass pathways | Ref. |
|---|---|---|---|---|---|---|
| 141# | 2.3.1.X | Thiamine-dependent dehydrogenase condensing glycolyl-CoA as an acceptor (e.g., evolved acetoin dehydrogenase complex) | glycolyl-CoA, D-glyceraldehyde (NAD(P)H) | D-xylulose (NAD(P), CoA) | D-xylulose dehydrogenase complex | [89] |
| 142# | 2.3.1.X | Thiamine-dependent dehydrogenase condensing glycolyl-CoA as an acceptor (e.g., evolved acetoin dehydrogenase complex) | glycolyl-CoA, D-glyceraldehyde 3-phosphate (NAD(P)H) | D-ribulose 5-phosphate (NAD(P), CoA) | D-ribulose 5-phosphate dehydrogenase complex | [89] |
| 143# | 2.3.1.X | Thiamine-dependent dehydrogenase condensing glycolyl-CoA as an acceptor (e.g., evolved acetoin dehydrogenase complex) | glycolyl-CoA, D-glyceraldehyde (NAD(P)H) | D-ribulose (NAD(P), CoA) | D-ribulose dehydrogenase complex | [89] |
| 144# | 2.3.1.X | Thiamine-dependent dehydrogenase condensing glycolyl-CoA as an acceptor (e.g., evolved acetoin dehydrogenase complex) | glycolyl-CoA, D-aldotetrose 4-phosphate (NAD(P)H) | D-ketohexose 6-phosphate (NAD(P), CoA) | D-ketohexose 6-phosphate dehydrogenase complex | [89] |
| 145# | 2.3.1.X | Thiamine-dependent dehydrogenase condensing glycolyl-CoA as an acceptor (e.g., evolved acetoin dehydrogenase complex) | glycolyl-CoA, D-aldotetrose (NAD(P)H) | D-ketohexose (NAD(P), CoA) | D-ketohexose dehydrogenase complex | [89] |
| 146# | 2.3.1.X | Thiamine-dependent dehydrogenase condensing glycolyl-CoA as an acceptor (e.g., evolved acetoin dehydrogenase complex) | glycolyl-CoA, D-aldopntose 5-phosphate (NAD(P)H) | D-ketoheptose 7-phosphate (NAD(P), CoA) | D-ketoheptose 7-phosphate dehydrogenase complex | [89] |
| 147# | 2.3.1.X | Thiamine-dependent dehydrogenase condensing glycolyl-CoA as an acceptor (e.g., evolved acetoin dehydrogenase complex) | glycolyl-CoA, D-aldopntose (NAD(P)H) | D-ketoheptose (NAD(P), CoA) | D-ketoheptose dehydrogenase complex | [89] |
| 148# | 2.3.1.X | Thiamine-dependent dehydrogenase condensing glycolyl-CoA as an acceptor (e.g., evolved acetoin dehydrogenase complex) | glycolyl-CoA, glycolaldehyde phosphate (NAD(P)H) | D/L-erythrulose 4-phosphate (NAD(P), CoA) | D/L-erythrulose 4-phosphate dehydrogenase complex | [89] |
| 149# | 2.3.1.X | Thiamine-dependent dehydrogenase condensing glycolyl-CoA as an acceptor (e.g., evolved acetoin dehydrogenase complex) | glycolyl-CoA, glycolaldehyde (NAD(P)H) | D-D/L-erythrulose (NAD(P), CoA) | D/L-erythrulose dehydrogenase complex | [89] |
| Z1# | 4.1.2.X | various aldolases | D-ketohexose 1,6-bisphosphate | D-glyceraldehyde 3-phosphate, dihydroxyacetone phosphate | D-ketohexose 1,6-bisphosphate aldolase | [90, 91] |
| Z2# | 3.1.3.X | various phosphatases | D-ketohexose 1,6-bisphosphate | D-ketohexose 1-phosphate, phosphate | D-ketohexose 1,6-bisphosphate 6-phosphatase | [84] |
| Z3# | 3.1.3.X | various phosphatases | D-ketohexose 1,6-bisphosphate | D-ketohexose 6-phosphate, phosphate | D-ketohexose 1,6-bisphosphate 1-phosphatase | [84] |
| Z4# | 5.4.2.X | various mutases | D-ketohexose 1-bisphosphate | D-ketohexose 6-bisphosphate | phosphohexomutase | [92] |
| Z5# | 3.1.3.X | various phosphatases | D-ketohexose 1-phosphate | D-ketohexose, phosphate | D-ketohexose 1-phosphatase | [84] |
| Z6# | 3.1.3.X | various phosphatases | D-ketohexose 6-phosphate | D-ketohexose, phosphate | D-ketohexose 6-phosphatase | [84] |
| Z7# | 4.1.2.X | various aldolases | D-ketohexose 1-phosphatase | dihydroxyacetone phosphate, D-glyceraldehyde | D-ketohexose 1-phosphatase aldolase | [90, 91] |
| Z8# | 4.1.2.X | various aldolases | D-ketohexose 6-phosphatase | dihydroxyacetone, D-glyceraldehyde 3-phosphate | D-ketohexose 6-phosphatase aldolase | [90, 91] |
| Z9# | 4.1.2.X | various aldolases | D-ketohexose | dihydroxyacetone, D-glyceraldehyde | D-ketohexose aldolase | [90, 91] |
| Z16# | 5.3.1.X | various sugar isomerases | D-glyceraldehyde | dihydroxyacetone | triose isomerase | [81, 82] |
| Z17# | 3.1.3.X | various phosphatases | D-glyceraldehyde 3-phosphate | D-glyceraldehyde, phosphate | D-glyceraldehyde 3-phosphatase | [84] |
| Z18# | 3.1.3.X | various phosphatases | dihydroxyacetone phosphate | dihydroxyacetone, phosphate | dihydroxyacetone phosphatase | [84] |

TABLE 3-continued

| Reaction/ Enzyme no. | EC no. of enzyme to be employed | Enzyme to be employed | Substrate(s) | Product(s) | Enzymatic activity within the photorespiration bypass pathways | Ref. |
|---|---|---|---|---|---|---|
| Z21# | 3.1.3.X | various phosphatases | D-sedoheptulose 1,7-bisphosphate | D-sedoheptulose 1-phosphate, phosphate | D-sedoheptulose 1,7-bisphosphate 7-phosphatase | [84] |
| Z22# | 3.1.3.X | various phosphatases | D-sedoheptulose 7-phosphate | D-sedoheptulose, phosphate | D-sedoheptulose 7-phosphatase | [84] |
| Z23# | 4.1.2.X | various aldolases | D-sedoheptulose 7-phosphate | D-erythrose 4-phosphate, dihydroxyacetone | D-sedoheptulose 7-phosphate aldolase | [93] |
| Z24# | 3.1.3.X | various phosphatases | D-erythrose 4-phosphate | D-erythrose, phosphate | D-erythrose 4-phosphatase | [84] |
| Z25# | 4.1.2.X | various aldolases | D-sedoheptulose | D-erythrose, dihydroxyacetone | D-sedoheptulose aldolase | [93] |
| Z26# | 3.1.3.X | various phosphatases | D-sedoheptulose 1-phosphate | D-sedoheptulose, phosphate | D-sedoheptulose 1-phosphatase | [84] |
| Z27# | 4.1.2.X | various aldolases | D-sedoheptulose 1-phosphate | D-erythrose, dihydroxyacetone phosphate | D-sedoheptulose 1-phosphate aldolase | [45] |
| Z28# | 5.1.3.X | various sugar epimerases | D-erythrose 4-phosphate or L-erythrose 4-phosphate | D-threose 4-phosphate or L-threose 4-phosphate | (D-erythrose or L-erythrose) 4-phosphate epimerase | [69] |
| Z29# | 5.3.1.X | various sugar isomerases | D-erythrose 4-phosphate or L-erythrose 4-phosphate | D-erythrulose 4-phosphate or L-erythrulose 4-phosphate | (D-erythrose or L-erythrose) 4-phosphate isomerase | [69] |
| Z30# | 5.3.1.X | various sugar isomerases | D-threose 4-phosphate or L-threose 4-phosphate | D-erythrulose 4-phosphate or L-erythrulose 4-phosphate | (D-threose or L-threose) 4-phosphate isomerase | [69] |
| Z31# | 5.1.3.X | various sugar epimerases | D-erythrose or L-erythrose | D-threose or L-threose | (D-erythrose or L-erythrose) epimerase | [81, 82] |
| Z32# | 5.3.1.X | various sugar isomerases | D-erythrose or L-erythrose | D-erythrulose or L-erythrulose | (D-erythrose or L-erythrose) isomerase | [81, 82] |
| Z33# | 5.3.1.X | various sugar isomerases | D-threose or L-threose | D-erythrulose or L-erythrulose | (D-threose or L-threose) isomerase | [81, 82] |
| Z34# | 1.1.1.X | various alcohol-sugar dehydrogenases | D-erythrose or L-erythrose 4-phosphate | erythritol 4-phosphate | (D-erythrose or L-erythrose) 4-phosphate reductase | [94-96] |
| Z35# | 1.1.1.X | various alcohol-sugar dehydrogenases | D-threose 4-phosphate or L-threose 4-phosphate | D-threitol 4-phosphate or L-threitol 4-phosphate | (D-threose or L-threose) 4-phosphate reductase | [94-96] |
| Z36# | 1.1.1.X | various alcohol-sugar dehydrogenases | D-erythrulose 4-phosphate or L-erythrulose 4-phosphate | erythritol 4-phosphate | (D-erythrulose or L-erythrulose) 4-phosphate reductase (erythritol 4-phosphate forming) | [94-96] |
| Z37# | 1.1.1.X | various alcohol-sugar dehydrogenases | D-erythrulose 4-phosphate or L-erythrulose 4-phosphate | D-threitol 4-phosphate or L-threitol 4-phosphate | (D-erythrulose or L-erythrulose) 4-phosphate reductase (D-threitol or L-threitol 4-phosphate forming) | [94-96] |
| Z38# | 5.1.3.X | various sugar epimerases | erythritol 4-phosphate | D-threitol 4-phosphate or L-threitol 4-phosphate | erythritol 4-phosphate epimerase | [97] |
| Z39# | 1.1.1.X | various alcohol-sugar dehydrogenases | D-erythrose or L-erythrose | erythritol | (D-erythrose or L-erythrose) reductase | [94-96] |
| Z40# | 1.1.1.X | various alcohol-sugar dehydrogenases | D-threose or L-threose | D-threitol or L-threitol | (D-threose or L-threose) reductase | [94-96] |
| Z41# | 1.1.1.X | various alcohol-sugar dehydrogenases | D-erythrulose or L-erythrulose | erythritol | (D-erythrulose or L-erythrulose) reductase (erythritol forming) | [94-96] |
| Z42# | 1.1.1.X | various alcohol-sugar dehydrogenases | D-erythrulose or L-erythrulose | D-threitol or L-threitol | (D-erythrulose or L-erythrulose) reductase (D-threitol or L-threitol forming) | [94-96] |
| Z43# | 5.1.3.X | various sugar epimerases | erythritol | D-threitol or L-threitol | erythritol epimerase | [97] |
| Z44# | 2.7.1.X | various sugar kinases | D-erythrose or L-erythrose (ATP) | D-erythrose 4-phosphate or L-erythrose 4-phosphate (ADP) | (D-erythrose or L-erythrose) kinase | [46, 68, 98] |
| Z45# | 2.7.1.X | various sugar kinases | D-threose or L-threose (ATP) | D-threose 4-phosphate or L-threose 4-phosphate (ADP) | (D-threose or L-threose) kinase | [68] |
| Z46# | 2.7.1.X | various sugar kinases | D-erythrulose or L-erythrulose (ATP) | D-erythrulose 4-phosphate or L-erythrulose 4-phosphate (ADP) | (D-erythrulose or L-erythrulose) kinase | [46, 68, 99] |
| Z47# | 2.7.1.X | various sugar kinases | erythritol (ATP) | Erythritol 4-phosphate (ADP) | erythritol kinase | [68] |

TABLE 3-continued

| Reaction/ Enzyme no. | EC no. of enzyme to be employed | Enzyme to be employed | Substrate(s) | Product(s) | Enzymatic activity within the photorespiration bypass pathways | Ref. |
| --- | --- | --- | --- | --- | --- | --- |
| Z48# | 2.7.1.X | various sugar kinases | D-threitol or L-threitol (ATP) | D-threitol 4-phosphate or L-threitol 4-phosphate (ADP) | (D-threitol or L-threitol) kinase | [68] |

REFERENCES LISTED IN TABLE 2 AND TABLE 3

1. Hardy P, Baldy P (1986) Corn phosphoglycolate phosphatase: purification and properties. Planta 168: 245-252.
2. Njau R K, Herndon C A, Hawes J W (2000) Novel beta-hydroxyacid dehydrogenases in *Escherichia coli* and *Haemophilus influenzae*. J Biol Chem 275: 38780-38786.
3. Boldt R, Edner C, Kolukisaoglu U, Hagemann M, Weckwerth W, et al. (2005) D-GLYCERATE 3-KINASE, the last unknown enzyme in the photorespiratory cycle in *Arabidopsis*, belongs to a novel kinase family. Plant Cell 17: 2413-2420.
4. Ghalambor M A, Heath E C (1962) The metabolism of L-fucose. II. The enzymatic cleavage of L-fuculose 1-phosphate. J Biol Chem 237: 2427-2433.
5. Allan W L, Clark S M, Hoover G J, Shelp B J (2009) Role of plant glyoxylate reductases during stress: a hypothesis. Biochem J 423: 15-22.
6. Kendziorek M, Paszkowski A (2008) Properties of serine: glyoxylate aminotransferase purified from *Arabidopsis thaliana* leaves. Acta Biochim Biophys Sin (Shanghai) 40: 102-110.
7. Jamai A, Salome P A, Schilling S H, Weber A P, McClung C R (2009) *Arabidopsis* photorespiratory serine hydroxymethyltransferase activity requires the mitochondrial accumulation of ferredoxin-dependent glutamate synthase. Plant Cell 21: 595-606.
8. Hanson A D, Gage D A, Shachar-Hill Y (2000) Plant one-carbon metabolism and its engineering. Trends Plant Sci 5: 206-213.
9. Timm S, Florian A, Jahnke K, Nunes-Nesi A, Fernie A R, et al. (2011) The hydroxypyruvate-reducing system in *Arabidopsis*: multiple enzymes for the same end. Plant Physiol 155: 694-705.
10. Carvalho Jde F, Madgwick P J, Powers S J, Keys A J, Lea P J, et al. (2011) An engineered pathway for glyoxylate metabolism in tobacco plants aimed to avoid the release of ammonia in photorespiration. BMC Biotechnol 11: 111.
11. Horinouchi N, Kawano T, Sakai T, Matsumoto S, Sasaki M, et al. (2009) Screening and characterization of a phosphopentomutase useful for enzymatic production of 2'-deoxyribonucleoside. N Biotechnol 26: 75-82.
12. Aono R, Sato T, Imanaka T, Atomi H (2015) A pentose bisphosphate pathway for nucleoside degradation in Archaea. Nat Chem Biol 11: 355-360.
13. Trethewey R N, Geigenberger P, Riedel K, Hajirezaei M R, Sonnewald U, et al. (1998) Combined expression of glucokinase and invertase in potato tubers leads to a dramatic reduction in starch accumulation and a stimulation of glycolysis. Plant J 15: 109-118.
14. Herbert M, Schnarrenberger C (1982) Purification and subunit structure of glucosephosphate isomerase 2 from spinach leaves and immunochemical comparison with other isomerases. Arch Biochem Biophys 217: 452-459.
15. Gonzali S, Pistelli L, De Bellis L, Alpi A (2001) Characterization of two *Arabidopsis thaliana* fructokinases. Plant Sci 160: 1107-1114.
16. Niessen M, Thiruveedhi K, Rosenkranz R, Kebeish R, Hirsch H J, et al. (2007) Mitochondrial glycolate oxidation contributes to photorespiration in higher plants. J Exp Bot 58: 2709-2715.
17. Goldman D S, Wagner M J (1962) Enzyme systems in the mycobacteria. XIII. Glycine dehydrogenase and the glyoxylic acid cycle. Biochim Biophys Acta 65: 297-306.
18. Cicchillo R M, Baker M A, Schnitzer E J, Newman E B, Krebs C, et al. (2004) *Escherichia coli* L-serine deaminase requires a [4Fe-4S] cluster in catalysis. J Biol Chem 279: 32418-32425.
19. Berman K M, Cohn M (1970) Phosphoenolpyruvate synthetase of *Escherichia coli*. Purification, some properties, and the role of divalent metal ions. J Biol Chem 245: 5309-5318.
20. Prabhakar V, Lottgert T, Gigolashvili T, Bell K, Flugge U I, et al. (2009) Molecular and functional characterization of the plastid-localized Phosphoenolpyruvate enolase (ENO1) from *Arabidopsis thaliana*. FEBS Lett 583: 983-991.
21. Zhao Z, Assmann S M (2011) The glycolytic enzyme, phosphoglycerate mutase, has critical roles in stomatal movement, vegetative growth, and pollen production in *Arabidopsis thaliana*. J Exp Bot 62: 5179-5189.
22. Merfort M, Herrmann U, Bringer-Meyer S, Sahm H (2006) High-yield 5-keto-D-gluconic acid formation is mediated by soluble and membrane-bound gluconate-5-dehydrogenases of *Gluconobacter oxydans*. Appl Microbiol Biotechnol 73: 443-451.
23. Meredith T C, Woodard R W (2005) Identification of GutQ from *Escherichia coli* as a D-arabinose 5-phosphate isomerase. Journal of Bacteriology 187: 6936-6942.
24. Smyth K M, Marchant A (2013) Conservation of the 2-keto-3-deoxymanno-octulosonic acid (Kdo) biosynthesis pathway between plants and bacteria. Carbohydrate Research 380: 70-75.
25. Volk W A (1962) Purification and properties of D-arabinokinase from *Propionibacterium pentosaceum*. J Biol Chem 237: 19-23.
26. Takeda K, Yoshida H, Takada G, Izumori K, Kamitori S (2008) Overexpression, purification, crystallization and preliminary X-ray crystal analysis of *Bacillus* pallidusD-arabinose isomerase. Acta Crystallogr Sect F Struct Biol Cryst Commun 64: 945-948.
27. LeBlanc D J, Mortlock R P (1971) Metabolism of D-arabinose: origin of a D-ribulokinase activity in *Escherichia coli*. J Bacteriol 106: 82-89.
28. Mustroph A, Sonnewald U, Biemelt S (2007) Characterisation of the ATP-dependent phosphofructokinase gene family from *Arabidopsis thaliana*. FEBS Lett 581: 2401-2410.
29. Kozak M, Hayward B, Borek D, Bonthron D T, Jaskolski M (2001) Expression, purification and preliminary crys- 30. Veiga-da-Cunha M, Hoyoux A, Van Schaftingen E (2000) Overexpression and purification of fructose-1-phosphate kinase from *Escherichia coli*: application to the assay of fructose 1-phosphate. Protein Expr Purif 19: 48-52.
31. Kardon T, Stroobant V, Veiga-da-Cunha M, Schaftingen E V (2008) Characterization of mammalian sedoheptulokinase and mechanism of formation of erythritol in sedoheptulokinase deficiency. FEBS Lett 582: 3330-3334.
32. Sakasegawa S, Hagemeier C H, Thauer R K, Essen L O, Shima S (2004) Structural and functional analysis of the gpsA gene product of *Archaeoglobus fulgidus*: a glycerol-3-phosphate dehydrogenase with an unusual NADP+ preference. Protein Sci 13: 3161-3171.
33. Chen M, Thelen J J (2010) The plastid isoform of triose phosphate isomerase is required for the postgerminative transition from heterotrophic to autotrophic growth in *Arabidopsis*. Plant Cell 22: 77-90.
34. Shen W, Wei Y, Dauk M, Tan Y, Taylor D C, et al. (2006) Involvement of a glycerol-3-phosphate dehydrogenase in modulating the NADH/NAD+ ratio provides evidence of a mitochondrial glycerol-3-phosphate shuttle in *Arabidopsis*. Plant Cell 18: 422-441.
35. Caparros-Martin J A, McCarthy-Suarez I, Culianez-Macia F A (2013) HAD hydrolase function unveiled by substrate screening: enzymatic characterization of *Arabidopsis thaliana* subclass I phosphosugar phosphatase AtSgpp. Planta 237: 943-954.
36. Durnin G, Clomburg J, Yeates Z, Alvarez P J, Zygourakis K, et al. (2009) Understanding and harnessing the microaerobic metabolism of glycerol in *Escherichia coli*. Biotechnol Bioeng 103: 148-161.
37. Mininno M, Brugiere S, Pautre V, Gilgen A, Ma S, et al. (2012) Characterization of chloroplastic fructose 1,6-bisphosphate aldolases as lysine-methylated proteins in plants. J Biol Chem 287: 21034-21044.
38. Rosenthal D M, Locke A M, Khozaei M, Raines C A, Long S P, et al. (2011) Overexpressing the C(3) photosynthesis cycle enzyme Sedoheptulose-1-7 Bisphosphatase improves photosynthetic carbon gain and yield under fully open air CO(2) fumigation (FACE). BMC Plant Biol 11: 123.
39. Soucaille P, Dischert W (2011) Method for polymerising glycolic acid with microorganisms. Metabolic Explorer.
40. Tran T H, Hsiao Y S, Jo J, Chou C Y, Dietrich L E, et al. (2015) Structure and function of a single-chain, multi-domain long-chain acyl-CoA carboxylase. Nature 518: 120-124.
41. Baker P, Carere J, Seah S Y (2012) Substrate specificity, substrate channeling, and allostery in BphJ: an acylating aldehyde dehydrogenase associated with the pyruvate aldolase BphI. Biochemistry 51: 4558-4567.
42. Burton R M, Stadtman E R (1953) The oxidation of acetaldehyde to acetyl coenzyme A. J Biol Chem 202: 873-890.
43. Sohling B, Gottschalk G (1993) Purification and characterization of a coenzyme-A-dependent succinate-semialdehyde dehydrogenase from *Clostridium kluyveri*. Eur J Biochem 212: 121-127.
44. Lee L V, Gerratana B, Cleland W W (2001) Substrate specificity and kinetic mechanism of *Escherichia coli* ribulokinase. Arch Biochem Biophys 396: 219-224.
45. Windle C L, Muller M, Nelson A, Berry A (2014) Engineering aldolases as biocatalysts. Curr Opin Chem Biol 19: 25-33.
46. Herz S, Kis K, Bacher A, Rohdich F (2002) A tomato enzyme catalyzing the phosphorylation of 3,4-dihydroxy-2-butanone. Phytochemistry 60: 3-11.
47. Henstra A M, Dijkema C, Stams A J (2007) *Archaeoglobus fulgidus* couples CO oxidation to sulfate reduction and acetogenesis with transient formate accumulation. Environ Microbiol 9: 1836-1841.
48. Lyer P, Ferry J G (2005) Acetate Kinase From *Methanosarcina thermophila*, a Key Enzyme for Methanogenesis. In: Barredo J L, editor. Microbial Enzymes and Biotransformations. pp. 239-246.
49. Fife T H, Rikihisa T (1970) Reaction of glyceraldehyde 3-phosphate dehydrogenase with aliphatic aldehydes. Biochemistry 9: 4064-4067.
50. Armstrong J M, Trentham D R (1976) The reactions of D-glyceraldehyde 3-phosphate with thiols and the holoenzyme of D-glyceraldehyde 3-phosphate dehydrogenase and of inorganic phosphate with the acyl-holoenzyme. Biochem J 159: 513-527.
51. Byers L D (1978) Enantiomeric specificity of glyceraldehyde 3-phosphate dehydrogenase. Arch Biochem Biophys 186: 335-342.
52. Castano-Cerezo S, Pastor J M, Renilla S, Bernal V, Iborra J L, et al. (2009) An insight into the role of phosphotransacetylase (pta) and the acetate/acetyl-CoA node in *Escherichia coli*. Microb Cell Fact 8: 54.
53. Venkitasubramanian P, Daniels L, Rosazza J P (2007) Reduction of carboxylic acids by *Nocardia* aldehyde oxidoreductase requires a phosphopantetheinylated enzyme. J Biol Chem 282: 478-485.
54. Tompa P, Hong P T, Vas M (1986) The phosphate group of 3-phosphoglycerate accounts for conformational changes occurring on binding to 3-phosphoglycerate kinase. Enzyme inhibition and thiol reactivity studies. Eur J Biochem 154: 643-649.
55. Vas M (1990) Modelling of substrate binding to 3-phosphoglycerate kinase with analogues of 3-phosphoglycerate. Eur J Biochem 194: 639-645.
56. Szilagyi A N, Vas M (1998) Anion activation of 3-phosphoglycerate kinase requires domain closure. Biochemistry 37: 8551-8563.
57. Koffas M A, Jung G Y, Aon J C, Stephanopoulos G (2002) Effect of pyruvate carboxylase overexpression on the physiology of *Corynebacterium glutamicum*. Appl Environ Microbiol 68: 5422-5428.
58. Grover S D, Canellas P F, Wedding R T (1981) Purification of NAD malic enzyme from potato and investigation of some physical and kinetic properties. Arch Biochem Biophys 209: 396-407.
59. Ghalambor M A, Heath E C (1966) L-Fuculose 1-Phosphate Aldolase Methods Enzymol 9: 538-542.
60. Saito Y, Ashida H, Kojima C, Tamura H, Matsumura H, et al. (2007) Enzymatic characterization of 5-methylthioribose 1-phosphate isomerase from *Bacillus* subtilis. Biosci Biotechnol Biochem 71: 2021-2028.
61. Erb T J, Evans B S, Cho K, Warlick B P, Sriram J, et al. (2012) A RubisCO-like protein links SAM metabolism with isoprenoid biosynthesis. Nat Chem Biol 8: 926-932.
62. Imker H J, Singh J, Warlick B P, Tabita F R, Gerlt J A (2008) Mechanistic diversity in the RuBisCO superfamily: a novel isomerization reaction catalyzed by the RuBisCO-like protein from *Rhodospirillum rubrum*. Biochemistry 47: 11171-11173.

63. Kim Y M, Chang Y H, Choi N S, Kim Y, Song J J, et al. (2009) Cloning, expression, and characterization of a new deoxyribose 5-phosphate aldolase from *Yersinia* sp. EA015. Protein Expr Purif 68: 196-200.
64. Fiedler E, Golbik R, Schneider G, Tittmann K, Neef H, et al. (2001) Examination of donor substrate conversion in yeast transketolase. J Biol Chem 276: 16051-16058.
65. Sevostyanova I A, Solovjeva O N, Kochetov G A (2004) A hitherto unknown transketolase-catalyzed reaction. Biochem Biophys Res Commun 313: 771-774.
66. Li S, Xu N, Liu L, Chen J (2014) Engineering of carboligase activity reaction in *Candida glabrata* for acetoin production. Metab Eng 22: 32-39.
67. Ebner M, Stütz A E (1997) Glucose isomerase catalysed isomerisation reactions of (2R, 3R)-configured aldofuranoses into the corresponding open-chain 2-ketoses. Carbohydr Res 305: 331-336.
68. Bork P, Sander C, Valencia A (1993) Convergent evolution of similar enzymatic function on different protein folds: the hexokinase, ribokinase, and galactokinase families of sugar kinases. Protein Sci 2: 31-40.
69. Terada T, Mukae H, Ohashi K, Hosomi S, Mizoguchi T, et al. (1985) Characterization of an enzyme which catalyzes isomerization and epimerization of D-erythrose 4-phosphate. Eur J Biochem 148: 345-351.
70. Hesslinger C, Fairhurst S A, Sawers G (1998) Novel keto acid formate-lyase and propionate kinase enzymes are components of an anaerobic pathway in *Escherichia coli* that degrades L-threonine to propionate. Mol Microbiol 27: 477-492.
71. Sawers G, Hesslinger C, Muller N, Kaiser M (1998) The glycyl radical enzyme TdcE can replace pyruvate formate-lyase in glucose fermentation. J Bacteriol 180: 3509-3516.
72. Fukuda E, Wakagi T (2002) Substrate recognition by 2-oxoacid:ferredoxin oxidoreductase from *Sulfolobus* sp. strain 7. Biochim Biophys Acta 1597: 74-80.
73. Dhamankar H, Tarasova Y, Martin C H, Prather K L (2014) Engineering *E. coli* for the biosynthesis of 3-hydroxy-gamma-butyrolactone (3HBL) and 3,4-dihydroxybutyric acid (3,4-DHBA) as value-added chemicals from glucose as a sole carbon source. Metab Eng 25: 72-81.
74. Boynton Z L, Bennet G N, Rudolph F B (1996) Cloning, sequencing, and expression of clustered genes encoding beta-hydroxybutyryl-coenzyme A (CoA) dehydrogenase, crotonase, and butyryl-CoA dehydrogenase from *Clostridium acetobutylicum* ATCC 824. J Bacteriol 178: 3015-3024.
75. Alexson S E, Nedergaard J (1988) A novel type of short- and medium-chain acyl-CoA hydrolases in brown adipose tissue mitochondria. J Biol Chem 263: 13564-13571.
76. Samland A K, Baier S, Schurmann M, Inoue T, Huf S, et al. (2012) Conservation of structure and mechanism within the transaldolase enzyme family. FEBS J 279: 766-778.
77. Sprenger G A, Schorken U, Sprenger G, Sahm H (1995) Transketolase A of *Escherichia coli* K12. Purification and properties of the enzyme from recombinant strains. Eur J Biochem 230: 525-532.
78. Garrabou X, Castillo J A, Guerard-Helaine C, Parella T, Joglar J, et al. (2009) Asymmetric self- and cross-aldol reactions of glycolaldehyde catalyzed by D-fructose-6-phosphate aldolase. Angew Chem Int Ed Engl 48: 5521-5525.
79. Samland A K, Rale M, Sprenger G A, Fessner W D (2011) The transaldolase family: new synthetic opportunities from an ancient enzyme scaffold. Chembiochem 12: 1454-1474.
80. Castillo J A, Guérard-Hélaine C, Gutiérrez M, Garrabou X, Sancelme M, et al. (2010) A Mutant D-Fructose-6-Phosphate Aldolase (Ala129Ser) with Improved Affinity towards Dihydroxyacetone for the Synthesis of Polyhydroxylated Compounds. Adv Synth Catal 352: 1039-1046.
81. Vuolanto A, Pastinen O, Schoemaker H E, Leisola M (2002) C-2 epimer formation of tetrose, pentose and hexose sugars by xylose isomerase. Biocatalysis and Biotransformation 20: 235-240.
82. Leang K, Takada G, Fukai Y, Morimoto K, Granstrom T B, et al. (2004) Novel reactions of L-rhamnose isomerase from *Pseudomonas stutzeri* and its relation with D-xylose isomerase via substrate specificity. Biochim Biophys Acta 1674: 68-77.
83. Kato N (1990) 3-Hexulose-6-phosphate synthase from *Mycobacterium gastri* MB19. Methods Enzymol 188: 397-401.
84. Kuznetsova E, Proudfoot M, Gonzalez C F, Brown G, Omelchenko M V, et al. (2006) Genome-wide analysis of substrate specificities of the *Escherichia coli* haloacid dehalogenase-like phosphatase family. J Biol Chem 281: 36149-36161.
85. Akana J, Fedorov A A, Fedorov E, Novak W R, Babbitt P C, et al. (2006) D-Ribulose 5-phosphate 3-epimerase: functional and structural relationships to members of the ribulose-phosphate binding (beta/alpha)8-barrel superfamily. Biochemistry 45: 2493-2503.
86. Taylor E J, Charnock S J, Colby J, Davies G J, Black G W (2001) Cloning, purification and characterization of the 6-phospho-3-hexulose isomerase YckF from *Bacillus subtilis*. Acta Crystallogr D Biol Crystallogr 57: 1138-1140.
87. Lu Z, Feng X, Song L, Han Y, Kim A, et al. (2005) Diversity of function in the isocitrate lyase enzyme superfamily: the *Dianthus caryophyllus* petal death protein cleaves alpha-keto and alpha-hydroxycarboxylic acids. Biochemistry 44: 16365-16376.
88. Rudolph F B, Purich D L, Fromm H J (1968) Coenzyme A-linked aldehyde dehydrogenase from *Escherichia coli*. I. Partial purification, properties, and kinetic studies of the enzyme. J Biol Chem 243: 5539-5545.
89. Oppermann F B, Schmidt B, Steinbuchel A (1991) Purification and characterization of acetoin:2,6-dichlorophenolindophenol oxidoreductase, dihydrolipoamide dehydrogenase, and dihydrolipoamide acetyltransferase of the *Pelobacter carbinolicus* acetoin dehydrogenase enzyme system. J Bacteriol 173: 757-767.
90. Szwergold B S, Ugurbil K, Brown T R (1995) Properties of fructose-1,6-bisphosphate aldolase from *Escherichia coli*: an NMR analysis. Arch Biochem Biophys 317: 244-252.
91. LowKam C, Liotard B, Sygusch J (2010) Structure of a class I tagatose-1,6-bisphosphate aldolase: investigation into an apparent loss of stereospecificity. J Biol Chem 285: 21143-21152.
92. Yoon S S, Park S H, Kim Y C, Shin M, Chong C K, et al. (2008) Cloning and characterization of phosphoglucomutase and phosphomannomutase derived from *Sphingomonas chungbukensis* DJ77. J Biochem 144: 507-512.
93. Nakahigashi K, Toya Y, Ishii N, Soga T, Hasegawa M, et al. (2009) Systematic phenome analysis of *Escherichia* coli multiple-knockout mutants reveals hidden reactions in central carbon metabolism. Mol Syst Biol 5: 306.
94. Flynn T G, Cromlish J A (1982) Glycerol dehydrogenase from rabbit muscle. Methods Enzymol 89 Pt D: 237-242.
95. Kahle C, Schneider K H, Giffhorn F (1992) Pentitol metabolism of *Rhodobacter sphaeroides* Si4: purification and characterization of a ribitol dehydrogenase. J Gen Microbiol 138: 1277-1281.
96. Tiwari M K, Moon H J, Jeya M, Lee J K (2010) Cloning and characterization of a thermostable xylitol dehydrogenase from *Rhizobium etli* CFN42. Appl Microbiol Biotechnol 87: 571-581.
97. Ito S (2009) Features and applications of microbial sugar epimerases. Appl Microbiol Biotechnol 84: 1053-1060.
98. Siebold C, Garcia-Alles L F, Erni B, Baumann U (2003) A mechanism of covalent substrate binding in the x-ray structure of subunit K of the *Escherichia coli* dihydroxyacetone kinase. Proc Natl Acad Sci USA 100: 8188-8192.
99. Flanagan T, Waites M J (1992) Purification and characterization of d-xylulokinase from the pentose-fermenting yeast *Pichia stipitis* NCYC 1541. Enzyme Microb Technol 14: 975-979.
100. Di Luccio E, Petschacher B, Voegtli J, Chou H T, Stahlberg H, et al. (2007) Structural and kinetic studies of induced fit in xylulose kinase from *Escherichia coli*. J Mol Biol 365: 783-798.

Table 4.

Table 4 shows enzymes used for the synthetic photorespiratory bypass pathway illustrated in Example 6. The abbreviations (abbr.) defined herein are used in the Figures and/or corresponding Figure descriptions of FIGS. 7 to 11.

TABLE 4

| enzyme | organism | abbr. | NCBI accession no. |
|---|---|---|---|
| propionyl-CoA transferase | *Ralstonia eutropha* | $PCT_{Re}$ | CAJ93797.1 |
| propionyl-CoA transferase | *Clostridium propionicum* | $PCT_{Cp}$ | CAB77207.1 |
| propionyl-CoA carboxylase | *Methylobacterium extorquens* | $PCC_{Me}$ | WP_003599287.1 (pccA subunit); WP_003597263.1 (pccB subunit) |
| malonyl-CoA reductase | *Chloroflexus aurantiacus* | $MCR_{Ca}$ | AAS20429.1 |
| malonyl-CoA reductase | *Erythrobacter* sp. NAP1 | $MCR_{E}$ | WP_007163680.1 |

In addition to the above mentioned enzymes also the mutant variant $PCC_{Me}$_D407I_Y143H was employed. This protein comprises the WT sequence of the pccA subunit and a pccB subunit comprising the amino acid substitutions D407I and Y143H (wherein the respective number indicates the amino acid position in the amino acid sequence of pccB as disclosed in the NCBI entry having the accession code WP_003597263.1.

Table 5.

Table 5 summarizes the enzymes employed in Example 6 and their kinetical properties ($K_m$ (substrate) and $v_{max}$) as determined in Example 6.

TABLE 5

| enzyme | $K_m$ (substrate) | $v_{max}$ |
|---|---|---|
| $PCT_{Re}$ | 51.7 ± 9.6 mM (glycolate) | 1.3 ± 0.07 U mg$^{-1}$ |
| $PCT_{Cp}$ | 149 ± 35 mM (glycolate) | 0.03 ± 0.003 U mg$^{-1}$ |
| $PCC_{Me}$ D407I Y143H | 1.0 ± 0.15 mM (glycolyl-CoA) | 1.5 ± 0.09 U mg$^{-1}$ |
| $MCR_{Ca}$ | 0.03 ± 0.003 mM (tartronyl-CoA) | 0.6 ± 0.01 U mg$^{-1}$ |
| $MCR_{E}$ | 0.18 ± 0.04 mM (tartronyl-CoA) | 0.23 ± 0.01 U mg$^{-1}$ |

The invention claimed is:

1. A cell expressing enzymes which allow the conversion of 2-phosphoglycolate (2-PG) into an intermediate compound of the Calvin-Benson-Bassham Cycle (CBBC) without releasing $CO_2$,
wherein said cell is a genetically engineered cell that provides a photorespiration bypass pathway for said conversion of 2-PG into said intermediate compound of the CBBC without releasing $CO_2$, by expressing said enzymes, wherein said photorespiration bypass pathway comprises expressing at least one enzyme catalyzing a non-native reaction; and
wherein said conversion of 2-PG into an intermediate compound of the CBBC is achieved by enzymatic conversion of 2-PG into glycolyl-CoA and the further enzymatic conversion of glycolyl-CoA into said intermediate compound of the CBBC.

2. The cell of claim 1, wherein said pathway for said conversion of 2-PG into an intermediate compound of the CBBC involves ten or less enzymatic conversions.

3. The cell of claim 1, which exhibits the CBBC under aerobic conditions.

4. An organism comprising at least one cell of claim 1, wherein said organism is a plant, algae, cyanobacteria, or a bacterium.

5. The cell of claim 1, wherein said intermediate compound of the CBBC is selected from the group consisting of: D-glycerate 3-phosphate, D-ribulose 5-phosphate, D-ribulose 1,5-bisphosphate, D-erythrose 4-phosphate, D-ribose 5-phosphate, and D-xylulose 5-phosphate.

6. The cell of claim 1 comprising an organelle, wherein said organelle is a chloroplast comprising at least one of said enzymes.

7. The cell of claim 1, which is genetically engineered so as to express at least one of said enzymes.

8. The organism of claim 4, wherein the organism is a C3 plant.

9. A method for producing the cell of claim 1, wherein said method comprises a step of genetically engineering a cell so as to express at least one of said enzymes.

10. A method of enzymatically converting 2-PG into an intermediate compound of the CBBC in a cell without releasing $CO_2$, comprising the step of providing a cell of claim 1.

11. The cell of claim 1, wherein said enzymatic conversion of 2-PG into glycolyl-CoA is achieved by:
   a) enzymatic conversion of 2-PG into glycolate and further enzymatic conversion of glycolate into glycolyl-CoA,
   b) enzymatic conversion of 2-PG into glycolate, further enzymatic conversion of glycolate into glycolyl phosphate, and further enzymatic conversion of glycolyl phosphate into glycolyl-CoA,
   c) enzymatic conversion of 2-PG into glycolate, further enzymatic conversion of glycolate into glycolyl phosphate, further enzymatic conversion of glycolyl phosphate into glycolaldehyde, and further enzymatic conversion of glycolaldehyde into glycolyl-CoA, or
   d) enzymatic conversion of 2-PG into glycolate, further enzymatic conversion of glycolate into glycolaldehyde, and further enzymatic conversion of glycolaldehyde into glycolyl-CoA.

12. The cell of claim 11, wherein said enzymatic conversion of 2-PG into glycolyl-CoA includes at least one of: said enzymatic conversion of glycolate into glycolyl-CoA by a CoA-transferase (EC 2.8.3.X), said enzymatic conversion of glycolate into glycolyl-CoA by a propionyl-CoA transferase (EC 2.8.3.1), said enzymatic conversion of glycolate into glycolyl-CoA by an ADP-forming or AMP-forming CoA ligase (EC 6.2.1.X), said enzymatic conversion of glycolate into glycolyl-CoA by a propionate-CoA ligase (EC 6.2.1.17), said enzymatic conversion of glycolate into glycolyl phosphate by a carboxy kinase (EC 2.7.2.X), said enzymatic conversion of glycolate into glycolyl phosphate by an acetate kinase (EC 2.7.2.1.), said enzymatic conversion of glycolyl phosphate into glycolyl-CoA by a phosphate acyltransferase (EC 2.3.1.X), said enzymatic conversion of glycolyl phosphate into glycolyl-CoA by a phosphate acetyltransferase (EC 2.3.1.8), said enzymatic conversion of glycolaldehyde into glycolyl-CoA by an acylating aldehyde dehydrogenase (EC 1.2.1.X), said enzymatic conversion of glycolaldehyde into glycolyl-CoA by an acetaldehyde dehydrogenase (acylating) (EC 1.2.1.10), said enzymatic conversion of glycolyl phosphate into glycolaldehyde by glyceraldehyde 3-phosphate dehydrogenase (EC 1.2.1.12), or said enzymatic conversion of glycolate into glycolaldehyde by an ATP- and NAD(P)H-dependent carboxylic acid reductase (EC 1.2.1.X).

13. The cell of claim 1, wherein said intermediate compound of the CBBC is D-glycerate 3-phosphate, and wherein said enzymatic conversion of glycolyl-CoA into D-glycerate 3-phosphate is achieved by:
   a) enzymatic conversion of glycolyl-CoA into tartronyl-CoA, further enzymatic conversion of tartronyl-CoA into tartronate semialdehyde, further enzymatic conversion of tartronate semialdehyde into D-glycerate, and further enzymatic conversion of D-glycerate into D-glycerate 3-phosphate, or
   b) enzymatic conversion of glycolyl-CoA into hydroxypyruvate, further enzymatic conversion of hydroxypyruvate into D-glycerate, and further enzymatic conversion of D-glycerate into D-glycerate 3-phosphate.

14. The cell of claim 13, wherein said enzymatic conversion of glycolyl-CoA into D-glycerate 3-phosphate includes at least one of: said enzymatic conversion of glycolyl-CoA into tartronyl-CoA by a biotin-dependent acyl-CoA carboxylase (EC 6.4.1.X), said enzymatic conversion of glycolyl-CoA into tartronyl-CoA by a propionyl-CoA carboxylase (EC 6.4.1.3), said enzymatic conversion of tartronyl-CoA into tartronate semialdehyde by an acylating aldehyde dehydrogenase (EC 1.2.1.X) said enzymatic conversion of tartronyl-CoA into tartronate semialdehyde by a malonyl-CoA reductase (EC 1.2.1.75), said enzymatic conversion of glycolyl-CoA into hydroxypyruvate by a pyruvate synthase (EC 1.2.7.1), or said enzymatic conversion of glycolyl-CoA into hydroxypyruvate by a pyruvate formate lyase (EC 2.3.1.54).

15. The cell of claim 1, wherein said intermediate compound of the CBBC is D-ribulose 1,5-bisphosphate, and wherein said enzymatic conversion of glycolyl-CoA into D-ribulose 1,5-bisphosphate is achieved by:
   a) enzymatic conversion of glycolyl-CoA into glycolaldehyde, further enzymatic conversion of glycolaldehyde into D-ribulose 1-phosphate, and further enzymatic conversion of D-ribulose 1-phosphate into D-ribulose 1,5-bisphosphate,
   b) enzymatic conversion of glycolyl-CoA into glycolyl phosphate, further enzymatic conversion of glycolyl phosphate into glycolaldehyde, further enzymatic conversion of glycolaldehyde into D-ribulose 1-phosphate, and further enzymatic conversion of D-ribulose 1-phosphate into D-ribulose 1,5-bisphosphate,
   c) enzymatic conversion of glycolyl-CoA into glycolaldehyde, further enzymatic conversion of glycolaldehyde into D-ribulose 1-phosphate, further enzymatic conversion of D-ribulose 1-phosphate into D-ribose 1-phosphate, further enzymatic conversion of D-ribose 1-phosphate into D-ribose 1,5-bisphosphate, and further enzymatic conversion of D-ribose 1,5-bisphosphate into D-ribulose 1,5-bisphosphate, or
   d) enzymatic conversion of glycolyl-CoA into glycolyl phosphate, further enzymatic conversion of glycolyl phosphate into glycolaldehyde, further enzymatic conversion of glycolaldehyde into D-ribulose 1-phosphate, further enzymatic conversion of D-ribulose 1-phosphate into D-ribose 1-phosphate, further enzymatic conversion of D-ribose 1-phosphate into D-ribose 1,5-bisphosphate, and further enzymatic conversion of D-ribose 1,5-bisphosphate into D-ribulose 1,5-bisphosphate.

16. The cell of claim 15, wherein said enzymatic conversion of glycolyl-CoA into D-ribulose 1,5-bisphosphate includes at least one of: said enzymatic conversion of glycolyl-CoA into glycolaldehyde by an acylating aldehyde dehydrogenase (EC 1.2.1.X), said enzymatic conversion of glycolyl-CoA into glycolaldehyde by an acetaldehyde dehydrogenase (acylating) (EC 1.2.1.10), said enzymatic conversion of D-ribulose 1-phosphate into D-ribulose 1,5-bisphosphate by a 1-phosphofructokinase (EC 2.7.1.56), said enzymatic conversion of D-ribulose 1-phosphate into D-ribulose 1,5-bisphosphate by a ribulokinase (EC 2.7.1.16), said enzymatic conversion of glycolyl-CoA into glycolyl phosphate by a phosphate acyltransferase (EC 2.3.1.X), said enzymatic conversion of glycolyl-CoA into glycolyl phosphate by a phosphate acetyltransferase (EC 2.3.1.8), said enzymatic conversion of glycolyl phosphate into glycolaldehyde by a phosphorylating glyceraldehyde 3-phosphate dehydrogenase (EC 1.2.1.12), said enzymatic conversion of D-ribulose 1-phosphate into D-ribose 1-phosphate by a 5-methylthio-D-ribulose 1-phosphate 1,2- isomerase, or said enzymatic conversion of D-ribulose 1-phosphate into D-ribose 1-phosphate by Rru_A0360.

17. The cell of claim 1, wherein said intermediate compound of the CBBC is D-erythrose 4-phosphate, and wherein said enzymatic conversion of glycolyl-CoA into D-erythrose 4-phosphate is achieved by:
  a) enzymatic conversion of glycolyl-CoA into glycolaldehyde, further enzymatic conversion of glycolaldehyde into D-erythrose, and further enzymatic conversion of D-erythrose into D-erythrose 4-phosphate,
  b) enzymatic conversion of glycolyl-CoA into glycolyl phosphate, further enzymatic conversion of glycolyl phosphate into glycolaldehyde, further enzymatic conversion of glycolaldehyde into D-erythrose, and further enzymatic conversion of D-erythrose into D-erythrose 4-phosphate, or
  c) enzymatic conversion of glycolyl-CoA into 2,4-dihydroxy-3-oxo-butyryl-CoA, further enzymatic conversion of 2,4-dihydroxy-3-oxo-butyryl-CoA into 2,3,4-trihydroxy-3-oxo-butyryl-CoA, further enzymatic conversion of 2,3,4-trihydroxy-3-oxo-butyryl-CoA into a D-aldotetrose, and further enzymatic conversion of said D-aldotetrose into D-erythrose 4-phosphate, wherein said D-aldotetrose is D-erythrose or D-threose.

18. The cell of claim 17, wherein said enzymatic conversion of glycolyl-CoA into D-erythrose 4-phosphate includes at least one of: said enzymatic conversion of glycolyl-CoA into glycolaldehyde by an acylating aldehyde dehydrogenase (EC 1.2.1.X), said enzymatic conversion of glycolyl-CoA into glycolaldehyde by an acylating aldehyde dehydrogenase by acetaldehyde dehydrogenase (acylating) (EC 1.2.1.10), said enzymatic conversion of glycolaldehyde into D-erythrose by an aldolase (EC 4.1.2.X), said enzymatic conversion of glycolaldehyde into D-erythrose by a fructose 6-phosphate aldolase, said enzymatic conversion of glycolaldehyde into D-erythrose by a xylulose 1-phosphate aldolase, said enzymatic conversion of D-erythrose into D-erythrose 4-phosphate by a dihydroxyacetone kinase (EC 2.7.1.29), said enzymatic conversion of glycolyl-CoA into glycolyl phosphate by a phosphate acyltransferase (EC 2.3.1.X), said enzymatic conversion of glycolyl-CoA into glycolyl phosphate by a phosphate acetyltransferase (EC 2.3.1.8), said enzymatic conversion of glycolyl phosphate into glycolaldehyde by a phosphorylating glyceraldehyde 3-phosphate dehydrogenase (EC 1.2.1.12), said enzymatic conversion of glycolyl-CoA into 2,4-dihydroxy-3-oxo-butyryl-CoA by an acetyl-CoA C-acetyltransferase (EC 2.3.1.9), said enzymatic conversion of glycolyl-CoA into 2,4-dihydroxy-3-oxo-butyryl-CoA by the acetyl-CoA C-acetyltransferase bktB from *Cupriavidus necator* (EC 2.3.1.9), said enzymatic conversion of 2,4-dihydroxy-3-oxo-butyryl-CoA into 2,3,4-trihydroxy-3-oxo-butyryl-CoA by a 3-hydroxybutyryl-CoA dehydrogenase (EC 1.1.1.157), said enzymatic conversion of 2,3,4-trihydroxy-3-oxo-butyryl-CoA into D-aldotetrose by an aldehyde dehydrogenase (acetylating, EC 1.2.1.X), said enzymatic conversion of said D-aldotetrose into D-erythrose 4-phosphate by a sugar kinase (EC 2.7.1.X) wherein said D-aldotetrose is D-erythrose, said enzymatic conversion of said D-aldotetrose into D-erythrose 4-phosphate by a dihydroxyacetone kinase (EC 2.7.1.29) wherein said D-aldotetrose is D-erythrose, said enzymatic conversion of said D-aldotetrose into D-erythrose 4-phosphate by a sugar isomerase/epimerase (EC 5.3.1.X) and a sugar kinase (EC 2.7.1.X) wherein said D-aldotetrose is D-threose, said enzymatic conversion of said D-aldotetrose into D-erythrose 4-phosphate by xylose isomerase (EC 5.3.1.5) and a sugar kinase (EC 2.7.1.X) wherein said D-aldotetrose is D-threose, said enzymatic conversion of said D-aldotetrose into D-erythrose 4-phosphate by L-rhamnose isomerase (EC 5.3.1.14) and a sugar kinase (EC 2.7.1.X), wherein said D-aldotetrose is D-threose, said enzymatic conversion of said D-aldotetrose into D-erythrose 4-phosphate by a sugar isomerase/epimerase (EC 5.3.1.X) and a dihydroxyacetone kinase (EC 2.7.1.29) wherein said D-aldotetrose is D-threose, said enzymatic conversion of said D-aldotetrose into D-erythrose 4-phosphate by xylose isomerase (EC 5.3.1.5) and a dihydroxyacetone kinase (EC 2.7.1.29) wherein said D-aldotetrose is D-threose, said enzymatic conversion of said D-aldotetrose into D-erythrose 4-phosphate by L-rhamnose isomerase (EC 5.3.1.14) and a dihydroxyacetone kinase (EC 2.7.1.29) wherein said D-aldotetrose is D-threose, or said enzymatic conversion of said D-threose into D-erythrose 4-phosphate by a sugar kinase (EC 2.7.1.X) and a sugar phosphate epimerase (EC 5.3.1.X).

19. The cell of claim 1, wherein said intermediate compound of the CBBC is D-ribose 5-phosphate, and wherein said enzymatic conversion of glycolyl-CoA into D-ribose 5-phosphate is achieved by:
  a) enzymatic conversion of glycolyl-CoA into glycolaldehyde, further enzymatic conversion of glycolaldehyde into D-ribulose 1-phosphate, further enzymatic conversion of D-ribulose 1-phosphate into D-ribose 1-phosphate, and further enzymatic conversion of D-ribose 1-phosphate into D-ribose 5-phosphate, or
  b) enzymatic conversion of glycolyl-CoA into glycolyl phosphate, further enzymatic conversion of glycolyl phosphate into glycolaldehyde, further enzymatic conversion of glycolaldehyde into D-ribulose 1-phosphate, further enzymatic conversion of D-ribulose 1-phosphate into D-ribose 1-phosphate, and further enzymatic conversion of D-ribose 1-phosphate into D-ribose 5-phosphate.

20. The cell of claim 19, wherein said enzymatic conversion of glycolyl-CoA into D-ribose 5-phosphate includes at least one of: said enzymatic conversion of glycolyl-CoA into glycolaldehyde by an acylating aldehyde dehydrogenase (EC 1.2.1.X), said enzymatic conversion of glycolyl-CoA into glycolaldehyde by an acetaldehyde dehydrogenase (acylating) (EC 1.2.1.10), said enzymatic conversion of D-ribulose 1-phosphate into D-ribose 1-phosphate by a 5-methylthio-D-ribulose 1-phosphate 1,2-isomerase, said enzymatic conversion of D-ribulose 1-phosphate into D-ribose 1-phosphate by Rru_A0360, said enzymatic conversion of glycolyl-CoA into glycolyl phosphate by a phosphate acyltransferase (EC 2.3.1.X), said enzymatic conversion of glycolyl-CoA into glycolyl phosphate by a phosphate acetyltransferase (EC 2.3.1.8), or said enzymatic conversion of glycolyl phosphate into glycolaldehyde by a phosphorylating glyceraldehyde 3-phosphate dehydrogenase (EC 1.2.1.12).

21. The cell of claim 1, wherein said intermediate compound of the CBBC is D-ribulose 5-phosphate, and wherein said enzymatic conversion of glycolyl-CoA into D-ribulose 5-phosphate is achieved by:
  a) enzymatic conversion of glycolyl-CoA into glycolaldehyde, further enzymatic conversion of glycolaldehyde into D-arabinose 5-phosphate, and further enzymatic conversion of D-arabinose 5-phosphate into D-ribulose 5-phosphate, or
  b) enzymatic conversion of glycolyl-CoA into glycolyl phosphate, further enzymatic conversion of glycolyl phosphate into glycolaldehyde, further enzymatic conversion of glycolaldehyde into D-arabinose 5-phosphate, and further enzymatic conversion of D-arabinose 5-phosphate into D-ribulose 5-phosphate.

22. The cell of claim 21, wherein said enzymatic conversion of glycolyl-CoA into D-ribulose 5-phosphate includes at least one of: said enzymatic conversion of glycolyl-CoA into glycolaldehyde by an acylating aldehyde dehydrogenase (EC 1.2.1.X), said enzymatic conversion of glycolyl-CoA into glycolaldehyde by an acetaldehyde dehydrogenase (acylating) (EC 1.2.1.10), said enzymatic conversion of glycolaldehyde into D-arabinose 5-phosphate by an aldolase (EC 4.1.2.X), said enzymatic conversion of glycolaldehyde into D-arabinose 5-phosphate by fructose 6-phosphate aldolase (EC 4.1.2.X), said enzymatic conversion of glycolyl-CoA into glycolyl phosphate by a phosphate acyltransferase (EC 2.3.1.X), said enzymatic conversion of glycolyl-CoA into glycolyl phosphate by a phosphate acetyltransferase (EC 2.3.1.8), or said enzymatic conversion of glycolyl phosphate into glycolaldehyde by a phosphorylating glyceraldehyde 3-phosphate dehydrogenase (EC 1.2.1.12).

23. The cell of claim 1, wherein said intermediate compound of the CBBC is D-xylulose 5-phosphate, and wherein said enzymatic conversion of glycolyl-CoA into D-xylulose 5-phosphate is achieved by:
   a) enzymatic conversion of glycolyl-CoA into glycolaldehyde, further enzymatic conversion of glycolaldehyde into D-xylulose, and further enzymatic conversion of D-xylulose into D-xylulose 5-phosphate,
   b) enzymatic conversion of glycolyl-CoA into glycolyl phosphate, further enzymatic conversion of glycolyl phosphate into glycolaldehyde, further enzymatic conversion of glycolaldehyde into D-xylulose, and further enzymatic conversion of D-xylulose into D-xylulose 5-phosphate,
   c) enzymatic conversion of glycolyl-CoA into glycolaldehyde, and further enzymatic conversion of glycolaldehyde into D-xylulose 5-phosphate, or
   d) enzymatic conversion of glycolyl-CoA into glycolyl phosphate, further enzymatic conversion of glycolyl phosphate into glycolaldehyde, and further enzymatic conversion of glycolaldehyde into D-xylulose 5-phosphate.

24. The cell of claim 23, wherein said enzymatic conversion of glycolyl-CoA into D-xylulose 5-phosphate includes at least one of: said enzymatic conversion of glycolyl-CoA into glycolaldehyde by an acylating aldehyde dehydrogenase (EC 1.2.1.X), said enzymatic conversion of glycolyl-CoA into glycolaldehyde by an acetaldehyde dehydrogenase (acylating) (EC 1.2.1.10), said enzymatic conversion of glycolaldehyde into D-xylulose by a transaldolase (EC 2.2.1.2), said enzymatic conversion of glycolyl-CoA into glycolyl phosphate by a phosphate acyltransferase (EC 2.3.1.X), said enzymatic conversion of glycolyl-CoA into glycolyl phosphate by a phosphate acetyltransferase (EC 2.3.1.8), said enzymatic conversion of glycolyl phosphate into glycolaldehyde by a phosphorylating glyceraldehyde 3-phosphate dehydrogenase (EC 1.2.1.12), or said enzymatic conversion of glycolaldehyde into D-xylulose 5-phosphate by a transketolase (2.2.1.2).

25. The cell of claim 1, wherein said intermediate compound of the CBBC is D-glycerate 3-phosphate, and wherein:
   said enzymatic conversion of 2-PG into glycolyl-CoA is achieved by enzymatic conversion of 2-PG into glycolate and further enzymatic conversion of glycolate into glycolyl-CoA; and
   said enzymatic conversion of glycolyl-CoA into D-glycerate 3-phosphate is achieved by enzymatic conversion of glycolyl-CoA into tartronyl-CoA, further enzymatic conversion of tartronyl-CoA into tartronate semialdehyde, further enzymatic conversion of tartronate semialdehyde into D-glycerate, and further enzymatic conversion of D-glycerate into D-glycerate 3-phosphate.

26. The cell of claim 25, wherein said enzymatic conversion of glycolate into glycolyl-CoA is achieved by a CoA-transferase (EC 2.8.3.X) or an ADP-forming or AMP-forming CoA ligase (EC 6.2.1.X), said enzymatic conversion of glycolyl-CoA into tartronyl-CoA is achieved by a biotin-dependent acyl-CoA carboxylase (EC 6.4.1.X), and said enzymatic conversion of tartronyl-CoA into tartronate semialdehyde is achieved by an acylating aldehyde dehydrogenase (EC 1.2.1.X).

27. The cell of claim 26, wherein said enzymatic conversion of glycolate into glycolyl-CoA is achieved by propionyl-CoA transferase (EC 2.8.3.1) or propionate-CoA ligase (EC 6.2.1.17), said enzymatic conversion of glycolyl-CoA into tartronyl-CoA is achieved by propionyl-CoA carboxylase (EC 6.4.1.3), and said enzymatic conversion of tartronyl-CoA into tartronate semialdehyde is achieved by malonyl-CoA reductase (EC 1.2.1.75).

28. The cell of claim 1, wherein said further enzymatic conversion of glycolyl-CoA into said intermediate compound of the CBBC comprises enzymatic conversion of said glycolyl-CoA into tartronyl-CoA and further enzymatic conversion of said tartronyl-CoA into said intermediate compound of the CBBC or enzymatic conversion of said glycolyl-CoA into glycolaldehyde and further enzymatic conversion of said glycolaldehyde into said intermediate compound of the CBBC.

* * * * *

SEQUENCE LISTING

<160> NUMBER OF SEQ ID NOS: 26

<210> SEQ ID NO 1
<211> LENGTH: 2004
<212> TYPE: DNA
<213> ORGANISM: Methylobacterium extorquens
<220> FEATURE:
<223> OTHER INFORMATION: Coding sequence of pccA gene
<220> FEATURE:
<221> NAME/KEY: CDS
<222> LOCATION: 1..2004

<223> OTHER INFORMATION: /transl_table=11

<400> SEQUENCE: 1

```
atg ttc gat aag atc ctg att gcc aac cgg ggc gaa atc gcc tgc cgt      48
Met Phe Asp Lys Ile Leu Ile Ala Asn Arg Gly Glu Ile Ala Cys Arg
1               5                   10                  15 atc atc aag acg gcc cag aaa atg ggc atc aag acg gtg gcg gtc tat      96
Ile Ile Lys Thr Ala Gln Lys Met Gly Ile Lys Thr Val Ala Val Tyr
            20                  25                  30 tcg gac gcc gac cgt gat gcg gtc cac gtc gcg atg gcc gac gag gcg     144
Ser Asp Ala Asp Arg Asp Ala Val His Val Ala Met Ala Asp Glu Ala
        35                  40                  45 gtg cat atc ggc ccg gcg ccc gct gcg cag tcc tac ctt ctg atc gaa     192
Val His Ile Gly Pro Ala Pro Ala Ala Gln Ser Tyr Leu Leu Ile Glu
    50                  55                  60 aag atc atc gac gcc tgc aag cag acc ggc gcc caa gcg gtc cat ccg     240
Lys Ile Ile Asp Ala Cys Lys Gln Thr Gly Ala Gln Ala Val His Pro
65                  70                  75                  80 ggc tac ggc ttc ctt tcc gag cgc gag tcc ttc ccc aag gcg ctg gcg     288
Gly Tyr Gly Phe Leu Ser Glu Arg Glu Ser Phe Pro Lys Ala Leu Ala
                85                  90                  95 gaa gcg ggc atc gtc ttt atc ggc ccc aat ccg ggt gcc atc gcc gcc     336
Glu Ala Gly Ile Val Phe Ile Gly Pro Asn Pro Gly Ala Ile Ala Ala
            100                 105                 110 atg ggc gac aag atc gaa tcg aag aag gcc gcg gcc gcg gcc gag gtc     384
Met Gly Asp Lys Ile Glu Ser Lys Lys Ala Ala Ala Ala Ala Glu Val
        115                 120                 125 tcg acg gtg ccg ggc ttc ctc ggc gtg atc gag agc ccc gag cac gcc     432
Ser Thr Val Pro Gly Phe Leu Gly Val Ile Glu Ser Pro Glu His Ala
    130                 135                 140 gtg acg atc gcc gat gag atc ggc tat ccg gtg atg atc aag gcg tcg     480
Val Thr Ile Ala Asp Glu Ile Gly Tyr Pro Val Met Ile Lys Ala Ser
145                 150                 155                 160 gcg ggc ggc ggc ggc aag ggt atg cgc atc gcc gaa tcg gcc gat gag     528
Ala Gly Gly Gly Gly Lys Gly Met Arg Ile Ala Glu Ser Ala Asp Glu
                165                 170                 175 gtc gcc gag ggc ttc gcc cgc gcc aag tcc gag gcc tcg tcc tcc ttc     576
Val Ala Glu Gly Phe Ala Arg Ala Lys Ser Glu Ala Ser Ser Ser Phe
            180                 185                 190 ggc gac gac cgc gtc ttc gtg gaa aag ttc atc acc gac ccg cgc cac     624
Gly Asp Asp Arg Val Phe Val Glu Lys Phe Ile Thr Asp Pro Arg His
        195                 200                 205 atc gag atc cag gtg atc ggc gat aag cac ggc aac gtg atc tat ctc     672
Ile Glu Ile Gln Val Ile Gly Asp Lys His Gly Asn Val Ile Tyr Leu
    210                 215                 220 ggt gag cgc gag tgc tcg atc cag cgc cgc aac cag aag gtc atc gag     720
Gly Glu Arg Glu Cys Ser Ile Gln Arg Arg Asn Gln Lys Val Ile Glu
225                 230                 235                 240 gag gcg ccg tcg ccg ctc ctc gac gaa gag acg cgc cgc aag atg ggc     768
Glu Ala Pro Ser Pro Leu Leu Asp Glu Glu Thr Arg Arg Lys Met Gly
                245                 250                 255 gag cag gcg gtc gcg ctc gcc aag gcc gtg aat tac gac tcc gcc ggc     816
Glu Gln Ala Val Ala Leu Ala Lys Ala Val Asn Tyr Asp Ser Ala Gly
            260                 265                 270 acc gtc gag ttc gtc gcc ggc cag gac aag tcg ttc tac ttc ctc gaa     864
Thr Val Glu Phe Val Ala Gly Gln Asp Lys Ser Phe Tyr Phe Leu Glu
        275                 280                 285 atg aac acc cgc ctg cag gtg gag cac ccg gtc acc gag atg atc acc     912
Met Asn Thr Arg Leu Gln Val Glu His Pro Val Thr Glu Met Ile Thr
    290                 295                 300
```

```
ggg ctc gac ctc gtc gag ctg atg atc cgg gtg gcc gcc ggc gag aag    960
Gly Leu Asp Leu Val Glu Leu Met Ile Arg Val Ala Ala Gly Glu Lys
305                 310                 315                 320 ctg ccg ctg tcg cag gat cag gtg aag ctc gac ggc tgg gcg gtc gag   1008
Leu Pro Leu Ser Gln Asp Gln Val Lys Leu Asp Gly Trp Ala Val Glu
                325                 330                 335 agc cgc gtc tat gcc gag gat ccg acc cgc aac ttc ctg ccc tcg atc   1056
Ser Arg Val Tyr Ala Glu Asp Pro Thr Arg Asn Phe Leu Pro Ser Ile
            340                 345                 350 ggt cgg ctg act acc tac cag ccg ccg gag gag ggc ccg ctc ggc ggg   1104
Gly Arg Leu Thr Thr Tyr Gln Pro Pro Glu Glu Gly Pro Leu Gly Gly
        355                 360                 365 gcg atc gtg cgc aac gat acc ggc gtg gag gag ggc ggc gag atc gcg   1152
Ala Ile Val Arg Asn Asp Thr Gly Val Glu Glu Gly Gly Glu Ile Ala
370                 375                 380 atc cac tac gat ccg atg att gcc aag ctc gta acc tgg gcg ccg acc   1200
Ile His Tyr Asp Pro Met Ile Ala Lys Leu Val Thr Trp Ala Pro Thr
385                 390                 395                 400 cgg ttg gaa gcc atc gaa gcg cag gcg acc gcg ctc gac gcc ttc gcc   1248
Arg Leu Glu Ala Ile Glu Ala Gln Ala Thr Ala Leu Asp Ala Phe Ala
                405                 410                 415 atc gag ggc atc cgc cac aac atc ccc ttc ctc gcc acc ctg atg gcc   1296
Ile Glu Gly Ile Arg His Asn Ile Pro Phe Leu Ala Thr Leu Met Ala
            420                 425                 430 cat ccc cgc tgg cgc gac ggc cgg ctc tcg acg ggc ttc atc aag gaa   1344
His Pro Arg Trp Arg Asp Gly Arg Leu Ser Thr Gly Phe Ile Lys Glu
        435                 440                 445 gag ttc ccc gaa ggc ttc atc gca ccc gag ccc gag ggg ccg gtc gct   1392
Glu Phe Pro Glu Gly Phe Ile Ala Pro Glu Pro Glu Gly Pro Val Ala
450                 455                 460 cat cgg ctc gcg gcg gtg gcg gcg gcg atc gat cac aag ctc aac atc   1440
His Arg Leu Ala Ala Val Ala Ala Ala Ile Asp His Lys Leu Asn Ile
465                 470                 475                 480 cgc aag cgc ggc atc tcc ggc cag atg cgc gac ccg agc ctg ctg acc   1488
Arg Lys Arg Gly Ile Ser Gly Gln Met Arg Asp Pro Ser Leu Leu Thr
                485                 490                 495 ttc cag cgc gag cgc gtg gtg gtg ctc tcc ggc cag cgc ttc aac gtc   1536
Phe Gln Arg Glu Arg Val Val Val Leu Ser Gly Gln Arg Phe Asn Val
            500                 505                 510 acc gtc gat cct gac ggc gac gac ctc ctc gtc acc ttc gac gac ggt   1584
Thr Val Asp Pro Asp Gly Asp Asp Leu Leu Val Thr Phe Asp Asp Gly
        515                 520                 525 acg aca gcc ccg gtg cgc agc gcg tgg cgc ccc ggt gcg ccg gtc tgg   1632
Thr Thr Ala Pro Val Arg Ser Ala Trp Arg Pro Gly Ala Pro Val Trp
530                 535                 540 agc ggt acg gtc gga gat cag tcg gtc gcg atc cag gtg cgt ccg ctc   1680
Ser Gly Thr Val Gly Asp Gln Ser Val Ala Ile Gln Val Arg Pro Leu
545                 550                 555                 560 ctc aac ggt gtg ttc ctg cag cat gcg ggc gcg gcg gaa gcg cgg        1728
Leu Asn Gly Val Phe Leu Gln His Ala Gly Ala Ala Glu Ala Arg
                565                 570                 575 gtg ttc acc cgc cgc gag gcc gaa ctc gcc gac ctg atg ccg gtc aag   1776
Val Phe Thr Arg Arg Glu Ala Glu Leu Ala Asp Leu Met Pro Val Lys
            580                 585                 590 gag aat gcc ggc tcc ggc aag cag ctc ctt tgc ccg atg ccc ggc ctg   1824
Glu Asn Ala Gly Ser Gly Lys Gln Leu Leu Cys Pro Met Pro Gly Leu
        595                 600                 605 gtc aag cag atc atg gtc agc gag ggc cag gag gtg aag aac ggc gag   1872
Val Lys Gln Ile Met Val Ser Glu Gly Gln Glu Val Lys Asn Gly Glu
```

```
                   610                 615                 620
ccg ctg gcc atc gtc gag gcg atg aag atg gag aac gtg ctg cgc gcc      1920
Pro Leu Ala Ile Val Glu Ala Met Lys Met Glu Asn Val Leu Arg Ala
625                 630                 635                 640 gaa cgc gac ggc acc atc tcc aag atc gcc gcc aag gaa ggc gac agc      1968
Glu Arg Asp Gly Thr Ile Ser Lys Ile Ala Ala Lys Glu Gly Asp Ser
                645                 650                 655 ctc gcc gtc gat gcc gtg atc ctg gaa ttc gcc tga                      2004
Leu Ala Val Asp Ala Val Ile Leu Glu Phe Ala
                660                 665
```

<210> SEQ ID NO 2
<211> LENGTH: 667
<212> TYPE: PRT
<213> ORGANISM: Methylobacterium extorquens
<220> FEATURE:
<223> OTHER INFORMATION: [CDS]:1..2004 from SEQ ID NO 1

<400> SEQUENCE: 2

```
Met Phe Asp Lys Ile Leu Ile Ala Asn Arg Gly Glu Ile Ala Cys Arg
1               5                   10                  15

Ile Ile Lys Thr Ala Gln Lys Met Gly Ile Lys Thr Val Ala Val Tyr
            20                  25                  30

Ser Asp Ala Asp Arg Asp Ala Val His Val Ala Met Ala Asp Glu Ala
        35                  40                  45

Val His Ile Gly Pro Ala Pro Ala Gln Ser Tyr Leu Leu Ile Glu
    50                  55                  60

Lys Ile Ile Asp Ala Cys Lys Gln Thr Gly Ala Gln Ala Val His Pro
65                  70                  75                  80

Gly Tyr Gly Phe Leu Ser Glu Arg Glu Ser Phe Pro Lys Ala Leu Ala
                85                  90                  95

Glu Ala Gly Ile Val Phe Ile Gly Pro Asn Pro Gly Ala Ile Ala Ala
            100                 105                 110

Met Gly Asp Lys Ile Glu Ser Lys Lys Ala Ala Ala Ala Glu Val
        115                 120                 125

Ser Thr Val Pro Gly Phe Leu Gly Val Ile Glu Ser Pro Glu His Ala
    130                 135                 140

Val Thr Ile Ala Asp Glu Ile Gly Tyr Pro Val Met Ile Lys Ala Ser
145                 150                 155                 160

Ala Gly Gly Gly Gly Lys Gly Met Arg Ile Ala Glu Ser Ala Asp Glu
                165                 170                 175

Val Ala Glu Gly Phe Ala Arg Ala Lys Ser Glu Ala Ser Ser Phe
            180                 185                 190

Gly Asp Asp Arg Val Phe Val Glu Lys Phe Ile Thr Asp Pro Arg His
        195                 200                 205

Ile Glu Ile Gln Val Ile Gly Asp Lys His Gly Asn Val Ile Tyr Leu
    210                 215                 220

Gly Glu Arg Glu Cys Ser Ile Gln Arg Asn Gln Lys Val Ile Glu
225                 230                 235                 240

Glu Ala Pro Ser Pro Leu Leu Asp Glu Thr Arg Arg Lys Met Gly
                245                 250                 255

Glu Gln Ala Val Ala Leu Ala Lys Ala Val Asn Tyr Asp Ser Ala Gly
            260                 265                 270

Thr Val Glu Phe Val Ala Gly Gln Asp Lys Ser Phe Tyr Phe Leu Glu
        275                 280                 285

Met Asn Thr Arg Leu Gln Val Glu His Pro Val Thr Glu Met Ile Thr
```

```
                290                 295                 300
Gly Leu Asp Leu Val Glu Leu Met Ile Arg Val Ala Ala Gly Glu Lys
305                 310                 315                 320

Leu Pro Leu Ser Gln Asp Gln Val Lys Leu Asp Gly Trp Ala Val Glu
                325                 330                 335

Ser Arg Val Tyr Ala Glu Asp Pro Thr Arg Asn Phe Leu Pro Ser Ile
                340                 345                 350

Gly Arg Leu Thr Thr Tyr Gln Pro Pro Glu Glu Gly Pro Leu Gly Gly
                355                 360                 365

Ala Ile Val Arg Asn Asp Thr Gly Val Glu Glu Gly Glu Ile Ala
            370                 375                 380

Ile His Tyr Asp Pro Met Ile Ala Lys Leu Val Thr Trp Ala Pro Thr
385                 390                 395                 400

Arg Leu Glu Ala Ile Glu Ala Gln Ala Thr Ala Leu Asp Ala Phe Ala
                405                 410                 415

Ile Glu Gly Ile Arg His Asn Ile Pro Phe Leu Ala Thr Leu Met Ala
                420                 425                 430

His Pro Arg Trp Arg Asp Gly Arg Leu Ser Thr Gly Phe Ile Lys Glu
                435                 440                 445

Glu Phe Pro Glu Gly Phe Ile Ala Pro Glu Pro Gly Pro Val Ala
450                 455                 460

His Arg Leu Ala Ala Val Ala Ala Ala Ile Asp His Lys Leu Asn Ile
465                 470                 475                 480

Arg Lys Arg Gly Ile Ser Gly Gln Met Arg Asp Pro Ser Leu Leu Thr
                485                 490                 495

Phe Gln Arg Glu Arg Val Val Val Leu Ser Gly Gln Arg Phe Asn Val
                500                 505                 510

Thr Val Asp Pro Asp Gly Asp Asp Leu Leu Val Thr Phe Asp Asp Gly
                515                 520                 525

Thr Thr Ala Pro Val Arg Ser Ala Trp Arg Pro Gly Ala Pro Val Trp
                530                 535                 540

Ser Gly Thr Val Gly Asp Gln Ser Val Ala Ile Gln Val Arg Pro Leu
545                 550                 555                 560

Leu Asn Gly Val Phe Leu Gln His Ala Gly Ala Ala Ala Glu Ala Arg
                565                 570                 575

Val Phe Thr Arg Arg Glu Ala Glu Leu Ala Asp Leu Met Pro Val Lys
                580                 585                 590

Glu Asn Ala Gly Ser Gly Lys Gln Leu Leu Cys Pro Met Pro Gly Leu
                595                 600                 605

Val Lys Gln Ile Met Val Ser Glu Gly Gln Glu Val Lys Asn Gly Glu
610                 615                 620

Pro Leu Ala Ile Val Glu Ala Met Lys Met Glu Asn Val Leu Arg Ala
625                 630                 635                 640

Glu Arg Asp Gly Thr Ile Ser Lys Ile Ala Lys Glu Gly Asp Ser
                645                 650                 655

Leu Ala Val Asp Ala Val Ile Leu Glu Phe Ala
                660                 665

<210> SEQ ID NO 3
<211> LENGTH: 1533
<212> TYPE: DNA
<213> ORGANISM: Methylobacterium extorquens
<220> FEATURE:
<223> OTHER INFORMATION: Coding sequence of pccB gene
<220> FEATURE:
```

```
<221> NAME/KEY: CDS
<222> LOCATION: 1..1533
<223> OTHER INFORMATION: /transl_table=11

<400> SEQUENCE: 3
```

| | | | | | | | | | | | | | | | | |
|---|---|---|---|---|---|---|---|---|---|---|---|---|---|---|---|---|
| atg | aag | gac | att | ctc | gag | aag | ctt | gag | gag | cgt | cgc | gca | cag | gcc | cgt | 48 |
| Met | Lys | Asp | Ile | Leu | Glu | Lys | Leu | Glu | Glu | Arg | Arg | Ala | Gln | Ala | Arg | |
| 1 | | | | 5 | | | | | 10 | | | | | 15 | | |
| ctc | ggc | ggc | ggg | gaa | aag | cgg | ctc | gag | gcg | cag | cac | aag | cgc | ggc | aag | 96 |
| Leu | Gly | Gly | Gly | Glu | Lys | Arg | Leu | Glu | Ala | Gln | His | Lys | Arg | Gly | Lys | |
| | | | 20 | | | | | 25 | | | | | 30 | | | |
| ctc | acg | gcg | cgc | gag | cgc | atc | gaa | ctc | ctg | ctc | gac | cac | ggg | tcg | ttc | 144 |
| Leu | Thr | Ala | Arg | Glu | Arg | Ile | Glu | Leu | Leu | Leu | Asp | His | Gly | Ser | Phe | |
| | | 35 | | | | | 40 | | | | | 45 | | | | |
| gag | gag | ttc | gac | atg | ttc | gtg | cag | cac | cgc | tcc | acc | gat | ttc | ggc | atg | 192 |
| Glu | Glu | Phe | Asp | Met | Phe | Val | Gln | His | Arg | Ser | Thr | Asp | Phe | Gly | Met | |
| 50 | | | | | 55 | | | | | 60 | | | | | | |
| gag | aag | cag | aag | atc | ccc | ggc | gac | ggc | gtc | gtc | acc | ggc | tgg | ggc | acc | 240 |
| Glu | Lys | Gln | Lys | Ile | Pro | Gly | Asp | Gly | Val | Val | Thr | Gly | Trp | Gly | Thr | |
| 65 | | | | | 70 | | | | | 75 | | | | | 80 | |
| gtg | aac | ggg | cgc | acc | gtc | ttc | ctg | ttc | tcg | aag | gac | ttc | acg | gtg | ttc | 288 |
| Val | Asn | Gly | Arg | Thr | Val | Phe | Leu | Phe | Ser | Lys | Asp | Phe | Thr | Val | Phe | |
| | | | | 85 | | | | | 90 | | | | | 95 | | |
| ggc | ggc | tcg | ctc | tcc | gag | gcg | cac | gca | gcc | aag | atc | gtt | aag | gtc | cag | 336 |
| Gly | Gly | Ser | Leu | Ser | Glu | Ala | His | Ala | Ala | Lys | Ile | Val | Lys | Val | Gln | |
| | | | 100 | | | | | 105 | | | | | 110 | | | |
| gac | atg | gcg | ctg | aag | atg | cgc | gcc | ccg | atc | atc | ggc | atc | ttc | gat | gcc | 384 |
| Asp | Met | Ala | Leu | Lys | Met | Arg | Ala | Pro | Ile | Ile | Gly | Ile | Phe | Asp | Ala | |
| | | 115 | | | | | 120 | | | | | 125 | | | | |
| ggc | ggt | gcg | cgc | atc | cag | gag | ggc | gtg | gcc | gcg | ctc | ggc | ggc | tac | ggc | 432 |
| Gly | Gly | Ala | Arg | Ile | Gln | Glu | Gly | Val | Ala | Ala | Leu | Gly | Gly | Tyr | Gly | |
| | | 130 | | | | | 135 | | | | | 140 | | | | |
| gag | gtg | ttc | cgc | cgc | aac | gtc | gct | gcc | tcc | ggc | gtg | atc | ccg | cag | atc | 480 |
| Glu | Val | Phe | Arg | Arg | Asn | Val | Ala | Ala | Ser | Gly | Val | Ile | Pro | Gln | Ile | |
| 145 | | | | | 150 | | | | | 155 | | | | | 160 | |
| tcg | gtc | atc | atg | ggg | ccg | tgc | gcg | ggc | ggc | gac | gtg | tac | tcg | ccg | gcc | 528 |
| Ser | Val | Ile | Met | Gly | Pro | Cys | Ala | Gly | Gly | Asp | Val | Tyr | Ser | Pro | Ala | |
| | | | | 165 | | | | | 170 | | | | | 175 | | |
| atg | acc | gac | ttc | atc | ttc | atg | gtg | cgt | gac | acg | agc | tac | atg | ttc | gtg | 576 |
| Met | Thr | Asp | Phe | Ile | Phe | Met | Val | Arg | Asp | Thr | Ser | Tyr | Met | Phe | Val | |
| | | | 180 | | | | | 185 | | | | | 190 | | | |
| acc | ggc | ccc | gac | gtg | gtg | aag | acc | gtc | acc | aac | gag | gtc | gtg | acc | gcc | 624 |
| Thr | Gly | Pro | Asp | Val | Val | Lys | Thr | Val | Thr | Asn | Glu | Val | Val | Thr | Ala | |
| | | 195 | | | | | 200 | | | | | 205 | | | | |
| gag | gaa | ctc | ggc | ggc | gcc | aag | gtc | cac | acc | tcg | aaa | tcc | tcg | atc | gcc | 672 |
| Glu | Glu | Leu | Gly | Gly | Ala | Lys | Val | His | Thr | Ser | Lys | Ser | Ser | Ile | Ala | |
| 210 | | | | | 215 | | | | | 220 | | | | | | |
| gac | ggc | tcg | ttc | gag | aac | gac | gtc | gag | gcg | atc | ctc | cag | atc | cgc | cgc | 720 |
| Asp | Gly | Ser | Phe | Glu | Asn | Asp | Val | Glu | Ala | Ile | Leu | Gln | Ile | Arg | Arg | |
| 225 | | | | | 230 | | | | | 235 | | | | | 240 | |
| ctg | ctc | gac | ttc | ctg | ccc | gcg | aac | aac | atc | gag | ggc | gtg | ccg | gag | atc | 768 |
| Leu | Leu | Asp | Phe | Leu | Pro | Ala | Asn | Asn | Ile | Glu | Gly | Val | Pro | Glu | Ile | |
| | | | | 245 | | | | | 250 | | | | | 255 | | |
| gag | agc | ttc | gac | gac | gtc | aac | cgc | ctc | gac | aag | tcg | ctc | gac | acg | ctg | 816 |
| Glu | Ser | Phe | Asp | Asp | Val | Asn | Arg | Leu | Asp | Lys | Ser | Leu | Asp | Thr | Leu | |
| | | | 260 | | | | | 265 | | | | | 270 | | | |
| atc | ccg | gac | aac | ccg | aac | aag | ccc | tac | gac | atg | ggc | gag | ctg | atc | cgc | 864 |
| Ile | Pro | Asp | Asn | Pro | Asn | Lys | Pro | Tyr | Asp | Met | Gly | Glu | Leu | Ile | Arg | |
| | | 275 | | | | | 280 | | | | | 285 | | | | |
| cgg | gtc | gtg | gac | gaa | ggc | gac | ttc | ttc | gag | atc | cag | gcg | gct | tac | gcc | 912 |

```
                    Arg Val Val Asp Glu Gly Asp Phe Phe Glu Ile Gln Ala Ala Tyr Ala
                                    290                 295                 300 cgc aat att atc acc ggc ttc ggc cgc gtc gag ggc cgc acc gtc ggt              960
Arg Asn Ile Ile Thr Gly Phe Gly Arg Val Glu Gly Arg Thr Val Gly
305                 310                 315                 320 ttc gtc gcc aac cag ccg ctg gtg ctg gcc ggc gtg ctt gat tcg gac             1008
Phe Val Ala Asn Gln Pro Leu Val Leu Ala Gly Val Leu Asp Ser Asp
                325                 330                 335 gcc tcc cgg aag gcg gcc cgc ttc gtg cgc ttc tgc aac gcc ttc tcg             1056
Ala Ser Arg Lys Ala Ala Arg Phe Val Arg Phe Cys Asn Ala Phe Ser
                340                 345                 350 atc ccg atc gtc acc ttc gtg gac gtg ccg ggc ttc ctg ccg ggc acg             1104
Ile Pro Ile Val Thr Phe Val Asp Val Pro Gly Phe Leu Pro Gly Thr
                355                 360                 365 gcg cag gaa tat ggc ggc ctg atc aag cac ggc gcc aag ctg ctc ttc             1152
Ala Gln Glu Tyr Gly Gly Leu Ile Lys His Gly Ala Lys Leu Leu Phe
370                 375                 380 gcc tac agc caa gcc acc gtg ccg ctc gtg acc atc atc acc cgc aag             1200
Ala Tyr Ser Gln Ala Thr Val Pro Leu Val Thr Ile Ile Thr Arg Lys
385                 390                 395                 400 gcc ttc ggc ggc gcc tac gac gtc atg gcc tcc aag cat gtc ggc gcc             1248
Ala Phe Gly Gly Ala Tyr Asp Val Met Ala Ser Lys His Val Gly Ala
                405                 410                 415 gac ctg aac tac gcg tgg ccg acg gcg cag atc gcg gtg atg ggc gcc             1296
Asp Leu Asn Tyr Ala Trp Pro Thr Ala Gln Ile Ala Val Met Gly Ala
                420                 425                 430 aag ggc gct gtc gag atc atc ttc cgc gcc gag atc ggc gat gcg gac             1344
Lys Gly Ala Val Glu Ile Ile Phe Arg Ala Glu Ile Gly Asp Ala Asp
                435                 440                 445 aag atc gcc gag cgg acc aaa gaa tac gag gac cgc ttc ctc tcg ccc             1392
Lys Ile Ala Glu Arg Thr Lys Glu Tyr Glu Asp Arg Phe Leu Ser Pro
450                 455                 460 ttc gtg gcg gcg gag cgc ggc tac atc gac gag gtg atc atg ccc cac             1440
Phe Val Ala Ala Glu Arg Gly Tyr Ile Asp Glu Val Ile Met Pro His
465                 470                 475                 480 tcc acc cgc aag cgg atc gcg cgg gcg ctc ggg atg ctg cgc acc aag             1488
Ser Thr Arg Lys Arg Ile Ala Arg Ala Leu Gly Met Leu Arg Thr Lys
                485                 490                 495 gag atg gag cag ccc tgg aag aag cac gac aac atc ccg ctc tga               1533
Glu Met Glu Gln Pro Trp Lys Lys His Asp Asn Ile Pro Leu
                500                 505                 510

<210> SEQ ID NO 4
<211> LENGTH: 510
<212> TYPE: PRT
<213> ORGANISM: Methylobacterium extorquens
<220> FEATURE:
<223> OTHER INFORMATION: [CDS]:1..1533 from SEQ ID NO 3

<400> SEQUENCE: 4

Met Lys Asp Ile Leu Glu Lys Leu Glu Glu Arg Arg Ala Gln Ala Arg
1               5                   10                  15

Leu Gly Gly Gly Glu Lys Arg Leu Glu Ala Gln His Lys Arg Gly Lys
                20                  25                  30

Leu Thr Ala Arg Glu Arg Ile Glu Leu Leu Asp His Gly Ser Phe
                35                  40                  45

Glu Glu Phe Asp Met Phe Val Gln His Arg Ser Thr Asp Phe Gly Met
50                  55                  60

Glu Lys Gln Lys Ile Pro Gly Asp Gly Val Val Thr Gly Trp Gly Thr
65                  70                  75                  80
```

```
Val Asn Gly Arg Thr Val Phe Leu Phe Ser Lys Asp Phe Thr Val Phe
                85                  90                  95

Gly Gly Ser Leu Ser Glu Ala His Ala Ala Lys Ile Val Lys Val Gln
            100                 105                 110

Asp Met Ala Leu Lys Met Arg Ala Pro Ile Ile Gly Ile Phe Asp Ala
        115                 120                 125

Gly Gly Ala Arg Ile Gln Glu Gly Val Ala Ala Leu Gly Gly Tyr Gly
    130                 135                 140

Glu Val Phe Arg Arg Asn Val Ala Ala Ser Gly Val Ile Pro Gln Ile
145                 150                 155                 160

Ser Val Ile Met Gly Pro Cys Ala Gly Gly Asp Val Tyr Ser Pro Ala
                165                 170                 175

Met Thr Asp Phe Ile Phe Met Val Arg Asp Thr Ser Tyr Met Phe Val
            180                 185                 190

Thr Gly Pro Asp Val Val Lys Thr Val Thr Asn Glu Val Val Thr Ala
        195                 200                 205

Glu Glu Leu Gly Gly Ala Lys Val His Thr Ser Lys Ser Ser Ile Ala
    210                 215                 220

Asp Gly Ser Phe Glu Asn Asp Val Glu Ala Ile Leu Gln Ile Arg Arg
225                 230                 235                 240

Leu Leu Asp Phe Leu Pro Ala Asn Asn Ile Glu Gly Val Pro Glu Ile
                245                 250                 255

Glu Ser Phe Asp Asp Val Asn Arg Leu Asp Lys Ser Leu Asp Thr Leu
            260                 265                 270

Ile Pro Asp Asn Pro Asn Lys Pro Tyr Asp Met Gly Leu Ile Arg
        275                 280                 285

Arg Val Val Asp Glu Gly Asp Phe Phe Glu Ile Gln Ala Ala Tyr Ala
    290                 295                 300

Arg Asn Ile Ile Thr Gly Phe Gly Arg Val Glu Gly Arg Thr Val Gly
305                 310                 315                 320

Phe Val Ala Asn Gln Pro Leu Val Leu Ala Gly Val Leu Asp Ser Asp
                325                 330                 335

Ala Ser Arg Lys Ala Ala Arg Phe Val Arg Phe Cys Asn Ala Phe Ser
            340                 345                 350

Ile Pro Ile Val Thr Phe Val Asp Val Pro Gly Phe Leu Pro Gly Thr
        355                 360                 365

Ala Gln Glu Tyr Gly Gly Leu Ile Lys His Gly Ala Lys Leu Leu Phe
    370                 375                 380

Ala Tyr Ser Gln Ala Thr Val Pro Leu Val Thr Ile Ile Thr Arg Lys
385                 390                 395                 400

Ala Phe Gly Gly Ala Tyr Asp Val Met Ala Ser Lys His Val Gly Ala
                405                 410                 415

Asp Leu Asn Tyr Ala Trp Pro Thr Ala Gln Ile Ala Val Met Gly Ala
            420                 425                 430

Lys Gly Ala Val Glu Ile Ile Phe Arg Ala Glu Ile Gly Asp Ala Asp
        435                 440                 445

Lys Ile Ala Glu Arg Thr Lys Glu Tyr Glu Asp Arg Phe Leu Ser Pro
    450                 455                 460

Phe Val Ala Ala Glu Arg Gly Tyr Ile Asp Glu Val Ile Met Pro His
465                 470                 475                 480

Ser Thr Arg Lys Arg Ile Ala Arg Ala Leu Gly Met Leu Arg Thr Lys
                485                 490                 495
```

```
                                       Glu Met Glu Gln Pro Trp Lys Lys His Asp Asn Ile Pro Leu
                                                       500                 505                 510

<210> SEQ ID NO 5
<211> LENGTH: 1533
<212> TYPE: DNA
<213> ORGANISM: Artificial Sequence
<220> FEATURE:
<223> OTHER INFORMATION: Nucleic acid sequence encoding the mutant
      variant pccB_D407I_Y143H of pccB protein from Methylobacterium
      extorquens
<220> FEATURE:
<221> NAME/KEY: CDS
<222> LOCATION: 1..1533
<223> OTHER INFORMATION: /transl_table=1

<400> SEQUENCE: 5 atg aag gac atc ctc gag aag ctt gag gag cgt cgc gca cag gcc cgt       48
Met Lys Asp Ile Leu Glu Lys Leu Glu Glu Arg Arg Ala Gln Ala Arg
1               5                   10                  15 ctc ggc ggc ggg gaa aag cgg ctc gag gcg cag cac aag cgc ggc aag       96
Leu Gly Gly Gly Glu Lys Arg Leu Glu Ala Gln His Lys Arg Gly Lys
            20                  25                  30 ctc acg gcg cgc gag cgc atc gaa ctc ctg ctc gac cac ggg tcg ttc      144
Leu Thr Ala Arg Glu Arg Ile Glu Leu Leu Leu Asp His Gly Ser Phe
        35                  40                  45 gag gag ttc gac atg ttc gtg cag cac cgc tcc acc gat ttc ggc atg      192
Glu Glu Phe Asp Met Phe Val Gln His Arg Ser Thr Asp Phe Gly Met
50                  55                  60 gag aag cag aag atc ccc ggc gac ggc gtc gtc acc ggc tgg ggc acc      240
Glu Lys Gln Lys Ile Pro Gly Asp Gly Val Val Thr Gly Trp Gly Thr
65                  70                  75                  80 gtg aac ggg cgc acc gtc ttc ctg ttc tcg aag gac ttc acg gtg ttc      288
Val Asn Gly Arg Thr Val Phe Leu Phe Ser Lys Asp Phe Thr Val Phe
                85                  90                  95 ggc ggc tcg ctc tcc gag gcg cac gca gcc aag atc gtt aag gtc cag      336
Gly Gly Ser Leu Ser Glu Ala His Ala Ala Lys Ile Val Lys Val Gln
            100                 105                 110 gac atg gcg ctg aag atg cgc gcc ccg atc atc ggc atc ttc gat gcc      384
Asp Met Ala Leu Lys Met Arg Ala Pro Ile Ile Gly Ile Phe Asp Ala
        115                 120                 125 ggc ggt gcg cgc atc cag gag ggc gtg gcc gcg ctc ggc ggc cac ggc      432
Gly Gly Ala Arg Ile Gln Glu Gly Val Ala Ala Leu Gly Gly His Gly
130                 135                 140 gag gtg ttc cgc cgc aac gtc gct gcc tcc ggc gtg atc ccg cag atc      480
Glu Val Phe Arg Arg Asn Val Ala Ala Ser Gly Val Ile Pro Gln Ile
145                 150                 155                 160 tcg gtc atc atg ggg ccg tgc gcg ggc ggc gac gtg tac tcg ccg gcc      528
Ser Val Ile Met Gly Pro Cys Ala Gly Gly Asp Val Tyr Ser Pro Ala
                165                 170                 175 atg acc gac ttc atc ttc atg gtg cgt gac acg agc tac atg ttc gtg      576
Met Thr Asp Phe Ile Phe Met Val Arg Asp Thr Ser Tyr Met Phe Val
            180                 185                 190 acc ggc ccc gac gtg gtg aag acc gtc acc aac gag gtc gtg acc gcc      624
Thr Gly Pro Asp Val Val Lys Thr Val Thr Asn Glu Val Val Thr Ala
        195                 200                 205 gag gaa ctc ggc ggc gcc aag gtc cac acc tcg aaa tcc tcg atc gcc      672
Glu Glu Leu Gly Gly Ala Lys Val His Thr Ser Lys Ser Ser Ile Ala
210                 215                 220 gac ggc tcg ttc gag aac gac gtc gag gcg atc ctc cag atc cgc cgc      720
Asp Gly Ser Phe Glu Asn Asp Val Glu Ala Ile Leu Gln Ile Arg Arg
225                 230                 235                 240
```

```
ctg ctc gac ttc ctg ccc gcg aac aac atc gag ggc gtg ccg gag atc      768
Leu Leu Asp Phe Leu Pro Ala Asn Asn Ile Glu Gly Val Pro Glu Ile
                    245                 250                 255 gag agc ttc gac gac gtc aac cgc ctc gac aag tcg ctc gac acg ctg      816
Glu Ser Phe Asp Asp Val Asn Arg Leu Asp Lys Ser Leu Asp Thr Leu
                260                 265                 270 atc ccg gac aac ccg aac aag ccc tac gac atg ggc gag ctg atc cgc      864
Ile Pro Asp Asn Pro Asn Lys Pro Tyr Asp Met Gly Glu Leu Ile Arg
            275                 280                 285 cgg gtc gtg gac gaa ggc gac ttc ttc gag atc cag gcg gct tac gcc      912
Arg Val Val Asp Glu Gly Asp Phe Phe Glu Ile Gln Ala Ala Tyr Ala
        290                 295                 300 cgc aat att atc acc ggc ttc ggc cgc gtc gag ggc cgc acc gtc ggt      960
Arg Asn Ile Ile Thr Gly Phe Gly Arg Val Glu Gly Arg Thr Val Gly
305                 310                 315                 320 ttc gtc gcc aac cag ccg ctg gtg ctg gcc ggc gtg ctt gat tcg gac     1008
Phe Val Ala Asn Gln Pro Leu Val Leu Ala Gly Val Leu Asp Ser Asp
                325                 330                 335 gcc tcc cgg aag gcg gcc cgc ttc gtg cgc ttc tgc aac gcc ttc tcg     1056
Ala Ser Arg Lys Ala Ala Arg Phe Val Arg Phe Cys Asn Ala Phe Ser
                340                 345                 350 atc ccg atc gtc acc ttc gtg gac gtg ccg ggc ttc ctg ccg ggc acg     1104
Ile Pro Ile Val Thr Phe Val Asp Val Pro Gly Phe Leu Pro Gly Thr
            355                 360                 365 gcg cag gaa tat ggc ggc ctg atc aag cac ggc gcc aag ctg ctc ttc     1152
Ala Gln Glu Tyr Gly Gly Leu Ile Lys His Gly Ala Lys Leu Leu Phe
        370                 375                 380 gcc tac agc caa gcc acc gtg ccg ctc gtg acc atc atc acc cgc aag     1200
Ala Tyr Ser Gln Ala Thr Val Pro Leu Val Thr Ile Ile Thr Arg Lys
385                 390                 395                 400 gcc ttc ggc ggc gcc tac atc gtc atg gcc tcc aag cat gtc ggc gcc     1248
Ala Phe Gly Gly Ala Tyr Ile Val Met Ala Ser Lys His Val Gly Ala
                405                 410                 415 gac ctg aac tac gcg tgg ccg acg gcg cag atc gcg gtg atg ggc gcc     1296
Asp Leu Asn Tyr Ala Trp Pro Thr Ala Gln Ile Ala Val Met Gly Ala
                420                 425                 430 aag ggc gct gtc gag atc atc ttc cgc gcc gag atc ggc gat gcg gac     1344
Lys Gly Ala Val Glu Ile Ile Phe Arg Ala Glu Ile Gly Asp Ala Asp
            435                 440                 445 aag atc gcc gag cgg acc aaa gaa tac gag gac cgc ttc ctc tcg ccc     1392
Lys Ile Ala Glu Arg Thr Lys Glu Tyr Glu Asp Arg Phe Leu Ser Pro
        450                 455                 460 ttc gtg gcg gcg gag cgc ggc tac atc gac gag gtg atc atg ccc cac     1440
Phe Val Ala Ala Glu Arg Gly Tyr Ile Asp Glu Val Ile Met Pro His
465                 470                 475                 480 tcc acc cgc aag cgg atc gcg cgg gcg ctc ggg atg ctg cgc acc aag     1488
Ser Thr Arg Lys Arg Ile Ala Arg Ala Leu Gly Met Leu Arg Thr Lys
                485                 490                 495 gag atg gag cag ccc tgg aag aag cac gac aac atc ccg ctc tga        1533
Glu Met Glu Gln Pro Trp Lys Lys His Asp Asn Ile Pro Leu
                500                 505                 510

<210> SEQ ID NO 6
<211> LENGTH: 510
<212> TYPE: PRT
<213> ORGANISM: Artificial Sequence
<220> FEATURE:
<223> OTHER INFORMATION: [CDS]:1..1533 from SEQ ID NO 5

<400> SEQUENCE: 6

Met Lys Asp Ile Leu Glu Lys Leu Glu Glu Arg Arg Ala Gln Ala Arg
```

-continued

```
1               5                   10                  15
Leu Gly Gly Gly Glu Lys Arg Leu Glu Ala Gln His Lys Arg Gly Lys
                20                  25                  30
Leu Thr Ala Arg Glu Arg Ile Glu Leu Leu Asp His Gly Ser Phe
                35                  40                  45
Glu Glu Phe Asp Met Phe Val Gln His Arg Ser Thr Asp Phe Gly Met
            50                  55                  60
Glu Lys Gln Lys Ile Pro Gly Asp Gly Val Val Thr Gly Trp Gly Thr
65                  70                  75                  80
Val Asn Gly Arg Thr Val Phe Leu Phe Ser Lys Asp Phe Thr Val Phe
                85                  90                  95
Gly Gly Ser Leu Ser Glu Ala His Ala Ala Lys Ile Val Lys Val Gln
            100                 105                 110
Asp Met Ala Leu Lys Met Arg Ala Pro Ile Ile Gly Ile Phe Asp Ala
            115                 120                 125
Gly Gly Ala Arg Ile Gln Glu Gly Val Ala Ala Leu Gly Gly His Gly
            130                 135                 140
Glu Val Phe Arg Arg Asn Val Ala Ala Ser Gly Val Ile Pro Gln Ile
145                 150                 155                 160
Ser Val Ile Met Gly Pro Cys Ala Gly Gly Asp Val Tyr Ser Pro Ala
                165                 170                 175
Met Thr Asp Phe Ile Phe Met Val Arg Asp Thr Ser Tyr Met Phe Val
                180                 185                 190
Thr Gly Pro Asp Val Val Lys Thr Val Thr Asn Glu Val Val Thr Ala
                195                 200                 205
Glu Glu Leu Gly Gly Ala Lys Val His Thr Ser Lys Ser Ser Ile Ala
210                 215                 220
Asp Gly Ser Phe Glu Asn Asp Val Glu Ala Ile Leu Gln Ile Arg Arg
225                 230                 235                 240
Leu Leu Asp Phe Leu Pro Ala Asn Asn Ile Glu Gly Val Pro Glu Ile
                245                 250                 255
Glu Ser Phe Asp Asp Val Asn Arg Leu Asp Lys Ser Leu Asp Thr Leu
                260                 265                 270
Ile Pro Asp Asn Pro Asn Lys Pro Tyr Asp Met Gly Glu Leu Ile Arg
            275                 280                 285
Arg Val Val Asp Glu Gly Asp Phe Phe Glu Ile Gln Ala Ala Tyr Ala
290                 295                 300
Arg Asn Ile Ile Thr Gly Phe Gly Arg Val Glu Gly Arg Thr Val Gly
305                 310                 315                 320
Phe Val Ala Asn Gln Pro Leu Val Leu Ala Gly Val Leu Asp Ser Asp
                325                 330                 335
Ala Ser Arg Lys Ala Ala Arg Phe Val Arg Phe Cys Asn Ala Phe Ser
                340                 345                 350
Ile Pro Ile Val Thr Phe Val Asp Val Pro Gly Phe Leu Pro Gly Thr
                355                 360                 365
Ala Gln Glu Tyr Gly Gly Leu Ile Lys His Gly Ala Lys Leu Leu Phe
            370                 375                 380
Ala Tyr Ser Gln Ala Thr Val Pro Leu Val Thr Ile Ile Thr Arg Lys
385                 390                 395                 400
Ala Phe Gly Gly Ala Tyr Ile Val Met Ala Ser Lys His Val Gly Ala
                405                 410                 415
Asp Leu Asn Tyr Ala Trp Pro Thr Ala Gln Ile Ala Val Met Gly Ala
                420                 425                 430
```

```
Lys Gly Ala Val Glu Ile Ile Phe Arg Ala Glu Ile Gly Asp Ala Asp
            435                 440                 445

Lys Ile Ala Glu Arg Thr Lys Glu Tyr Glu Asp Arg Phe Leu Ser Pro
        450                 455                 460

Phe Val Ala Ala Glu Arg Gly Tyr Ile Asp Val Ile Met Pro His
465                 470                 475                 480

Ser Thr Arg Lys Arg Ile Ala Arg Ala Leu Gly Met Leu Arg Thr Lys
                485                 490                 495

Glu Met Glu Gln Pro Trp Lys Lys His Asp Asn Ile Pro Leu
            500                 505                 510

<210> SEQ ID NO 7
<211> LENGTH: 3663
<212> TYPE: DNA
<213> ORGANISM: Chloroflexus aurantiacus
<220> FEATURE:
<223> OTHER INFORMATION: Coding sequence of the gene encoding
      malonyl-CoA reductase
<220> FEATURE:
<221> NAME/KEY: CDS
<222> LOCATION: 1..3663
<223> OTHER INFORMATION: /transl_table=11

<400> SEQUENCE: 7 atg agc gga aca gga cga ctg gca gga aag att gcg tta att acc ggt      48
Met Ser Gly Thr Gly Arg Leu Ala Gly Lys Ile Ala Leu Ile Thr Gly
1               5                   10                  15 ggc gcc ggc aat atc ggc agt gaa ttg aca cgt cgc ttt ctc gca gag     96
Gly Ala Gly Asn Ile Gly Ser Glu Leu Thr Arg Arg Phe Leu Ala Glu
                20                  25                  30 gga gcg acg gtc att att agt gga cgg aat cgg gcg aag ttg acc gca    144
Gly Ala Thr Val Ile Ile Ser Gly Arg Asn Arg Ala Lys Leu Thr Ala
            35                  40                  45 ctg gcc gaa cgg atg cag gca gag gca gga gtg ccg gca aag cgc atc    192
Leu Ala Glu Arg Met Gln Ala Glu Ala Gly Val Pro Ala Lys Arg Ile
        50                  55                  60 gat ctc gaa gtc atg gat ggg agt gat ccg gtc gcg gta cgt gcc ggt    240
Asp Leu Glu Val Met Asp Gly Ser Asp Pro Val Ala Val Arg Ala Gly
65                  70                  75                  80 atc gaa gcg att gtg gcc cgt cac ggc cag atc gac att ctg gtc aac    288
Ile Glu Ala Ile Val Ala Arg His Gly Gln Ile Asp Ile Leu Val Asn
                85                  90                  95 aat gca gga agt gcc ggt gcc cag cgt cgt ctg gcc gag att cca ctc    336
Asn Ala Gly Ser Ala Gly Ala Gln Arg Arg Leu Ala Glu Ile Pro Leu
            100                 105                 110 act gaa gct gaa tta ggc cct ggc gcc gaa gag acg ctt cat gcc agc    384
Thr Glu Ala Glu Leu Gly Pro Gly Ala Glu Glu Thr Leu His Ala Ser
        115                 120                 125 atc gcc aat tta ctt ggt atg gga tgg cat ctg atg cgt att gcg gca    432
Ile Ala Asn Leu Leu Gly Met Gly Trp His Leu Met Arg Ile Ala Ala
    130                 135                 140 cct cat atg ccg gta gga agt gcg gtc atc aat gtc tcg acc atc ttt    480
Pro His Met Pro Val Gly Ser Ala Val Ile Asn Val Ser Thr Ile Phe
145                 150                 155                 160 tca cgg gct gag tac tac ggg cgg att ccg tat gtc acc cct aaa gct    528
Ser Arg Ala Glu Tyr Tyr Gly Arg Ile Pro Tyr Val Thr Pro Lys Ala
                165                 170                 175 gct ctt aat gct cta tct caa ctt gct gcg cgt gag tta ggt gca cgt    576
Ala Leu Asn Ala Leu Ser Gln Leu Ala Ala Arg Glu Leu Gly Ala Arg
            180                 185                 190
```

```
                                                            -continued ggc atc cgc gtt aat acg atc ttt ccc ggc ccg att gaa agt gat cgc        624
Gly Ile Arg Val Asn Thr Ile Phe Pro Gly Pro Ile Glu Ser Asp Arg
        195                 200                 205 atc cgt aca gtg ttc cag cgt atg gat cag ctc aag ggg cgg ccc gaa        672
Ile Arg Thr Val Phe Gln Arg Met Asp Gln Leu Lys Gly Arg Pro Glu
210                 215                 220 ggc gac aca gcg cac cat ttt ttg aac acc atg cga ttg tgt cgt gcc        720
Gly Asp Thr Ala His His Phe Leu Asn Thr Met Arg Leu Cys Arg Ala
225                 230                 235                 240 aac gac cag ggc gcg ctt gaa cgt cgg ttc ccc tcc gtc ggt gat gtg        768
Asn Asp Gln Gly Ala Leu Glu Arg Arg Phe Pro Ser Val Gly Asp Val
            245                 250                 255 gca gac gcc gct gtc ttt ctg gcc agt gcc gaa tcc gcc gct ctc tcc        816
Ala Asp Ala Ala Val Phe Leu Ala Ser Ala Glu Ser Ala Ala Leu Ser
                260                 265                 270 ggt gag acg att gag gtt acg cac gga atg gag ttg ccg gcc tgc agt        864
Gly Glu Thr Ile Glu Val Thr His Gly Met Glu Leu Pro Ala Cys Ser
        275                 280                 285 gag acc agc ctg ctg gcc cgt act gat ctg cgc acg att gat gcc agt        912
Glu Thr Ser Leu Leu Ala Arg Thr Asp Leu Arg Thr Ile Asp Ala Ser
290                 295                 300 ggc cgc acg acg ctc atc tgc gcc ggc gac cag att gaa gag gtg atg        960
Gly Arg Thr Thr Leu Ile Cys Ala Gly Asp Gln Ile Glu Glu Val Met
305                 310                 315                 320 gcg ctc acc ggt atg ttg cgt acc tgt ggg agt gaa gtg atc atc ggc       1008
Ala Leu Thr Gly Met Leu Arg Thr Cys Gly Ser Glu Val Ile Ile Gly
            325                 330                 335 ttc cgt tcg gct gcg gcg ctg gcc cag ttc gag cag gca gtc aat gag       1056
Phe Arg Ser Ala Ala Ala Leu Ala Gln Phe Glu Gln Ala Val Asn Glu
                340                 345                 350 agt cgg cgg ctg gcc ggc gca gac ttt acg cct ccc att gcc ttg cca       1104
Ser Arg Arg Leu Ala Gly Ala Asp Phe Thr Pro Pro Ile Ala Leu Pro
        355                 360                 365 ctc gat cca cgc gat ccg gca aca att gac gct gtc ttc gat tgg ggg       1152
Leu Asp Pro Arg Asp Pro Ala Thr Ile Asp Ala Val Phe Asp Trp Gly
370                 375                 380 gcc ggc gag aat acc ggc ggg att cat gca gcg gtg att ctg cct gct       1200
Ala Gly Glu Asn Thr Gly Gly Ile His Ala Ala Val Ile Leu Pro Ala
385                 390                 395                 400 acc agt cac gaa ccg gca ccg tgc gtg att gag gtt gat gat gag cgg       1248
Thr Ser His Glu Pro Ala Pro Cys Val Ile Glu Val Asp Asp Glu Arg
            405                 410                 415 gtg ctg aat ttt ctg gcc gat gaa atc acc ggg aca att gtg att gcc       1296
Val Leu Asn Phe Leu Ala Asp Glu Ile Thr Gly Thr Ile Val Ile Ala
                420                 425                 430 agt cgc ctg gcc cgt tac tgg cag tcg caa cgg ctt acc ccc ggc gca       1344
Ser Arg Leu Ala Arg Tyr Trp Gln Ser Gln Arg Leu Thr Pro Gly Ala
        435                 440                 445 cgt gcg cgt ggg ccg cgt gtc att ttt ctc tcg aac ggt gcc gat caa       1392
Arg Ala Arg Gly Pro Arg Val Ile Phe Leu Ser Asn Gly Ala Asp Gln
450                 455                 460 aat ggg aat gtt tac gga cgc att caa agt gcc gct atc ggt cag ctc       1440
Asn Gly Asn Val Tyr Gly Arg Ile Gln Ser Ala Ala Ile Gly Gln Leu
465                 470                 475                 480 att cgt gtg tgg cgt cac gag gct gaa ctt gac tat cag cgt gcc agc       1488
Ile Arg Val Trp Arg His Glu Ala Glu Leu Asp Tyr Gln Arg Ala Ser
            485                 490                 495 gcc gcc ggt gat cat gtg ctg ccg ccg gta tgg gcc aat cag att gtg       1536
Ala Ala Gly Asp His Val Leu Pro Pro Val Trp Ala Asn Gln Ile Val
                500                 505                 510
```

```
cgc ttc gct aac cgc agc ctt gaa ggg tta gaa ttt gcc tgt gcc tgg    1584
Arg Phe Ala Asn Arg Ser Leu Glu Gly Leu Glu Phe Ala Cys Ala Trp
        515                 520                 525 aca gct caa ttg ctc cat agt caa cgc cat atc aat gag att acc ctc    1632
Thr Ala Gln Leu Leu His Ser Gln Arg His Ile Asn Glu Ile Thr Leu
530                 535                 540 aac atc cct gcc aac att agc gcc acc acc ggc gca cgc agt gca tcg    1680
Asn Ile Pro Ala Asn Ile Ser Ala Thr Thr Gly Ala Arg Ser Ala Ser
545                 550                 555                 560 gtc gga tgg gcg gaa agc ctg atc ggg ttg cat ttg ggg aaa gtt gcc    1728
Val Gly Trp Ala Glu Ser Leu Ile Gly Leu His Leu Gly Lys Val Ala
                565                 570                 575 ttg att acc ggt ggc agc gcc ggt att ggt ggg cag atc ggg cgc ctc    1776
Leu Ile Thr Gly Gly Ser Ala Gly Ile Gly Gly Gln Ile Gly Arg Leu
            580                 585                 590 ctg gct ttg agt ggc gcg cgc gtg atg ctg gca gcc cgt gat cgg cat    1824
Leu Ala Leu Ser Gly Ala Arg Val Met Leu Ala Ala Arg Asp Arg His
        595                 600                 605 aag ctc gaa cag atg cag gcg atg atc caa tct gag ctg gct gag gtg    1872
Lys Leu Glu Gln Met Gln Ala Met Ile Gln Ser Glu Leu Ala Glu Val
    610                 615                 620 ggg tat acc gat gtc gaa gat cgc gtc cac att gca ccg ggc tgc gat    1920
Gly Tyr Thr Asp Val Glu Asp Arg Val His Ile Ala Pro Gly Cys Asp
625                 630                 635                 640 gtg agt agc gaa gcg cag ctt gcg gat ctt gtt gaa cgt acc ctg tca    1968
Val Ser Ser Glu Ala Gln Leu Ala Asp Leu Val Glu Arg Thr Leu Ser
                645                 650                 655 gct ttt ggc acc gtc gat tat ctg atc aac aac gcc ggg atc gcc ggt    2016
Ala Phe Gly Thr Val Asp Tyr Leu Ile Asn Asn Ala Gly Ile Ala Gly
            660                 665                 670 gtc gaa gag atg gtt atc gat atg cca gtt gag gga tgg cgc cat acc    2064
Val Glu Glu Met Val Ile Asp Met Pro Val Glu Gly Trp Arg His Thr
        675                 680                 685 ctc ttc gcc aat ctg atc agc aac tac tcg ttg atg cgc aaa ctg gcg    2112
Leu Phe Ala Asn Leu Ile Ser Asn Tyr Ser Leu Met Arg Lys Leu Ala
    690                 695                 700 ccg ttg atg aaa aaa cag ggt agc ggt tac atc ctt aac gtc tca tca    2160
Pro Leu Met Lys Lys Gln Gly Ser Gly Tyr Ile Leu Asn Val Ser Ser
705                 710                 715                 720 tac ttt ggc ggt gaa aaa gat gcg gcc att ccc tac ccc aac cgt gcc    2208
Tyr Phe Gly Gly Glu Lys Asp Ala Ala Ile Pro Tyr Pro Asn Arg Ala
                725                 730                 735 gat tac gcc gtc tcg aag gct ggt cag cgg gca atg gcc gaa gtc ttt    2256
Asp Tyr Ala Val Ser Lys Ala Gly Gln Arg Ala Met Ala Glu Val Phe
            740                 745                 750 gcg cgc ttc ctt ggc ccg gag ata cag atc aat gcc att gcg ccg ggt    2304
Ala Arg Phe Leu Gly Pro Glu Ile Gln Ile Asn Ala Ile Ala Pro Gly
        755                 760                 765 ccg gtc gaa ggt gat cgc ttg cgc ggt acc ggt gaa cgt ccc ggc ctc    2352
Pro Val Glu Gly Asp Arg Leu Arg Gly Thr Gly Glu Arg Pro Gly Leu
    770                 775                 780 ttt gcc cgt cgg gcg cgg ctg att ttg gag aac aag cgg ctg aat gag    2400
Phe Ala Arg Arg Ala Arg Leu Ile Leu Glu Asn Lys Arg Leu Asn Glu
785                 790                 795                 800 ctt cac gct gct ctt atc gcg gct gcg cgc acc gat gag cga tct atg    2448
Leu His Ala Ala Leu Ile Ala Ala Ala Arg Thr Asp Glu Arg Ser Met
                805                 810                 815 cac gaa ctg gtt gaa ctg ctc tta ccc aat gat gtg gcc gca cta gag    2496
His Glu Leu Val Glu Leu Leu Leu Pro Asn Asp Val Ala Ala Leu Glu
```

-continued

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     | 820 |     |     |     | 825 |     |     |     | 830 |     |     |     |     |     |     |      |
| cag | aat | ccc | gca | gca | cct | acc | gcg | ttg | cgt | gaa | ctg | gca | cga | cgt | ttt | 2544 |
| Gln | Asn | Pro | Ala | Ala | Pro | Thr | Ala | Leu | Arg | Glu | Leu | Ala | Arg | Arg | Phe |      |
|     |     | 835 |     |     |     | 840 |     |     |     | 845 |     |     |     |     |     |      |
| cgc | agc | gaa | ggc | gat | ccg | gcg | gca | tca | tca | agc | agt | gcg | ctg | ctg | aac | 2592 |
| Arg | Ser | Glu | Gly | Asp | Pro | Ala | Ala | Ser | Ser | Ser | Ser | Ala | Leu | Leu | Asn |      |
|     | 850 |     |     |     |     | 855 |     |     |     |     | 860 |     |     |     |     |      |
| cgt | tca | att | gcc | gct | aaa | ttg | ctg | gct | cgt | ttg | cat | aat | ggt | ggc | tat | 2640 |
| Arg | Ser | Ile | Ala | Ala | Lys | Leu | Leu | Ala | Arg | Leu | His | Asn | Gly | Gly | Tyr |      |
| 865 |     |     |     |     | 870 |     |     |     |     | 875 |     |     |     |     | 880 |      |
| gtg | ttg | cct | gcc | gac | atc | ttt | gca | aac | ctg | cca | aac | ccg | ccc | gat | ccc | 2688 |
| Val | Leu | Pro | Ala | Asp | Ile | Phe | Ala | Asn | Leu | Pro | Asn | Pro | Pro | Asp | Pro |      |
|     |     |     |     | 885 |     |     |     |     | 890 |     |     |     |     | 895 |     |      |
| ttc | ttc | acc | cga | gcc | cag | att | gat | cgc | gag | gct | cgc | aag | gtt | cgt | gac | 2736 |
| Phe | Phe | Thr | Arg | Ala | Gln | Ile | Asp | Arg | Glu | Ala | Arg | Lys | Val | Arg | Asp |      |
|     |     |     | 900 |     |     |     |     | 905 |     |     |     |     | 910 |     |     |      |
| ggc | atc | atg | ggg | atg | ctc | tac | ctg | caa | cgg | atg | ccg | act | gag | ttt | gat | 2784 |
| Gly | Ile | Met | Gly | Met | Leu | Tyr | Leu | Gln | Arg | Met | Pro | Thr | Glu | Phe | Asp |      |
|     |     | 915 |     |     |     |     | 920 |     |     |     |     | 925 |     |     |     |      |
| gtc | gca | atg | gcc | acc | gtc | tat | tac | ctt | gcc | gac | cgc | aat | gtc | agt | ggt | 2832 |
| Val | Ala | Met | Ala | Thr | Val | Tyr | Tyr | Leu | Ala | Asp | Arg | Asn | Val | Ser | Gly |      |
|     | 930 |     |     |     |     | 935 |     |     |     |     | 940 |     |     |     |     |      |
| gag | aca | ttc | cac | cca | tca | ggt | ggt | ttg | cgt | tac | gaa | cgc | acc | cct | acc | 2880 |
| Glu | Thr | Phe | His | Pro | Ser | Gly | Gly | Leu | Arg | Tyr | Glu | Arg | Thr | Pro | Thr |      |
| 945 |     |     |     |     | 950 |     |     |     |     | 955 |     |     |     |     | 960 |      |
| ggt | ggc | gaa | ctc | ttc | ggc | ttg | ccc | tca | ccg | gaa | cgg | ctg | gcg | gag | ctg | 2928 |
| Gly | Gly | Glu | Leu | Phe | Gly | Leu | Pro | Ser | Pro | Glu | Arg | Leu | Ala | Glu | Leu |      |
|     |     |     |     | 965 |     |     |     |     | 970 |     |     |     |     | 975 |     |      |
| gtc | gga | agc | acg | gtc | tat | ctg | ata | ggt | gaa | cat | ctg | act | gaa | cac | ctt | 2976 |
| Val | Gly | Ser | Thr | Val | Tyr | Leu | Ile | Gly | Glu | His | Leu | Thr | Glu | His | Leu |      |
|     |     |     | 980 |     |     |     |     | 985 |     |     |     |     | 990 |     |     |      |
| aac | ctg | ctt | gcc | cgt | gcg | tac | ctc | gaa | cgt | tac | ggg | gca | cgt | cag | gta | 3024 |
| Asn | Leu | Leu | Ala | Arg | Ala | Tyr | Leu | Glu | Arg | Tyr | Gly | Ala | Arg | Gln | Val |      |
|     |     | 995 |     |     |     |     | 1000|     |     |     |     | 1005|     |     |     |      |
| gtg | atg | att | gtt | gag | aca | gaa | acc | ggg | gca | gag | aca | atg | cgt | cgc | ttg | 3072 |
| Val | Met | Ile | Val | Glu | Thr | Glu | Thr | Gly | Ala | Glu | Thr | Met | Arg | Arg | Leu |      |
|     | 1010|     |     |     |     | 1015|     |     |     |     | 1020|     |     |     |     |      |
| ctc | cac | gat | cac | gtc | gag | gct | ggt | cgg | ctg | atg | act | att | gtg | gcc | ggt | 3120 |
| Leu | His | Asp | His | Val | Glu | Ala | Gly | Arg | Leu | Met | Thr | Ile | Val | Ala | Gly |      |
| 1025|     |     |     |     | 1030|     |     |     |     | 1035|     |     |     |     | 1040|      |
| gat | cag | atc | gaa | gcc | gct | atc | gac | cag | gct | atc | act | cgc | tac | ggt | cgc | 3168 |
| Asp | Gln | Ile | Glu | Ala | Ala | Ile | Asp | Gln | Ala | Ile | Thr | Arg | Tyr | Gly | Arg |      |
|     |     |     |     | 1045|     |     |     |     | 1050|     |     |     |     | 1055|     |      |
| cca | ggg | ccg | gtc | gtc | tgt | acc | ccc | ttc | cgg | cca | ctg | ccg | acg | gta | cca | 3216 |
| Pro | Gly | Pro | Val | Val | Cys | Thr | Pro | Phe | Arg | Pro | Leu | Pro | Thr | Val | Pro |      |
|     |     |     | 1060|     |     |     |     | 1065|     |     |     |     | 1070|     |     |      |
| ctg | gtc | ggg | cgt | aaa | gac | agt | gac | tgg | agc | aca | gtg | ttg | agt | gag | gct | 3264 |
| Leu | Val | Gly | Arg | Lys | Asp | Ser | Asp | Trp | Ser | Thr | Val | Leu | Ser | Glu | Ala |      |
|     |     | 1075|     |     |     |     | 1080|     |     |     |     | 1085|     |     |     |      |
| gaa | ttt | gcc | gag | ttg | tgc | gaa | cac | cag | ctc | acc | cac | cat | ttc | cgg | gta | 3312 |
| Glu | Phe | Ala | Glu | Leu | Cys | Glu | His | Gln | Leu | Thr | His | His | Phe | Arg | Val |      |
|     | 1090|     |     |     |     | 1095|     |     |     |     | 1100|     |     |     |     |      |
| gcg | cgc | aag | att | gcc | ctg | agt | gat | ggt | gcc | agt | ctc | gcg | ctg | gtc | act | 3360 |
| Ala | Arg | Lys | Ile | Ala | Leu | Ser | Asp | Gly | Ala | Ser | Leu | Ala | Leu | Val | Thr |      |
| 1105|     |     |     |     | 1110|     |     |     |     | 1115|     |     |     |     | 1120|      |
| ccc | gaa | act | acg | gct | acc | tca | act | acc | gag | caa | ttt | gct | ctg | gct | aac | 3408 |
| Pro | Glu | Thr | Thr | Ala | Thr | Ser | Thr | Thr | Glu | Gln | Phe | Ala | Leu | Ala | Asn |      |
|     |     |     |     | 1125|     |     |     |     | 1130|     |     |     |     | 1135|     |      |
| ttc | atc | aaa | acg | acc | ctt | cac | gct | ttt | acg | gct | acg | att | ggt | gtc | gag | 3456 |

```
                Phe Ile Lys Thr Thr Leu His Ala Phe Thr Ala Thr Ile Gly Val Glu
                            1140                1145                1150 agc gaa aga act gct cag cgc att ctg atc aat caa gtc gat ctg acc          3504
Ser Glu Arg Thr Ala Gln Arg Ile Leu Ile Asn Gln Val Asp Leu Thr
            1155                1160                1165 cgg cgt gcg cgt gcc gaa gag ccg cgt gat ccg cac gag cgt caa caa          3552
Arg Arg Ala Arg Ala Glu Glu Pro Arg Asp Pro His Glu Arg Gln Gln
        1170                1175                1180 gaa ctg gaa cgt ttt atc gag gca gtc ttg ctg gtc act gca cca ctc          3600
Glu Leu Glu Arg Phe Ile Glu Ala Val Leu Leu Val Thr Ala Pro Leu
1185                1190                1195                1200 ccg cct gaa gcc gat acc cgt tac gcc ggg cgg att cat cgc gga cgg          3648
Pro Pro Glu Ala Asp Thr Arg Tyr Ala Gly Arg Ile His Arg Gly Arg
                1205                1210                1215 gcg att acc gtg taa                                                      3663
Ala Ile Thr Val
        1220

<210> SEQ ID NO 8
<211> LENGTH: 1220
<212> TYPE: PRT
<213> ORGANISM: Chloroflexus aurantiacus
<220> FEATURE:
<223> OTHER INFORMATION: [CDS]:1..3663 from SEQ ID NO 7

<400> SEQUENCE: 8

Met Ser Gly Thr Gly Arg Leu Ala Gly Lys Ile Ala Leu Ile Thr Gly
1               5                   10                  15

Gly Ala Gly Asn Ile Gly Ser Glu Leu Thr Arg Arg Phe Leu Ala Glu
            20                  25                  30

Gly Ala Thr Val Ile Ile Ser Gly Arg Asn Arg Ala Lys Leu Thr Ala
        35                  40                  45

Leu Ala Glu Arg Met Gln Ala Glu Ala Gly Val Pro Ala Lys Arg Ile
    50                  55                  60

Asp Leu Glu Val Met Asp Gly Ser Asp Pro Val Ala Val Arg Ala Gly
65                  70                  75                  80

Ile Glu Ala Ile Val Ala Arg His Gly Gln Ile Asp Ile Leu Val Asn
                85                  90                  95

Asn Ala Gly Ser Ala Gly Ala Gln Arg Arg Leu Ala Glu Ile Pro Leu
            100                 105                 110

Thr Glu Ala Glu Leu Gly Pro Gly Ala Glu Glu Thr Leu His Ala Ser
        115                 120                 125

Ile Ala Asn Leu Leu Gly Met Gly Trp His Leu Met Arg Ile Ala Ala
    130                 135                 140

Pro His Met Pro Val Gly Ser Ala Val Ile Asn Val Ser Thr Ile Phe
145                 150                 155                 160

Ser Arg Ala Glu Tyr Tyr Gly Arg Ile Pro Tyr Val Thr Pro Lys Ala
                165                 170                 175

Ala Leu Asn Ala Leu Ser Gln Leu Ala Ala Arg Glu Leu Gly Ala Arg
            180                 185                 190

Gly Ile Arg Val Asn Thr Ile Phe Pro Gly Pro Ile Glu Ser Asp Arg
        195                 200                 205

Ile Arg Thr Val Phe Gln Arg Met Asp Gln Leu Lys Gly Arg Pro Glu
    210                 215                 220

Gly Asp Thr Ala His His Phe Leu Asn Thr Met Arg Leu Cys Arg Ala
225                 230                 235                 240

Asn Asp Gln Gly Ala Leu Glu Arg Arg Phe Pro Ser Val Gly Asp Val
```

-continued

```
                245                 250                 255
Ala Asp Ala Ala Val Phe Leu Ala Ser Ala Glu Ser Ala Ala Leu Ser
                260                 265                 270

Gly Glu Thr Ile Glu Val Thr His Gly Met Glu Leu Pro Ala Cys Ser
                275                 280                 285

Glu Thr Ser Leu Leu Ala Arg Thr Asp Leu Arg Thr Ile Asp Ala Ser
    290                 295                 300

Gly Arg Thr Thr Leu Ile Cys Ala Gly Asp Gln Ile Glu Glu Val Met
305                 310                 315                 320

Ala Leu Thr Gly Met Leu Arg Thr Cys Gly Ser Glu Val Ile Ile Gly
                325                 330                 335

Phe Arg Ser Ala Ala Ala Leu Ala Gln Phe Glu Gln Ala Val Asn Glu
                340                 345                 350

Ser Arg Arg Leu Ala Gly Ala Asp Phe Thr Pro Pro Ile Ala Leu Pro
                355                 360                 365

Leu Asp Pro Arg Asp Pro Ala Thr Ile Asp Ala Val Phe Asp Trp Gly
    370                 375                 380

Ala Gly Glu Asn Thr Gly Gly Ile His Ala Ala Val Ile Leu Pro Ala
385                 390                 395                 400

Thr Ser His Glu Pro Ala Pro Cys Val Ile Glu Val Asp Asp Glu Arg
                405                 410                 415

Val Leu Asn Phe Leu Ala Asp Glu Ile Thr Gly Thr Ile Val Ile Ala
                420                 425                 430

Ser Arg Leu Ala Arg Tyr Trp Gln Ser Gln Arg Leu Thr Pro Gly Ala
                435                 440                 445

Arg Ala Arg Gly Pro Arg Val Ile Phe Leu Ser Asn Gly Ala Asp Gln
    450                 455                 460

Asn Gly Asn Val Tyr Gly Arg Ile Gln Ser Ala Ala Ile Gly Gln Leu
465                 470                 475                 480

Ile Arg Val Trp Arg His Glu Ala Glu Leu Asp Tyr Gln Arg Ala Ser
                485                 490                 495

Ala Ala Gly Asp His Val Leu Pro Pro Val Trp Ala Asn Gln Ile Val
                500                 505                 510

Arg Phe Ala Asn Arg Ser Leu Glu Gly Leu Glu Phe Ala Cys Ala Trp
                515                 520                 525

Thr Ala Gln Leu Leu His Ser Gln Arg His Ile Asn Glu Ile Thr Leu
    530                 535                 540

Asn Ile Pro Ala Asn Ile Ser Ala Thr Thr Gly Ala Arg Ser Ala Ser
545                 550                 555                 560

Val Gly Trp Ala Glu Ser Leu Ile Gly Leu His Leu Gly Lys Val Ala
                565                 570                 575

Leu Ile Thr Gly Gly Ser Ala Gly Ile Gly Gly Gln Ile Gly Arg Leu
                580                 585                 590

Leu Ala Leu Ser Gly Ala Arg Val Met Leu Ala Ala Arg Asp Arg His
                595                 600                 605

Lys Leu Glu Gln Met Gln Ala Met Ile Gln Ser Glu Leu Ala Glu Val
    610                 615                 620

Gly Tyr Thr Asp Val Glu Asp Arg Val His Ile Ala Pro Gly Cys Asp
625                 630                 635                 640

Val Ser Ser Glu Ala Gln Leu Ala Asp Leu Val Glu Arg Thr Leu Ser
                645                 650                 655

Ala Phe Gly Thr Val Asp Tyr Leu Ile Asn Asn Ala Gly Ile Ala Gly
                660                 665                 670
```

-continued

```
Val Glu Glu Met Val Ile Asp Met Pro Val Glu Gly Trp Arg His Thr
            675                 680                 685
Leu Phe Ala Asn Leu Ile Ser Asn Tyr Ser Leu Met Arg Lys Leu Ala
            690                 695                 700
Pro Leu Met Lys Lys Gln Gly Ser Gly Tyr Ile Leu Asn Val Ser Ser
705                 710                 715                 720
Tyr Phe Gly Gly Glu Lys Asp Ala Ala Ile Pro Tyr Pro Asn Arg Ala
                725                 730                 735
Asp Tyr Ala Val Ser Lys Ala Gly Gln Arg Ala Met Ala Glu Val Phe
                740                 745                 750
Ala Arg Phe Leu Gly Pro Glu Ile Gln Ile Asn Ala Ile Ala Pro Gly
            755                 760                 765
Pro Val Glu Gly Asp Arg Leu Arg Gly Thr Gly Glu Arg Pro Gly Leu
            770                 775                 780
Phe Ala Arg Arg Ala Arg Leu Ile Leu Glu Asn Lys Arg Leu Asn Glu
785                 790                 795                 800
Leu His Ala Ala Leu Ile Ala Ala Ala Arg Thr Asp Glu Arg Ser Met
                805                 810                 815
His Glu Leu Val Glu Leu Leu Leu Pro Asn Asp Val Ala Ala Leu Glu
            820                 825                 830
Gln Asn Pro Ala Ala Pro Thr Ala Leu Arg Glu Leu Ala Arg Arg Phe
            835                 840                 845
Arg Ser Glu Gly Asp Pro Ala Ala Ser Ser Ser Ala Leu Leu Asn
850                 855                 860
Arg Ser Ile Ala Ala Lys Leu Leu Ala Arg Leu His Asn Gly Gly Tyr
865                 870                 875                 880
Val Leu Pro Ala Asp Ile Phe Ala Asn Leu Pro Asn Pro Pro Asp Pro
                885                 890                 895
Phe Phe Thr Arg Ala Gln Ile Asp Arg Glu Ala Arg Lys Val Arg Asp
                900                 905                 910
Gly Ile Met Gly Met Leu Tyr Leu Gln Arg Met Pro Thr Glu Phe Asp
            915                 920                 925
Val Ala Met Ala Thr Val Tyr Tyr Leu Ala Asp Arg Asn Val Ser Gly
            930                 935                 940
Glu Thr Phe His Pro Ser Gly Gly Leu Arg Tyr Glu Arg Thr Pro Thr
945                 950                 955                 960
Gly Gly Glu Leu Phe Gly Leu Pro Ser Pro Glu Arg Leu Ala Glu Leu
                965                 970                 975
Val Gly Ser Thr Val Tyr Leu Ile Gly Glu His Leu Thr Glu His Leu
            980                 985                 990
Asn Leu Leu Ala Arg Ala Tyr Leu Glu Arg Tyr Gly Ala Arg Gln Val
            995                 1000                1005
Val Met Ile Val Glu Thr Glu Thr Gly Ala Glu Thr Met Arg Arg Leu
     1010                1015                1020
Leu His Asp His Val Glu Ala Gly Arg Leu Met Thr Ile Val Ala Gly
1025                1030                1035                1040
Asp Gln Ile Glu Ala Ala Ile Asp Gln Ala Ile Thr Arg Tyr Gly Arg
                1045                1050                1055
Pro Gly Pro Val Val Cys Thr Pro Phe Arg Pro Leu Pro Thr Val Pro
                1060                1065                1070
Leu Val Gly Arg Lys Asp Ser Asp Trp Ser Thr Val Leu Ser Glu Ala
            1075                1080                1085
```

|       |       |       |       |       |       |       |       |       |       |       |     |
|-------|-------|-------|-------|-------|-------|-------|-------|-------|-------|-------|-----|
| Glu   | Phe   | Ala   | Glu   | Leu   | Cys   | Glu   | His   | Gln   | Leu   | Thr   | His His Phe Arg Val |

Glu Phe Ala Glu Leu Cys Glu His Gln Leu Thr His His Phe Arg Val
    1090            1095            1100

Ala Arg Lys Ile Ala Leu Ser Asp Gly Ala Ser Leu Ala Leu Val Thr
1105            1110            1115            1120

Pro Glu Thr Thr Ala Thr Ser Thr Thr Glu Gln Phe Ala Leu Ala Asn
            1125            1130            1135

Phe Ile Lys Thr Thr Leu His Ala Phe Thr Ala Thr Ile Gly Val Glu
            1140            1145            1150

Ser Glu Arg Thr Ala Gln Arg Ile Leu Ile Asn Gln Val Asp Leu Thr
            1155            1160            1165

Arg Arg Ala Arg Ala Glu Glu Pro Arg Asp Pro His Glu Arg Gln Gln
1170            1175            1180

Glu Leu Glu Arg Phe Ile Glu Ala Val Leu Leu Val Thr Ala Pro Leu
1185            1190            1195            1200

Pro Pro Glu Ala Asp Thr Arg Tyr Ala Gly Arg Ile His Arg Gly Arg
            1205            1210            1215

Ala Ile Thr Val
        1220

<210> SEQ ID NO 9
<211> LENGTH: 3654
<212> TYPE: DNA
<213> ORGANISM: Erythrobacter sp.
<220> FEATURE:
<223> OTHER INFORMATION: Coding sequence of the gene encoding
      malonyl-CoA reductase from Erythrobacter sp. NAP1
<220> FEATURE:
<221> NAME/KEY: CDS
<222> LOCATION: 1..3654
<223> OTHER INFORMATION: /transl_table=11

<400> SEQUENCE: 9 atg agc aaa gaa gga aac gcc gcc aag ggt cgt ctc gaa ggt aag gtc     48
Met Ser Lys Glu Gly Asn Ala Ala Lys Gly Arg Leu Glu Gly Lys Val
1               5                   10                  15 gcg ctg atc acg ggg gcg gca ggc aat ctc ggc aac gag ata tcg cgt     96
Ala Leu Ile Thr Gly Ala Ala Gly Asn Leu Gly Asn Glu Ile Ser Arg
            20                  25                  30 gcc ttt gcc cgc gaa ggc gcc ttt gtg gtg atg acg ggg cgc acc gaa    144
Ala Phe Ala Arg Glu Gly Ala Phe Val Val Met Thr Gly Arg Thr Glu
        35                  40                  45 gag cgt att tct gcg gcg cgc gaa cag ctc atc gcg gac acc ggc gtc    192
Glu Arg Ile Ser Ala Ala Arg Glu Gln Leu Ile Ala Asp Thr Gly Val
    50                  55                  60 gcg cct gag cga atc gac acc gcc gtc ctc gat ggc ggc aat cca gat    240
Ala Pro Glu Arg Ile Asp Thr Ala Val Leu Asp Gly Gly Asn Pro Asp
65                  70                  75                  80 tcg atc cgc gca gcg atg gca aag ctt cgc aaa gaa tat ggc cgg atc    288
Ser Ile Arg Ala Ala Met Ala Lys Leu Arg Lys Glu Tyr Gly Arg Ile
                85                  90                  95 gat atc ctc atc aac aat gca ggt tct gct ggc ccc aag cag ccg ctc    336
Asp Ile Leu Ile Asn Asn Ala Gly Ser Ala Gly Pro Lys Gln Pro Leu
            100                 105                 110 cac aac gta ccg ctc agc cct cag gag atg gaa gcg tgc ggc gat acc    384
His Asn Val Pro Leu Ser Pro Gln Glu Met Glu Ala Cys Gly Asp Thr
        115                 120                 125 gag acc gtc cgc gat gcg atg ctc aat atc ctt ggc gtg acc tgg aac    432
Glu Thr Val Arg Asp Ala Met Leu Asn Ile Leu Gly Val Thr Trp Asn
    130                 135                 140 atg gcg cgc atc gtt gcg ccc atg atg ccg gtg ggc ggc gct atg gtg    480
Met Ala Arg Ile Val Ala Pro Met Met Pro Val Gly Gly Ala Met Val

```
                Met Ala Arg Ile Val Ala Pro Met Met Pro Val Gly Gly Ala Met Val
                145                 150                 155                 160 aat atc tcg acg att ttc agc cac acg cgc tat tac gga cgc acg gct           528
Asn Ile Ser Thr Ile Phe Ser His Thr Arg Tyr Tyr Gly Arg Thr Ala
                    165                 170                 175 tat gtc gtg ccc aag gct gcg ctg aac gcg cta tcg aac cag ctt gcc           576
Tyr Val Val Pro Lys Ala Ala Leu Asn Ala Leu Ser Asn Gln Leu Ala
                180                 185                 190 agc gag ctc gga ccg cgc ggc atc cgc gtg aac act gtc ttc ccc ggc           624
Ser Glu Leu Gly Pro Arg Gly Ile Arg Val Asn Thr Val Phe Pro Gly
            195                 200                 205 ccg att gaa agc gac cgc atc cgc acc gtt ttt gcc gcg atg gac gag           672
Pro Ile Glu Ser Asp Arg Ile Arg Thr Val Phe Ala Ala Met Asp Glu
        210                 215                 220 gtg cag agc cag ccc aag gac acg acc gca aac tac ttc acc ggt cgc           720
Val Gln Ser Gln Pro Lys Asp Thr Thr Ala Asn Tyr Phe Thr Gly Arg
225                 230                 235                 240 atg gcg ctc acc cgc agc gtc aac gga aag gta gac ggc aag cct ctg           768
Met Ala Leu Thr Arg Ser Val Asn Gly Lys Val Asp Gly Lys Pro Leu
                    245                 250                 255 ccc aac cca aag gat atc gcg ggg acg tgc ctg ttc ctt gcc agt gag           816
Pro Asn Pro Lys Asp Ile Ala Gly Thr Cys Leu Phe Leu Ala Ser Glu
                260                 265                 270 gaa gcc gca gga att gcg ggc gag gaa gtg gac gtg acc cac ggt cta           864
Glu Ala Ala Gly Ile Ala Gly Glu Glu Val Asp Val Thr His Gly Leu
            275                 280                 285 tcc gcc aac cgc acc tcg gca tcg acc tat atg acc cgg cca tca atg           912
Ser Ala Asn Arg Thr Ser Ala Ser Thr Tyr Met Thr Arg Pro Ser Met
        290                 295                 300 cgc tcg ctc gac ggg gcg ggt ctc aat atc ttc atc gtc tcg gga gag           960
Arg Ser Leu Asp Gly Ala Gly Leu Asn Ile Phe Ile Val Ser Gly Glu
305                 310                 315                 320 aac tgg gac gat gcg ctg gtc gcc gct cac acg ctg atc gga tca ggc          1008
Asn Trp Asp Asp Ala Leu Val Ala Ala His Thr Leu Ile Gly Ser Gly
                    325                 330                 335 gca aag gtg cgc ctt ggc ctc gct cgc aat gcc gac gtt gcg cag gcc          1056
Ala Lys Val Arg Leu Gly Leu Ala Arg Asn Ala Asp Val Ala Gln Ala
                340                 345                 350 aat gcg cgg ctg aaa gcg caa ggg att ggc gag gag ctg acc gtc acc          1104
Asn Ala Arg Leu Lys Ala Gln Gly Ile Gly Glu Glu Leu Thr Val Thr
            355                 360                 365 cgc ttc aac cgc gca gag ccc gat gcg atg gaa gac gcg ctc gcc gcg          1152
Arg Phe Asn Arg Ala Glu Pro Asp Ala Met Glu Asp Ala Leu Ala Ala
        370                 375                 380 ttt tcg ggc gat gtc gac ggg gcg atc acc ggc gcg atc atc ctg ccg          1200
Phe Ser Gly Asp Val Asp Gly Ala Ile Thr Gly Ala Ile Ile Leu Pro
385                 390                 395                 400 gtc aag cca tcg ggc cac ttc acc gga tcg ctg ctc gcc gcc gac gat          1248
Val Lys Pro Ser Gly His Phe Thr Gly Ser Leu Leu Ala Ala Asp Asp
                    405                 410                 415 gat acc gtt acg aag ttc atg gac acc gag ctt gtg ggc gcg att gca          1296
Asp Thr Val Thr Lys Phe Met Asp Thr Glu Leu Val Gly Ala Ile Ala
                420                 425                 430 gtc tcg cga agc ctt gcg cgg tat tgg cat ggg cga gag gat ctc cag          1344
Val Ser Arg Ser Leu Ala Arg Tyr Trp His Gly Arg Glu Asp Leu Gln
            435                 440                 445 tcc cct ccc cgc tgc gtg ttc atg acc aat ccg ggc gat ccc ttg ggc          1392
Ser Pro Pro Arg Cys Val Phe Met Thr Asn Pro Gly Asp Pro Leu Gly
        450                 455                 460
```

```
aat tcc ttc gcc tcg gtc ctc tcc gcc ggc atc acc cag ctg atc cgc    1440
Asn Ser Phe Ala Ser Val Leu Ser Ala Gly Ile Thr Gln Leu Ile Arg
465             470                 475                 480 atc tgg cgc gat gag gaa cgc gtg cag gcg ggc aat ggc tcg acc gag    1488
Ile Trp Arg Asp Glu Glu Arg Val Gln Ala Gly Asn Gly Ser Thr Glu
                485                 490                 495 cac gcc gtg tgg tcg aac cag atc gtg cgc cac acc aac acc gaa gac    1536
His Ala Val Trp Ser Asn Gln Ile Val Arg His Thr Asn Thr Glu Asp
            500                 505                 510 gag aac acc cgc ttt gcc tcg ggc cat gcc acc cgc gtt ctc ttc cgc    1584
Glu Asn Thr Arg Phe Ala Ser Gly His Ala Thr Arg Val Leu Phe Arg
        515                 520                 525 gaa cag cac atc gcc gag atc gac ctc aag ctg ccc gcg aat atc agc    1632
Glu Gln His Ile Ala Glu Ile Asp Leu Lys Leu Pro Ala Asn Ile Ser
    530                 535                 540 gag gaa acc gga tcg cgc aag gcc atg gtc ggc ttt gcc gag aac atc    1680
Glu Glu Thr Gly Ser Arg Lys Ala Met Val Gly Phe Ala Glu Asn Ile
545                 550                 555                 560 acc ggg cta cac ctt ggc aag gtt gct ttc atc acc ggc ggc tct gcc    1728
Thr Gly Leu His Leu Gly Lys Val Ala Phe Ile Thr Gly Gly Ser Ala
                565                 570                 575 ggg atc ggc ggc cag gtg gcg cgc ttg ctc gcg ctc gca ggc gca aag    1776
Gly Ile Gly Gly Gln Val Ala Arg Leu Leu Ala Leu Ala Gly Ala Lys
                580                 585                 590 gtg atg atg gtc gca agg cgc gaa agc gag ctt gtc gcc gcc cgt gac    1824
Val Met Met Val Ala Arg Arg Glu Ser Glu Leu Val Ala Ala Arg Asp
            595                 600                 605 cgg atc gtg ggt gag ctt cag gat atc ggc ttc gcg ggc gtt gaa cgc    1872
Arg Ile Val Gly Glu Leu Gln Asp Ile Gly Phe Ala Gly Val Glu Arg
        610                 615                 620 cgg gtc aaa tac atg gcc gac atc gac gtc agc gac ttc gcc tcg ctc    1920
Arg Val Lys Tyr Met Ala Asp Ile Asp Val Ser Asp Phe Ala Ser Leu
625                 630                 635                 640 gac aag gcg gtt gac gcg acg ctc gag gag ttc ggg cgg att gat tac    1968
Asp Lys Ala Val Asp Ala Thr Leu Glu Glu Phe Gly Arg Ile Asp Tyr
                645                 650                 655 ctc atc aat aac gca ggc gtt gcg ggc gcc gag gac atg gtg atc gac    2016
Leu Ile Asn Asn Ala Gly Val Ala Gly Ala Glu Asp Met Val Ile Asp
                660                 665                 670 atg gag ccc gag gca tgg cgc ttc acg ctc gat gcg aac ctt atc tcc    2064
Met Glu Pro Glu Ala Trp Arg Phe Thr Leu Asp Ala Asn Leu Ile Ser
            675                 680                 685 aat tac cat ctg atg cag cgc gtc gtg ccg ctg atg aag gaa cag ggc    2112
Asn Tyr His Leu Met Gln Arg Val Val Pro Leu Met Lys Glu Gln Gly
        690                 695                 700 tcg ggc tac gtc ctc aat gtc tcg tcc tat ttc ggc ggt gaa aag ttc    2160
Ser Gly Tyr Val Leu Asn Val Ser Ser Tyr Phe Gly Gly Glu Lys Phe
705                 710                 715                 720 ctc gcg gtc gcc tac ccc aac cgc gcc gat tat gga ctg tcg aaa gcg    2208
Leu Ala Val Ala Tyr Pro Asn Arg Ala Asp Tyr Gly Leu Ser Lys Ala
                725                 730                 735 ggc cag cgt gcg atg gtc gag gcg ttc tcg ccg ttc ctc ggg cca gag    2256
Gly Gln Arg Ala Met Val Glu Ala Phe Ser Pro Phe Leu Gly Pro Glu
                740                 745                 750 gta cag tgc aac gcc att gcg ccg ggc cct gtc gat ggc gac cgt ttg    2304
Val Gln Cys Asn Ala Ile Ala Pro Gly Pro Val Asp Gly Asp Arg Leu
            755                 760                 765 tcc ggc acc ggg gga aaa ccc ggc ctg ttc cag cgc cgc gcc aag ctg    2352
Ser Gly Thr Gly Gly Lys Pro Gly Leu Phe Gln Arg Arg Ala Lys Leu
        770                 775                 780
```

-continued

| | |
|---|---|
| atc ctt gag aac aag cga ctg aat gcg gtc tat tcc gca gtc atc cac<br>Ile Leu Glu Asn Lys Arg Leu Asn Ala Val Tyr Ser Ala Val Ile His<br>785                      790                          795                      800 | 2400 |
| gcg atc cgc gag ggc ggc gat gcg gcg aaa atc ctg acg cga ttg tcg<br>Ala Ile Arg Glu Gly Gly Asp Ala Ala Lys Ile Leu Thr Arg Leu Ser<br>                        805                          810                          815 | 2448 |
| cgc aat tcg acc tcg acc ctc agc cat gac gca gaa gca ccc gag gaa<br>Arg Asn Ser Thr Ser Thr Leu Ser His Asp Ala Glu Ala Pro Glu Glu<br>                  820                          825                          830 | 2496 |
| ctg cgc aag ctc gca ctc gac ttc gca tcg cag ggt gat ggg ctg tgc<br>Leu Arg Lys Leu Ala Leu Asp Phe Ala Ser Gln Gly Asp Gly Leu Cys<br>835                      840                          845 | 2544 |
| acg tgg gat cag tat ctc ctg acc gac gcg atg gcg cag cgt ttg ctc<br>Thr Trp Asp Gln Tyr Leu Leu Thr Asp Ala Met Ala Gln Arg Leu Leu<br>850                      855                          860 | 2592 |
| gtc cgt ctt cag ctt ggc ggc ttc ctg ctc ggc tcg aac gaa tgg gcg<br>Val Arg Leu Gln Leu Gly Gly Phe Leu Leu Gly Ser Asn Glu Trp Ala<br>865                      870                          875                      880 | 2640 |
| agc ctg tcg agc agc gag cag acg tgg ctc aaa ctc tcg cct ccc gat<br>Ser Leu Ser Ser Ser Glu Gln Thr Trp Leu Lys Leu Ser Pro Pro Asp<br>                  885                          890                          895 | 2688 |
| gac aag ccc ttc ctc ccc gct gcg cag gtc gac aag gtc gca aac ggc<br>Asp Lys Pro Phe Leu Pro Ala Ala Gln Val Asp Lys Val Ala Asn Gly<br>            900                          905                          910 | 2736 |
| gtc ggc aag ggc gtg atc tcg cag ctt cac ctt ggt gcg atg ccg acc<br>Val Gly Lys Gly Val Ile Ser Gln Leu His Leu Gly Ala Met Pro Thr<br>                  915                          920                          925 | 2784 |
| gag gcg gag gtg gcg caa gcg acc gtc ttc ttc ctc gcc gac cgc gct<br>Glu Ala Glu Val Ala Gln Ala Thr Val Phe Phe Leu Ala Asp Arg Ala<br>930                      935                          940 | 2832 |
| gtg agc ggg gaa acc ttc atg ccg tca ggc ggc ctc cgg gtc gaa cgc<br>Val Ser Gly Glu Thr Phe Met Pro Ser Gly Gly Leu Arg Val Glu Arg<br>945                      950                          955                      960 | 2880 |
| tcc aac acc gag cgc gag atg ttc ggc agc ccc aag caa gag cgc atc<br>Ser Asn Thr Glu Arg Glu Met Phe Gly Ser Pro Lys Gln Glu Arg Ile<br>                  965                          970                          975 | 2928 |
| gac aag atg aag ggg aaa acc gtc tgg atc atc ggc gag cac ctg tcc<br>Asp Lys Met Lys Gly Lys Thr Val Trp Ile Ile Gly Glu His Leu Ser<br>            980                          985                          990 | 2976 |
| gat tat gtc gct gcg act atc gaa gag ctc gtt tca ggc tgc ggc gtc<br>Asp Tyr Val Ala Ala Thr Ile Glu Glu Leu Val Ser Gly Cys Gly Val<br>            995                          1000                    1005 | 3024 |
| gcc aag gtc gtg ctg atc gcc aag gac aag tcc ggc gaa aag gcg gtg<br>Ala Lys Val Val Leu Ile Ala Lys Asp Lys Ser Gly Glu Lys Ala Val<br>            1010                        1015                    1020 | 3072 |
| cgc gac cag ttg ccc aac gac ctt tcg aaa gac gcg ctc gaa gtg ctg<br>Arg Asp Gln Leu Pro Asn Asp Leu Ser Lys Asp Ala Leu Glu Val Leu<br>1025                    1030                      1035                    1040 | 3120 |
| atc gcg ggt gat ggg ctt gag gaa gcg atg gac gag gcg ctt ggc cat<br>Ile Ala Gly Asp Gly Leu Glu Glu Ala Met Asp Glu Ala Leu Gly His<br>                  1045                      1050                    1055 | 3168 |
| tgg ggc aag ccc acg acg gtc ctg tcc atg ccg ggt gaa ccc ttg ccc<br>Trp Gly Lys Pro Thr Thr Val Leu Ser Met Pro Gly Glu Pro Leu Pro<br>            1060                        1065                    1070 | 3216 |
| gat cac ctg ttc gaa ggc ggc aac ccg ctt tcg acc aag gat ttc gcg<br>Asp His Leu Phe Glu Gly Gly Asn Pro Leu Ser Thr Lys Asp Phe Ala<br>1075                    1080                      1085 | 3264 |
| cat atg gtc gag gcg aac atc acc cgc cac tat cgc gtg acg cgc aag<br>His Met Val Glu Ala Asn Ile Thr Arg His Tyr Arg Val Thr Arg Lys | 3312 |

```
                1090                1095               1100
gcg tcg ctt tat gac gga tgc caa gtc gtg ttg gtg tcg ccg gac gtg        3360
Ala Ser Leu Tyr Asp Gly Cys Gln Val Val Leu Val Ser Pro Asp Val
1105                1110                1115                1120 ccg tac ggc tcc gat ggc ccc gga gtg gcg ctc gcc aat ttc gtg aag        3408
Pro Tyr Gly Ser Asp Gly Pro Gly Val Ala Leu Ala Asn Phe Val Lys
            1125                1130                1135 acg agc ctg cac gct ttc acc gcg acg gtt gcg gtg gag aat gag agg        3456
Thr Ser Leu His Ala Phe Thr Ala Thr Val Ala Val Glu Asn Glu Arg
        1140                1145                1150 ttg gtc cac gat gtg ccg gtc aac cag atc aac ctc acc cgc cgt gtc        3504
Leu Val His Asp Val Pro Val Asn Gln Ile Asn Leu Thr Arg Arg Val
    1155                1160                1165 tcg agc gag gag ccg cgc gat gct gac gaa cat gcc gag gag ctt agg        3552
Ser Ser Glu Glu Pro Arg Asp Ala Asp Glu His Ala Glu Glu Leu Arg
1170                1175                1180 cgc ttc acc cgc gct gtt ctg ttg gtc ggc gca ccg ctg ccc gat gcg        3600
Arg Phe Thr Arg Ala Val Leu Leu Val Gly Ala Pro Leu Pro Asp Ala
1185                1190                1195                1200 cag gac tcg cgc tac cgc tcg aag atc tat cgc ggc acg tcg atg acg        3648
Gln Asp Ser Arg Tyr Arg Ser Lys Ile Tyr Arg Gly Thr Ser Met Thr
            1205                1210                1215 gtc tag                                                                 3654
Val <210> SEQ ID NO 10
<211> LENGTH: 1217
<212> TYPE: PRT
<213> ORGANISM: Erythrobacter sp.
<220> FEATURE:
<223> OTHER INFORMATION: [CDS]:1..3654 from SEQ ID NO 9

<400> SEQUENCE: 10

Met Ser Lys Glu Gly Asn Ala Ala Lys Gly Arg Leu Glu Gly Lys Val
1               5                   10                  15

Ala Leu Ile Thr Gly Ala Ala Gly Asn Leu Gly Asn Glu Ile Ser Arg
            20                  25                  30

Ala Phe Ala Arg Glu Gly Ala Phe Val Val Met Thr Gly Arg Thr Glu
        35                  40                  45

Glu Arg Ile Ser Ala Ala Arg Glu Gln Leu Ile Ala Asp Thr Gly Val
    50                  55                  60

Ala Pro Glu Arg Ile Asp Thr Ala Val Leu Asp Gly Gly Asn Pro Asp
65                  70                  75                  80

Ser Ile Arg Ala Ala Met Ala Lys Leu Arg Lys Glu Tyr Gly Arg Ile
                85                  90                  95

Asp Ile Leu Ile Asn Asn Ala Gly Ser Ala Gly Pro Lys Gln Pro Leu
            100                 105                 110

His Asn Val Pro Leu Ser Pro Gln Glu Met Glu Ala Cys Gly Asp Thr
        115                 120                 125

Glu Thr Val Arg Asp Ala Met Leu Asn Ile Leu Gly Val Thr Trp Asn
    130                 135                 140

Met Ala Arg Ile Val Ala Pro Met Met Pro Val Gly Gly Ala Met Val
145                 150                 155                 160

Asn Ile Ser Thr Ile Phe Ser His Thr Arg Tyr Tyr Gly Arg Thr Ala
                165                 170                 175

Tyr Val Val Pro Lys Ala Ala Leu Asn Ala Leu Ser Asn Gln Leu Ala
            180                 185                 190

Ser Glu Leu Gly Pro Arg Gly Ile Arg Val Asn Thr Val Phe Pro Gly
```

```
            195                 200                 205
Pro Ile Glu Ser Asp Arg Ile Arg Thr Val Phe Ala Ala Met Asp Glu
210                 215                 220

Val Gln Ser Gln Pro Lys Asp Thr Thr Ala Asn Tyr Phe Thr Gly Arg
225                 230                 235                 240

Met Ala Leu Thr Arg Ser Val Asn Gly Lys Val Asp Gly Lys Pro Leu
                245                 250                 255

Pro Asn Pro Lys Asp Ile Ala Gly Thr Cys Leu Phe Leu Ala Ser Glu
            260                 265                 270

Glu Ala Ala Gly Ile Ala Gly Glu Val Asp Val Thr His Gly Leu
        275                 280                 285

Ser Ala Asn Arg Thr Ser Ala Ser Thr Tyr Met Thr Arg Pro Ser Met
290                 295                 300

Arg Ser Leu Asp Gly Ala Gly Leu Asn Ile Phe Ile Val Ser Gly Glu
305                 310                 315                 320

Asn Trp Asp Asp Ala Leu Val Ala Ala His Thr Leu Ile Gly Ser Gly
                325                 330                 335

Ala Lys Val Arg Leu Gly Leu Ala Arg Asn Ala Asp Val Ala Gln Ala
            340                 345                 350

Asn Ala Arg Leu Lys Ala Gln Gly Ile Gly Glu Leu Thr Val Thr
        355                 360                 365

Arg Phe Asn Arg Ala Glu Pro Asp Ala Met Glu Asp Ala Leu Ala Ala
370                 375                 380

Phe Ser Gly Asp Val Asp Gly Ala Ile Thr Gly Ala Ile Ile Leu Pro
385                 390                 395                 400

Val Lys Pro Ser Gly His Phe Thr Gly Ser Leu Leu Ala Ala Asp Asp
                405                 410                 415

Asp Thr Val Thr Lys Phe Met Asp Thr Glu Leu Val Gly Ala Ile Ala
            420                 425                 430

Val Ser Arg Ser Leu Ala Arg Tyr Trp His Gly Arg Glu Asp Leu Gln
        435                 440                 445

Ser Pro Pro Arg Cys Val Phe Met Thr Asn Pro Gly Asp Pro Leu Gly
450                 455                 460

Asn Ser Phe Ala Ser Val Leu Ser Ala Gly Ile Thr Gln Leu Ile Arg
465                 470                 475                 480

Ile Trp Arg Asp Glu Glu Arg Val Gln Ala Gly Asn Gly Ser Thr Glu
                485                 490                 495

His Ala Val Trp Ser Asn Gln Ile Val Arg His Thr Asn Thr Glu Asp
            500                 505                 510

Glu Asn Thr Arg Phe Ala Ser Gly His Ala Thr Arg Val Leu Phe Arg
        515                 520                 525

Glu Gln His Ile Ala Glu Ile Asp Leu Lys Leu Pro Ala Asn Ile Ser
530                 535                 540

Glu Glu Thr Gly Ser Arg Lys Ala Met Val Gly Phe Ala Glu Asn Ile
545                 550                 555                 560

Thr Gly Leu His Leu Gly Lys Val Ala Phe Ile Thr Gly Gly Ser Ala
                565                 570                 575

Gly Ile Gly Gly Gln Val Ala Arg Leu Leu Ala Leu Ala Gly Ala Lys
            580                 585                 590

Val Met Met Val Ala Arg Arg Glu Ser Glu Leu Val Ala Ala Arg Asp
        595                 600                 605

Arg Ile Val Gly Glu Leu Gln Asp Ile Gly Phe Ala Gly Val Glu Arg
610                 615                 620
```

```
Arg Val Lys Tyr Met Ala Asp Ile Asp Val Ser Asp Phe Ala Ser Leu
625                 630                 635                 640

Asp Lys Ala Val Asp Ala Thr Leu Glu Glu Phe Gly Arg Ile Asp Tyr
            645                 650                 655

Leu Ile Asn Asn Ala Gly Val Ala Gly Ala Glu Asp Met Val Ile Asp
                660                 665                 670

Met Glu Pro Glu Ala Trp Arg Phe Thr Leu Asp Ala Asn Leu Ile Ser
        675                 680                 685

Asn Tyr His Leu Met Gln Arg Val Pro Leu Met Lys Glu Gln Gly
            690                 695                 700

Ser Gly Tyr Val Leu Asn Val Ser Ser Tyr Phe Gly Glu Lys Phe
705                 710                 715                 720

Leu Ala Val Ala Tyr Pro Asn Arg Ala Asp Tyr Gly Leu Ser Lys Ala
                725                 730                 735

Gly Gln Arg Ala Met Val Glu Ala Phe Ser Pro Phe Leu Gly Pro Glu
            740                 745                 750

Val Gln Cys Asn Ala Ile Ala Pro Gly Pro Val Asp Gly Asp Arg Leu
        755                 760                 765

Ser Gly Thr Gly Lys Pro Gly Leu Phe Gln Arg Arg Ala Lys Leu
            770                 775                 780

Ile Leu Glu Asn Lys Arg Leu Asn Ala Val Tyr Ser Ala Val Ile His
785                 790                 795                 800

Ala Ile Arg Glu Gly Gly Asp Ala Ala Lys Ile Leu Thr Arg Leu Ser
                805                 810                 815

Arg Asn Ser Thr Ser Thr Leu Ser His Asp Ala Glu Ala Pro Glu Glu
            820                 825                 830

Leu Arg Lys Leu Ala Leu Asp Phe Ala Ser Gln Gly Asp Gly Leu Cys
        835                 840                 845

Thr Trp Asp Gln Tyr Leu Leu Thr Asp Ala Met Ala Gln Arg Leu Leu
        850                 855                 860

Val Arg Leu Gln Leu Gly Gly Phe Leu Leu Gly Ser Asn Glu Trp Ala
865                 870                 875                 880

Ser Leu Ser Ser Ser Glu Gln Thr Trp Leu Lys Leu Ser Pro Pro Asp
                885                 890                 895

Asp Lys Pro Phe Leu Pro Ala Ala Gln Val Asp Lys Val Ala Asn Gly
            900                 905                 910

Val Gly Lys Gly Val Ile Ser Gln Leu His Leu Gly Ala Met Pro Thr
        915                 920                 925

Glu Ala Glu Val Ala Gln Ala Thr Val Phe Phe Leu Ala Asp Arg Ala
        930                 935                 940

Val Ser Gly Glu Thr Phe Met Pro Ser Gly Gly Leu Arg Val Glu Arg
945                 950                 955                 960

Ser Asn Thr Glu Arg Glu Met Phe Gly Ser Pro Lys Gln Glu Arg Ile
            965                 970                 975

Asp Lys Met Lys Gly Lys Thr Val Trp Ile Ile Gly Glu His Leu Ser
        980                 985                 990

Asp Tyr Val Ala Ala Thr Ile Glu Glu Leu Val Ser Gly Cys Gly Val
        995                 1000                1005

Ala Lys Val Val Leu Ile Ala Lys Asp Lys Ser Gly Glu Lys Ala Val
    1010                1015                1020

Arg Asp Gln Leu Pro Asn Asp Leu Ser Lys Asp Ala Leu Glu Val Leu
1025                1030                1035                1040
```

-continued

```
Ile Ala Gly Asp Gly Leu Glu Glu Ala Met Asp Glu Ala Leu Gly His
                1045                1050                1055

Trp Gly Lys Pro Thr Thr Val Leu Ser Met Pro Gly Glu Pro Leu Pro
            1060                1065                1070

Asp His Leu Phe Glu Gly Gly Asn Pro Leu Ser Thr Lys Asp Phe Ala
        1075                1080                1085

His Met Val Glu Ala Asn Ile Thr Arg His Tyr Arg Val Thr Arg Lys
    1090                1095                1100

Ala Ser Leu Tyr Asp Gly Cys Gln Val Val Leu Val Ser Pro Asp Val
1105                1110                1115                1120

Pro Tyr Gly Ser Asp Gly Pro Gly Val Ala Leu Ala Asn Phe Val Lys
                1125                1130                1135

Thr Ser Leu His Ala Phe Thr Ala Thr Val Ala Val Glu Asn Glu Arg
            1140                1145                1150

Leu Val His Asp Val Pro Val Asn Gln Ile Asn Leu Thr Arg Arg Val
        1155                1160                1165

Ser Ser Glu Glu Pro Arg Asp Ala Asp Glu His Ala Glu Glu Leu Arg
    1170                1175                1180

Arg Phe Thr Arg Ala Val Leu Leu Val Gly Ala Pro Leu Pro Asp Ala
1185                1190                1195                1200

Gln Asp Ser Arg Tyr Arg Ser Lys Ile Tyr Arg Gly Thr Ser Met Thr
                1205                1210                1215

Val

<210> SEQ ID NO 11
<211> LENGTH: 1629
<212> TYPE: DNA
<213> ORGANISM: Ralstonia eutropha H16
<220> FEATURE:
<223> OTHER INFORMATION: Coding sequence of the gene encoding
      propionyl-CoA transferase
<220> FEATURE:
<221> NAME/KEY: CDS
<222> LOCATION: 1..1629
<223> OTHER INFORMATION: /transl_table=11

<400> SEQUENCE: 11 atg aag gtg atc acc gca cgc gaa gcg gcg gca ctg gtg cag gac ggc      48
Met Lys Val Ile Thr Ala Arg Glu Ala Ala Ala Leu Val Gln Asp Gly
1               5                   10                  15 tgg acc gtg gcc agc gcg ggc ttt gtc ggc gcc ggc cat gcc gag gcc      96
Trp Thr Val Ala Ser Ala Gly Phe Val Gly Ala Gly His Ala Glu Ala
            20                  25                  30 gtg acc gag gcg ctg gag cag cgc ttc ctg cag agc ggg ctg ccg cgc     144
Val Thr Glu Ala Leu Glu Gln Arg Phe Leu Gln Ser Gly Leu Pro Arg
        35                  40                  45 gac ctg acg ctg gtg tac tcg gcc ggg cag ggc gac cgc ggc gcg cgc     192
Asp Leu Thr Leu Val Tyr Ser Ala Gly Gln Gly Asp Arg Gly Ala Arg
    50                  55                  60 ggc gtg aac cac ttc ggc aat gcc ggc atg acc gcc agc atc gtc ggc     240
Gly Val Asn His Phe Gly Asn Ala Gly Met Thr Ala Ser Ile Val Gly
65                  70                  75                  80 ggc cac tgg cgc tcg gcc acg cgg ctg gcc acg ctg gcc atg gcc gag     288
Gly His Trp Arg Ser Ala Thr Arg Leu Ala Thr Leu Ala Met Ala Glu
                85                  90                  95 cag tgc gag ggc tac aac ctg ccg cag ggc gtg ctg acg cac cta tac     336
Gln Cys Glu Gly Tyr Asn Leu Pro Gln Gly Val Leu Thr His Leu Tyr
            100                 105                 110 cgc gcc atc gcc ggc ggc aag ccc ggc gtg atg acc aag atc ggc ctg     384
```

```
                Arg Ala Ile Ala Gly Gly Lys Pro Gly Val Met Thr Lys Ile Gly Leu
                                115                 120                 125 cac acc ttc gtc gac ccg cgc acc gcg cag gat gcg cgc tac cac ggc          432
His Thr Phe Val Asp Pro Arg Thr Ala Gln Asp Ala Arg Tyr His Gly
            130                 135                 140 ggc gcc gtc aac gag cgc gcg cgc cag gcc att gcc gag ggc aag gca          480
Gly Ala Val Asn Glu Arg Ala Arg Gln Ala Ile Ala Glu Gly Lys Ala
145                 150                 155                 160 tgc tgg gtc gat gcg gtc gac ttc cgc ggc gac gaa tac ctg ttc tac          528
Cys Trp Val Asp Ala Val Asp Phe Arg Gly Asp Glu Tyr Leu Phe Tyr
                165                 170                 175 ccg agc ttc ccg atc cac tgc gcg ctg atc cgc tgc acc gcg gcc gac          576
Pro Ser Phe Pro Ile His Cys Ala Leu Ile Arg Cys Thr Ala Ala Asp
            180                 185                 190 gcc cgc ggc aac ctc agc acc cat cgc gaa gcc ttc cac cat gag ctg          624
Ala Arg Gly Asn Leu Ser Thr His Arg Glu Ala Phe His His Glu Leu
        195                 200                 205 ctg gcg atg gcg cag gcg gcc cac aac tcg ggc ggc atc gtg atc gcg          672
Leu Ala Met Ala Gln Ala Ala His Asn Ser Gly Gly Ile Val Ile Ala
    210                 215                 220 cag gtg gaa agc ctg gtc gac cac cac gag atc ctg cag gcc atc cac          720
Gln Val Glu Ser Leu Val Asp His His Glu Ile Leu Gln Ala Ile His
225                 230                 235                 240 gtg ccc ggc atc ctg gtc gac tac gtg gtg gtc tgc gac aac ccc gcc          768
Val Pro Gly Ile Leu Val Asp Tyr Val Val Val Cys Asp Asn Pro Ala
                245                 250                 255 aac cac cag atg acg ttt gcc gag tcc tac aac ccg gcc tac gtg acg          816
Asn His Gln Met Thr Phe Ala Glu Ser Tyr Asn Pro Ala Tyr Val Thr
            260                 265                 270 cca tgg caa ggc gag gca gcg gtg gcc gaa gcg gaa gcg gcg ccg gtg          864
Pro Trp Gln Gly Glu Ala Ala Val Ala Glu Ala Glu Ala Ala Pro Val
        275                 280                 285 gct gcc ggc ccg ctc gac gcg cgc acc atc gtg cag cgc cgt gcg gtg          912
Ala Ala Gly Pro Leu Asp Ala Arg Thr Ile Val Gln Arg Arg Ala Val
    290                 295                 300 atg gaa ctg gcg cgc cgt gcg ccg cgc gtg gtc aac ctg ggc gtg ggc          960
Met Glu Leu Ala Arg Arg Ala Pro Arg Val Val Asn Leu Gly Val Gly
305                 310                 315                 320 atg ccg gca gcg gtc ggc atg ctg gcg cac cag gcc ggg ctg gac ggc         1008
Met Pro Ala Ala Val Gly Met Leu Ala His Gln Ala Gly Leu Asp Gly
                325                 330                 335 ttc acg ctg acc gtc gag gcc ggc ccc atc ggc ggc acg ccc gcg gat         1056
Phe Thr Leu Thr Val Glu Ala Gly Pro Ile Gly Gly Thr Pro Ala Asp
            340                 345                 350 ggc ctc agc ttc ggt gcc tcg gcc tac ccg gag gcg gtg gtg gat cag         1104
Gly Leu Ser Phe Gly Ala Ser Ala Tyr Pro Glu Ala Val Val Asp Gln
        355                 360                 365 ccc gcg cag ttc gat ttc tac gag ggc ggc ggc atc gac ctg gcc atc         1152
Pro Ala Gln Phe Asp Phe Tyr Glu Gly Gly Gly Ile Asp Leu Ala Ile
    370                 375                 380 ctc ggc ctg gcc gag ctg gat ggc cac ggc aac gtc aat gtc agc aag         1200
Leu Gly Leu Ala Glu Leu Asp Gly His Gly Asn Val Asn Val Ser Lys
385                 390                 395                 400 ttc ggc gaa ggc gag ggc gca tcg att gcc ggc gtc ggc ggc ttt atc         1248
Phe Gly Glu Gly Glu Gly Ala Ser Ile Ala Gly Val Gly Gly Phe Ile
                405                 410                 415 aac atc acg cag agc gcg cgc gcg gtg gtg ttc atg ggc acg ctg acg         1296
Asn Ile Thr Gln Ser Ala Arg Ala Val Val Phe Met Gly Thr Leu Thr
            420                 425                 430
```

```
gcg ggc ggg ctg gaa gtc cgc gcc ggc gac ggc ggc ctg cag atc gtg      1344
Ala Gly Gly Leu Glu Val Arg Ala Gly Asp Gly Gly Leu Gln Ile Val
        435                 440                 445 cgc gaa ggc cgc gtg aag aag atc gtg cct gag gtg tcg cac ctg agc      1392
Arg Glu Gly Arg Val Lys Lys Ile Val Pro Glu Val Ser His Leu Ser
450                 455                 460 ttc aac ggg ccc tat gtg gcg tcg ctc ggc atc ccg gtg ctg tac atc      1440
Phe Asn Gly Pro Tyr Val Ala Ser Leu Gly Ile Pro Val Leu Tyr Ile
465                 470                 475                 480 acc gag cgc gcg gtg ttc gag atg cgc gct ggc gca gac ggc gaa gcc      1488
Thr Glu Arg Ala Val Phe Glu Met Arg Ala Gly Ala Asp Gly Glu Ala
                485                 490                 495 cgc ctc acg ctg gtc gag atc gcc ccc ggc gtg gac ctg cag cgc gac      1536
Arg Leu Thr Leu Val Glu Ile Ala Pro Gly Val Asp Leu Gln Arg Asp
            500                 505                 510 gtg ctc gac cag tgc tcg acg ccc atc gcc gtt gcg cag gac ctg cgc      1584
Val Leu Asp Gln Cys Ser Thr Pro Ile Ala Val Ala Gln Asp Leu Arg
        515                 520                 525 gaa atg gat gcg cgg ctg ttc cag gcc ggg ccc ctg cac ctg taa          1629
Glu Met Asp Ala Arg Leu Phe Gln Ala Gly Pro Leu His Leu
    530                 535                 540

<210> SEQ ID NO 12
<211> LENGTH: 542
<212> TYPE: PRT
<213> ORGANISM: Ralstonia eutropha H16
<220> FEATURE:
<223> OTHER INFORMATION: [CDS]:1..1629 from SEQ ID NO 11

<400> SEQUENCE: 12

Met Lys Val Ile Thr Ala Arg Glu Ala Ala Ala Leu Val Gln Asp Gly
1               5                   10                  15

Trp Thr Val Ala Ser Ala Gly Phe Val Gly Ala Gly His Ala Glu Ala
            20                  25                  30

Val Thr Glu Ala Leu Glu Gln Arg Phe Leu Gln Ser Gly Leu Pro Arg
        35                  40                  45

Asp Leu Thr Leu Val Tyr Ser Ala Gly Gln Gly Asp Arg Gly Ala Arg
    50                  55                  60

Gly Val Asn His Phe Gly Asn Ala Gly Met Thr Ala Ser Ile Val Gly
65                  70                  75                  80

Gly His Trp Arg Ser Ala Thr Arg Leu Ala Thr Leu Ala Met Ala Glu
                85                  90                  95

Gln Cys Glu Gly Tyr Asn Leu Pro Gln Gly Val Leu Thr His Leu Tyr
            100                 105                 110

Arg Ala Ile Ala Gly Gly Lys Pro Gly Val Met Thr Lys Ile Gly Leu
        115                 120                 125

His Thr Phe Val Asp Pro Arg Thr Ala Gln Asp Ala Arg Tyr His Gly
    130                 135                 140

Gly Ala Val Asn Glu Arg Ala Arg Gln Ala Ile Ala Glu Gly Lys Ala
145                 150                 155                 160

Cys Trp Val Asp Ala Val Asp Phe Arg Gly Asp Glu Tyr Leu Phe Tyr
                165                 170                 175

Pro Ser Phe Pro Ile His Cys Ala Leu Ile Arg Cys Thr Ala Ala Asp
            180                 185                 190

Ala Arg Gly Asn Leu Ser Thr His Arg Glu Ala Phe His His Glu Leu
        195                 200                 205

Leu Ala Met Ala Gln Ala Ala His Asn Ser Gly Gly Ile Val Ile Ala
    210                 215                 220
```

Gln Val Glu Ser Leu Val Asp His His Glu Ile Leu Gln Ala Ile His
225                 230                 235                 240

Val Pro Gly Ile Leu Val Asp Tyr Val Val Cys Asp Asn Pro Ala
            245                 250                 255

Asn His Gln Met Thr Phe Ala Glu Ser Tyr Asn Pro Tyr Val Thr
        260                 265                 270

Pro Trp Gln Gly Glu Ala Ala Val Ala Glu Ala Glu Ala Pro Val
    275                 280                 285

Ala Ala Gly Pro Leu Asp Ala Arg Thr Ile Val Gln Arg Arg Ala Val
290                 295                 300

Met Glu Leu Ala Arg Arg Ala Pro Arg Val Val Asn Leu Gly Val Gly
305                 310                 315                 320

Met Pro Ala Ala Val Gly Met Leu Ala His Gln Ala Gly Leu Asp Gly
            325                 330                 335

Phe Thr Leu Thr Val Glu Ala Gly Pro Ile Gly Gly Thr Pro Ala Asp
        340                 345                 350

Gly Leu Ser Phe Gly Ala Ser Ala Tyr Pro Glu Ala Val Val Asp Gln
    355                 360                 365

Pro Ala Gln Phe Asp Phe Tyr Glu Gly Gly Ile Asp Leu Ala Ile
370                 375                 380

Leu Gly Leu Ala Glu Leu Asp Gly His Gly Asn Val Asn Val Ser Lys
385                 390                 395                 400

Phe Gly Glu Gly Glu Gly Ala Ser Ile Ala Gly Val Gly Gly Phe Ile
            405                 410                 415

Asn Ile Thr Gln Ser Ala Arg Ala Val Val Phe Met Gly Thr Leu Thr
        420                 425                 430

Ala Gly Gly Leu Glu Val Arg Ala Gly Asp Gly Gly Leu Gln Ile Val
    435                 440                 445

Arg Glu Gly Arg Val Lys Lys Ile Val Pro Glu Val Ser His Leu Ser
450                 455                 460

Phe Asn Gly Pro Tyr Val Ala Ser Leu Gly Ile Pro Val Leu Tyr Ile
465                 470                 475                 480

Thr Glu Arg Ala Val Phe Glu Met Arg Ala Gly Ala Asp Gly Glu Ala
            485                 490                 495

Arg Leu Thr Leu Val Glu Ile Ala Pro Gly Val Asp Leu Gln Arg Asp
        500                 505                 510

Val Leu Asp Gln Cys Ser Thr Pro Ile Ala Val Ala Gln Asp Leu Arg
    515                 520                 525

Glu Met Asp Ala Arg Leu Phe Gln Ala Gly Pro Leu His Leu
530                 535                 540

<210> SEQ ID NO 13
<211> LENGTH: 1584
<212> TYPE: DNA
<213> ORGANISM: [Clostridium] propionicum
<220> FEATURE:
<223> OTHER INFORMATION: Coding sequence of the gene encoding
    propionyl-CoA transferase
<220> FEATURE:
<221> NAME/KEY: CDS
<222> LOCATION: 1..1584
<223> OTHER INFORMATION: /transl_table=11

<400> SEQUENCE: 13 atg ctc gag atg aga aag gtt ccc att att acc gca gat gag gct gca     48
Met Leu Glu Met Arg Lys Val Pro Ile Ile Thr Ala Asp Glu Ala Ala
1               5                   10                  15

-continued

```
aag ctt att aaa gac ggt gat aca gtt aca aca agt ggt ttc gtt gga      96
Lys Leu Ile Lys Asp Gly Asp Thr Val Thr Thr Ser Gly Phe Val Gly
         20                  25                  30 aat gca atc cct gag gct ctt gat aga gct gta gaa aaa aga ttc tta     144
Asn Ala Ile Pro Glu Ala Leu Asp Arg Ala Val Glu Lys Arg Phe Leu
     35                  40                  45 gaa aca ggc gaa ccc aaa aac att aca tat gtt tat tgt ggt tct caa     192
Glu Thr Gly Glu Pro Lys Asn Ile Thr Tyr Val Tyr Cys Gly Ser Gln
 50                  55                  60 ggt aac aga gac gga aga ggt gct gag cac ttt gct cat gaa ggc ctt     240
Gly Asn Arg Asp Gly Arg Gly Ala Glu His Phe Ala His Glu Gly Leu
 65                  70                  75                  80 tta aaa cgt tac atc gct ggt cac tgg gct aca gtt cct gct ttg ggt     288
Leu Lys Arg Tyr Ile Ala Gly His Trp Ala Thr Val Pro Ala Leu Gly
                 85                  90                  95 aaa atg gct atg gaa aat aaa atg gaa gca tat aat gta tct cag ggt     336
Lys Met Ala Met Glu Asn Lys Met Glu Ala Tyr Asn Val Ser Gln Gly
            100                 105                 110 gca ttg tgt cat ttg ttc cgt gat ata gct tct cat aag cca ggc gta     384
Ala Leu Cys His Leu Phe Arg Asp Ile Ala Ser His Lys Pro Gly Val
        115                 120                 125 ttt aca aag gta ggt atc ggt act ttc att gac ccc aga aat ggc ggc     432
Phe Thr Lys Val Gly Ile Gly Thr Phe Ile Asp Pro Arg Asn Gly Gly
    130                 135                 140 ggt aaa gta aat gat att acc aaa gaa gat att gtt gaa ttg gta gag     480
Gly Lys Val Asn Asp Ile Thr Lys Glu Asp Ile Val Glu Leu Val Glu
145                 150                 155                 160 att aag ggt cag gaa tat tta ttc tac cct gct ttt cct att cat gta     528
Ile Lys Gly Gln Glu Tyr Leu Phe Tyr Pro Ala Phe Pro Ile His Val
                165                 170                 175 gct ctt att cgt ggt act tac gct gat gaa agc gga aat atc aca ttt     576
Ala Leu Ile Arg Gly Thr Tyr Ala Asp Glu Ser Gly Asn Ile Thr Phe
            180                 185                 190 gag aaa gaa gtt gct cct ctg gaa gga act tca gta tgc cag gct gtt     624
Glu Lys Glu Val Ala Pro Leu Glu Gly Thr Ser Val Cys Gln Ala Val
        195                 200                 205 aaa aac agt ggc ggt atc gtt gta gtt cag gtt gaa aga gta gta aaa     672
Lys Asn Ser Gly Gly Ile Val Val Val Gln Val Glu Arg Val Val Lys
    210                 215                 220 gct ggt act ctt gac cct cgt cat gta aaa gtt cca gga att tat gtt     720
Ala Gly Thr Leu Asp Pro Arg His Val Lys Val Pro Gly Ile Tyr Val
225                 230                 235                 240 gac tat gtt gtt gtt gct gac cca gaa gat cat cag caa tct tta gat     768
Asp Tyr Val Val Val Ala Asp Pro Glu Asp His Gln Gln Ser Leu Asp
                245                 250                 255 tgt gaa tat gat cct gca tta tca ggc gag cat aga aga cct gaa gtt     816
Cys Glu Tyr Asp Pro Ala Leu Ser Gly Glu His Arg Arg Pro Glu Val
            260                 265                 270 gtt gga gaa cca ctt cct ttg agt gca aag aaa gtt att ggt cgt cgt     864
Val Gly Glu Pro Leu Pro Leu Ser Ala Lys Lys Val Ile Gly Arg Arg
        275                 280                 285 ggt gcc att gaa tta gaa aaa gat gtt gct gta aat tta ggt gtt ggt     912
Gly Ala Ile Glu Leu Glu Lys Asp Val Ala Val Asn Leu Gly Val Gly
    290                 295                 300 gcg cct gaa tat gta gca agt gtt gct gat gaa gaa ggt atc gtt gat     960
Ala Pro Glu Tyr Val Ala Ser Val Ala Asp Glu Glu Gly Ile Val Asp
305                 310                 315                 320 ttt atg act tta act gct gaa agt ggt gct att ggt ggt gtt cct gct    1008
Phe Met Thr Leu Thr Ala Glu Ser Gly Ala Ile Gly Gly Val Pro Ala
```

|  |  |  |  |  |  |  |  |  |  |  |  |  |  |  |  |
|---|---|---|---|---|---|---|---|---|---|---|---|---|---|---|---|
|  |  |  | 325 |  |  |  | 330 |  |  |  | 335 |  |  |  |  |
| ggt | ggc | gtt | cgc | ttt | ggt | gct | tct | tat | aat | gcg | gat | gca | ttg | atc | gat | 1056 |
| Gly | Gly | Val | Arg | Phe | Gly | Ala | Ser | Tyr | Asn | Ala | Asp | Ala | Leu | Ile | Asp |
|  |  |  | 340 |  |  |  | 345 |  |  |  | 350 |  |  |  |  |
| caa | ggt | tat | caa | ttc | gat | tac | tat | gat | ggc | ggc | gga | tta | gac | ctt | tgc | 1104 |
| Gln | Gly | Tyr | Gln | Phe | Asp | Tyr | Tyr | Asp | Gly | Gly | Gly | Leu | Asp | Leu | Cys |
|  |  |  | 355 |  |  |  | 360 |  |  |  | 365 |  |  |  |  |
| tat | tta | ggc | tta | gct | gaa | tgc | gat | gaa | aaa | ggc | aat | atc | aac | gtt | tca | 1152 |
| Tyr | Leu | Gly | Leu | Ala | Glu | Cys | Asp | Glu | Lys | Gly | Asn | Ile | Asn | Val | Ser |
|  |  |  | 370 |  |  |  | 375 |  |  |  | 380 |  |  |  |  |
| aga | ttt | ggc | cct | cgt | atc | gct | ggt | tgt | ggt | ggt | ttc | atc | aac | att | aca | 1200 |
| Arg | Phe | Gly | Pro | Arg | Ile | Ala | Gly | Cys | Gly | Gly | Phe | Ile | Asn | Ile | Thr |
| 385 |  |  |  | 390 |  |  |  | 395 |  |  |  | 400 |  |  |  |
| cag | aat | aca | cct | aag | gta | ttc | ttc | tgt | ggt | act | ttc | aca | gca | ggt | ggc | 1248 |
| Gln | Asn | Thr | Pro | Lys | Val | Phe | Phe | Cys | Gly | Thr | Phe | Thr | Ala | Gly | Gly |
|  |  |  |  | 405 |  |  |  | 410 |  |  |  | 415 |  |  |  |
| tta | aag | gtt | aaa | att | gaa | gat | ggc | aag | gtt | att | att | gtt | caa | gaa | ggc | 1296 |
| Leu | Lys | Val | Lys | Ile | Glu | Asp | Gly | Lys | Val | Ile | Ile | Val | Gln | Glu | Gly |
|  |  |  | 420 |  |  |  | 425 |  |  |  | 430 |  |  |  |  |
| aag | cag | aaa | aaa | ttc | ttg | aaa | gct | gtt | gag | cag | att | aca | ttc | aat | ggt | 1344 |
| Lys | Gln | Lys | Lys | Phe | Leu | Lys | Ala | Val | Glu | Gln | Ile | Thr | Phe | Asn | Gly |
|  |  |  | 435 |  |  |  | 440 |  |  |  | 445 |  |  |  |  |
| gac | gtt | gca | ctt | gct | aat | aag | caa | caa | gta | act | tat | att | aca | gaa | aga | 1392 |
| Asp | Val | Ala | Leu | Ala | Asn | Lys | Gln | Gln | Val | Thr | Tyr | Ile | Thr | Glu | Arg |
|  | 450 |  |  |  | 455 |  |  |  | 460 |  |  |  |  |  |  |
| tgc | gta | ttc | ctt | ttg | aag | gaa | gat | ggt | ttg | cac | tta | tct | gaa | att | gca | 1440 |
| Cys | Val | Phe | Leu | Leu | Lys | Glu | Asp | Gly | Leu | His | Leu | Ser | Glu | Ile | Ala |
| 465 |  |  |  | 470 |  |  |  | 475 |  |  |  | 480 |  |  |  |
| cct | ggt | att | gat | ttg | cag | aca | cag | att | ctt | gac | gtt | atg | gat | ttt | gca | 1488 |
| Pro | Gly | Ile | Asp | Leu | Gln | Thr | Gln | Ile | Leu | Asp | Val | Met | Asp | Phe | Ala |
|  |  |  | 485 |  |  |  | 490 |  |  |  | 495 |  |  |  |  |
| cct | att | att | gac | aga | gat | gca | aac | ggc | caa | atc | aaa | ttg | atg | gac | gct | 1536 |
| Pro | Ile | Ile | Asp | Arg | Asp | Ala | Asn | Gly | Gln | Ile | Lys | Leu | Met | Asp | Ala |
|  |  |  | 500 |  |  |  | 505 |  |  |  | 510 |  |  |  |  |
| gct | ttg | ttt | gca | gaa | ggc | tta | atg | ggt | ctg | aag | gaa | atg | aag | tcc | tga | 1584 |
| Ala | Leu | Phe | Ala | Glu | Gly | Leu | Met | Gly | Leu | Lys | Glu | Met | Lys | Ser |  |
|  |  |  | 515 |  |  |  | 520 |  |  |  | 525 |  |  |  |  |

<210> SEQ ID NO 14
<211> LENGTH: 527
<212> TYPE: PRT
<213> ORGANISM: [Clostridium] propionicum
<220> FEATURE:
<223> OTHER INFORMATION: [CDS]:1..1584 from SEQ ID NO 13

<400> SEQUENCE: 14

Met Leu Glu Met Arg Lys Val Pro Ile Ile Thr Ala Asp Glu Ala Ala
1               5                   10                  15

Lys Leu Ile Lys Asp Gly Asp Thr Val Thr Thr Ser Gly Phe Val Gly
            20                  25                  30

Asn Ala Ile Pro Glu Ala Leu Asp Arg Ala Val Glu Lys Arg Phe Leu
        35                  40                  45

Glu Thr Gly Glu Pro Lys Asn Ile Thr Tyr Val Tyr Cys Gly Ser Gln
    50                  55                  60

Gly Asn Arg Asp Gly Arg Gly Ala Glu His Phe Ala His Glu Gly Leu
65                  70                  75                  80

Leu Lys Arg Tyr Ile Ala Gly His Trp Ala Thr Val Pro Ala Leu Gly
                85                  90                  95

Lys Met Ala Met Glu Asn Lys Met Glu Ala Tyr Asn Val Ser Gln Gly

```
            100                 105                 110
Ala Leu Cys His Leu Phe Arg Asp Ile Ala Ser His Lys Pro Gly Val
        115                 120                 125

Phe Thr Lys Val Gly Ile Gly Thr Phe Ile Asp Pro Arg Asn Gly Gly
        130                 135                 140

Gly Lys Val Asn Asp Ile Thr Lys Glu Asp Ile Val Glu Leu Val Glu
145                 150                 155                 160

Ile Lys Gly Gln Glu Tyr Leu Phe Tyr Pro Ala Phe Pro Ile His Val
                    165                 170                 175

Ala Leu Ile Arg Gly Thr Tyr Ala Asp Glu Ser Gly Asn Ile Thr Phe
                180                 185                 190

Glu Lys Glu Val Ala Pro Leu Glu Gly Thr Ser Val Cys Gln Ala Val
            195                 200                 205

Lys Asn Ser Gly Gly Ile Val Val Gln Val Glu Arg Val Val Lys
        210                 215                 220

Ala Gly Thr Leu Asp Pro Arg His Val Lys Val Pro Gly Ile Tyr Val
225                 230                 235                 240

Asp Tyr Val Val Ala Asp Pro Glu Asp His Gln Gln Ser Leu Asp
                    245                 250                 255

Cys Glu Tyr Asp Pro Ala Leu Ser Gly Glu His Arg Arg Pro Glu Val
                260                 265                 270

Val Gly Glu Pro Leu Pro Leu Ser Ala Lys Lys Val Ile Gly Arg Arg
                275                 280                 285

Gly Ala Ile Glu Leu Glu Lys Asp Val Ala Val Asn Leu Gly Val Gly
        290                 295                 300

Ala Pro Glu Tyr Val Ala Ser Val Ala Asp Glu Glu Gly Ile Val Asp
305                 310                 315                 320

Phe Met Thr Leu Thr Ala Glu Ser Gly Ala Ile Gly Gly Val Pro Ala
                    325                 330                 335

Gly Gly Val Arg Phe Gly Ala Ser Tyr Asn Ala Asp Ala Leu Ile Asp
                340                 345                 350

Gln Gly Tyr Gln Phe Asp Tyr Tyr Asp Gly Gly Gly Leu Asp Leu Cys
            355                 360                 365

Tyr Leu Gly Leu Ala Glu Cys Asp Glu Lys Gly Asn Ile Asn Val Ser
370                 375                 380

Arg Phe Gly Pro Arg Ile Ala Gly Cys Gly Gly Phe Ile Asn Ile Thr
385                 390                 395                 400

Gln Asn Thr Pro Lys Val Phe Phe Cys Gly Thr Phe Thr Ala Gly Gly
                405                 410                 415

Leu Lys Val Lys Ile Glu Asp Gly Lys Val Ile Val Gln Glu Gly
                420                 425                 430

Lys Gln Lys Lys Phe Leu Lys Ala Val Glu Gln Ile Thr Phe Asn Gly
            435                 440                 445

Asp Val Ala Leu Ala Asn Lys Gln Val Thr Tyr Ile Thr Glu Arg
450                 455                 460

Cys Val Phe Leu Leu Lys Glu Asp Gly Leu His Leu Ser Glu Ile Ala
465                 470                 475                 480

Pro Gly Ile Asp Leu Gln Thr Gln Ile Leu Asp Val Met Asp Phe Ala
                    485                 490                 495

Pro Ile Ile Asp Arg Asp Ala Asn Gly Gln Ile Lys Leu Met Asp Ala
                500                 505                 510

Ala Leu Phe Ala Glu Gly Leu Met Gly Leu Lys Glu Met Lys Ser
            515                 520                 525
```

<210> SEQ ID NO 15
<211> LENGTH: 2004
<212> TYPE: DNA
<213> ORGANISM: Artificial Sequence
<220> FEATURE:
<223> OTHER INFORMATION: Nucleic acid sequence of pccA gene from
      Methylobacterium extorquens with mutated NcoI restriction site

<400> SEQUENCE: 15

```
atgttcgata agatcctgat tgccaaccgg ggcgaaatcg cctgccgtat catcaagacg      60
gcccagaaaa tgggcatcaa gacggtggcg gtctattcgg acgccgaccg tgatgcggtc     120
cacgtcgcga tggccgacga ggcggtgcat atcggcccgg cgcccgctgc gcagtcctac     180
cttctgatcg aaaagatcat cgacgcctgc aagcagaccg cgcccaagc ggtccatccg      240
ggctacggct tcctttccga gcgcgagtcc ttccccaagg cgctggcgga agcgggcatc     300
gtctttatcg cccccaatcc gggtgccatc gccgcaatgg gcgacaagat cgaatcgaag     360
aaggccgcgg ccgcggccga ggtctcgacg gtgccgggct cctcggcgt gatcgagagc      420
cccgagcacg ccgtgacgat cgccgatgag atcggctatc cggtgatgat caaggcgtcg     480
gcgggcggcg gcgcaaggg tatgcgcatc gccgaatcgg ccgatgaggt cgccgagggc     540
ttcgcccgcg ccaagtccga ggcctcgtcc tccttcggcg acgaccgcgt cttcgtggaa     600
aagttcatca ccgacccgcg ccacatcgag atccaggtga tcggcgataa gcacggcaac     660
gtgatctatc tcggtgagcg cgagtgctcg atccagcgcc gcaaccagaa ggtcatcgag     720
gaggcgccgt cgccgctcct cgacgaagag acgcgccgca agatgggcga gcaggcggtc     780
gcgctcgcca aggccgtgaa ttacgactcc gccggcaccg tcgagttcgt cgccggccag     840
gacaagtcgt tctacttcct cgaaatgaac cccgcctgc aggtggagca cccggtcacc      900
gagatgatca ccgggctcga cctcgtcgag ctgatgatcc gggtggccgc cggcgagaag     960
ctgccgctgt cgcaggatca ggtgaagctc gacggctggg cggtcgagag ccgcgtctat    1020
gccgaggatc cgacccgcaa cttcctgccc tcgatcggtc ggctgactac ctaccagccg    1080
ccggaggagg gcccgctcgg cggggcgatc gtgcgcaacg ataccggcgt ggaggagggc    1140
ggcgagatcg cgatccacta cgatccgatg attgccaagc tcgtaacctg gcgcgccacc    1200
cggttggaag ccatcgaagc gcaggcgacc gcgctcgacg ccttcgccat cgagggcatc    1260
cgccacaaca tcccttcct cgccaccctg atggcccatc ccgctggcg cgacggccgg     1320
ctctcgacgg gcttcatcaa ggaagagttc cccgaaggct tcatcgcacc cgagcccgag    1380
gggccggtcg ctcatcggct cgcggcggtg gcggcggcga tcgatcacaa gctcaacatc    1440
cgcaagcgcg gcatctccgg ccagatgcgc gacccgagcc tgctgacctt ccagcgcgag    1500
cgcgtggtgg tgctctccgg ccagcgcttc aacgtcaccg tcgatcctga cggcgacgac    1560
ctcctcgtca ccttcgacga cggtacgaca gccccggtgc gcagcgcgtg gcgcccggt     1620
gcgccggtct ggagcggtac ggtcggagat cagtcggtcg cgatccaggt gcgtccgctc    1680
ctcaacggtg tgttcctgca gcatgcgggc gcggcggcgg aagcgcgggt gttcacccgc    1740
cgcgaggccg aactcgccga cctgatgccg gtcaaggaga atgccggctc cggcaagcag    1800
ctcctttgcc cgatgccgg cctggtcaag cagatcatgg tcagcgaggg ccaggaggtg    1860
aagaacggcg agccgctggc catcgtcgag gcgatgaaga tggagaacgt gctgcgcgcc    1920
gaacgcgacg gcaccatctc caagatcgcc gccaaggaag cgacagcct cgccgtcgat    1980
gccgtgatcc tggaattcgc ctga                                          2004
```

```
<210> SEQ ID NO 16
<211> LENGTH: 30
<212> TYPE: DNA
<213> ORGANISM: Artificial Sequence
<220> FEATURE:
<223> OTHER INFORMATION: Primer for mutating NcoI restriction site in
      the pccA gene from Methylobacterium extorquens

<400> SEQUENCE: 16
ggtgccatcg ccgcaatggg cgacaagatc                                      30

<210> SEQ ID NO 17
<211> LENGTH: 30
<212> TYPE: DNA
<213> ORGANISM: Artificial Sequence
<220> FEATURE:
<223> OTHER INFORMATION: Primer for mutating NcoI restriction site in
      the pccA gene from Methylobacterium extorquens

<400> SEQUENCE: 17
gatcttgtcg cccattgcgg cgatggcacc                                      30

<210> SEQ ID NO 18
<211> LENGTH: 32
<212> TYPE: DNA
<213> ORGANISM: Artificial Sequence
<220> FEATURE:
<223> OTHER INFORMATION: Primer for amplifying the pccA gene from
      Methylobacterium extorquens

<400> SEQUENCE: 18
cggctgccat atgttcgata agatcctgat tg                                   32

<210> SEQ ID NO 19
<211> LENGTH: 32
<212> TYPE: DNA
<213> ORGANISM: Artificial Sequence
<220> FEATURE:
<223> OTHER INFORMATION: Primer for amplifying the pccA gene from
      Methylobacterium extorquens

<400> SEQUENCE: 19
catgcgtggt acctcaggcg aattccagga tc                                   32

<210> SEQ ID NO 20
<211> LENGTH: 6558
<212> TYPE: DNA
<213> ORGANISM: Artificial Sequence
<220> FEATURE:
<223> OTHER INFORMATION: Nucleic acid sequence of the pTE100 vector

<400> SEQUENCE: 20 gacccttctcc gacgctcacc gggctggttg ccctcgccgc tgggctggcg gccgtctatg     60
gccctgcaaa cgcgccagaa acgccgtcga agccgtgtgc gagacaccgc ggccgccggc    120
gttgtggata cctcgcggaa aacttggccc tcactgacag atgaggggcg gacgttgaca    180
cttgaggggc cgactcaccc ggcgcggcgt tgacagatga ggggcaggct cgatttcggc    240
cggcgacgtg gagctggcca gcctcgcaaa tcggcgaaaa cgcctgattt tacgcgagtt    300
tcccacagat gatgtggaca agcctgggga taagtgccct gcggtattga cacttgaggg    360
gcgcgactac tgacagatga ggggcgcgat ccttgacact tgaggggcag agtgctgaca    420
gatgaggggc gcacctattg acatttgagg ggctgtccac aggcagaaaa tccagcattt    480
```

-continued

```
gcaagggttt ccgcccgttt ttcggccacc gctaacctgt cttttaacct gcttttaaac      540
caatatttat aaaccttgtt tttaaccagg gctgcgccct gtgcgcgtga ccgcgcacgc      600 cgaaggggg  tgcccccct  tctcgaaccc tcccggcccg ctaacgcggg cctcccatcc      660 ccccagggc  tgcgccctc  ggccgcgaac ggcctcaccc caaaaatggc agccaagctg      720
accacttctg cgctcggccc ttccggctgg ctggtttatt gctgataaat ctggagccgg      780
tgagcgtggg tctcgcggta tcattgcagc actgggcca  gatggtaagc cctcccgtat      840
cgtagttatc tacacgacgg ggagtcaggc aactatggat gaacgaaata gacagatcgc      900
tgagataggt gcctcactga ttaagcattg gtaactgtca gaccaagttt actcatatat      960
actttagatt gatttaaaac ttcatttta atttaaaagg atctaggtga agatccttt      1020 tgataatctc atgaccaaaa tcccttaacg tgagttttcg ttccactgag cgtcagaccc      1080
cgtagaaaag atcaaaggat cttcttgaga tcctttttt  ctgcgcgtaa tctgctgctt      1140
gcaaacaaaa aaaccaccgc taccagcggt ggtttgtttg ccggatcaag agctaccaac      1200
tctttttccg aaggtaactg gcttcagcag agcgcagata ccaaatactg ttcttctagt      1260
gtagccgtag ttaggccacc acttcaagaa ctctgtagca ccgcctacat acctcgctct      1320
gctaatcctg ttaccagtgg ctgctgccag tggcgataag tcgtgtctta ccgggttgga      1380
ctcaagacga tagttaccgg ataaggcgca gcggtcgggc tgaacggggg gttcgtgcac      1440
acagcccagc ttggagcgaa cgacctacac cgaactgaga tacctacagc gtgagctatg      1500
agaaagcgcc acgcttcccg aagggagaaa ggcggacagg tatccggtaa gcggcagggt      1560
cggaacagga gagcgcacga gggagcttcc agggggaaac gcctggtatc tttatagtcc      1620
tgtcgggttt cgccacctct gacttgagcg tcgatttttg tgatgctcgt caggggggcg      1680
gagcctatgg aaaaacgcca gcaacgcggc cttttacgg  ttcctggcct tttgctggcc      1740
ttttgctcac atggaattct gtacatctag aaataagaag gagatataat taatccatgg      1800
caattgaagc ttagatcttg actagtcctg caggtaccta attcactggc cgtcgtttta      1860
caacgtcgtg actgggaaaa ccctggcgtt acccaactta atcgccttgc agcacatccc      1920
cctttcgcca gctggcgtaa tagcgaagag gcccgcaccg atcgcccttc ccaacagttg      1980
cgcagcctga atggcgaatg gcgcctgatg cggtatttc tccttacgca tctgtgcggt      2040
atttcacacc gcatatggtg cactctcagt acaatctgct ctgatgccgc atagttaagc      2100
cagccccgac acccgccaac acccgctgac gcgccctgac gggcttgtct gctcccggca      2160
tccgcttaca gacaagctgt gaccgtctcc gggagctgca tgtgtcagag gttttcaccg      2220
tcatcaccga aacgcgcgag acgaaagggc ctcgtgatac gcctattttt ataggttaat      2280
gtcatgataa taatggtttc ttagcaccct ttctcggtcc ttcaacgttc ctgacaacga      2340
gcctcctttt cgccaatcca tcgacaatca ccgcgagtcc ctgctcgaac gctgcgtccg      2400
gaccggcttc gtcgaaggcg tctatcgcgg cccgcaacag cggcgagagc ggagcctgtt      2460
caacggtgcc gccgcgctcg ccggcatcgc tgtcgccggc ctgctcctca gcacggccc       2520 caacagtgaa gtagctgatt gtcatcagcg cattgacggc gtccccggcc gaaaaacccg      2580
cctcgcagag gaagcgaagc tgcgcgtcgg ccgtttccat ctgcggtgcg cccggtcgcg      2640
tgccggcatg gatgcgcgcg ccatcgcggt aggcgagcag cgcctgcctg aagctgcggg      2700
cattcccgat cagaaatgag cgccagtcgt cgtcggctct cggcaccgaa tgcgtatgat      2760
tctccgccag catggcttcg gccagtgcgt cgagcagcgc ccgcttgttc ctgaagtgcc      2820
agtaaagcgc cggctgctga accccaacc  gttccgccag tttgcgtgtc gtcagaccgt      2880
```

```
ctacgccgac ctcgttcaac aggtccaggg cggcacggat cactgtattc ggctgcaact    2940
ttgtcatgct tgacacttta tcactgataa acataatatg tccaccaact tatcagtgat    3000
aaagaatccg cgcgttcaat cggaccagcg gaggctggtc cggaggccag acgtgaaacc    3060
caacataccc ctgatcgtaa ttctgagcac tgtcgcgctc gacgctgtcg gcatcggcct    3120
gattatgccg gtgctgccgg gcctcctgcg cgatctggtt cactcgaacg acgtcaccgc    3180
ccactatggc attctgctgg cgctgtatgc gttggtgcaa tttgcctgcg cacctgtgct    3240
gggcgcgctg tcggatcgtt cgggcggcg gccaatcttg ctcgtctcgc tggccggcgc    3300
cactgtcgac tacgccatca tggcgacagc gcctttcctt tgggttctct atatcgggcg    3360
gatcgtggcc ggcatcaccg gggcgactgg ggcggtagcc ggcgcttata ttgccgatat    3420
cactgatggc gatgagcgcg cgcggcactt cggcttcatg agcgcctgtt tcgggttcgg    3480
gatggtcgcg ggacctgtgc tcggtgggct gatgggcggt ttctcccccc acgctccgtt    3540
cttcgccgcg gcagccttga acggcctcaa tttcctgacg ggctgtttcc ttttgccgga    3600
gtcgcacaaa ggcgaacgcc ggccgttacg ccgggaggct ctcaacccgc tcgcttcgtt    3660
ccggtgggcc cggggcatga ccgtcgtcgc cgccctgatg gcggtcttct tcatcatgca    3720
acttgtcgga caggtgccgg ccgcgctttg ggtcattttc ggcgaggatc gctttcactg    3780
ggacgcgacc acgatcggca tttcgcttgc cgcatttggc attctgcatt cactcgccca    3840
ggcaatgatc accggccctg tagccgcccg gctcggcgaa aggcgggcac tcatgctcgg    3900
aatgattgcc gacggcacag gctacatcct gcttgccttc gcgacacggg gatggatggc    3960
gttcccgatc atggtcctgc ttgcttcggg tggcatcgga atgccggcgc tgcaagcaat    4020
gttgtccagg caggtggatg aggaacgtca ggggcagctg caaggctcac tggcggcgct    4080
caccagcctg acctcgatcg tcggaccccc cctcttcacg gcgatctatg cggcttctat    4140
aacaacgtgg aacgggtggg catggattgc aggcgctgcc ctctacttgc tctgcctgcc    4200
ggcgctgcgt cgcgggcttt ggagcggcgc agggcaacga gccgatcgct gatcgtggaa    4260
acgataggcc tatgccatgc gggtcaaggc gacttccggc aagctatacg cgccctagaa    4320
ttgtcaattt taatcctctg tttatcggca gttcgtagag cgcgccgtgc gtcccgagcg    4380
atactgagcg aagcaagtgc gtcgagcagt gcccgcttgt tcctgaaatg ccagtaaagc    4440
gctggctgct gaaccccag ccggaactga ccccacaagg ccctagcgtt tgcaatgcac    4500
caggtcatca ttgacccagg cgtgttccac caggccgctg cctcgcaact cttcgcaggc    4560
ttcgccgacc tgctcgcgcc acttcttcac gcgggtggaa tccgatccgc acatgaggcg    4620
gaaggtttcc agcttgagcg ggtacggctc ccggtgcgag ctgaaatagt cgaacatccg    4680
tcgggccgtc ggcgacagct tgcggtactt ctcccatatg aatttcgtgt agtggtcgcc    4740
agcaaacagc acgacgattt cctcgtcgat caggacctgg caacgggacg ttttcttgcc    4800
acggtccagg acgcggaagc ggtgcagcag cgacaccgat tccaggtgcc caacgcggtc    4860
ggacgtgaag cccatcgccg tcgcctgtag gcgcgacagg cattcctcgg ccttcgtgta    4920
ataccggcca ttgatcgacc agcccaggtc ctggcaaagc tcgtagaacg tgaaggtgat    4980
cggctcgccg atagggtgc gcttcgcgta ctccaacacc tgctgccaca ccagttcgtc    5040
atcgtcggcc cgcagctcga cgccggtgta ggtgatcttc acgtccttgt tgacgtggaa    5100
aatgaccttg ttttgcagcg cctcgcgcgg gattttcttg ttgcgcgtgg tgaacagggc    5160
agagcgggcc gtgtcgtttg gcatcgctcg catcgtgtcc ggccacggcg caatatcgaa    5220
```

-continued

```
caaggaaagc tgcatttcct tgatctgctg cttcgtgtgt ttcagcaacg cggcctgctt    5280
ggcctcgctg acctgttttg ccaggtcctc gccggcggtt tttcgcttct tggtcgtcat    5340
agttcctcgc gtgtcgatgg tcatcgactt cgccaaacct gccgcctcct gttcgagacg    5400
acgcgaacgc tccacggcgg ccgatggcgc gggcagggca gggggagcca gttgcacgct    5460
gtcgcgctcg atcttggccg tagcttgctg gaccatcgag ccgacggact ggaaggtttc    5520
gcggggcgca cgcatgacgg tgcggcttgc gatggtttcg gcatcctcgg cggaaaaccc    5580
cgcgtcgatc agttcttgcc tgtatgcctt ccggtcaaac gtccgattca ttcaccctcc    5640
ttgcgggatt gccccgactc acgccggggc aatgtgccct tattcctgat ttgacccgcc    5700
tggtgccttg gtgtccagat aatccacctt atcggcaatg aagtcggtcc cgtagaccgt    5760
ctggccgtcc ttctcgtact tggtattccg aatcttgccc tgcacgaata ccagctccgc    5820
gaagtcgctc ttcttgatgg agcgcatggg gacgtgcttg gcaatcacgc gcaccccccg    5880
gccgttttag cggctaaaaa agtcatggct ctgccctcgg gcggaccacg cccatcatga    5940
ccttgccaag ctcgtcctgc ttctcttcga tcttcgccag cagggcgagg atcgtggcat    6000
caccgaaccg cgccgtgcgc gggtcgtcgg tgagccagag tttcagcagg ccgcccaggc    6060
ggcccaggtc gccattgatg cgggccagct cgcggacgtg ctcatagtcc acgacgcccg    6120
tgattttgta gccctggccg acggccagca ggtaggccta caggctcatg ccggccgccg    6180
ccgccttttc ctcaatcgct cttcgttcgt ctggaaggca gtacaccttg ataggtgggc    6240
tgcccttcct ggttggcttg gtttcatcag ccatccgctt gccctcatct gttacgccgg    6300
cggtagccgg ccagcctcgc agagcaggat tcccgttgag caccgccagg tgcgaataag    6360
ggacagtgaa gaggaacac ccgctcgcgg gtgggcctac ttcacctatc ctgcccggct    6420
gacgccgttg gatacaccaa ggaaagtcta cacgaaccct ttggcaaaat cctgtatatc    6480
gtgcgaaaaa ggatggatat accgaaaaaa tcgctataat gaccccgaag cagggttatg    6540
cagcggaaaa gatccgtc                                                 6558
```

<210> SEQ ID NO 21
<211> LENGTH: 44
<212> TYPE: DNA
<213> ORGANISM: Artificial Sequence
<220> FEATURE:
<223> OTHER INFORMATION: Primer for introducing the nucleic acid
      exchange into the pccB gene resulting in the amino acid exchange
      D407I

<400> SEQUENCE: 21
caaggccttc ggcggcgcct acatcgtcat ggcctccaag catg                    44

<210> SEQ ID NO 22
<211> LENGTH: 30
<212> TYPE: DNA
<213> ORGANISM: Artificial Sequence
<220> FEATURE:
<223> OTHER INFORMATION: Primer for introducing the nucleic acid
      exchange into the pccB gene resulting in the amino acid exchange
      Y143H

<400> SEQUENCE: 22
gcgctcggcg gccacggcga ggtgttccgc                                    30

<210> SEQ ID NO 23
<211> LENGTH: 7467
<212> TYPE: DNA
<213> ORGANISM: Artificial Sequence
<220> FEATURE:
<223> OTHER INFORMATION: pSEVA321 plasmid comprising between position 115 and 3827 a nucleic acid sequence that is codon-optimized for E.coli and encodes for malonyl-CoA reductase from Erythrobacter sp. NAP1

<400> SEQUENCE: 23

| | | | | | |
|---|---|---|---|---|---|
| ttaattaaag | atctcgatcc | cgcgaaatta | atacgactca | ctatagggga | attgtgagcg | 60 |
| gataacaatt | cccctctaga | aataattttg | tttaacttta | agaaggagat | ataccatggc | 120 |
| gtggagccac | ccgcagttcg | agaagggaag | cggccatatc | gaaggtcgtc | atatgagcaa | 180 |
| agaaggcaac | gcggctaaag | gtcgcctgga | gggcaaagtt | gctctgatca | ccggcgcagc | 240 |
| cggtaacctg | ggcaacgaaa | tctctcgtgc | ttttgctcgt | gagggtgcat | tcgtggttat | 300 |
| gactggtcgt | accgaagaac | gtatctctgc | tgcacgcgaa | cagctgatcg | ccgacaccgg | 360 |
| cgtagcgccg | gaacgtatcg | atactgctgt | gctggacggc | ggtaacccgg | actctatccg | 420 |
| cgcagcgatg | gctaaactgc | gtaaagagta | tggccgcatc | gacatcctga | tcaacaacgc | 480 |
| tggctctgcg | ggccctaaac | agccgctgca | caacgttccg | ctgtctccac | aggaaatgga | 540 |
| ggcatgtggt | gacaccgaga | ctgtacgtga | cgctatgctg | aacatcctgg | gtgttacctg | 600 |
| gaacatggca | cgcatcgtag | ccccgatgat | gccggttggc | ggtgcaatgg | ttaacatctc | 660 |
| taccatcttt | tctcacacac | gttactacgg | tcgtactgcg | tacgtagttc | gaaaagctgc | 720 |
| cctaaacgct | ctgtccaacc | agctggcctc | tgaactgggg | ccgcgtggca | tccgcgttaa | 780 |
| caccgtattc | ccgggtccta | ttgagtctga | ccgtatccgt | accgttttcg | ctgcaatgga | 840 |
| cgaggtacaa | tctcagccga | agatactacc | gcaaactac | tttactggtc | gtatggctct | 900 |
| gactcgttct | gtaaatggca | aggttgacgg | taaaccgctg | ccgaacccga | agatatcgc | 960 |
| aggcacttgt | ctgttccttg | caagcgaaga | ggctgcaggt | atcgcgggtg | aagaagtgga | 1020 |
| cgtgacccac | ggtctgagcg | ctaaccgtac | cagcgctagc | acgtatatga | cccgcccgtc | 1080 |
| tatgcgttct | ctggacggtg | cgggtctgaa | catcttcatc | gtttctggcg | aaaactggga | 1140 |
| cgacgccctg | gttgcagctc | acaccctgat | tggttccggt | gcaaaggtac | gtctgggtct | 1200 |
| ggcgcgtaac | gcagatgtag | cacaggctaa | cgcacgtctc | aaagcacagg | gcatcggtga | 1260 |
| agaactgacc | gttacacgtt | ttaaccgtgc | tgagccggac | gcaatggaag | acgctctggc | 1320 |
| tgcattcagc | ggcgacgtag | acggtgctat | cactggcgca | atcatcctgc | cggtaaaacc | 1380 |
| ttctggtcac | ttcactggtt | ctctgctggc | tgcagacgac | gataccgtta | ccaaattcat | 1440 |
| ggacacggag | ctggtgggtg | ctattgcagt | gtctcgctct | ctggcgcgct | attggcacgg | 1500 |
| ccgtgaagac | ctgcagtctc | cgccgcgctg | tgttttcatg | accaacccgg | gtgacccgct | 1560 |
| gggtaatagt | ttcgcatccg | tactgagcgc | aggtatcact | cagctgatcc | gcatctggcg | 1620 |
| tgacgaggaa | cgtgtgcagg | cgggtaacgg | ctctactgaa | cacgcagttt | ggtctaacca | 1680 |
| gatcgttcgt | cataccaaca | ctgaagacga | aaacacccgc | ttcgcatccg | gtcacgcaac | 1740 |
| tcgtgttctt | ttccgtgagc | agcacatcgc | tgaaatcgac | ctgaaactgc | cggccaacat | 1800 |
| ctctgaggaa | accggttctc | gcaaagcaat | ggtaggcttc | gcggaaaaca | tcactggcct | 1860 |
| gcatctgggt | aaagtagctt | tcatcaccgg | tggctctgcg | ggtatcggcg | gtcaggttgc | 1920 |
| acgtctgctg | gcgctggcag | gtgcgaaggt | tatgatggtt | gcacgtcgcg | aatctgaact | 1980 |
| ggtagctgca | cgtgaccgta | tcgttggtga | actgcaggac | atcggtttcg | caggcgttga | 2040 |
| gcgtcgtgta | aaatacatgg | cagacatcga | cgtttctgac | ttcgcatccc | tggataaagc | 2100 |
| tgtagacgca | actctggaag | agttcggtcg | tatcgactat | ctgatcaaca | acgctggtgt | 2160 |

```
ggctggtgct gaagacatgg taattgacat ggaaccggaa gcctggcgtt ttaccctgga    2220
cgctaacctt atctctaact atcacctgat gcagcgtgtg gtgccgctta tgaaagagca    2280
aggttctggc tacgtactga acgttagctc ttatttcggt ggcgaaaaat tcctggcagt    2340
agcttacccg aaccgtgcag actatggtct gtctaaggca ggtcagcgcg cgatggttga    2400
agcattctcc cctttccttg gcccggaggt acagtgcaac gctatcgctc cgggtccggt    2460
tgacggtgac cgtctctctg gtaccggcgg taaaccgggc tgttccagc gccgcgctaa     2520 actgatcctg gaaaacaaac gtctgaacgc tgtttattct gctgtaatcc atgcaatccg    2580
tgagggtggc gacgctgcaa aaatcctgac ccgcctgtct cgcaactcca cttctactct    2640
gtctcacgac gcagaagctc cggaagaact gcgtaagctg gcactggact tcgcgtccca    2700
gggtgacggc ctgtgcacct gggaccagta cctgctcacg gacgcgatgg cacagcgcct    2760
gctggttcgt ctgcagttgg gtggcttcct tctgggttcc aacgagtggg catccctgag    2820
ctcttccgaa cagacctggc tgaaactgtc tccgccggac gacaagccgt tcctgccggc    2880
agcacaggta gacaaagtag ccaacggtgt tggtaaaggt gttatctccc agctgcacct    2940
gggtgcaatg ccgaccgagg ctgaagtggc acaggctacc gtattcttcc tggcagaccg    3000
tgctgtgtct ggtgaaacgt tcatgccgag cggcggtctg cgcgtagaac gttctaacac    3060
tgaacgtgag atgttcggtt ctccgaaaca ggaacgtatc gataaaatga aggtaaaac    3120 cgtttggatc atcggcgaac acctgtctga ctatgtagca gcgactatcg aggagctggt    3180
ttccggttgc ggtgtagcaa aagtagttct gatcgctaaa gacaaatctg gtgaaaaagc    3240
agttcgtgac caactgccga cgacctgtc taaagacgct ctggaagttc tgatcgctgg    3300
tgacggtctg gaagaagcaa tggacgaggc actgggccac tggggtaaac caacaacggt    3360
tctgtctatg ccgggcgagc cgctgccgga ccacctgttc gaaggtggta cccgctgtc    3420 cactaaagac ttcgctcaca tggtcgaagc taacatcacc cgccactacc gtgttacccg    3480
taaagcatct ctgtacgacg gttgtcaggt agttctggtt tccccggacg taccatacgg    3540
ctctgacggc ccgggtgttg ctctggcaaa cttcgtgaaa acttctctgc atgcgtttac    3600
cgctactgtg gctgttgaaa acgagcgcct ggtacatgat gtcccggtta accagatcaa    3660
ccttacccgt cgtgtttcct ccaggaacc gcgcgacgcg gacgaacacg cagaagaact    3720
gcgccgtttc acccgtgcag tactgctggt gggtgctccg ctgccggacg cgcaggacag    3780
ccgctaccgc tctaaaatct accgcggtac ctccatgact gtataactcg aggatccggc    3840
tgctaacaaa gcccgaaagg aagctgagtt ggctgctgcc accgctgagc aataactagc    3900
ataacccctt ggggcctcta acgggtctt gagggggttttt tgactagtc ttggactcct    3960 gttgatagat ccagtaatga cctcagaact ccatctggat ttgttcagaa cgctcggttg    4020
ccgccgggcg ttttttattg gtgagaatcc aggggtcccc aataattacg atttaaattg    4080
gcgaaaatga cgttgatc ggcacgtaag aggttccaac tttcaccata atgaaataag    4140
atcactaccg ggcgtattt ttgagttatc gagattttca ggagctaagg aagctaaaat    4200
ggagaaaaaa atcactggat ataccaccgt tgatatatcc caatggcatc gtaaagaaca    4260
ttttgaggca tttcagtcag ttgctcaatg tacctataac cagaccgttc agctggatat    4320
tacggccttt ttaaagaccg taaagaaaaa taagcacaag ttttatccgg cctttattca    4380
cattcttgcc cgcctgatga atgctcatcc ggaatttcgt atggcaatga aagacgtga    4440 gctggtgata tgggatagtg ttcacccttg ttacaccgtt ttccatgagc aaactgaaac    4500
```

```
gttttcatcg ctctggagtg aataccacga cgatttccgg cagtttctac acatatattc   4560
gcaagatgtg gcgtgttacg gtgaaaacct ggcctatttc cctaaagggt ttattgagaa   4620
tatgtttttc gtctcagcca atccctgggt gagtttcacc agttttgatt taaacgtggc   4680
caatatggac aacttcttcg cccccgtttt caccatgggc aaatattata cgcaaggcga   4740
caaggtgctg atgccgctgg cgattcaggt tcatcatgcc gtttgtgatg gcttccatgt   4800
cggcagaatg cttaatgaat tacaacagta ctgcgatgag tggcagggcg gggcgtaatt   4860
tgacttttgt ccttttccgc tgcataaccc tgcttcgggg tcattatagc gatttttttcg   4920 gtatatccat cctttttcgc acgatataca ggattttgcc aaagggttcg tgtagacttt   4980
ccttggtgta tccaacggcg tcagccgggc aggataggtg aagtaggccc acccgcgagc   5040
gggtgttcct tcttcactgt cccttattcg cacctggcgg tgctcaacgg gaatcctgct   5100
ctgcgaggct ggccgtaggc cggccgcgat gcaggtgggc gctgaacccc cagccggaac   5160 tgacccccaca aggccctagc gtttgcaatg caccaggtca tcattgaccc aggcgtgttc   5220
caccaggccg ctgcctcgca actcttcgca ggcttcgccg acctgctcgc gccacttctt   5280
cacgcgggtg gaatccgatc cgcacatgag gcggaaggtt tccagcttga gcgggtacgg   5340
ctcccggtgc gagctgaaat agtcgaacat ccgtcgggcc gtcggcgaca gcttgcggta   5400
cttctcccat atgaatttcg tgtagtggtc gccagcaaac agcacgacga ttcctcgtc    5460 gatcaggacc tggcaacggg acgttttctt gccacggtcc aggacgcgga agcggtgcag   5520
cagcgacacc gattccaggt gcccaacgcg gtcggacgtg aagcccatcg ccgtcgcctg   5580
taggcgcgac aggcattcct cggccttcgt gtaataccgg ccattgatcg accagcccag   5640
gtcctggcaa agctcgtaga acgtgaaggt gatcggctcg ccgataggggg tgcgcttcgc   5700 gtactccaac acctgctgcc acaccagttc gtcatcgtcg gcccgcagct cgacgccggt   5760
gtaggtgatc ttcacgtcct tgttgacgtg gaaaatgacc ttgttttgca gcgcctcgcg   5820
cgggattttc ttgttgcgcg tggtgaacag ggcagagcgg gccgtgtcgt ttggcatcgc   5880
tcgcatcgtg tccggccacg gcgcaatatc gaacaaggaa agctgcattt ccttgatctg   5940
ctgcttcgtg tgtttcagca acgcggcctg cttggcttcg ctgacctgtt ttgccaggtc   6000
ctcgccggcg gttttttcgct tcttggtcgt catagttcct cgcgtgtcga tggtcatcga   6060
cttcgccaaa cctgccgcct cctgttcgag acgacgcgaa cgctccacgg cggccgatgg   6120
cgcgggcagg gcagggggag ccagttgcac gctgtcgcgc tcgatcttgg ccgtagcttg   6180
ctggactatc gagccgacgg actggaaggt ttcgcggggc gcacgcatga cggtgcggct   6240
tgcgatggtt tcggcatcct cggcggaaaa ccccgcgtcg atcagttctt gcctgtatgc   6300
cttccggtca aacgtccgat tcattcaccc tccttgcggg attgccccgg aattaattcc   6360
ccggatcgat ccgtcgatct tgatcccctg cgccatcaga tccttggcgg caagaaagcc   6420
atccagttta ctttgcaggg cttcccaacc ttaccagagg gcgccccagc tgcaattcc    6480 ggttcgcttg ctgtccataa aaccgcccag tctagctatc gccatgtaag cccactgcaa   6540
gctacctgct ttctctttgc gcttgcgttt tccttgtcc agatagccca gtagctgaca    6600
ttcatccggg gtcagcaccg tttctgcgga ctggctttct acgtggctgc catttttggg   6660
gtgaggccgt tcgcggccga ggggcgcagc ccctgggggg atgggaggcc cgcgttagcg   6720
ggccgggagg gttcgagaag ggggggcacc cccttcggc gtgcgcggtc acgcgcacag    6780
ggcgcagccc tggttaaaaa caaggtttat aaatatttggt ttaaaagcag gttaaaagac   6840
aggttagcgg tggccgaaaa acgggcggaa acccttgcaa atgctggatt ttctgcctgt   6900
```

-continued

```
ggacagcccc tcaaatgtca ataggtgcgc ccctcatctg tcagcactct gcccctcaag    6960
tgtcaaggat cgcgcccctc atctgtcagt agtcgcgccc ctcaagtgtc aataccgcag    7020
ggcacttatc cccaggcttg tccacatcat ctgtgggaaa ctcgcgtaaa atcaggcgtt    7080
ttcgccgatt tgcgaggctg gccagctcca cgtcgccggc cgaaatcgag cctgcccctc    7140
atctgtcaac gccgcgccgg gtgagtcggc ccctcaagtg tcaacgtccg ccctcatct    7200 gtcagtgagg gccaagtttt ccgcgaggta tccacaacgc cggcggccct acatggctct    7260
gctgtagtga gtgggttgcg ctccggcagc ggtcctgatc ccccgcagaa aaaaggatc    7320 tcaagaagat cctttgatct tttctacggc gcgcccagct gtctagggcg gcggatttgt    7380
cctactcagg agagcgttca ccgacaaaca acagataaaa cgaaaggccc agtctttcga    7440
ctgagccttt cgttttattt gatgcct                                         7467
```

<210> SEQ ID NO 24
<211> LENGTH: 32
<212> TYPE: DNA
<213> ORGANISM: Artificial Sequence
<220> FEATURE:
<223> OTHER INFORMATION: Forward Primer for amplifying the pccB gene
      from Methylobacterium extorquens genomic DNA

<400> SEQUENCE: 24

```
gaccgtgcat atgaaggaca tcctcgagaa gc                                     32
```

<210> SEQ ID NO 25
<211> LENGTH: 33
<212> TYPE: DNA
<213> ORGANISM: Artificial Sequence
<220> FEATURE:
<223> OTHER INFORMATION: Reverse Primer for amplifying the pccB gene
      from Methylobacterium extorquens genomic DNA

<400> SEQUENCE: 25

```
gatacatgaa ttctcagagc gggatgttgt cgt                                    33
```

<210> SEQ ID NO 26
<211> LENGTH: 6997
<212> TYPE: DNA
<213> ORGANISM: Artificial Sequence
<220> FEATURE:
<223> OTHER INFORMATION: pET16b plasmid comprising between position 180
      and 1765 the nucleic acid sequence encoding the propionyl-CoA
      transferase of Clostridium propionicum

<400> SEQUENCE: 26

```
tagaggatcg agatctcgat cccgcgaaat taatacgact cactataggg gaattgtgag      60
cggataacaa ttcccctcta gaaataattt tgtttaactt taagaaggag atataccatg     120
ggccatcatc atcatcatca tcatcatcat cacagcagcg gccatatcga aggtcgtcat     180
atgctcgaga tgaaaaggt tcccattatt accgcagatg aggctgcaaa gcttattaaa     240
gacggtgata cagttacaac aagtggtttc gttggaaatg caatccctga ggctcttgat     300
agagctgtag aaaaaagatt cttagaaaca ggcgaaccca aaacattac atatgtttat     360 tgtggttctc aaggtaacag agacggaaga ggtgctgagc actttgctca tgaaggcctt     420
ttaaaacgtt acatcgctgg tcactgggct acagttcctg ctttgggtaa aatggctatg     480
gaaaataaaa tggaagcata taatgtatct cagggtgcat tgtgtcattt gttccgtgat     540
atagcttctc ataagccagg cgtatttaca aaggtaggta tcggtacttt cattgacccc     600
```

```
agaaatggcg gcggtaaagt aaatgatatt accaaagaag atattgttga attggtagag      660
attaagggtc aggaatattt attctaccct gcttttccta ttcatgtagc tcttattcgt      720
ggtacttacg ctgatgaaag cggaaatatc acatttgaga aagaagttgc tcctctggaa      780
ggaacttcag tatgccaggc tgttaaaaac agtggcggta tcgttgtagt tcaggttgaa      840
agagtagtaa aagctggtac tcttgacccc cgtcatgtaa aagttccagg aatttatgtt      900
gactatgttt tgttgctga cccagaagat catcagcaat ctttagattg tgaatatgat      960
cctgcattat caggcgagca tagaagacct gaagttgttg agaaccact tcctttgagt     1020 gcaaagaaag ttattggtcg tcgtggtgcc attgaattag aaaaagatgt tgctgtaaat     1080
ttaggtgttg gtgcgcctga atatgtagca agtgttgctg atgaagaagg tatcgttgat     1140
tttatgactt taactgctga aagtggtgct attggtggtg ttcctgctgg tggcgttcgc     1200
tttggtgctt cttataatgc ggatgcattg atcgatcaag ttatcaatt cgattactat     1260 gatggcggcg gcttagacct ttgctattta ggcttagctg aatgcgatga aaaaggcaat     1320
atcaacgttt caagatttgg ccctcgtatc gctggttgtg gtggtttcat caacattaca     1380
cagaatacac ctaaggtatt cttctgtggt actttcacag caggtggctt aaaggttaaa     1440
attgaagatg gcaaggttat tattgttcaa gaaggcaagc agaaaaaatt cttgaaagct     1500
gttgagcaga ttacattcaa tggtgacgtt gcacttgcta ataagcaaca agtaacttat     1560
attacagaaa gatgcgtatt cctttttgaag gaagatgggtt tgcacttatc tgaaattgca     1620
cctggtattg atttgcagac acagattctt gacgttatgg attttgcacc tattattgac     1680
agagatgcaa acgccaaat caaattgatg gacgctgctg tgtttgcaga aggcttaatg     1740
ggtctgaagg aaatgaagtc ctgaaagctt atcgatgata agctgtcaaa catgagaatt     1800
cttgaagacg aaagggcctc gtgatacgcc tatttttata ggttaatgtc atgataataa     1860
tggtttctta gacgtcaggt ggcactttttc ggggaaatgt gcgcggaacc cctatttgtt     1920
tatttttcta aatacattca aatatgtatc cgctcatgag acaataaccc tgataaatgc     1980
ttcaataata ttgaaaaagg aagagtatga gtattcaaca tttccgtgtc gcccttattc     2040
ccttttttgc ggcattttgc cttcctgttt ttgctcaccc agaaacgctg gtgaaagtaa     2100
aagatgctga agatcagttg ggtgcacgag tgggttacat cgaactggat ctcaacagcg     2160
gtaagatcct tgagagttttt cgccccgaag aacgttttcc aatgatgagc acttttaaag     2220
ttctgctatg tggcgcggta ttatcccgtg ttgacgccgg caagagcaa ctcggtcgcc     2280 gcatacacta ttctcagaat gacttggttg agtactcacc agtcacagaa aagcatctta     2340
cggatggcat gacagtaaga gaattatgca gtgctgccat aaccatgagt gataacactg     2400
cggccaactt acttctgaca acgatcggag gaccgaagga gctaaccgct tttttgcaca     2460
acatggggga tcatgtaact cgccttgatc gttgggaacc ggagctgaat gaagccatac     2520
caaacgacga gcgtgacacc acgatgcctg cagcaatggc aacaacgttg cgcaaactat     2580
taactggcga actacttact ctagcttccc ggcaacaatt aatagactgg atggaggcgg     2640
ataaagttgc aggaccactt ctgcgctcgg cccttccggc tggctggttt attgctgata     2700
aatctggagc cggtgagcgt gggtctcgcg gtatcattgc agcactgggg ccagatggta     2760
agccctcccg tatcgtagtt atctacacga cggggagtca ggcaactatg gatgaacgaa     2820
atagacagat cgctgagata ggtgcctcac tgattaagca ttggtaactg tcagaccaag     2880
tttactcata tatactttag attgatttaa aacttcattt ttaatttaaa aggatctagg     2940
tgaagatcct tttttgataat ctcatgacca aaatccctta acgtgagttt tcgttccact     3000
```

```
gagcgtcaga ccccgtagaa aagatcaaag gatcttcttg agatcctttt tttctgcgcg   3060
taatctgctg cttgcaaaca aaaaaaccac cgctaccagc ggtggtttgt ttgccggatc   3120
aagagctacc aactcttttt ccgaaggtaa ctggcttcag cagagcgcag ataccaaata   3180
ctgtccttct agtgtagccg tagttaggcc accacttcaa gaactctgta gcaccgccta   3240
catacctcgc tctgctaatc ctgttaccag tggctgctgc cagtggcgat aagtcgtgtc   3300
ttaccgggtt ggactcaaga cgatagttac cggataaggc gcagcggtcg ggctgaacgg   3360
ggggttcgtg cacacagccc agcttggagc gaacgaccta caccgaactg agatacctac   3420
agcgtgagct atgagaaagc gccacgcttc ccgaagggag aaaggcggac aggtatccgg   3480
taagcggcag ggtcggaaca ggagagcgca cgagggagct tccaggggga aacgcctggt   3540
atctttatag tcctgtcggg tttcgccacc tctgacttga gcgtcgattt ttgtgatgct   3600
cgtcaggggg cggagcccta tggaaaaacg ccagcaacgc ggccttttta cggttcctgg   3660
ccttttgctg gccttttgct cacatgttct ttcctgcgtt atcccctgat tctgtggata   3720
accgtattac cgcctttgag tgagctgata ccgctcgccg cagccgaacg accgagcgca   3780
gcgagtcagt gagcgaggaa gcggaagagc gcctgatgcg gtattttctc cttacgcatc   3840
tgtgcggtat ttcacaccgc atatatggtg cactctcagt acaatctgct ctgatgccgc   3900
atagttaagc cagtatacac tccgctatcg ctacgtgact gggtcatggc tgcgccccga   3960
cacccgccaa cacccgctga cgcgccctga cgggcttgtc tgctcccggc atccgcttac   4020
agacaagctg tgaccgtctc cgggagctgc atgtgtcaga ggttttcacc gtcatcaccg   4080
aaacgcgcga ggcagctgcg gtaaagctca tcagcgtggt cgtgaagcga ttcacagatg   4140
tctgcctgtt catccgcgtc cagctcgttg agtttctcca gaagcgttaa tgtctggctt   4200
ctgataaagc gggccatgtt aagggcggtt ttttcctgtt tggtcactga tgcctccgtg   4260
taagggggat ttctgttcat gggggtaatg ataccgatga acgagagag gatgctcacg   4320 atacgggtta ctgatgatga acatgcccgg ttactggaac gttgtgaggg taaacaactg   4380
gcggtatgga tgcggcggga ccagagaaaa atcactcagg gtcaatgcca gcgcttcgtt   4440
aatacagatg taggtgttcc acagggtagc cagcagcatc ctgcgatgca gatccggaac   4500
ataatggtgc agggcgctga cttccgcgtt tccagacttt acgaaacacg gaaaccgaag   4560
accattcatg ttgttgctca ggtcgcagac gttttgcagc agcagtcgct tcacgttcgc   4620
tcgcgtatcg gtgattcatt ctgctaacca gtaaggcaac cccgccagcc tagccgggtc   4680
ctcaacgaca ggagcacgat catgcgcacc cgtggccagg acccaacgct gcccgagatg   4740
cgccgcgtgc ggctgctgga gatggcggac gcgatggata tgttctgcca agggttggtt   4800
tgcgcattca cagttctccg caagaattga ttggctccaa ttcttggagt ggtgaatccg   4860
ttagcgaggt gccgccggct tccattcagg tcgaggtggc ccggctccat gcaccgcgac   4920
gcaacgcggg gaggcagaca aggtataggg cggcgcctac aatccatgcc aacccgttcc   4980
atgtgctcgc cgaggcggca taaatcgccg tgacgatcag cggtccagtg atcgaagtta   5040
ggctggtaag agccgcgagc gatccttgaa gctgtccctg atggtcgtca tctacctgcc   5100
tggacagcat ggcctgcaac gcgggcatcc cgatgccgcc ggaagcgaga agaatcataa   5160
tggggaaggc catccagcct cgcgtcgcga acgccagcaa gacgtagccc agcgcgtcgg   5220
ccgccatgcc ggcgataatg gcctgcttct cgccgaaacg tttggtggcg gaccagtga   5280 cgaaggcttg agcgagggcg tgcaagattc cgaataccgc aagcgacagg ccgatcatcg   5340
```

-continued

```
tcgcgctcca gcgaaagcgg tcctcgccga aaatgaccca gagcgctgcc ggcacctgtc    5400
ctacgagttg catgataaag aagacagtca taagtgcggc gacgatagtc atgcccgcg     5460 cccaccggaa ggagctgact gggttgaagg ctctcaaggg catcggtcga gatcccggtg    5520
cctaatgagt gagctaactt acattaattg cgttgcgctc actgcccgct ttccagtcgg    5580
gaaacctgtc gtgccagctg cattaatgaa tcggccaacg cgcggggaga ggcggtttgc    5640
gtattgggcg ccagggtggt ttttcttttc accagtgaga cgggcaacag ctgattgccc    5700
ttcaccgcct ggccctgaga gagttgcagc aagcggtcca cgctggtttg ccccagcagg    5760
cgaaaatcct gtttgatggt ggttaacggc gggatataac atgagctgtc ttcggtatcg    5820
tcgtatccca ctaccgagat atccgcacca acgcgcagcc cggactcggt aatggcgcgc    5880
attgcgccca cgccatctg atcgttggca accagcatcg cagtgggaac gatgccctca     5940
ttcagcattt gcatggtttg ttgaaaaccg gacatggcac tccagtcgcc ttcccgttcc    6000
gctatcggct gaatttgatt gcgagtgaga tatttatgcc agccagccag acgcagacgc    6060
gccgagacag aacttaatgg gcccgctaac agcgcgattt gctggtgacc caatgcgacc    6120
agatgctcca cgcccagtcg cgtaccgtct tcatgggaga aaataatact gttgatgggt    6180
gtctggtcag agacatcaag aaataacgcc ggaacattag tgcaggcagc ttccacagca    6240
atggcatcct ggtcatccag cggatagtta atgatcagcc cactgacgcg ttgcgcgaga    6300
agattgtgca ccgccgcttt acaggcttcg acgccgcttc gttctaccat cgacaccacc    6360
acgctggcac ccagttgatc ggcgcgagat ttaatcgccg cgacaatttg cgacggcgcg    6420
tgcagggcca gactggaggt ggcaacgcca atcagcaacg actgtttgcc cgccagttgt    6480
tgtgccacgc ggttgggaat gtaattcagc tccgccatcg ccgcttccac ttttccgc      6540 gttttcgcag aaacgtggct ggcctggttc accacgcggg aaacggtctg ataagagaca    6600
ccggcatact ctgcgacatc gtataacgtt actggtttca cattcaccac cctgaattga    6660
ctctcttccg ggcgctatca tgccataccg cgaaaggttt tgcgccattc gatggtgtcc    6720
gggatctcga cgctctccct tatgcgactc ctgcattagg aagcagccca gtagtaggtt    6780
gaggccgttg agcaccgccg ccgcaaggaa tggtgcatgc aaggagatgg cgcccaacag    6840
tcccccggcc acggggcctg ccaccatacc cacgccgaaa caagcgctca tgagcccgaa    6900
gtggcgagcc cgatcttccc catcggtgat gtcggcgata taggcgccag caaccgcacc    6960
tgtggcgccg gtgatgccgg ccacgatgcg tccggcg                             6997
```